US009802988B2

(12) United States Patent
Donnenberg

(10) Patent No.: US 9,802,988 B2
(45) Date of Patent: *Oct. 31, 2017

(54) ENGINEERED TYPE IV PILIN OF CLOSTRIDIUM DIFFICILE

(71) Applicant: University of Maryland, Baltimore, Baltimore, MD (US)

(72) Inventor: Michael Donnenberg, Baltimore, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/259,413

(22) Filed: Apr. 23, 2014

(65) Prior Publication Data

US 2014/0227314 A1    Aug. 14, 2014

Related U.S. Application Data

(63) Continuation-in-part of application No. 13/974,825, filed on Aug. 23, 2013, now Pat. No. 9,310,381, which is a continuation of application No. 13/321,399, filed as application No. PCT/US2010/035664 on May 20, 2010, now Pat. No. 8,518,415.

(60) Provisional application No. 61/179,747, filed on May 20, 2009.

(51) Int. Cl.
| C07K 14/33 | (2006.01) |
| A61K 39/08 | (2006.01) |
| G01N 33/569 | (2006.01) |
| C07K 16/12 | (2006.01) |

(52) U.S. Cl.
CPC .............. *C07K 14/33* (2013.01); *A61K 39/08* (2013.01); *C07K 16/1282* (2013.01); *C07K 2317/20* (2013.01); *C07K 2317/33* (2013.01); *G01N 33/56911* (2013.01); *G01N 2333/33* (2013.01)

(58) Field of Classification Search
None
See application file for complete search history.

(56) References Cited

U.S. PATENT DOCUMENTS

| 6,248,329 | B1 | 6/2001 | Chandrashekar et al. |
| 6,290,960 | B1 | 9/2001 | Kink |
| 8,518,415 | B2 | 8/2013 | Donnenberg |
| 2004/0101531 | A1 | 5/2004 | Curtiss, III |
| 2013/0337003 | A1 | 12/2013 | Donnenberg |

FOREIGN PATENT DOCUMENTS

| WO | WO 99/55875 | * 11/1999 |
| WO | WO 0285295 | * 10/2002 |
| WO | 2004/099250 | 11/2004 |
| WO | 2007/026247 | 3/2007 |
| WO | 2008/127296 | 10/2008 |

OTHER PUBLICATIONS

Uniprot Accesion #Q185H8 Jul. 25, 2006.*
Uniprot Accesion #Q180D8 Jul. 25, 2006.*
Uniprot Accesion #Q181B2 Jul. 25, 2006.*
Dupont et al., New advances in Clostridium difficile infection: changing epidemiology, diagnosis, treatment and control, Current Opinion in Infectious Disease, 21: 500-507 (Oct. 2008).
Proft et al., Pili in Gram-negative and Gram-positive bacteria-structure,assembly and their role in disease, Cell. Mol. Life Sci., 66: 613-635 (Oct. 2008).
Uniprot Accession No. Q180D8. Uniprot Database sequence added Jul. 25, 2006.
Varga et al., Type IV pili-dependent gliding motility in the Gram-positive pathogen Clostridium perfringens and other Clostridia, Molecular Microbiology, 62: 680-694 (2006).
Office Action from U.S. Appl. No. 13/321,399, mailed Oct. 25, 2012.
Office Action from U.S. Appl. No. 13/321,399, mailed Aug. 28, 2012.
Van Dissel et al., Bovine antibody-enriched whey to aid in the prevention of a relapse of Clostridium difficile-associated diarrhoea, Journal of Medical Microbiology, 54(2):197-205 (2005).
Torres et al., Evaluation of formalin-inactivated Costridium difficile vaccines administered by parental and mucosal routes of immunization in hamsters, Infection and Immunity, 63(12): 4619-4627 (1995).
UniProt Accession No. Q181B2. Uniprot Database sequence added Jul. 25, 2006.
UniProt Accession No. Q185H8. Uniprot Database sequence added Jul. 25, 2006.
Craig et al., Type IV pili: paradoxes in form and function, Current Opinion in Structural Biology, 18(2):267-277 (Apr. 2008).
Gerd Döring et al., Vaccines and immunotherapy against Pseudomonas aeruginosa, Vaccine, 26(8):1011-1024 (Feb. 2008).
Telford et al., Pili in gram positive pathogens, Nature Reviews Microbiology, 4(7):509-519 (2006).
Office Action from U.S. Appl. No. 13/974,825, mailed May 7, 2014.
Boslego, J.W et al., Efficacy Trial of a Parenteral Gonococcal Pilus Vaccine in Men, Vaccine, 9(3):154-162 (1991).
Official Communication from European Application No. 10778421.7, dated Apr. 13, 2017.

* cited by examiner

*Primary Examiner* — Oluwatosin Ogunbiyi
(74) *Attorney, Agent, or Firm* — Nevrivy Patent Law Group P.L.L.C.

(57) ABSTRACT

The present invention relates to engineered *Clostridium difficile* type IV pilin (tfp) genes, type IV pilin proteins which can serve as a diagnostic marker for identification of patients infected with *C. difficile*, and vaccines comprising type IV pilin proteins, antigenic fragments and variants thereof for therapeutic interventions.

15 Claims, 10 Drawing Sheets

FIG. 5

SEQUENCE LISTING

```
<160> NUMBER OF SEQ ID NOS: 118

<210> SEQ ID NO 1
<211> LENGTH: 522
<212> TYPE: DNA
<213> ORGANISM: Clostridium difficile

<400> SEQUENCE: 1
atgaagttaa aaaagaataa aaaaggtttc actttagtgg aattattggt agtaattgca      60
attataggta tattagcagt agtggcagtt ccagctttat ttagtaatat aaacaaggct     120
aaggtagcaa gtgttgagtc tgattatagt tcaattaaga gtgcagcatt atcttattat     180
tcagatacta ataaaatacc agttacacca gatggtcaaa ctggtttaaa tgttttagag     240
acttatatgg aatctcttcc tgataaagct gatataggtg gagaatataa attgattaaa     300
gttggtaata aattagtatt acagataggt aaagatggtg aaggagttac cttaacagaa     360
```

```
gcgcaatcag caaaattatt gagtgatata ggtaaagata aaatatatac aggtgttaca      420
ggagataatt ttggagagca attaaaagat actacaaaaa tagataataa agctctatat      480
atagtactta tagataatac tgtgatggat tcaacaaaat ag                         522

<210> SEQ ID NO 2
<211> LENGTH: 173
<212> TYPE: PRT
<213> ORGANISM: Clostridium difficile

<400> SEQUENCE: 2

Met Lys Leu Lys Lys Asn Lys Lys Gly Phe Thr Leu Val Glu Leu Leu
1               5                   10                  15

Val Val Ile Ala Ile Ile Gly Ile Leu Ala Val Val Ala Val Pro Ala
            20                  25                  30

Leu Phe Ser Asn Ile Asn Lys Ala Lys Val Ala Ser Val Glu Ser Asp
        35                  40                  45

Tyr Ser Ser Ile Lys Ser Ala Ala Leu Ser Tyr Tyr Ser Asp Thr Asn
    50                  55                  60

Lys Ile Pro Val Thr Pro Asp Gly Gln Thr Gly Leu Asn Val Leu Glu
65                  70                  75                  80

Thr Tyr Met Glu Ser Leu Pro Asp Lys Ala Asp Ile Gly Gly Glu Tyr
                85                  90                  95

Lys Leu Ile Lys Val Gly Asn Lys Leu Val Leu Gln Ile Gly Lys Asp
            100                 105                 110

Gly Glu Gly Val Thr Leu Thr Glu Ala Gln Ser Ala Lys Leu Leu Ser
        115                 120                 125

Asp Ile Gly Lys Asp Lys Ile Tyr Thr Gly Val Thr Gly Asp Asn Phe
    130                 135                 140

Gly Glu Gln Leu Lys Asp Thr Thr Lys Ile Asp Asn Lys Ala Leu Tyr
145                 150                 155                 160

Ile Val Leu Ile Asp Asn Thr Val Met Asp Ser Thr Lys
                165                 170

<210> SEQ ID NO 3
<211> LENGTH: 558
<212> TYPE: DNA
<213> ORGANISM: Artificial Sequence
<220> FEATURE:
<223> OTHER INFORMATION: Synthetic polynucleotide

<400> SEQUENCE: 3
atgcaccatc atcatcatca ttcttctggt ctggtgccac gcggttctgg tatgaaagaa       60
accgctgctg ctaaattcga acgccagcac atggacagcc cagatctggg taccgacgac      120
gacgacaagg ccatgggttc taacatcaac aaagctaaag ttgcttctgt tgaatctgac      180
tactcttcta tcaaatctgc tgctctgtct tactactctg acaccaacaa atcccggtt       240 accccggacg gtcagaccgg tctgaacgtt ctggaaacct acatggaatc tctgccggac      300
aaagctgaca tcggtggtga atacaaactg atcaaagttg gtaacaaact ggttctgcag      360
atcggtaaag acggtgaagg tgttaccctg accgaagctc agtctgctaa actgctgtct      420
gacatcggta agacaaaat ctacaccggt gttaccggtg acaacttcgg tgaacagctg      480
aaagacacca ccaaaatcga caacaaagct ctgtacatcg ttctgatcga caacaccgtt      540
atggactcta ccaaatag                                                    558

<210> SEQ ID NO 4
```

```
<211> LENGTH: 185
<212> TYPE: PRT
<213> ORGANISM: Artificial Sequence
<220> FEATURE:
<223> OTHER INFORMATION: Synthetic polypeptide

<400> SEQUENCE: 4

Met His His His His His Ser Ser Gly Leu Val Pro Arg Gly Ser
1               5                   10                  15

Gly Met Lys Glu Thr Ala Ala Lys Phe Glu Arg Gln His Met Asp
            20                  25                  30

Ser Pro Asp Leu Gly Thr Asp Asp Asp Lys Ala Met Gly Ser Asn
        35                  40                  45

Ile Asn Lys Ala Lys Val Ala Ser Val Glu Ser Asp Tyr Ser Ser Ile
    50                  55                  60

Lys Ser Ala Ala Leu Ser Tyr Tyr Ser Asp Thr Asn Lys Ile Pro Val
65                  70                  75                  80

Thr Pro Asp Gly Gln Thr Gly Leu Asn Val Leu Glu Thr Tyr Met Glu
                85                  90                  95

Ser Leu Pro Asp Lys Ala Asp Ile Gly Gly Glu Tyr Lys Leu Ile Lys
            100                 105                 110

Val Gly Asn Lys Leu Val Leu Gln Ile Gly Lys Asp Gly Glu Gly Val
            115                 120                 125

Thr Leu Thr Glu Ala Gln Ser Ala Lys Leu Leu Ser Asp Ile Gly Lys
    130                 135                 140

Asp Lys Ile Tyr Thr Gly Val Thr Gly Asp Asn Phe Gly Glu Gln Leu
145                 150                 155                 160

Lys Asp Thr Thr Lys Ile Asp Asn Lys Ala Leu Tyr Ile Val Leu Ile
                165                 170                 175

Asp Asn Thr Val Met Asp Ser Thr Lys
            180                 185

<210> SEQ ID NO 5
<211> LENGTH: 522
<212> TYPE: DNA
<213> ORGANISM: Clostridium difficile

<400> SEQUENCE: 5
atgaagttaa aaagaataa aaaaggtttc actttagtgg aattattggt agtaattgca      60
attataggta tattagcagt agtggcagtt ccagctttat ttagtaatat aaacaaggct    120
aaggtagcaa gtgttgagtc tgattatagt tcagttaaga gtgctgcatt atccttatat    180
tcagatacta ataagatacc agttacacca gatggtcaaa ctggtttaag tgttttagaa    240
acttatatgg agtctcttcc tgataaagct gatataggtg gagaatataa attgattaaa    300
gttggtagta aattggtatt acagataggt acaaatactg agggagttac cttaacagaa    360
gcacaatcag caaaattatt gagtgatata ggtgaaaaaa aaatatatac aagcgctaca    420
acaaatagtt tgggagatcc attaacaagt aatacaaaaa tagataataa agttctatat    480
atagtactta tagataatac tgtgatggac acaacaaaat ag                       522

<210> SEQ ID NO 6
<211> LENGTH: 173
<212> TYPE: PRT
<213> ORGANISM: Clostridium difficile

<400> SEQUENCE: 6

Met Lys Leu Lys Lys Asn Lys Lys Gly Phe Thr Leu Val Glu Leu Leu
```

```
              1               5                  10                 15
         Val Val Ile Ala Ile Ile Gly Ile Leu Ala Val Val Ala Val Pro Ala
                          20                  25                  30

Leu Phe Ser Asn Ile Asn Lys Ala Lys Val Ala Ser Val Glu Ser Asp
                     35                  40                  45

Tyr Ser Ser Val Lys Ser Ala Ala Leu Ser Tyr Tyr Ser Asp Thr Asn
                 50                  55                  60

Lys Ile Pro Val Thr Pro Asp Gly Gln Thr Gly Leu Ser Val Leu Glu
         65                  70                  75                  80

Thr Tyr Met Glu Ser Leu Pro Asp Lys Ala Asp Ile Gly Gly Glu Tyr
                             85                  90                  95

Lys Leu Ile Lys Val Gly Ser Lys Leu Val Leu Gln Ile Gly Thr Asn
                         100                 105                 110

Thr Glu Gly Val Thr Leu Thr Glu Ala Gln Ser Ala Lys Leu Leu Ser
                     115                 120                 125

Asp Ile Gly Glu Lys Lys Ile Tyr Thr Ser Ala Thr Thr Asn Ser Leu
                 130                 135                 140

Gly Asp Pro Leu Thr Ser Asn Thr Lys Ile Asp Asn Lys Val Leu Tyr
         145                 150                 155                 160

Ile Val Leu Ile Asp Asn Thr Val Met Asp Thr Thr Lys
                             165                 170
```

<210> SEQ ID NO 7
<211> LENGTH: 558
<212> TYPE: DNA
<213> ORGANISM: Artificial Sequence
<220> FEATURE:
<223> OTHER INFORMATION: Synthetic polynucleotide

<400> SEQUENCE: 7

```
atgcaccatc atcatcatca ttcttctggt ctggtgccac gcggttctgg tatgaaagaa    60
accgctgctg ctaaattcga acgccagcac atggacagcc agatctgggt accgacgac    120
gacgacaagg ccatgggttc taacatcaac aaagctaaag ttgcttctgt tgaatctgac   180
tactcttctg ttaaatctgc tgctctgtct tactactctg acaccaacaa aatcccggtt   240
accccggacg gtcagaccgg tctgtctgtt ctggaaacct acatggaatc tctgccggac   300
aaagctgaca tcggtggtga atacaaactg atcaaagttg gttctaaact ggttctgcag   360
atcggtacca acaccgaagg tgttaccctg accgaagctc agtctgctaa actgctgtct   420
gacatcggtg aaaaaaaaat ctacacctct gctaccacca ctctctgggt gacccgctg   480
acctctaaca ccaaaatcga caacaaagtt ctgtacatcg ttctgatcga caacaccgtt   540
atggacacca ccaaatag                                                  558
```

<210> SEQ ID NO 8
<211> LENGTH: 185
<212> TYPE: PRT
<213> ORGANISM: Artificial Sequence
<220> FEATURE:
<223> OTHER INFORMATION: Synthetic polypeptide

<400> SEQUENCE: 8

```
         Met His His His His His His Ser Ser Gly Leu Val Pro Arg Gly Ser
         1               5                  10                  15

Gly Met Lys Glu Thr Ala Ala Ala Lys Phe Glu Arg Gln His Met Asp
                         20                  25                  30

Ser Pro Asp Leu Gly Thr Asp Asp Asp Asp Lys Ala Met Gly Ser Asn
```

```
                35                  40                  45
Ile Asn Lys Ala Lys Val Ala Ser Val Glu Ser Asp Tyr Ser Ser Val
    50                  55                  60

Lys Ser Ala Ala Leu Ser Tyr Tyr Ser Asp Thr Asn Lys Ile Pro Val
65                  70                  75                  80

Thr Pro Asp Gly Gln Thr Gly Leu Ser Val Leu Glu Thr Tyr Met Glu
                85                  90                  95

Ser Leu Pro Asp Lys Ala Asp Ile Gly Gly Glu Tyr Lys Leu Ile Lys
            100                 105                 110

Val Gly Ser Lys Leu Val Leu Gln Ile Gly Thr Asn Thr Glu Gly Val
        115                 120                 125

Thr Leu Thr Glu Ala Gln Ser Ala Lys Leu Leu Ser Asp Ile Gly Glu
    130                 135                 140

Lys Lys Ile Tyr Thr Ser Ala Thr Thr Asn Ser Leu Gly Asp Pro Leu
145                 150                 155                 160

Thr Ser Asn Thr Lys Ile Asp Asn Lys Val Leu Tyr Ile Val Leu Ile
                165                 170                 175

Asp Asn Thr Val Met Asp Thr Thr Lys
            180                 185

<210> SEQ ID NO 9
<211> LENGTH: 522
<212> TYPE: DNA
<213> ORGANISM: Clostridium difficile

<400> SEQUENCE: 9
atgaagttaa aaagaataa aaaaggtttc actttagtgg aattattggt agtaattgca      60
attataggta tattagcagt agtggcagtt ccagctttat ttagtaatat aaacaaggct    120
aaggtagcaa gtgttgagtc tgattatagt tcaattaaga gtgcagcatt atcttattat    180
tcagatacta taaaatacc agttacacca gatggtcaaa ctggtttaaa tgttttagag    240
acttatatgg aatctcttcc tgataaagct gatataggtg gagaatataa attgattaaa    300
gttggtaata attagtgatt acagataggt aaagatggtg aaggagttac cttaacagaa    360
gcgcaatcag caaaattatt gagtgataga ggtaaagata aatatatac aggtgttaca    420 ggagataatt ttggagagca attaaaagat actacaaaaa tagataataa agctctatat    480
atagtactta tagataatac tgtgatggat tcaacaaaat ag                       522

<210> SEQ ID NO 10
<211> LENGTH: 173
<212> TYPE: PRT
<213> ORGANISM: Clostridium difficile

<400> SEQUENCE: 10

Met Lys Leu Lys Lys Asn Lys Lys Gly Phe Thr Leu Val Glu Leu Leu
1               5                   10                  15

Val Val Ile Ala Ile Ile Gly Ile Leu Ala Val Ala Val Pro Ala
            20                  25                  30

Leu Phe Ser Asn Ile Asn Lys Ala Lys Val Ala Ser Val Glu Ser Asp
        35                  40                  45

Tyr Ser Ser Ile Lys Ser Ala Ala Leu Ser Tyr Tyr Ser Asp Thr Asn
    50                  55                  60

Lys Ile Pro Val Thr Pro Asp Gly Gln Thr Gly Leu Asn Val Leu Glu
65                  70                  75                  80

Thr Tyr Met Glu Ser Leu Pro Asp Lys Ala Asp Ile Gly Gly Glu Tyr
```

```
                    85                  90                  95
Lys Ile Lys Val Gly Asn Lys Leu Val Gln Ile Gly Lys Asp
            100                 105                 110

Gly Glu Gly Val Thr Leu Thr Glu Ala Gln Ser Ala Lys Leu Leu Ser
            115                 120                 125

Asp Ile Gly Lys Asp Lys Ile Tyr Thr Gly Val Thr Gly Asp Asn Phe
        130                 135                 140

Gly Glu Gln Leu Lys Asp Thr Thr Lys Ile Asp Asn Lys Ala Leu Tyr
145                 150                 155                 160

Ile Val Leu Ile Asp Asn Thr Val Met Asp Ser Thr Lys
                165                 170
```

<210> SEQ ID NO 11
<211> LENGTH: 558
<212> TYPE: DNA
<213> ORGANISM: Artificial Sequence
<220> FEATURE:
<223> OTHER INFORMATION: Synthetic polynucleotide

<400> SEQUENCE: 11

```
atgcaccatc atcatcatca ttcttctggt ctggtgccac gcggttctgg tatgaaagaa    60
accgctgctg ctaaattcga acgccagcac atggacagcc agatctggg taccgacgac    120
gacgacaagg ccatgggttc taacatcaac aaagctaaag ttgcttctgt tgaatctgac    180
tactcttcta tcaaatctgc tgctctgtct tactactctg acaccaacaa atcccggtt     240
accccggacg gtcagaccgg tctgaacgtt ctggaaacct acatggaatc tctgccggac    300
aaagctgaca tcggtggtga atacaaactg atcaaagttg gtaacaaact ggttctgcag    360
atcggtaaag acggtgaagg tgttaccctg accgaagctc agtctgctaa actgctgtct    420
gacatcggta agacaaaat ctacaccggt gttaccggtg acaacttcgg tgaacagctg    480
aaagacacca ccaaaatcga caacaaagct ctgtacatcg ttctgatcga caacaccgtt    540
atggactcta ccaaatag                                                  558
```

<210> SEQ ID NO 12
<211> LENGTH: 185
<212> TYPE: PRT
<213> ORGANISM: Artificial Sequence
<220> FEATURE:
<223> OTHER INFORMATION: Synthetic polypeptide

<400> SEQUENCE: 12

```
Met His His His His His His Ser Ser Gly Leu Val Pro Arg Gly Ser
1               5                   10                  15

Gly Met Lys Glu Thr Ala Ala Ala Lys Phe Glu Arg Gln His Met Asp
            20                  25                  30

Ser Pro Asp Leu Gly Thr Asp Asp Asp Lys Ala Met Gly Ser Asn
        35                  40                  45

Ile Asn Lys Ala Lys Val Ala Ser Val Glu Ser Asp Tyr Ser Ser Ile
    50                  55                  60

Lys Ser Ala Ala Leu Ser Tyr Tyr Ser Asp Thr Asn Lys Ile Pro Val
65                  70                  75                  80

Thr Pro Asp Gly Gln Thr Gly Leu Asn Val Leu Glu Thr Tyr Met Glu
                85                  90                  95

Ser Leu Pro Asp Lys Ala Asp Ile Gly Gly Glu Tyr Lys Leu Ile Lys
            100                 105                 110

Val Gly Asn Lys Leu Val Leu Gln Ile Gly Lys Asp Gly Glu Gly Val
```

```
            115                 120                 125
Thr Leu Thr Glu Ala Gln Ser Ala Lys Leu Leu Ser Asp Ile Gly Lys
    130                 135                 140

Asp Lys Ile Tyr Thr Gly Val Thr Gly Asp Asn Phe Gly Glu Gln Leu
145                 150                 155                 160

Lys Asp Thr Thr Lys Ile Asp Asn Lys Ala Leu Tyr Ile Val Leu Ile
                165                 170                 175

Asp Asn Thr Val Met Asp Ser Thr Lys
            180                 185

<210> SEQ ID NO 13
<211> LENGTH: 516
<212> TYPE: DNA
<213> ORGANISM: Clostridium difficile

<400> SEQUENCE: 13
atgaagttaa aaagaataa aaaaggtttc actttagtgg aattattggt agtaattgca      60
attataggta tattagcagt agtggcagtt ccagctttat ttagtaatat aaacaaggct    120
aaggtagcaa gtgttgagtc tgattatagt tcagttaaga gtgcagcatt atcttattat    180
tcagatacta taagatacc agttacacca gatggtcaaa ctggtttaag tgttttagag    240
acttatatgg agtctctgcc tgataaagct gatataggtg aaaatataa attgattaaa    300 gttggtaata aattggtatt acagataggt acaaatactg aaggagttac cttaacagaa    360
gcacaatcag caaaattatt gagtgatata ggtgaaaata aatatatac aaatgcagct    420 cttagtgcta aattaacatc tactacaaag gtaaataatg aagctttata tatagttctt    480
atagataata ttgtaatgga tcaacaagga gcttaa                              516

<210> SEQ ID NO 14
<211> LENGTH: 171
<212> TYPE: PRT
<213> ORGANISM: Clostridium difficile

<400> SEQUENCE: 14

Met Lys Leu Lys Lys Asn Lys Lys Gly Phe Thr Leu Val Glu Leu Leu
1               5                   10                  15

Val Val Ile Ala Ile Ile Gly Ile Leu Ala Val Val Ala Val Pro Ala
            20                  25                  30

Leu Phe Ser Asn Ile Asn Lys Ala Lys Val Ala Ser Val Glu Ser Asp
        35                  40                  45

Tyr Ser Ser Val Lys Ser Ala Ala Leu Ser Tyr Tyr Ser Asp Thr Asn
    50                  55                  60

Lys Ile Pro Val Thr Pro Asp Gly Gln Thr Gly Leu Ser Val Leu Glu
65                  70                  75                  80

Thr Tyr Met Glu Ser Leu Pro Asp Lys Ala Asp Ile Gly Gly Lys Tyr
                85                  90                  95

Lys Leu Ile Lys Val Gly Asn Lys Leu Val Leu Gln Ile Gly Thr Asn
            100                 105                 110

Thr Glu Gly Val Thr Leu Thr Glu Ala Gln Ser Ala Lys Leu Leu Ser
        115                 120                 125

Asp Ile Gly Glu Asn Lys Ile Tyr Thr Asn Ala Leu Ser Ala Lys
    130                 135                 140

Leu Thr Ser Thr Thr Lys Val Asn Asn Glu Ala Leu Tyr Ile Val Leu
145                 150                 155                 160

Ile Asp Asn Ile Val Met Asp Gln Gln Gly Ala
                165                 170
```

<210> SEQ ID NO 15
<211> LENGTH: 552
<212> TYPE: DNA
<213> ORGANISM: Artificial Sequence
<220> FEATURE:
<223> OTHER INFORMATION: Synthetic polynucleotide

<400> SEQUENCE: 15

```
atgcaccatc atcatcatca ttcttctggt ctggtgccac gcggttctgg tatgaaagaa      60
accgctgctg ctaaattcga acgccagcac atggacagcc agatctggg taccgacgac      120
gacgacaagg ccatgggttc taacatcaac aaagctaaag ttgcttctgt tgaatctgac     180
tactcttctg ttaaatctgc tgctctgtct tactactctg acaccaacaa aatcccggtt     240
accccggacg gtcagaccgg tctgtctgtt ctggaaacct acatggaatc tctgccggac     300
aaagctgaca tcggtggtaa atacaaactg atcaaagttg gtaacaaact ggttctgcag     360
atcggtacca caccgaagg tgttaccctg accgaagctc agtctgctaa actgctgtct     420
gacatcggtg aaaacaaaat ctacaccaac gctgctctgt ctgctaaact gacctctacc     480
accaaagtta acaacgaagc tctgtacatc gttctgatcg acaacatcgt tatggaccag     540
cagggtgctt aa                                                          552
```

<210> SEQ ID NO 16
<211> LENGTH: 183
<212> TYPE: PRT
<213> ORGANISM: Artificial Sequence
<220> FEATURE:
<223> OTHER INFORMATION: Synthetic polypeptide

<400> SEQUENCE: 16

```
Met His His His His His His Ser Ser Gly Leu Val Pro Arg Gly Ser
1               5                   10                  15

Gly Met Lys Glu Thr Ala Ala Ala Lys Phe Glu Arg Gln His Met Asp
            20                  25                  30

Ser Pro Asp Leu Gly Thr Asp Asp Asp Asp Lys Ala Met Gly Ser Asn
        35                  40                  45

Ile Asn Lys Ala Lys Val Ala Ser Val Glu Ser Asp Tyr Ser Ser Val
    50                  55                  60

Lys Ser Ala Ala Leu Ser Tyr Tyr Ser Asp Thr Asn Lys Ile Pro Val
65                  70                  75                  80

Thr Pro Asp Gly Gln Thr Gly Leu Ser Val Leu Glu Thr Tyr Met Glu
                85                  90                  95

Ser Leu Pro Asp Lys Ala Asp Ile Gly Gly Lys Tyr Lys Leu Ile Lys
            100                 105                 110

Val Gly Asn Lys Leu Val Leu Gln Ile Gly Thr Asn Thr Glu Gly Val
        115                 120                 125

Thr Leu Thr Glu Ala Gln Ser Ala Lys Leu Leu Ser Asp Ile Gly Glu
    130                 135                 140

Asn Lys Ile Tyr Thr Asn Ala Ala Leu Ser Ala Lys Leu Thr Ser Thr
145                 150                 155                 160

Thr Lys Val Asn Asn Glu Ala Leu Tyr Ile Val Leu Ile Asp Asn Ile
                165                 170                 175

Val Met Asp Gln Gln Gly Ala
            180
```

<210> SEQ ID NO 17
<211> LENGTH: 513
<212> TYPE: DNA
<213> ORGANISM: Clostridium difficile

<400> SEQUENCE: 17

```
atgaagttaa agaagaataa aaaaggtttc actttagtgg aattattggt agtaattgca      60
attataggta tattagcagt agtggcagtt ccagctttat ttagtaatat aaataaggct     120
aaggtagcaa gtgttgagtc tgattatagt tcaattaaga gtgcagcatt atcttattat     180
tcagatacta taagatgcc agctacaaca tcaaatcctg tagatttaga aaatttaaaa     240
acttatatgg aaagtcttcc tgataaagca gatataggtg gagagtatca attacttttg     300
gttgggaata agttagtttt acaaataaat gatgctacat taacaggagc gcaatcaacg     360
aagttattga gtgatttagg taatgataag atatacaaaa ctataggtag cgatgataag     420
cttacagatt tattaactac caatgaaaaa ttagataata aggttctata tttagttctt     480
atagataatg ctgagatgga ttcaacaaaa taa                                 513
```

<210> SEQ ID NO 18
<211> LENGTH: 170
<212> TYPE: PRT
<213> ORGANISM: Clostridium difficile

<400> SEQUENCE: 18

```
Met Lys Leu Lys Lys Asn Lys Lys Gly Phe Thr Leu Val Glu Leu Leu
1               5                   10                  15
Val Val Ile Ala Ile Ile Gly Ile Leu Ala Val Val Ala Val Pro Ala
            20                  25                  30
Leu Phe Ser Asn Ile Asn Lys Ala Lys Val Ala Ser Val Glu Ser Asp
        35                  40                  45
Tyr Ser Ser Ile Lys Ser Ala Ala Leu Ser Tyr Tyr Ser Asp Thr Asn
    50                  55                  60
Lys Met Pro Ala Thr Thr Ser Asn Pro Val Asp Leu Glu Asn Leu Lys
65                  70                  75                  80
Thr Tyr Met Glu Ser Leu Pro Asp Lys Ala Asp Ile Gly Gly Glu Tyr
                85                  90                  95
Gln Leu Leu Leu Val Gly Asn Lys Leu Val Leu Gln Ile Asn Asp Ala
            100                 105                 110
Thr Leu Thr Gly Ala Gln Ser Thr Lys Leu Leu Ser Asp Leu Gly Asn
        115                 120                 125
Asp Lys Ile Tyr Lys Thr Ile Gly Ser Asp Asp Lys Leu Thr Asp Leu
    130                 135                 140
Leu Thr Thr Asn Glu Lys Leu Asp Asn Lys Val Leu Tyr Leu Val Leu
145                 150                 155                 160
Ile Asp Asn Ala Glu Met Asp Ser Thr Lys
                165                 170
```

<210> SEQ ID NO 19
<211> LENGTH: 549
<212> TYPE: DNA
<213> ORGANISM: Artificial Sequence
<220> FEATURE:
<223> OTHER INFORMATION: Synthetic polynucleotide

<400> SEQUENCE: 19

```
atgcaccatc atcatcatca ttcttctggt ctggtgccac gcggttctgg tatgaaagaa      60
accgctgctg ctaaattcga acgccagcac atggacagcc agatctgggt accgacgac     120
```

```
gacgacaagg ccatgggttc taacatcaac aaagctaaag ttgcttctgt tgaatctgac    180
tactcttcta tcaaatctgc tgctctgtct tactactctg acaccaacaa aatgccggct    240
accacctcta acccggttga cctggaaaac ctgaaaacct acatggaatc tctgccggac    300
aaagctgaca tcgtggtga ataccagctg ctgctggttg taacaaaact ggttctgcag    360
```

```
aaagctgaca tcgtggtga  ataccagctg ctgctggttg taacaaaact ggttctgcag    360
atcaacgacg ctaccctgac cggtgctcag tctaccaaac tgctgtctga cctgggtaac    420
gacaaaatct acaaaaccat cggttctgac gacaaactga ccgacctgct gaccaccaac    480
gaaaaactgg acaacaaagt tctgtacctg gttctgatcg acaacgctga atggactct     540 accaaataa                                                             549
```

<210> SEQ ID NO 20
<211> LENGTH: 182
<212> TYPE: PRT
<213> ORGANISM: Artificial Sequence
<220> FEATURE:
<223> OTHER INFORMATION: Synthetic polypeptide

<400> SEQUENCE: 20

```
Met His His His His His Ser Ser Gly Leu Val Pro Arg Gly Ser
1               5                   10                  15

Gly Met Lys Glu Thr Ala Ala Ala Lys Phe Glu Arg Gln His Met Asp
            20                  25                  30

Ser Pro Asp Leu Gly Thr Asp Asp Asp Lys Ala Met Gly Ser Asn
        35                  40                  45

Ile Asn Lys Ala Lys Val Ala Ser Val Glu Ser Asp Tyr Ser Ser Ile
50                  55                  60

Lys Ser Ala Ala Leu Ser Tyr Tyr Ser Asp Thr Asn Lys Met Pro Ala
65                  70                  75                  80

Thr Thr Ser Asn Pro Val Asp Leu Glu Asn Leu Lys Thr Tyr Met Glu
                85                  90                  95

Ser Leu Pro Asp Lys Ala Asp Ile Gly Gly Glu Tyr Gln Leu Leu Leu
            100                 105                 110

Val Gly Asn Lys Leu Val Leu Gln Ile Asn Asp Ala Thr Leu Thr Gly
        115                 120                 125

Ala Gln Ser Thr Lys Leu Leu Ser Asp Leu Gly Asn Asp Lys Ile Tyr
    130                 135                 140

Lys Thr Ile Gly Ser Asp Asp Lys Leu Thr Asp Leu Leu Thr Thr Asn
145                 150                 155                 160

Glu Lys Leu Asp Asn Lys Val Leu Tyr Leu Val Leu Ile Asp Asn Ala
                165                 170                 175

Glu Met Asp Ser Thr Lys
            180
```

<210> SEQ ID NO 21
<211> LENGTH: 360
<212> TYPE: DNA
<213> ORGANISM: Clostridium difficile

<400> SEQUENCE: 21

```
ttgataaatt tgataaataa aaaacgaaaa ggatttacac ttgttgaaat gattgtagta     60
gtaactattt taggcgttat atctagtata gcattagtta agtatagtaa ggttcaagaa    120
agtgccaaat taaatgcaga ctatacgaat gctgctaata tagtaactgc agctagcatg    180
gcaattaatg atgatgaaaa gacaatagac tctctaagtg tagaaacatt gaaggaaaag    240
```

```
ggatacctaa atactgttcc agttcctcag agtacatcag gtaaattcga acttgtcata    300
aatgatagcg aacagatat aagcgtaaat ataaattcta acaattttta tccaaaataa     360
```

<210> SEQ ID NO 22
<211> LENGTH: 119
<212> TYPE: PRT
<213> ORGANISM: Clostridium difficile

<400> SEQUENCE: 22

```
Met Ile Asn Leu Ile Asn Lys Lys Arg Lys Gly Phe Thr Leu Val Glu
1               5                   10                  15

Met Ile Val Val Val Thr Ile Leu Gly Val Ile Ser Ser Ile Ala Leu
            20                  25                  30

Val Lys Tyr Ser Lys Val Gln Glu Ser Ala Lys Leu Asn Ala Asp Tyr
        35                  40                  45

Thr Asn Ala Ala Asn Ile Val Thr Ala Ala Ser Met Ala Ile Asn Asp
    50                  55                  60

Asp Glu Lys Thr Ile Asp Ser Leu Ser Val Glu Thr Leu Lys Glu Lys
65                  70                  75                  80

Gly Tyr Leu Asn Thr Val Pro Val Pro Gln Ser Thr Ser Gly Lys Phe
                85                  90                  95

Glu Leu Val Ile Asn Asp Ser Gly Thr Asp Ile Ser Val Asn Ile Asn
            100                 105                 110

Ser Lys Gln Phe Tyr Pro Lys
        115
```

<210> SEQ ID NO 23
<211> LENGTH: 399
<212> TYPE: DNA
<213> ORGANISM: Artificial Sequence
<220> FEATURE:
<223> OTHER INFORMATION: Synthetic polynucleotide

<400> SEQUENCE: 23

```
atgcaccatc atcatcatca ttcttctggt ctggtgccac gcggttctgg tatgaaagaa    60
accgctgctg ctaaattcga acgccagcac atggacagcc agatctggg taccgacgac    120 gacgacaagg ccatgggtaa atactctaaa gttcaggaat ctgctaaact gaacgctgac    180
tacaccaacg ctgctaacat cgttaccgct gcttctatgg ctatcaacga cgacgaaaaa    240
accatcgact ctctgtctgt tgaaaccctg aaagaaaaag gttacctgaa caccgttccg    300
gttccgcagt ctacctctgg taaattcgaa ctggttatca acgactctgg taccgacatc    360
tctgttaaca tcaactctaa acagttctac ccgaaataa                           399
```

<210> SEQ ID NO 24
<211> LENGTH: 132
<212> TYPE: PRT
<213> ORGANISM: Artificial Sequence
<220> FEATURE:
<223> OTHER INFORMATION: Synthetic polypeptide

<400> SEQUENCE: 24

```
Met His His His His His His Ser Ser Gly Leu Val Pro Arg Gly Ser
1               5                   10                  15

Gly Met Lys Glu Thr Ala Ala Ala Lys Phe Glu Arg Gln His Met Asp
            20                  25                  30

Ser Pro Asp Leu Gly Thr Asp Asp Asp Asp Lys Ala Met Gly Lys Tyr
        35                  40                  45
```

Ser Lys Val Gln Glu Ser Ala Lys Leu Asn Ala Asp Tyr Thr Asn Ala
    50                  55                  60

Ala Asn Ile Val Thr Ala Ala Ser Met Ala Ile Asn Asp Asp Glu Lys
65                  70                  75                  80

Thr Ile Asp Ser Leu Ser Val Glu Thr Leu Lys Glu Lys Gly Tyr Leu
                85                  90                  95

Asn Thr Val Pro Val Pro Gln Ser Thr Ser Gly Lys Phe Glu Leu Val
            100                 105                 110

Ile Asn Asp Ser Gly Thr Asp Ile Ser Val Asn Ile Asn Ser Lys Gln
        115                 120                 125

Phe Tyr Pro Lys
    130

<210> SEQ ID NO 25
<211> LENGTH: 351
<212> TYPE: DNA
<213> ORGANISM: Clostridium difficile

<400> SEQUENCE: 25
ttgataaata aaaacgaaa aggatttaca cttgttgaaa tgattgtagt agtaactatt        60
ttaggagtta tatctagtat agcattagtt aagtatagta aggttcaaga agtgctaaa       120 ttaaatgcag actatacgaa tgctgctaat atagtaacag cagctagtat ggcaattaat       180
gatgatgaaa atataataga ctctctaagt gtagaagcat tgaaggaaaa gggataccta       240
aatactgttc cagttcctca gagtacatca ggtaaattcg aacttgttat aaatgataac       300
ggaacagata taagcgtgaa tataaattct aagcaatttt atccaaaata a               351

<210> SEQ ID NO 26
<211> LENGTH: 116
<212> TYPE: PRT
<213> ORGANISM: Clostridium difficile

<400> SEQUENCE: 26

Met Ile Asn Lys Lys Arg Lys Gly Phe Thr Leu Val Glu Met Ile Val
1               5                   10                  15

Val Val Thr Ile Leu Gly Val Ile Ser Ser Ile Ala Leu Val Lys Tyr
                20                  25                  30

Ser Lys Val Gln Glu Ser Ala Lys Leu Asn Ala Asp Tyr Thr Asn Ala
            35                  40                  45

Ala Asn Ile Val Thr Ala Ala Ser Met Ala Ile Asn Asp Asp Glu Asn
50                  55                  60

Ile Ile Asp Ser Leu Ser Val Glu Ala Leu Lys Glu Lys Gly Tyr Leu
65                  70                  75                  80

Asn Thr Val Pro Val Pro Gln Ser Thr Ser Gly Lys Phe Glu Leu Val
                85                  90                  95

Ile Asn Asp Asn Gly Thr Asp Ile Ser Val Asn Ile Asn Ser Lys Gln
            100                 105                 110

Phe Tyr Pro Lys
    115

<210> SEQ ID NO 27
<211> LENGTH: 399
<212> TYPE: DNA
<213> ORGANISM: Artificial Sequence
<220> FEATURE:
<223> OTHER INFORMATION: Synthetic polynucleotide

<400> SEQUENCE: 27

```
atgcaccatc atcatcatca ttcttctggt ctggtgccac gcggttctgg tatgaaagaa      60
accgctgctg ctaaattcga acgccagcac atggacagcc agatctggg taccgacgac     120 gacgacaagg ccatgggtaa atactctaaa gttcaggaat ctgctaaact gaacgctgac     180
tacaccaacg ctgctaacat cgttaccgct gcttctatgg ctatcaacga cgacgaaaac     240
atcatcgact ctctgtctgt tgaagctctg aagaaaaag gttacctgaa caccgttccg      300
gttccgcagt ctacctctgg taaattcgaa ctggttatca acgacaacgg taccgacatc     360
tctgttaaca tcaactctaa acagttctac ccgaaataa                            399
```

<210> SEQ ID NO 28
<211> LENGTH: 132
<212> TYPE: PRT
<213> ORGANISM: Artificial Sequence
<220> FEATURE:
<223> OTHER INFORMATION: Synthetic polypeptide

<400> SEQUENCE: 28

```
Met His His His His His Ser Ser Gly Leu Val Pro Arg Gly Ser
1               5                   10                  15

Gly Met Lys Glu Thr Ala Ala Ala Lys Phe Glu Arg Gln His Met Asp
            20                  25                  30

Ser Pro Asp Leu Gly Thr Asp Asp Asp Lys Ala Met Gly Lys Tyr
        35                  40                  45

Ser Lys Val Gln Glu Ser Ala Lys Leu Asn Ala Asp Tyr Thr Asn Ala
    50                  55                  60

Ala Asn Ile Val Thr Ala Ala Ser Met Ala Ile Asn Asp Asp Glu Asn
65                  70                  75                  80

Ile Ile Asp Ser Leu Ser Val Glu Ala Leu Lys Glu Lys Gly Tyr Leu
                85                  90                  95

Asn Thr Val Pro Val Pro Gln Ser Thr Ser Gly Lys Phe Glu Leu Val
            100                 105                 110

Ile Asn Asp Asn Gly Thr Asp Ile Ser Val Asn Ile Asn Ser Lys Gln
        115                 120                 125

Phe Tyr Pro Lys
    130
```

<210> SEQ ID NO 29
<211> LENGTH: 495
<212> TYPE: DNA
<213> ORGANISM: Clostridium difficile

<400> SEQUENCE: 29

```
atgaaaaata aaaaggatt tactctagtg gaattattag tagtaattgc tataatagga      60
atattggcaa taatagcact tccagcatta tttaaaaata tagaaaaagc aaagatagct     120
aaacttgaag ctgatataag tgcaataaaa agtgcatctc ttagttacta tgctgatgaa     180
tccaagtata ctgatggagg aatgatatca tgggtaaaga aagatggaaa ataataata     240 aatgggggtt ttaaagatga cccattagca gataaaatag aaatttagg gatgccttat     300 aatggttcat atctgttaat gtcatctcct ggtcatgaaa aatatctaga attaagcata     360
cttccagaag gagaaataag caaagtggt ctagataaat taaaaaatga ttatggaaat     420
ttaatagaca taacgaacga tcaaaataaa ataaatattg taataaaact tttaaataat     480
aaatcgaata cttaa                                                      495
```

<210> SEQ ID NO 30
<211> LENGTH: 164
<212> TYPE: PRT
<213> ORGANISM: Clostridium difficile

<400> SEQUENCE: 30

```
Met Lys Asn Lys Lys Gly Phe Thr Leu Val Glu Leu Leu Val Val Ile
1               5                   10                  15

Ala Ile Ile Gly Ile Leu Ala Ile Ile Ala Leu Pro Ala Leu Phe Lys
            20                  25                  30

Asn Ile Glu Lys Ala Lys Ile Ala Lys Leu Glu Ala Asp Ile Ser Ala
        35                  40                  45

Ile Lys Ser Ala Ser Leu Ser Tyr Tyr Ala Asp Glu Ser Lys Tyr Thr
50                  55                  60

Asp Gly Gly Met Ile Ser Trp Val Lys Asp Gly Lys Ile Ile
65                  70                  75                  80

Asn Gly Gly Phe Lys Asp Asp Pro Leu Ala Asp Lys Ile Glu Asn Leu
                85                  90                  95

Gly Met Pro Tyr Asn Gly Ser Tyr Leu Leu Met Ser Ser Pro Gly His
            100                 105                 110

Glu Lys Tyr Leu Glu Leu Ser Ile Leu Pro Gly Glu Ile Ser Lys
        115                 120                 125

Ser Gly Leu Asp Lys Leu Lys Asn Asp Tyr Gly Asn Leu Ile Asp Ile
130                 135                 140

Thr Asn Asp Gln Asn Lys Ile Asn Ile Val Ile Lys Leu Leu Asn Asn
145                 150                 155                 160

Lys Ser Asn Thr
```

<210> SEQ ID NO 31
<211> LENGTH: 540
<212> TYPE: DNA
<213> ORGANISM: Artificial Sequence
<220> FEATURE:
<223> OTHER INFORMATION: Synthetic polynucleotide

<400> SEQUENCE: 31

```
atgcaccatc atcatcatca ttcttctggt ctggtgccac gcggttctgg tatgaaagaa      60
accgctgctg ctaaattcga acgccagcac atggacagcc cagatctggg taccgacgac     120
gacgacaagg ccatgggtaa aaacatcgaa aaagctaaaa tcgctaaact ggaagctgac     180
atctctgcta tcaaatctgc ttctctgtct tactacgctg acgaatctaa atacaccgac     240
ggtggtatga tctcttgggt taaaaaagac ggtaaaatca tcatcaacgg tggtttcaaa     300
gacgacccgc tggctgacaa aatcgaaaac ctgggtatgc cgtacaacgg ttcttacctg     360
ctgatgtctt ctccgggtca cgaaaaatac ctggaactgt ctatcctgcc ggaaggtgaa     420
atctctaaat ctggtctgga caaactgaaa aacgactacg gtaacctgat cgacatcacc     480
aacgaccaga caaaaatcaa catcgttatc aaactgctga caacaaatc taacacctaa     540
```

<210> SEQ ID NO 32
<211> LENGTH: 179
<212> TYPE: PRT
<213> ORGANISM: Artificial Sequence
<220> FEATURE:
<223> OTHER INFORMATION: Synthetic polypeptide

<400> SEQUENCE: 32

```
Met His His His His His His Ser Ser Gly Leu Val Pro Arg Gly Ser
1               5                   10                  15
```

```
Gly Met Lys Glu Thr Ala Ala Ala Lys Phe Glu Arg Gln His Met Asp
            20                  25                  30

Ser Pro Asp Leu Gly Thr Asp Asp Asp Lys Ala Met Gly Lys Asn
        35                  40                  45

Ile Glu Lys Ala Lys Ile Ala Lys Leu Glu Ala Asp Ile Ser Ala Ile
50                  55                  60

Lys Ser Ala Ser Leu Ser Tyr Tyr Ala Asp Glu Ser Lys Tyr Thr Asp
65                  70                  75                  80

Gly Gly Met Ile Ser Trp Val Lys Asp Gly Lys Ile Ile Ile Asn
                85                  90                  95

Gly Gly Phe Lys Asp Asp Pro Leu Ala Asp Lys Ile Glu Asn Leu Gly
            100                 105                 110

Met Pro Tyr Asn Gly Ser Tyr Leu Leu Met Ser Ser Pro Gly His Glu
            115                 120                 125

Lys Tyr Leu Glu Leu Ser Ile Leu Pro Glu Gly Glu Ile Ser Lys Ser
        130                 135                 140

Gly Leu Asp Lys Leu Lys Asn Asp Tyr Gly Asn Leu Ile Asp Ile Thr
145                 150                 155                 160

Asn Asp Gln Asn Lys Ile Asn Ile Val Ile Lys Leu Leu Asn Asn Lys
                165                 170                 175

Ser Asn Thr

<210> SEQ ID NO 33
<211> LENGTH: 495
<212> TYPE: DNA
<213> ORGANISM: Clostridium difficile

<400> SEQUENCE: 33
atgaaaaata aaaaggatt tactctagtg gaattattag tagtaattgc tataataggaa      60 atattggcaa tagtagcact tccagcatta tttaaaaata tagaaaaagc aaagatagct     120
aaacttgaag ctgatataag tgcaataaaa agtgcgtctc ttagctacta tgcagatgaa     180
tcaaaatata ctgatggagg aatgatatca tgggtaaaga agatggaaa ataataata      240 aatggtggct ttaaagatga cccattagca gataaaatag aaaatttagg tatgccttat     300
aatggttcat atctattaat gtcatctcct ggtcatgaaa aatatctaga attaagtata     360
cttccagaag gagaaataag caaaagtggt ctagataaat taaaaagtga ttatggaagt     420
tcaatagaca taagaacga tcaaaacaaa atagatattg taataaaact tttaaatgat     480
aaatcgaata cttaa                                                     495

<210> SEQ ID NO 34
<211> LENGTH: 164
<212> TYPE: PRT
<213> ORGANISM: Clostridium difficile

<400> SEQUENCE: 34

Met Lys Asn Lys Lys Gly Phe Thr Leu Val Glu Leu Leu Val Val Ile
1               5                   10                  15

Ala Ile Ile Gly Ile Leu Ala Ile Val Ala Leu Pro Ala Leu Phe Lys
            20                  25                  30

Asn Ile Glu Lys Ala Lys Ile Ala Lys Leu Glu Ala Asp Ile Ser Ala
        35                  40                  45

Ile Lys Ser Ala Ser Leu Ser Tyr Tyr Ala Asp Glu Ser Lys Tyr Thr
    50                  55                  60
```

```
Asp Gly Gly Met Ile Ser Trp Val Lys Lys Asp Gly Lys Ile Ile Ile
 65                  70                  75                  80

Asn Gly Gly Phe Lys Asp Asp Pro Leu Ala Asp Lys Ile Glu Asn Leu
                 85                  90                  95

Gly Met Pro Tyr Asn Gly Ser Tyr Leu Leu Met Ser Ser Pro Gly His
            100                 105                 110

Glu Lys Tyr Leu Glu Leu Ser Ile Leu Pro Glu Gly Glu Ile Ser Lys
        115                 120                 125

Ser Gly Leu Asp Lys Leu Lys Ser Asp Tyr Gly Ser Ser Ile Asp Ile
130                 135                 140

Lys Asn Asp Gln Asn Lys Ile Asp Ile Val Ile Lys Leu Leu Asn Asp
145                 150                 155                 160

Lys Ser Asn Thr
```

```
<210> SEQ ID NO 35
<211> LENGTH: 540
<212> TYPE: DNA
<213> ORGANISM: Artificial Sequence
<220> FEATURE:
<223> OTHER INFORMATION: Synthetic polynucleotide

<400> SEQUENCE: 35
atgcaccatc atcatcatca ttcttctggt ctggtgccac gcggttctgg tatgaaagaa    60
accgctgctg ctaaattcga acgccagcac atggacagcc agatctgggt accgacgac   120
gacgacaagg ccatgggtaa aaacatcgaa aaagctaaaa tcgctaaact ggaagctgac   180
atctctgcta tcaaatctgc ttctctgtct tactacgctg acgaatctaa atacaccgac   240
ggtggtatga tctcttgggt taaaaagac ggtaaaatca tcatcaacgg tggtttcaaa    300
gacgacccgc tggctgacaa aatcgaaaac ctgggtatgc cgtacaacgg ttcttacctg   360
ctgatgtctt ctccgggtca cgaaaaatac ctggaactgt ctatcctgcc ggaaggtgaa   420
atctctaaat ctggtctgga caaactgaaa tctgactacg gttcttctat cgacatcaaa   480
aacgaccaga acaaaatcga catcgttatc aaactgctga cgacaaatc taacacctaa   540
```

```
<210> SEQ ID NO 36
<211> LENGTH: 179
<212> TYPE: PRT
<213> ORGANISM: Artificial Sequence
<220> FEATURE:
<223> OTHER INFORMATION: Synthetic polypeptide

<400> SEQUENCE: 36

Met His His His His His His Ser Ser Gly Leu Val Pro Arg Gly Ser
  1               5                  10                  15

Gly Met Lys Glu Thr Ala Ala Ala Lys Phe Glu Arg Gln His Met Asp
             20                  25                  30

Ser Pro Asp Leu Gly Thr Asp Asp Asp Lys Ala Met Gly Lys Asn
         35                  40                  45

Ile Glu Lys Ala Lys Ile Ala Lys Leu Glu Ala Asp Ile Ser Ala Ile
 50                  55                  60

Lys Ser Ala Ser Leu Ser Tyr Tyr Ala Asp Glu Ser Lys Tyr Thr Asp
 65                  70                  75                  80

Gly Gly Met Ile Ser Trp Val Lys Lys Asp Gly Lys Ile Ile Ile Asn
             85                  90                  95

Gly Gly Phe Lys Asp Asp Pro Leu Ala Asp Lys Ile Glu Asn Leu Gly
            100                 105                 110
```

```
Met Pro Tyr Asn Gly Ser Tyr Leu Met Ser Ser Pro Gly His Glu
            115                 120                 125

Lys Tyr Leu Glu Leu Ser Ile Leu Pro Glu Gly Glu Ile Ser Lys Ser
    130                 135                 140

Gly Leu Asp Lys Leu Lys Ser Asp Tyr Gly Ser Ser Ile Asp Ile Lys
145                 150                 155                 160

Asn Asp Gln Asn Lys Ile Asp Ile Val Ile Lys Leu Leu Asn Asp Lys
                165                 170                 175

Ser Asn Thr
```

<210> SEQ ID NO 37
<211> LENGTH: 489
<212> TYPE: DNA
<213> ORGANISM: Clostridium difficile

<400> SEQUENCE: 37

```
atgaaaaata aaaaggatt tactctagtg gaattattag tagtaattgc tataatagga      60
atattggcaa tagtagcact tccagcatta tttaaaaata tagaaaaagc aaagatagct    120
aaacttgaag ctgatataag tgcaataaaa agtgcgtctc ttagctacta tgcagatgaa    180
tcaaaatata ctgaaggaaa cataaatatgg tggactaaaa aagatggaaa ataacagta    240 aactctggta ttggtgatga agacccttg gcacataaaa tagaaaattt aggcatgcct    300
tataatggtt cgtacacttt agtgtcatct aatggtagtg aagaatactt agaattaaac    360
ataattatag atggagaaat aagtaaaagt ggtctagata aattagaaga agattatggt    420
agttcaataa caataccaaa tgataaaaat atgataataa cttttttatc taataaatca    480
gacaattaa                                                             489
```

<210> SEQ ID NO 38
<211> LENGTH: 162
<212> TYPE: PRT
<213> ORGANISM: Clostridium difficile

<400> SEQUENCE: 38

```
Met Lys Asn Lys Lys Gly Phe Thr Leu Val Glu Leu Leu Val Val Ile
1               5                   10                  15

Ala Ile Ile Gly Ile Leu Ala Ile Val Ala Leu Pro Ala Leu Phe Lys
            20                  25                  30

Asn Ile Glu Lys Ala Lys Ile Ala Lys Leu Glu Ala Asp Ile Ser Ala
        35                  40                  45

Ile Lys Ser Ala Ser Leu Ser Tyr Tyr Ala Asp Glu Ser Lys Tyr Thr
    50                  55                  60

Glu Gly Asn Ile Ile Trp Trp Thr Lys Asp Gly Lys Ile Thr Val
65                  70                  75                  80

Asn Ser Gly Ile Gly Asp Glu Asp Pro Leu Ala His Lys Ile Glu Asn
                85                  90                  95

Leu Gly Met Pro Tyr Asn Gly Ser Tyr Thr Leu Val Ser Ser Asn Gly
            100                 105                 110

Ser Glu Glu Tyr Leu Glu Leu Asn Ile Ile Asp Gly Glu Ile Ser
        115                 120                 125

Lys Ser Gly Leu Asp Lys Leu Glu Glu Asp Tyr Gly Ser Ser Ile Thr
    130                 135                 140

Ile Pro Asn Asp Lys Asn Met Ile Ile Thr Phe Leu Ser Asn Lys Ser
145                 150                 155                 160

Asp Asn
```

<210> SEQ ID NO 39
<211> LENGTH: 534
<212> TYPE: DNA
<213> ORGANISM: Artificial Sequence
<220> FEATURE:
<223> OTHER INFORMATION: Synthetic polynucleotide

<400> SEQUENCE: 39

```
atgcaccatc atcatcatca ttcttctggt ctggtgccac gcggttctgg tatgaaagaa      60
accgctgctg ctaaattcga acgccagcac atggacagcc agatctggg taccgacgac      120
gacgacaagg ccatgggtaa aaacatcgaa aaagctaaaa tcgctaaact ggaagctgac      180
atctctgcta tcaaatctgc ttctctgtct tactacgctg acgaatctaa atacaccgaa      240
ggtaacatca tctggtggac caaaaaagac ggtaaaatca ccgttaactc tggtatcggt      300
gacgaagacc cgctggctca caaaatcgaa aacctgggta tgccgtacaa cggttcttac      360
accctggttt cttctaacgg ttctgaagaa tacctggaac tgaacatcat catcgacggt      420
gaaatctcta atctggtct ggacaaactg gaagaagact acggttcttc tatcaccatc      480
ccgaacgaca aaaacatgat catcaccttc ctgtctaaca atctgacaa ctaa            534
```

<210> SEQ ID NO 40
<211> LENGTH: 177
<212> TYPE: PRT
<213> ORGANISM: Artificial Sequence
<220> FEATURE:
<223> OTHER INFORMATION: Synthetic polypeptide

<400> SEQUENCE: 40

```
Met His His His His His Ser Ser Gly Leu Val Pro Arg Gly Ser
1               5                   10                  15

Gly Met Lys Glu Thr Ala Ala Ala Lys Phe Glu Arg Gln His Met Asp
            20                  25                  30

Ser Pro Asp Leu Gly Thr Asp Asp Asp Lys Ala Met Gly Lys Asn
        35                  40                  45

Ile Glu Lys Ala Lys Ile Ala Lys Leu Glu Ala Asp Ile Ser Ala Ile
50                  55                  60

Lys Ser Ala Ser Leu Ser Tyr Tyr Ala Asp Glu Ser Lys Tyr Thr Glu
65                  70                  75                  80

Gly Asn Ile Ile Trp Trp Thr Lys Lys Asp Gly Lys Ile Thr Val Asn
                85                  90                  95

Ser Gly Ile Gly Asp Glu Asp Pro Leu Ala His Lys Ile Glu Asn Leu
            100                 105                 110

Gly Met Pro Tyr Asn Gly Ser Tyr Thr Leu Val Ser Ser Asn Gly Ser
        115                 120                 125

Glu Glu Tyr Leu Glu Leu Asn Ile Ile Ile Asp Gly Glu Ile Ser Lys
    130                 135                 140

Ser Gly Leu Asp Lys Leu Glu Glu Asp Tyr Gly Ser Ser Ile Thr Ile
145                 150                 155                 160

Pro Asn Asp Lys Asn Met Ile Ile Thr Phe Leu Ser Asn Lys Ser Asp
                165                 170                 175

Asn
```

<210> SEQ ID NO 41
<211> LENGTH: 819
<212> TYPE: DNA
<213> ORGANISM: Clostridium difficile

<400> SEQUENCE: 41

```
atgggaatga ttattatgaa taaaaagggt tttacattaa ttgaattgtt ggtagttata    60
tctataatag gaattttagt tatagtagct gttccagcgt tatttagaaa tatagaaaaa   120
agtaaggcag ttacatgtct ttctaataga gaaaatataa agactcaaat tgttattgca   180
atggctgagg aatcaagtaa agacaagaat gaagtcataa agaggtatt agaaaacaaa    240
gatggtaagt actttgaaac agaaccaaag tgtaagtcag gtggaatata ttcagcaacg   300
tttgatgatg gttatgatgg aataactgga atagaaagca ttgcaaaagt gtatgttact   360
tgtacaaaac atccagatgg tattgaaatg gctagggata tacatcaaag tatgaaagat   420
ttgattgcat catttgcaca agacccttct ataataccag gagcttcaaa gggcaatgat   480
gattttagaa atatttatt agacaataaa tataaaaatg ggtggcctac aattccagat   540
gaatttaagg caaatatgg attaagtaag gatacactat atatacaacc atatgcatat   600
aatcctacta aatctgatgc tactgtagtt gtatttgcaa ataataagac tggaggtaat   660
tggtatactt ccctagttta cgattatgat gaaggtagat ggtataaagg taaaaatggt   720
atttctgttg caggtaggtc atgggatgtt gacacagata gtgttaagtc tgtaaaaaca   780
gagattcatt ctaaagaggg atggggtcct ttaaattaa                          819
```

<210> SEQ ID NO 42
<211> LENGTH: 272
<212> TYPE: PRT
<213> ORGANISM: Clostridium difficile

<400> SEQUENCE: 42

Met Gly Met Ile Ile Met Asn Lys Lys Gly Phe Thr Leu Ile Glu Leu
1 5 10 15

Leu Val Val Ile Ser Ile Ile Gly Ile Leu Val Ile Val Ala Val Pro
20 25 30

Ala Leu Phe Arg Asn Ile Glu Lys Ser Lys Ala Val Thr Cys Leu Ser
35 40 45

Asn Arg Glu Asn Ile Lys Thr Gln Ile Val Ile Ala Met Ala Glu Glu
50 55 60

Ser Ser Lys Asp Lys Asn Glu Val Ile Lys Glu Val Leu Glu Asn Lys
65 70 75 80

Asp Gly Lys Tyr Phe Glu Thr Glu Pro Lys Cys Lys Ser Gly Gly Ile
85 90 95

Tyr Ser Ala Thr Phe Asp Asp Gly Tyr Asp Gly Ile Thr Gly Ile Glu
100 105 110

Ser Ile Ala Lys Val Tyr Val Thr Cys Thr Lys His Pro Asp Gly Ile
115 120 125

Glu Met Ala Arg Asp Ile His Gln Ser Met Lys Asp Leu Ile Ala Ser
130 135 140

Phe Ala Gln Asp Pro Ser Ile Ile Pro Gly Ala Ser Lys Gly Asn Asp
145 150 155 160

Asp Phe Arg Lys Tyr Leu Leu Asp Asn Lys Tyr Lys Asn Gly Trp Pro
165 170 175

Thr Ile Pro Asp Glu Phe Lys Ala Lys Tyr Gly Leu Ser Lys Asp Thr
180 185 190

Leu Tyr Ile Gln Pro Tyr Ala Tyr Asn Pro Thr Lys Ser Asp Ala Thr
195 200 205

Val Val Val Phe Ala Asn Asn Lys Thr Gly Gly Asn Trp Tyr Thr Ser

Leu Val Tyr Asp Tyr Asp Glu Gly Arg Trp Tyr Lys Gly Lys Asn Gly
225                 230                 235                 240

Ile Ser Val Ala Gly Arg Ser Trp Asp Val Asp Thr Asp Ser Val Lys
                245                 250                 255

Ser Val Lys Thr Glu Ile His Ser Lys Glu Gly Trp Gly Pro Leu Asn
            260                 265                 270

<210> SEQ ID NO 43
<211> LENGTH: 852
<212> TYPE: DNA
<213> ORGANISM: Artificial Sequence
<220> FEATURE:
<223> OTHER INFORMATION: Synthetic polynucleotide

<400> SEQUENCE: 43
atgcaccatc atcatcatca ttcttctggt ctggtgccac gcggttctgg tatgaaagaa      60
accgctgctg ctaaattcga acgccagcac atggacagcc agatctggg taccgacgac     120
gacgacaagg ccatgggtcg taacatcgaa aaatctaaag ctgttacctg cctgtctaac     180
cgtgaaaaca tcaaaaccca gatcgttatc gctatggctg aagaatcttc taaagacaaa     240
aacgaagtta tcaaagaagt tctggaaaac aaagacggta atacttcga aaccgaaccg     300
aaatgcaaat ctggtggtat ctactctgct accttcgacg acggttacga cggtatcacc     360
ggtatcgaat ctatcgctaa agtttacgtt acctgcacca acacccgga cggtatcgaa     420
atggctcgtg acatccacca gtctatgaaa gacctgatcg cttctttcgc tcaggacccg     480
tctatcatcc cgggtgcttc taaaggtaac gacgacttcc gtaaatacct gctggacaac     540
aaatacaaaa acggttggcc gaccatcccg gacgaattca agctaaata cggtctgtct     600
aaagacaccc tgtacatcca gccgtacgct acaacccga ccaaatctga cgctaccgtt     660
gttgttttcg ctaacaacaa aaccggtggt aactggtaca cctctctggt ttacgactac     720
gacgaaggtc gttggtacaa aggtaaaaac ggtatctctg ttgctggtcg ttcttgggac     780
gttgacaccg actctgttaa atctgttaaa accgaaatcc actctaaaga aggttggggt     840
ccgctgaact aa                                                          852

<210> SEQ ID NO 44
<211> LENGTH: 283
<212> TYPE: PRT
<213> ORGANISM: Artificial Sequence
<220> FEATURE:
<223> OTHER INFORMATION: Synthetic polypeptide

<400> SEQUENCE: 44

Met His His His His His His Ser Ser Gly Leu Val Pro Arg Gly Ser
1               5                   10                  15

Gly Met Lys Glu Thr Ala Ala Ala Lys Phe Glu Arg Gln His Met Asp
            20                  25                  30

Ser Pro Asp Leu Gly Thr Asp Asp Asp Lys Ala Met Gly Arg Asn
        35                  40                  45

Ile Glu Lys Ser Lys Ala Val Thr Cys Leu Ser Asn Arg Glu Asn Ile
50                  55                  60

Lys Thr Gln Ile Val Ile Ala Met Ala Glu Glu Ser Ser Lys Asp Lys
65                  70                  75                  80

Asn Glu Val Ile Lys Glu Val Leu Glu Asn Lys Asp Gly Lys Tyr Phe
                85                  90                  95

```
Glu Thr Glu Pro Lys Cys Lys Ser Gly Ile Tyr Ser Ala Thr Phe
            100                 105                 110

Asp Asp Gly Tyr Asp Gly Ile Thr Gly Ile Glu Ser Ile Ala Lys Val
        115                 120                 125

Tyr Val Thr Cys Thr Lys His Pro Asp Gly Ile Glu Met Ala Arg Asp
    130                 135                 140

Ile His Gln Ser Met Lys Asp Leu Ile Ala Ser Phe Ala Gln Asp Pro
145                 150                 155                 160

Ser Ile Ile Pro Gly Ala Ser Lys Gly Asn Asp Phe Arg Lys Tyr
                165                 170                 175

Leu Leu Asp Asn Lys Tyr Lys Asn Gly Trp Pro Thr Ile Pro Asp Glu
            180                 185                 190

Phe Lys Ala Lys Tyr Gly Leu Ser Lys Asp Thr Leu Tyr Ile Gln Pro
        195                 200                 205

Tyr Ala Tyr Asn Pro Thr Lys Ser Asp Ala Thr Val Val Phe Ala
    210                 215                 220

Asn Asn Lys Thr Gly Gly Asn Trp Tyr Thr Ser Leu Val Tyr Asp Tyr
225                 230                 235                 240

Asp Glu Gly Arg Trp Tyr Lys Gly Lys Asn Gly Ile Ser Val Ala Gly
                245                 250                 255

Arg Ser Trp Asp Val Asp Thr Asp Ser Val Lys Ser Val Lys Thr Glu
            260                 265                 270

Ile His Ser Lys Glu Gly Trp Gly Pro Leu Asn
            275                 280

<210> SEQ ID NO 45
<211> LENGTH: 173
<212> TYPE: PRT
<213> ORGANISM: Clostridium difficile

<400> SEQUENCE: 45

Met Lys Leu Lys Lys Asn Lys Lys Gly Phe Thr Leu Val Glu Leu Leu
1               5                   10                  15

Val Val Ile Ala Ile Gly Ile Leu Ala Val Val Ala Val Pro Ala
            20                  25                  30

Leu Phe Ser Asn Ile Asn Lys Ala Lys Val Ala Ser Val Glu Ser Asp
        35                  40                  45

Tyr Ser Ser Val Lys Ser Ala Ala Leu Ser Tyr Tyr Ser Asp Thr Asn
    50                  55                  60

Lys Ile Pro Val Thr Pro Asp Gly Gln Thr Gly Leu Ser Val Leu Glu
65                  70                  75                  80

Thr Tyr Met Glu Ser Leu Pro Asp Lys Ala Asp Ile Gly Gly Lys Tyr
                85                  90                  95

Lys Leu Ile Lys Val Gly Asn Lys Leu Val Leu Gln Ile Gly Thr Asn
            100                 105                 110

Asp Glu Gly Val Thr Leu Thr Glu Ala Gln Ser Ala Lys Leu Leu Ser
        115                 120                 125

Asp Ile Gly Glu Asn Lys Ile Tyr Thr Ser Val Thr Ala Asp Asn Leu
    130                 135                 140

Gly Asn Pro Leu Thr Ser Asn Thr Lys Val Asp Asn Lys Val Leu Tyr
145                 150                 155                 160

Ile Val Leu Ile Asp Asn Thr Val Met Asp Ser Thr Lys
                165                 170

<210> SEQ ID NO 46
```

<211> LENGTH: 522
<212> TYPE: DNA
<213> ORGANISM: Clostridium difficile

<400> SEQUENCE: 46

```
atgaagttaa aaagaataa aaaggtttc actttagtgg aattattggt agtaattgca    60
attataggta tattagcagt agtggcagtt ccagctttat ttagtaatat aaacaaggct   120
aaggtagcaa gtgttgagtc tgattatagt tcagttaaga gtgcagcatt atcttattat   180
tcagatacta ataagatacc agttacacca gatggtcaaa ctggtttaag tgttttagag   240
acttatatgg agtctctgcc tgataaagct gataggtg gaaatataa attgattaaa      300 gttggtaata aattggtatt acagataggt acaaatgatg aaggagttac attaacagaa   360
gcacaatcag caaaattatt gagtgatata ggtgaaaata aatatatac aagtgttaca    420 gcagataatt tgggaaatcc attaacaagt aatacaaaag tagataataa agttctatat   480
atagtactta tagataatac tgtgatggac tcaacaaaat ag                      522
```

<210> SEQ ID NO 47
<211> LENGTH: 173
<212> TYPE: PRT
<213> ORGANISM: Clostridium difficile

<400> SEQUENCE: 47

```
Met Lys Leu Lys Lys Asn Lys Lys Gly Phe Thr Leu Val Glu Leu Leu
1               5                   10                  15

Val Val Ile Ala Ile Ile Gly Ile Leu Ala Val Val Ala Val Pro Ala
                20                  25                  30

Leu Phe Ser Asn Ile Asn Lys Ala Lys Val Ala Ser Val Glu Ser Asp
            35                  40                  45

Tyr Ser Ser Val Lys Ser Ala Ala Leu Ser Tyr Tyr Ser Asp Thr Asn
        50                  55                  60

Lys Ile Pro Val Thr Pro Asp Gly Gln Thr Gly Leu Asn Val Leu Glu
65                  70                  75                  80

Thr Tyr Met Glu Ser Leu Pro Asp Lys Ala Asp Ile Gly Gly Lys Tyr
                85                  90                  95

Lys Leu Ile Lys Val Gly Asn Lys Leu Val Leu Gln Ile Gly Lys Asp
            100                 105                 110

Gly Glu Gly Val Thr Leu Thr Glu Ala Gln Ser Ala Lys Leu Leu Ser
        115                 120                 125

Asp Ile Gly Lys Asp Lys Ile Tyr Thr Gly Val Thr Gly Asp Asn Phe
    130                 135                 140

Gly Asp Gln Leu Lys Asp Thr Thr Lys Ile Asp Asn Lys Ala Leu Tyr
145                 150                 155                 160

Ile Val Leu Ile Asp Asn Thr Val Met Asp Ser Thr Lys
                165                 170
```

<210> SEQ ID NO 48
<211> LENGTH: 173
<212> TYPE: PRT
<213> ORGANISM: Clostridium difficile

<400> SEQUENCE: 48

```
Met Lys Leu Lys Lys Asn Lys Lys Gly Phe Thr Leu Val Glu Leu Leu
1               5                   10                  15

Val Val Ile Ala Ile Ile Gly Ile Leu Ala Val Val Ala Val Pro Ala
                20                  25                  30
```

```
Leu Phe Ser Asn Ile Asn Lys Ala Lys Val Ala Ser Val Glu Ser Asp
            35                  40                  45

Tyr Ser Ser Val Lys Ser Ala Ala Leu Ser Tyr Tyr Ser Asp Thr Asn
 50                  55                  60

Lys Ile Pro Val Thr Pro Asp Gly Gln Thr Gly Leu Asn Val Leu Glu
 65                  70                  75                  80

Thr Tyr Met Glu Ser Leu Pro Asp Lys Ala Asp Ile Gly Gly Lys Tyr
                 85                  90                  95

Lys Leu Ile Lys Val Gly Asn Lys Leu Val Leu Gln Ile Gly Lys Asp
                100                 105                 110

Gly Glu Gly Val Thr Leu Thr Glu Ala Gln Ser Ala Lys Leu Leu Ser
            115                 120                 125

Asp Ile Gly Lys Asp Lys Ile Tyr Thr Gly Val Thr Gly Asp Asn Phe
        130                 135                 140

Gly Asp Gln Leu Lys Asp Thr Thr Lys Ile Asp Asn Lys Ala Leu Tyr
145                 150                 155                 160

Ile Val Leu Ile Asp Asn Thr Val Met Asp Ser Thr Lys
                165                 170

<210> SEQ ID NO 49
<211> LENGTH: 173
<212> TYPE: PRT
<213> ORGANISM: Clostridium difficile

<400> SEQUENCE: 49

Met Lys Leu Lys Lys Asn Lys Lys Gly Phe Thr Leu Val Glu Leu Leu
 1               5                  10                  15

Val Val Ile Ala Ile Ile Gly Ile Leu Ala Val Val Ala Val Pro Ala
                20                  25                  30

Leu Phe Ser Asn Ile Asn Lys Ala Lys Val Ala Ser Val Glu Ser Asp
            35                  40                  45

Tyr Ser Ser Val Lys Ser Ala Ala Leu Ser Tyr Tyr Ser Asp Thr Asn
 50                  55                  60

Lys Ile Pro Val Thr Pro Asp Gly Gln Thr Gly Leu Ser Val Leu Glu
 65                  70                  75                  80

Thr Tyr Met Glu Ser Leu Pro Asp Lys Ala Asp Ile Gly Gly Lys Tyr
                 85                  90                  95

Lys Leu Ile Lys Val Gly Asn Lys Leu Val Leu Gln Ile Gly Thr Asn
                100                 105                 110

Thr Glu Gly Val Thr Leu Thr Glu Ala Gln Ser Ala Lys Leu Leu Ser
            115                 120                 125

Asp Ile Gly Glu Asn Lys Ile Tyr Thr Ser Thr Thr Asn Ser Leu
        130                 135                 140

Gly Asn Pro Leu Thr Ser Asn Thr Lys Ile Asp Asn Asn Val Leu Tyr
145                 150                 155                 160

Ile Val Leu Ile Asp Asn Thr Val Met Asp Thr Thr Lys
                165                 170

<210> SEQ ID NO 50
<211> LENGTH: 173
<212> TYPE: PRT
<213> ORGANISM: Clostridium difficile

<400> SEQUENCE: 50

Met Lys Leu Lys Lys Asn Lys Lys Gly Phe Thr Leu Val Glu Leu Leu
 1               5                  10                  15
```

```
Val Val Ile Ala Ile Ile Gly Ile Leu Ala Val Ala Val Pro Ala
            20                  25                  30

Leu Phe Ser Asn Ile Asn Lys Ala Lys Val Ala Ser Val Glu Ser Asp
         35                  40                  45

Tyr Ser Ser Ile Lys Ser Ala Ala Leu Ser Tyr Tyr Ser Asp Thr Asn
 50                  55                  60

Lys Ile Pro Val Thr Pro Asp Gly Gln Thr Gly Leu Asn Val Leu Glu
 65                  70                  75                  80

Thr Tyr Met Glu Ser Leu Pro Asp Lys Ala Asp Ile Gly Gly Glu Tyr
                 85                  90                  95

Lys Leu Ile Lys Val Gly Asn Lys Leu Val Leu Gln Ile Gly Lys Asp
                100                 105                 110

Gly Glu Gly Val Thr Leu Thr Glu Ala Gln Ser Ala Lys Leu Leu Ser
            115                 120                 125

Asp Ile Gly Lys Asp Lys Ile Tyr Thr Gly Val Thr Gly Asp Asn Phe
        130                 135                 140

Gly Glu Gln Leu Lys Asp Thr Thr Lys Ile Asp Asn Lys Ala Leu Tyr
145                 150                 155                 160

Ile Val Leu Ile Asp Asn Thr Val Met Asp Ser Thr Lys
                165                 170

<210> SEQ ID NO 51
<211> LENGTH: 173
<212> TYPE: PRT
<213> ORGANISM: Clostridium difficile

<400> SEQUENCE: 51

Met Lys Leu Lys Lys Asn Lys Lys Gly Phe Thr Leu Val Glu Leu Leu
 1               5                  10                  15

Val Val Ile Ala Ile Ile Gly Ile Leu Ala Val Ala Val Pro Ala
            20                  25                  30

Leu Phe Ser Asn Ile Asn Lys Ala Lys Val Ala Ser Val Glu Ser Asp
         35                  40                  45

Tyr Ser Ser Ile Lys Ser Ala Ala Leu Ser Tyr Tyr Ser Asp Thr Asn
 50                  55                  60

Lys Ile Pro Val Thr Pro Asp Gly Gln Thr Gly Leu Asn Val Leu Glu
 65                  70                  75                  80

Thr Tyr Met Glu Ser Leu Pro Asp Lys Ala Asp Ile Gly Gly Glu Tyr
                 85                  90                  95

Lys Leu Ile Lys Val Gly Asn Lys Leu Val Leu Gln Ile Gly Lys Asp
                100                 105                 110

Gly Glu Gly Val Thr Leu Thr Glu Ala Gln Ser Ala Lys Leu Leu Ser
            115                 120                 125

Asp Ile Gly Lys Asp Lys Ile Tyr Thr Gly Val Thr Gly Asp Asn Phe
        130                 135                 140

Gly Glu Gln Leu Lys Asp Thr Thr Lys Ile Asp Asn Lys Ala Leu Tyr
145                 150                 155                 160

Ile Val Leu Ile Asp Asn Thr Val Met Asp Ser Thr Lys
                165                 170

<210> SEQ ID NO 52
<211> LENGTH: 162
<212> TYPE: PRT
<213> ORGANISM: Clostridium difficile

<400> SEQUENCE: 52
```

```
Met Lys Asn Lys Lys Gly Phe Thr Leu Val Glu Leu Leu Val Val Ile
1               5                   10                  15

Ala Ile Ile Gly Ile Leu Ala Ile Val Ala Leu Pro Ala Leu Phe Lys
            20                  25                  30

Asn Ile Glu Lys Ala Lys Ile Ala Lys Leu Glu Ala Asp Ile Ser Ala
        35                  40                  45

Ile Lys Ser Ala Ser Leu Ser Tyr Tyr Ala Asp Glu Ser Lys Tyr Thr
    50                  55                  60

Glu Gly Asn Ile Ile Trp Trp Thr Lys Lys Asp Gly Lys Ile Thr Val
65                  70                  75                  80

Asn Ser Gly Ile Gly Asp Glu Asp Pro Leu Ala His Lys Ile Glu Asn
                85                  90                  95

Leu Gly Met Pro Tyr Asn Gly Ser Tyr Thr Leu Val Ser Ser Asn Gly
            100                 105                 110

Ser Glu Glu Tyr Leu Glu Leu Asn Ile Ile Asp Gly Glu Ile Ser
        115                 120                 125

Lys Ser Gly Leu Asp Lys Leu Glu Glu Asp Tyr Gly Ser Ser Ile Lys
    130                 135                 140

Ile Pro Asn Asp Lys Asn Met Ile Ile Thr Phe Leu Ser Asn Lys Ser
145                 150                 155                 160

Asp Asn
```

<210> SEQ ID NO 53
<211> LENGTH: 267
<212> TYPE: PRT
<213> ORGANISM: Clostridium difficile

<400> SEQUENCE: 53

```
Met Asn Lys Lys Gly Phe Thr Leu Ile Glu Leu Leu Val Val Ile Ser
1               5                   10                  15

Ile Ile Gly Ile Leu Val Ile Val Ala Ile Pro Ala Leu Phe Arg Asn
            20                  25                  30

Ile Glu Lys Ser Lys Ala Val Thr Cys Leu Ser Asn Arg Glu Asn Ile
        35                  40                  45

Lys Thr Gln Ile Val Ile Ala Met Ala Glu Glu Ser Ser Lys Gly Lys
    50                  55                  60

Asn Glu Val Met Lys Glu Val Leu Glu Asn Lys Asp Gly Lys Tyr Phe
65                  70                  75                  80

Glu Thr Glu Pro Lys Cys Lys Ser Gly Gly Ile Tyr Ser Ala Thr Phe
                85                  90                  95

Asp Asp Gly Tyr Asp Gly Ile Thr Gly Ile Glu Ser Ile Ala Lys Val
            100                 105                 110

Tyr Val Thr Cys Thr Lys His Pro Asp Gly Val Glu Met Ala Arg Asp
        115                 120                 125

Ile His Gln Ser Met Lys Asp Leu Ile Ala Ser Phe Ser Gln Asp Pro
    130                 135                 140

Ser Ile Ile Pro Gly Ala Ser Lys Gly Asn Asp Asp Phe Arg Lys Tyr
145                 150                 155                 160

Leu Leu Asp Asn Lys Tyr Lys Asn Gly Trp Pro Thr Ile Pro Asp Glu
                165                 170                 175

Phe Lys Ala Lys Tyr Gly Leu Ser Lys Asp Thr Leu Tyr Ile Gln Pro
            180                 185                 190

Tyr Ala Tyr Ser Pro Thr Lys Ser Asp Ala Thr Val Val Val Phe Ala
        195                 200                 205
```

```
Asn Asn Lys Thr Gly Gly Asn Trp Tyr Thr Ser Leu Val Tyr Asp Tyr
    210                 215                 220

Asp Glu Gly Arg Trp Tyr Lys Gly Lys Asn Gly Ile Ser Val Ala Gly
225                 230                 235                 240

Arg Ser Trp Asp Val Asp Thr Asp Ser Val Lys Ser Val Lys Thr Glu
                245                 250                 255

Ile His Ser Lys Glu Gly Trp Gly Pro Leu Asn
            260                 265
```

<210> SEQ ID NO 54
<211> LENGTH: 272
<212> TYPE: PRT
<213> ORGANISM: Clostridium difficile

<400> SEQUENCE: 54

```
Met Gly Met Ile Ile Met Asn Lys Lys Gly Phe Thr Leu Ile Glu Leu
1               5                   10                  15

Leu Val Val Ile Ser Ile Gly Ile Leu Val Ile Val Ala Val Pro
            20                  25                  30

Ala Leu Phe Arg Asn Ile Glu Lys Ser Lys Ala Val Thr Cys Leu Ser
            35                  40                  45

Asn Arg Glu Asn Ile Lys Thr Gln Ile Val Ile Ala Met Ala Glu Glu
50                  55                  60

Gln Ser Lys Asp Lys Asn Glu Val Ile Lys Glu Val Leu Gln Asn Lys
65                  70                  75                  80

Asp Gly Lys Tyr Phe Glu Thr Glu Pro Lys Cys Lys Ser Gly Gly Ile
                85                  90                  95

Tyr Ser Ala Thr Phe Asp Asp Gly Tyr Asp Gly Ile Thr Gly Ile Glu
            100                 105                 110

Ser Ile Ala Lys Val Tyr Val Thr Cys Thr Lys His Pro Asp Gly Val
            115                 120                 125

Glu Met Ala Arg Asp Val His Gln Ser Met Lys Asp Leu Ile Ala Ser
130                 135                 140

Phe Ala Gln Asp Pro Ser Ile Ile Pro Gly Ala Ser Lys Gly Asn Asp
145                 150                 155                 160

Asp Phe Arg Lys Tyr Leu Leu Asp Asn Lys Tyr Lys Asn Gly Trp Pro
                165                 170                 175

Thr Ile Pro Asp Glu Phe Lys Ala Lys Tyr Gly Leu Ser Lys Asp Thr
            180                 185                 190

Leu Tyr Ile Gln Pro Tyr Ala Tyr Asn Pro Thr Lys Ser Asp Ala Thr
            195                 200                 205

Val Val Val Phe Ala Asn Asn Lys Thr Gly Gly Asn Trp Tyr Thr Ser
210                 215                 220

Leu Val Tyr Asp Tyr Asp Glu Gly Arg Trp Tyr Lys Gly Lys Asn Gly
225                 230                 235                 240

Ile Ser Val Ala Gly Arg Ser Trp Asp Val Asp Thr Asp Ser Ala Lys
                245                 250                 255

Ser Val Lys Thr Glu Ile His Ser Lys Glu Gly Trp Gly Pro Leu Asn
            260                 265                 270
```

<210> SEQ ID NO 55
<211> LENGTH: 272
<212> TYPE: PRT
<213> ORGANISM: Clostridium difficile

<400> SEQUENCE: 55

```
Met Gly Met Ile Ile Met Asn Lys Lys Gly Phe Thr Leu Ile Glu Leu
1               5                   10                  15

Leu Val Val Ile Ser Ile Ile Gly Ile Leu Val Ile Val Ala Val Pro
            20                  25                  30

Ala Leu Phe Arg Asn Ile Glu Lys Ser Lys Ala Val Thr Cys Leu Ser
        35                  40                  45

Asn Arg Glu Asn Ile Lys Thr Gln Ile Val Ile Ala Met Ala Glu Glu
    50                  55                  60

Ser Ser Lys Gly Lys Asn Glu Val Met Lys Val Leu Glu Asn Lys
65                  70                  75                  80

Asp Gly Lys Tyr Phe Glu Thr Glu Pro Lys Cys Lys Ser Gly Gly Ile
                85                  90                  95

Tyr Ser Ala Thr Phe Asp Asp Gly Tyr Asp Gly Ile Thr Gly Ile Glu
            100                 105                 110

Ser Ile Ala Lys Val Tyr Val Thr Cys Thr Lys His Pro Asp Gly Val
        115                 120                 125

Glu Met Ala Arg Asp Ile His Gln Ser Met Lys Asp Leu Ile Ala Ser
    130                 135                 140

Phe Ala Gln Asp Pro Ser Ile Ile Pro Gly Ala Ser Lys Gly Asn Asp
145                 150                 155                 160

Asp Phe Arg Lys Tyr Leu Leu Asp Asn Lys Tyr Lys Asn Gly Trp Pro
                165                 170                 175

Thr Ile Pro Asp Glu Phe Lys Ala Lys Tyr Gly Leu Ser Lys Asp Thr
            180                 185                 190

Leu Tyr Ile Gln Pro Tyr Ala Tyr Ser Pro Thr Lys Ser Asp Ala Thr
        195                 200                 205

Val Val Val Phe Ala Asn Asn Lys Thr Gly Gly Asn Trp Tyr Thr Ser
    210                 215                 220

Leu Val Tyr Asp Tyr Asp Glu Gly Arg Trp Tyr Lys Gly Lys Asn Gly
225                 230                 235                 240

Ile Ser Val Ala Gly Arg Ser Trp Asp Val Asp Thr Asp Ser Val Lys
                245                 250                 255

Ser Val Lys Thr Glu Ile His Ser Lys Glu Gly Trp Gly Pro Leu Asn
            260                 265                 270
```

<210> SEQ ID NO 56
<211> LENGTH: 272
<212> TYPE: PRT
<213> ORGANISM: Clostridium difficile

<400> SEQUENCE: 56

```
Met Gly Met Ile Ile Met Asn Lys Lys Gly Phe Thr Leu Ile Glu Leu
1               5                   10                  15

Leu Val Val Ile Ser Ile Ile Gly Ile Leu Val Ile Val Ala Val Pro
            20                  25                  30

Ala Leu Phe Arg Asn Ile Glu Lys Ser Lys Ala Val Thr Cys Leu Ser
        35                  40                  45

Asn Arg Glu Asn Ile Lys Thr Gln Ile Val Ile Ala Met Ala Glu Glu
    50                  55                  60

Pro Ser Lys Asp Lys Asn Lys Val Ile Lys Asp Val Leu Glu Asn Lys
65                  70                  75                  80

Asp Gly Lys Tyr Phe Glu Thr Glu Pro Lys Cys Lys Ser Gly Gly Ile
                85                  90                  95

Tyr Ser Ala Thr Phe Asp Asp Gly Tyr Asp Gly Ile Thr Gly Gly Glu
            100                 105                 110
```

Ser Ile Ala Lys Val Tyr Val Thr Cys Thr Glu His Pro Asp Gly Val
            115                 120

```
            210                 215                 220
Asp Glu Gly Arg Trp Tyr Lys Gly Lys Asn Gly Ile Ser Val Ala Gly
225                 230                 235                 240

Arg Ser Trp Asp Val Asp Thr Asp Ser Val Lys Ser Val Lys Thr Glu
                245                 250                 255

Ile His Ser Lys Glu Gly Trp Gly Pro Leu Asn
            260                 265

<210> SEQ ID NO 58
<211> LENGTH: 267
<212> TYPE: PRT
<213> ORGANISM: Clostridium difficile

<400> SEQUENCE: 58

Met Asn Lys Lys Gly Phe Thr Leu Ile Glu Leu Leu Val Val Ile Ser
1               5                   10                  15

Ile Ile Gly Ile Leu Val Ile Ala Val Pro Ala Leu Phe Arg Asn
                20                  25                  30

Ile Glu Lys Ser Lys Ala Val Thr Cys Leu Ser Asn Arg Glu Asn Ile
            35                  40                  45

Lys Thr Gln Ile Val Ile Ala Met Ala Glu Glu Ser Ser Lys Asp Lys
        50                  55                  60

Asn Glu Val Ile Lys Glu Val Leu Glu Asn Lys Asp Gly Lys Tyr Phe
65                  70                  75                  80

Glu Thr Glu Pro Lys Cys Lys Ser Gly Gly Ile Tyr Ser Ala Thr Phe
                85                  90                  95

Asp Asp Gly Tyr Asp Gly Ile Thr Gly Ile Glu Ser Ile Ala Lys Val
                100                 105                 110

Tyr Val Thr Cys Thr Lys His Pro Asp Gly Ile Glu Met Ala Arg Asp
            115                 120                 125

Ile His Gln Ser Met Lys Asp Leu Ile Ala Ser Phe Ala Gln Asp Pro
        130                 135                 140

Ser Ile Ile Pro Gly Ala Ser Lys Gly Asn Asp Asp Phe Arg Lys Tyr
145                 150                 155                 160

Leu Leu Asp Asn Lys Tyr Lys Asn Gly Trp Pro Thr Ile Pro Asp Glu
                165                 170                 175

Phe Lys Ala Lys Tyr Gly Leu Ser Lys Asp Thr Leu Tyr Ile Gln Pro
                180                 185                 190

Tyr Ala Tyr Asn Pro Thr Lys Ser Asp Ala Thr Val Val Phe Ala
            195                 200                 205

Asn Asn Lys Thr Gly Gly Asn Trp Tyr Thr Ser Leu Val Tyr Asp Tyr
        210                 215                 220

Asp Glu Gly Arg Trp Tyr Lys Gly Lys Asn Gly Ile Ser Val Ala Gly
225                 230                 235                 240

Arg Ser Trp Asp Val Asp Thr Asp Ser Val Lys Ser Val Lys Thr Glu
                245                 250                 255

Ile His Ser Lys Glu Gly Trp Gly Pro Leu Asn
            260                 265

<210> SEQ ID NO 59
<211> LENGTH: 267
<212> TYPE: PRT
<213> ORGANISM: Clostridium difficile

<400> SEQUENCE: 59

Met Asn Lys Lys Gly Phe Thr Leu Ile Glu Leu Leu Val Val Ile Ser
```

```
            1               5                  10                 15
        Ile Ile Gly Ile Leu Val Ile Val Ala Val Pro Ala Leu Phe Arg Asn
                        20                 25                 30

Ile Glu Lys Ser Lys Ala Val Thr Cys Leu Ser Asn Arg Glu Asn Ile
                        35                 40                 45

Lys Thr Gln Ile Val Ile Ala Met Ala Glu Glu Ser Ser Lys Asp Lys
                    50                 55                 60

Asn Glu Val Ile Lys Glu Val Leu Glu Asn Lys Asp Gly Lys Tyr Phe
        65                  70                 75                 80

Glu Thr Glu Pro Lys Cys Lys Ser Gly Gly Ile Tyr Ser Ala Thr Phe
                        85                 90                 95

Asp Asp Gly Tyr Asp Gly Ile Thr Gly Arg Glu Ser Ile Ala Lys Val
                        100                105                110

Tyr Val Thr Cys Thr Lys His Pro Asp Gly Val Glu Met Ala Arg Asp
                        115                120                125

Val His Gln Ser Met Lys Asp Leu Ile Ala Ser Phe Ala Gln Asp Pro
                    130                135                140

Ser Ile Ile Pro Gly Ala Ser Lys Gly Asn Asp Asp Phe Arg Lys Tyr
        145                 150                155                160

Leu Leu Asp Asn Lys Tyr Lys Asn Gly Trp Pro Thr Ile Pro Asp Glu
                        165                170                175

Phe Lys Ala Lys Tyr Gly Leu Ser Lys Asp Thr Leu Tyr Ile Gln Pro
                        180                185                190

Tyr Ala Tyr Asn Pro Thr Lys Ser Asp Ala Thr Val Val Val Phe Ala
                    195                200                205

Asn Asn Lys Thr Gly Gly Asn Trp Tyr Thr Ser Leu Val Tyr Asp Tyr
        210                 215                220

Asp Glu Gly Arg Trp Tyr Lys Gly Lys Asn Gly Ile Ser Val Ala Gly
        225                 230                235                240

Arg Ser Trp Asp Val Asp Thr Asp Ser Val Lys Ser Val Lys Thr Glu
                        245                250                255

Ile His Ser Lys Glu Gly Trp Gly Pro Leu Asn
                        260                265

<210> SEQ ID NO 60
<211> LENGTH: 267
<212> TYPE: PRT
<213> ORGANISM: Clostridium difficile

<400> SEQUENCE: 60

Met Asn Lys Lys Gly Phe Thr Leu Ile Glu Leu Leu Val Val Ile Ser
        1                   5                  10                 15

Ile Ile Gly Ile Leu Val Ile Val Ala Val Pro Ala Leu Phe Arg Asn
                        20                 25                 30

Ile Glu Lys Ser Lys Ala Val Thr Cys Leu Ser Asn Arg Glu Asn Ile
                        35                 40                 45

Lys Thr Gln Ile Val Ile Ala Met Ala Glu Glu Pro Ser Lys Asp Lys
                    50                 55                 60

Asn Lys Val Ile Lys Asp Val Leu Glu Asn Lys Asp Gly Lys Tyr Phe
        65                  70                 75                 80

Glu Thr Glu Pro Lys Cys Lys Ser Gly Gly Ile Tyr Ser Ala Thr Phe
                        85                 90                 95

Asp Asp Gly Tyr Asp Gly Ile Thr Gly Gly Glu Ser Ile Ala Lys Val
                        100                105                110
```

```
Tyr Val Thr Cys Thr Glu His Pro Asp Gly Val Glu Met Ala Arg Asp
            115                 120                 125

Val His Gln Ser Met Lys Asp Leu Ile Ala Ser Phe Ala Gln Asp Pro
    130                 135                 140

Ser Ile Ile Pro Gly Ala Ser Lys Ser Asn Asp Asp Phe Arg Lys Tyr
145                 150                 155                 160

Leu Leu Asp Asn Lys Tyr Lys Lys Gly Trp Pro Thr Ile Pro Asp Glu
                165                 170                 175

Phe Lys Ala Lys Tyr Gly Leu Ser Lys Asp Thr Leu Tyr Ile Gln Pro
            180                 185                 190

Tyr Ala Tyr Asn Pro Thr Lys Pro Asp Ala Thr Val Val Val Phe Ala
    195                 200                 205

Asn Asn Lys Thr Gly Gly Asn Trp Tyr Thr Ser Leu Val Tyr Asp Tyr
210                 215                 220

Asp Glu Gly Arg Trp Tyr Lys Gly Lys Asn Gly Ile Ser Val Ala Gly
225                 230                 235                 240

Arg Ser Trp Asp Val Asp Thr Asp Ser Val Lys Ser Val Lys Thr Glu
                245                 250                 255

Ile His Ser Lys Glu Gly Trp Gly Pro Leu Asn
            260                 265
```

<210> SEQ ID NO 61
<211> LENGTH: 528
<212> TYPE: DNA
<213> ORGANISM: Clostridium difficile

<400> SEQUENCE: 61

```
atgagtaaaa agaatagtga aagaggattt tccttaattg aagtgttagt agctatggct      60
attatgggaa ttgtactatt tgcatttttt aatattatca atactaataa caaagcaaac     120
actaaaaatg acacagatat aacttcctta aactatgtcc aaagtgaaat agaaaatcta     180
agagaaaaga taaaaagtgg agaatttgat tttgatagtt tagataaact agaagatgga     240
actgtcgtat atgaaaaatt aatagataaa tcaaaaaaag ttgtatatga taaagttctt     300
agtgaaggtg acgtgagctt atatgatact ccatatgaaa agattacaac aataaaagat     360
gaagatggta atttaatcga caaggaaat attacaaata agataaagac tattgtagaa     420
gataaaagtg gtcagatata taaaatagct gtaactggga aaagcatgaa tgactattca     480
agtaaaaaag aggttaaaat tgtaactgaa atatttaaag ataaataa                  528
```

<210> SEQ ID NO 62
<211> LENGTH: 528
<212> TYPE: DNA
<213> ORGANISM: Clostridium difficile

<400> SEQUENCE: 62

```
atgagtaaaa agaatagtga aagaggattt tccttaattg aagtgttagt agctatggct      60
attatgggaa ttgtactatt tgcatttttt aatattatca atactaataa caaagcaaac     120
actaaaaatg acacagatat aacttcctta aactatgttc aaagtgaaat agaaaatcta     180
agagaaaaga taaaaagtgg agaatttgat tttgatagtt tagataaact agaagatgga     240
actgtcgtat atgaaaaatt aatagataaa tcaaaaaaag ttgtatatga taaagttctt     300
agtgaaggtg atgtgagctt atatgatact ccatatgaaa agattacaac aataaaagat     360
gaagatggta atttaatcga caaggaaat attacaaata agataaagac tattgtagaa     420
gataaaagtg gtcagatata taaaatagct gtaactggga aaagcatgaa tgactattca     480
```

```
agtaaaaaag aggttaaaat tgtaactgaa atatttaaag ataaataa          528
```

<210> SEQ ID NO 63
<211> LENGTH: 175
<212> TYPE: PRT
<213> ORGANISM: Clostridium difficile

<400> SEQUENCE: 63

```
Met Ser Lys Lys Asn Ser Glu Arg Gly Phe Ser Leu Ile Glu Val Leu
1               5                   10                  15

Val Ala Met Ala Ile Met Gly Ile Val Leu Phe Ala Phe Phe Asn Ile
            20                  25                  30

Ile Asn Thr Asn Asn Lys Ala Asn Thr Lys Asn Asp Thr Asp Ile Thr
        35                  40                  45

Ser Leu Asn Tyr Val Gln Ser Glu Ile Glu Asn Leu Arg Glu Lys Ile
    50                  55                  60

Lys Ser Gly Glu Phe Asp Phe Asp Ser Leu Asp Lys Leu Glu Asp Gly
65                  70                  75                  80

Thr Val Val Tyr Glu Lys Leu Ile Asp Lys Ser Lys Lys Val Val Tyr
                85                  90                  95

Asp Lys Val Leu Ser Glu Gly Asp Val Ser Leu Tyr Asp Thr Pro Tyr
            100                 105                 110

Glu Lys Ile Thr Thr Ile Lys Asp Glu Asp Gly Asn Leu Ile Asp Lys
        115                 120                 125

Gly Asn Ile Thr Asn Lys Ile Lys Thr Ile Val Glu Asp Lys Ser Gly
    130                 135                 140

Gln Ile Tyr Lys Ile Ala Val Thr Gly Lys Ser Met Asn Asp Tyr Ser
145                 150                 155                 160

Ser Lys Lys Glu Val Lys Ile Val Thr Glu Ile Phe Lys Asp Lys
                165                 170                 175
```

<210> SEQ ID NO 64
<211> LENGTH: 528
<212> TYPE: DNA
<213> ORGANISM: Clostridium difficile

<400> SEQUENCE: 64

```
atgagtaaaa agaatagtga aagaggattt tccttaattg aagtgttagt agctatggct    60
attatgggaa ttgtactatt tgcattttt aatattatca atactaataa caaagcaaac   120
actaaaaatg acacagatat aacttcctta aactatgtcc aaagtgaaat agaaaatcta   180
agagaaaaga taaaagtgg agaatttgat tttgatagtt tagataaact agaagatgga   240
actgtcgtat atgaaaaatt aatagataaa tcaaaaaaag ttgtatatga taaagttctt   300
agtgaaggtg atgtgagctt atatgatact ccatatgaaa agattacaac aataaaagat   360
gaagatggta atttaatcga caaggaaat attacaaata agataaagac tattgtagaa   420
gataaaagtg gtcagatata taaaataact gtaactggaa aaagcatgaa tgactattca   480
agtaaaaaag aggttaaaat tgtaactgaa atatttaaag ataaataa             528
```

<210> SEQ ID NO 65
<211> LENGTH: 175
<212> TYPE: PRT
<213> ORGANISM: Clostridium difficile

<400> SEQUENCE: 65

```
Met Ser Lys Lys Asn Ser Glu Arg Gly Phe Ser Leu Ile Glu Val Leu
```

```
1               5                   10                  15
Val Ala Met Ala Ile Met Gly Ile Val Leu Phe Ala Phe Phe Asn Ile
                20                  25                  30

Ile Asn Thr Asn Asn Lys Ala Asn Thr Lys Asn Asp Thr Asp Ile Thr
                35                  40                  45

Ser Leu Asn Tyr Val Gln Ser Glu Ile Glu Asn Leu Arg Glu Lys Ile
    50                  55                  60

Lys Ser Gly Glu Phe Asp Phe Asp Ser Leu Asp Lys Leu Glu Asp Gly
65                  70                  75                  80

Thr Val Val Tyr Glu Lys Leu Ile Asp Lys Ser Lys Lys Val Val Tyr
                85                  90                  95

Asp Lys Val Leu Ser Glu Gly Asp Val Ser Leu Tyr Asp Thr Pro Tyr
                100                 105                 110

Glu Lys Ile Thr Thr Ile Lys Asp Glu Asp Gly Asn Leu Ile Asp Lys
                115                 120                 125

Gly Asn Ile Thr Asn Lys Ile Lys Thr Ile Val Glu Asp Lys Ser Gly
130                 135                 140

Gln Ile Tyr Lys Ile Thr Val Thr Gly Lys Ser Met Asn Asp Tyr Ser
145                 150                 155                 160

Ser Lys Lys Glu Val Lys Ile Val Thr Glu Ile Phe Lys Asp Lys
                165                 170                 175
```

<210> SEQ ID NO 66
<211> LENGTH: 175
<212> TYPE: PRT
<213> ORGANISM: Clostridium difficile

<400> SEQUENCE: 66

```
Met Ser Lys Lys Asn Ser Glu Arg Gly Phe Ser Leu Ile Glu Val Leu
1               5                   10                  15

Val Ala Met Ala Ile Met Gly Ile Val Leu Phe Ala Phe Phe Asn Ile
                20                  25                  30

Ile Asn Thr Asn Asn Lys Ala Asn Thr Lys Asn Asp Thr Asp Ile Thr
                35                  40                  45

Ser Leu Asn Tyr Val Gln Ser Glu Ile Glu Asn Leu Arg Glu Lys Ile
    50                  55                  60

Lys Ser Gly Glu Phe Asp Phe Asp Ser Leu Asp Lys Leu Glu Asp Gly
65                  70                  75                  80

Thr Val Val Tyr Glu Lys Leu Ile Asp Lys Ser Lys Lys Val Val Tyr
                85                  90                  95

Asp Lys Val Leu Ser Glu Ser Asp Val Ser Leu Tyr Asp Ile Pro Tyr
                100                 105                 110

Glu Lys Ile Thr Thr Ile Lys Asp Glu Asp Gly Asn Leu Ile Asp Lys
                115                 120                 125

Glu Asn Ile Thr Asn Lys Ile Lys Thr Ile Val Glu Asp Lys Ser Gly
130                 135                 140

Gln Ile Tyr Lys Val Ala Val Thr Gly Lys Ser Met Asn Asp Tyr Ser
145                 150                 155                 160

Ser Lys Lys Glu Val Lys Ile Val Thr Glu Ile Phe Lys Asp Lys
                165                 170                 175
```

<210> SEQ ID NO 67
<211> LENGTH: 175
<212> TYPE: PRT
<213> ORGANISM: Clostridium difficile -continued

<400> SEQUENCE: 67

Met Ser Lys Lys Asn Ser Lys Arg Gly Phe Ser Leu Ile Glu Val Leu
1               5                   10                  15

Val Ala Met Ala Ile Met Gly Ile Ile Leu Phe Ala Phe Phe Asn Ile
            20                  25                  30

Ile Asn Thr Asn Asn Lys Ala Asn Ile Lys Asn Asp Thr Asp Ile Asn
        35                  40                  45

Ser Leu Asn Tyr Val Gln Ser Glu Ile Glu Asn Leu Arg Glu Lys Ile
    50                  55                  60

Lys Ser Gly Glu Phe Asp Phe Asp Ser Leu Asp Lys Met Glu Asp Gly
65                  70                  75                  80

Thr Val Val Tyr Glu Lys Leu Ile Asp Lys Ser Lys Ile Val Tyr
                85                  90                  95

Asp Lys Val Leu Ser Glu Gly Asn Val Ser Leu Tyr Asp Thr Pro Tyr
            100                 105                 110

Glu Lys Ile Thr Thr Ile Lys Asp Glu Asp Gly Asn Leu Ile Asp Lys
        115                 120                 125

Glu Asn Ile Thr Asn Lys Ile Lys Thr Ile Val Glu Asp Lys Ser Gly
    130                 135                 140

Gln Ile Tyr Lys Ile Ala Val Thr Gly Lys Ser Met Asn Asp Tyr Ser
145                 150                 155                 160

Ser Lys Lys Glu Val Lys Ile Val Thr Glu Ile Phe Lys Asp Lys
                165                 170                 175

<210> SEQ ID NO 68
<211> LENGTH: 528
<212> TYPE: DNA
<213> ORGANISM: Clostridium difficile

<400> SEQUENCE: 68
atgagtaaaa agaatagtaa aagaggattt tccttaattg aagtgttagt agctatggct      60
attatgggaa ttatactatt tgcgtttttt aatattatca atactaataa taaagcaaat     120
attaaaaatg acacagatat aaattcctta aactatgtcc aaagtgaaat agaaaatcta     180
agagagaaga taaaaagtgg agaatttgat tttgatagtt tagataaaat ggaagatggg     240
actgtcgtat atgaaaaatt aatagataag tcaaaaaaaa ttgtgtatga taaagttctt     300
agtgagggta acgtgagctt atatgatact ccatatgaaa agattacaac aataaaagat     360
gaagatggta atttaatcga taaagaaaat attacaaata gataaagac tattgtagaa     420
gataaaagtg gtcagatata taaaatagct gtaactggga aaagcatgaa tgactattca     480
agtaaaaaag aagttaagat tgtaactgaa atatttaaag ataaataa                  528

<210> SEQ ID NO 69
<211> LENGTH: 175
<212> TYPE: PRT
<213> ORGANISM: Clostridium difficile

<400> SEQUENCE: 69

Met Ser Lys Lys Asn Ser Lys Arg Gly Phe Ser Leu Ile Glu Val Leu
1               5                   10                  15

Val Ala Met Ala Ile Met Gly Ile Ile Leu Phe Ala Phe Phe Asn Ile
            20                  25                  30

Ile Asn Thr Asn Asn Lys Ala Asn Ile Lys Asn Asp Thr Asp Ile Asn
        35                  40                  45

Ser Leu Asn Tyr Val Gln Ser Glu Ile Glu Asn Leu Arg Glu Lys Ile

```
              50                  55                  60
Lys Ser Gly Glu Phe Asp Phe Asp Ser Leu Asp Lys Met Glu Asp Gly
 65                  70                  75                  80

Thr Val Val Tyr Glu Lys Leu Ile Asp Lys Ser Lys Lys Ile Val Tyr
                 85                  90                  95

Asp Lys Val Leu Ser Glu Gly Asn Val Ser Leu Tyr Asp Thr Pro Tyr
            100                 105                 110

Glu Lys Ile Thr Thr Ile Lys Asp Gly Asp Gly Asn Leu Ile Asp Lys
        115                 120                 125

Glu Asn Ile Thr Asn Lys Ile Lys Thr Ile Val Glu Asp Lys Ser Gly
130                 135                 140

Gln Ile Tyr Lys Ile Ala Val Thr Gly Lys Ser Met Asn Asp Tyr Ser
145                 150                 155                 160

Ser Lys Lys Glu Val Lys Ile Val Thr Glu Ile Phe Lys Asp Lys
                165                 170                 175

<210> SEQ ID NO 70
<211> LENGTH: 567
<212> TYPE: DNA
<213> ORGANISM: Clostridium difficile

<400> SEQUENCE: 70
atgagtttgt acaaaaataa tgaaaaaggt cttactttat agaagtaat  aatagctgtt      60 tttatactga caatagtttt aagtatttct tataaagtgt tcaatggtat aacatcagca     120
gtaaaaaagc aacagattat tacagatgct caagtaaata ttaatctaat taataagtat     180
ctaaatagag atttggaaaa ctgtaaagag ctaactaaaa ctggttcagg taataattat     240
gaatacaata tagagatgcc agataatgtt gtaaaatatg aagtttctat agaaactaaa     300
aaaaatacag aggtatattc tgtaacgaga atccaaaaca atacaattga tacagaaaat     360
gaagttagag aagagataat ctataatcaa ccactagttc aaaacaataa agaaatgaag     420
gaaacaccat ttaaaataga aaagcaaact ggtaaatcta tttatactgt aagtatatac     480
tataatgaat cagtgcaaga aagtcataaa aatagcaatt taaataacaa aacttataca     540
tttgatgtta tgtcaagaat agggtaa                                         567

<210> SEQ ID NO 71
<211> LENGTH: 188
<212> TYPE: PRT
<213> ORGANISM: Clostridium difficile

<400> SEQUENCE: 71

Met Ser Leu Tyr Lys Asn Asn Glu Lys Gly Leu Thr Leu Leu Glu Val
  1               5                  10                  15

Ile Ile Ala Val Phe Ile Leu Thr Ile Val Leu Ser Ile Ser Tyr Lys
                 20                  25                  30

Val Phe Asn Gly Ile Thr Ser Ala Val Lys Lys Gln Gln Ile Ile Thr
             35                  40                  45

Asp Ala Gln Val Asn Ile Asn Leu Ile Asn Lys Tyr Leu Asn Arg Asp
         50                  55                  60

Leu Glu Asn Cys Lys Glu Leu Thr Lys Thr Gly Ser Gly Asn Asn Tyr
 65                  70                  75                  80

Glu Tyr Asn Ile Glu Met Pro Asp Asn Val Val Lys Tyr Glu Val Ser
                 85                  90                  95

Ile Glu Thr Lys Lys Asn Thr Glu Val Tyr Ser Val Thr Arg Ile Gln
            100                 105                 110
```

Asn Asn Thr Ile Asp Thr Glu Asn Glu Val Arg Glu Glu Ile Ile Tyr
            115                 120                 125

Asn Gln Pro Leu Val Gln Asn Asn Lys Glu Met Lys Glu Thr Pro Phe
        130                 135                 140

Lys Ile Glu Lys Gln Thr Gly Lys Ser Ile Tyr Thr Val Ser Ile Tyr
145                 150                 155                 160

Tyr Asn Glu Ser Val Gln Glu Ser His Lys Asn Ser Asn Leu Asn Asn
                165                 170                 175

Lys Thr Tyr Thr Phe Asp Val Met Ser Arg Ile Gly
            180                 185

<210> SEQ ID NO 72
<211> LENGTH: 567
<212> TYPE: DNA
<213> ORGANISM: Clostridium difficile

<400> SEQUENCE: 72
atgagtttgt acaaaaataa tgaaaaaggt cttactttat agaagtaat aatagctgtt      60 tttatactga caatagtttt aagtatttct tataaagtgt caatggtat aacatcagca     120 gtaaaaaagc aacagattat tacagatgct caagtaaata ttaatctaat taataagtat     180
ctaaatagag atttggaaaa ctgtaaagaa ctaactaaaa ctggttcagg taataattat     240
gaatacaata tagagatgcc agataatgtt gtaaatatg aagtttctat agaaactaaa     300
aaaaatacag aggtatattc tgtaacgaga atccaaaaca atacaattga tacagaaaat     360
gaagttagag aagagataat ctacaatcaa ccactagttc aaaacaataa agaaatgaag     420
gaaacaccat ttaaaataga aaagcaaact ggtaaatcta tttatactgt aagtatatac     480
tataatgaat cagtgcaaga aagtcataaa aatagcaatt taaataacaa aacttataca     540
tttgatgtta tgtcaagaat agggtaa                                        567

<210> SEQ ID NO 73
<211> LENGTH: 189
<212> TYPE: PRT
<213> ORGANISM: Clostridium difficile

<400> SEQUENCE: 73

Met Met Ser Leu Tyr Lys Asn Asn Glu Lys Gly Leu Thr Leu Leu Glu
1               5                   10                  15

Val Ile Ile Ala Val Phe Ile Leu Thr Ile Val Leu Ser Ile Ser Tyr
            20                  25                  30

Lys Val Phe Asn Gly Ile Thr Ser Ala Val Lys Lys Gln Gln Ile Ile
        35                  40                  45

Thr Asp Ala Gln Val Asn Ile Asn Leu Ile Asn Lys Tyr Leu Asn Arg
    50                  55                  60

Asp Leu Glu Asn Cys Lys Glu Leu Thr Lys Thr Gly Ser Gly Asn Asn
65                  70                  75                  80

Tyr Glu Tyr Asn Ile Glu Met Pro Asp Asn Val Val Lys Tyr Glu Val
                85                  90                  95

Ser Ile Glu Thr Lys Lys Asn Thr Glu Val Tyr Ser Val Thr Arg Ile
            100                 105                 110

Gln Asn Asn Thr Ile Asp Thr Glu Asn Glu Val Arg Glu Glu Ile Ile
        115                 120                 125

Tyr Asn Gln Pro Leu Val Gln Asn Asn Lys Glu Met Lys Glu Thr Pro
    130                 135                 140

Phe Lys Ile Glu Lys Gln Thr Gly Lys Ser Ile Tyr Thr Val Ser Ile
145                 150                 155                 160

Tyr Tyr Asn Glu Ser Val Gln Glu Ser His Lys Asn Ser Asn Leu Asn
                165                 170                 175

Asn Lys Thr Tyr Thr Phe Asp Val Met Ser Arg Ile Gly
            180                 185

<210> SEQ ID NO 74
<211> LENGTH: 188
<212> TYPE: PRT
<213> ORGANISM: Clostridium difficile

<400> SEQUENCE: 74

Met Ser Leu Tyr Lys Asn Asn Glu Lys Gly Leu Thr Leu Leu Glu Val
1               5                   10                  15

Ile Ile Ala Val Phe Ile Leu Thr Ile Val Leu Ser Ile Ser Tyr Lys
                20                  25                  30

Val Phe Asn Gly Ile Thr Ser Ala Val Lys Arg Gln Gln Ile Ile Thr
            35                  40                  45

Asp Ala Gln Val Asn Ile Asn Leu Ile Asn Lys Tyr Leu Asn Arg Asp
50                  55                  60

Leu Glu Asn Cys Lys Glu Leu Thr Lys Thr Gly Ser Gly Asn Asn Tyr
65                  70                  75                  80

Glu Tyr Asn Ile Glu Met Pro Asp Asn Val Val Lys Tyr Glu Val Ser
                85                  90                  95

Ile Glu Thr Lys Lys His Thr Glu Val Tyr Ser Val Thr Arg Ile Gln
            100                 105                 110

Lys Asn Thr Ile Asp Thr Glu Asn Glu Val Arg Glu Glu Ile Ile Tyr
        115                 120                 125

Asn Gln Pro Leu Val Gln Asn Asn Lys Glu Met Lys Glu Thr Pro Phe
130                 135                 140

Lys Ile Glu Lys Gln Thr Gly Lys Ser Ile Tyr Thr Val Ser Ile Tyr
145                 150                 155                 160

Tyr Asn Glu Ser Val Gln Glu Ser His Lys Asn Ile Asn Leu Asn Asn
                165                 170                 175

Lys Thr Tyr Thr Phe Asp Val Met Ser Arg Ile Gly
            180                 185

<210> SEQ ID NO 75
<211> LENGTH: 188
<212> TYPE: PRT
<213> ORGANISM: Clostridium difficile

<400> SEQUENCE: 75

Met Ser Leu Tyr Lys Asn Asn Glu Lys Gly Leu Thr Leu Leu Glu Val
1               5                   10                  15

Ile Ile Ala Val Phe Ile Leu Thr Ile Val Leu Ser Ile Ser Tyr Lys
                20                  25                  30

Val Phe Asn Gly Ile Thr Ser Ala Val Lys Lys Gln Gln Ile Ile Thr
            35                  40                  45

Asp Ala Gln Val Asn Ile Asn Leu Ile Asn Lys Tyr Leu Asn Arg Asp
50                  55                  60

Leu Glu Asn Cys Lys Glu Leu Thr Lys Thr Gly Ser Gly Ser Asn Tyr
65                  70                  75                  80

Glu Tyr Asn Ile Glu Thr Pro Asp Asn Ile Val Lys Tyr Glu Val Ser
                85                  90                  95

```
Ile Glu Thr Lys Lys Asn Thr Glu Val Tyr Ser Val Thr Arg Ile Glu
            100                 105                 110

Lys Asn Thr Ile Asp Thr Glu Asn Glu Val Arg Glu Glu Ile Ile Tyr
        115                 120                 125

Asn Gln Pro Leu Val Gln Asn Asn Lys Glu Met Lys Glu Thr Pro Phe
    130                 135                 140

Lys Ile Glu Lys Gln Thr Asp Lys Ser Ile Tyr Thr Val Ser Ile Phe
145                 150                 155                 160

Tyr Asn Glu Ser Val Gln Glu Gly His Lys Asn Ser Asn Leu Asn Asn
                165                 170                 175

Lys Thr Tyr Thr Phe Asp Val Met Ser Arg Ile Gly
        180                 185

<210> SEQ ID NO 76
<211> LENGTH: 567
<212> TYPE: DNA
<213> ORGANISM: Clostridium difficile

<400> SEQUENCE: 76
atgagtttgt acaaaaataa tgaaaaaggt cttactttat tagaagtaat aatagctgtt     60
tttatactga caatagtttt aagtatttct tataaagtgt tcaatggtat aacatcagca    120
gtaaaaaagc aacagattat tacagatgct caagtaaata ttaatctaat taataagtat    180
ctaaatagag atttggaaaa ctgtaaagag ctaactaaaa ctggttcagg taataattat    240
gaatacaata tagagatgcc agataatgtt gtaaaatatg aagtttctat agaaactaaa    300
aaaaatacag aggtatattc tgtaacgaga atccaaaaca atacaattga tacagaaaat    360
gaagttagag aagagataat ctataatcaa ccactagttc aaaacaataa agaaatgaag    420
gaaacaccat ttaaaataga aaagcaaact ggtaaatcta tttatactgt aagtatatac    480
tataatgaat cagtgcaaga agtcataaaa aatagcaatt taaataacaa aacttataca    540
tttgatgtta tgtcaagaat agggtaa                                        567

<210> SEQ ID NO 77
<211> LENGTH: 567
<212> TYPE: DNA
<213> ORGANISM: Clostridium difficile

<400> SEQUENCE: 77
atgagtttgt acaaaaataa tgaaaaaggt cttactttat tagaagtaat aatagctgtt     60
tttatactga caatagtttt aagtatttct tataaagtgt tcaatggtat aacatcagca    120
gtaaaaaagc aacagattat tacagatgct caagtaaata ttaatctaat taataagtat    180
ctaaatagag atttggaaaa ctgtaaagaa ctaactaaaa ctggttcagg taataattat    240
gaatacaata tagagatgcc agataatgtt gtaaaatatg aagtttctat agaaactaaa    300
aaaaatacag aggtatattc tgtaacgaga atccaaaaca atacaattga tacagaaaat    360
gaagttagag aagaaataat ctataatcaa ccactagttc aaaacaataa agaaatgaag    420
gaaacaccat ttaaaataga aaagcaaact ggtaaatcta tttatactgt aagtatatac    480
tataatgaat cagtgcaaga agtcataaaa aatagcaatt taaataacaa aacttataca    540
tttgatgtta tgtcaagaat agggtaa                                        567

<210> SEQ ID NO 78
<211> LENGTH: 186
<212> TYPE: PRT
<213> ORGANISM: Clostridium difficile
```

<400> SEQUENCE: 78

```
Met Tyr Lys Asn Asn Glu Lys Gly Leu Thr Leu Leu Glu Val Ile Ile
1               5                   10                  15

Ala Val Phe Ile Leu Thr Ile Val Leu Ser Ile Ser Tyr Lys Val Phe
            20                  25                  30

Asn Gly Ile Thr Ser Ala Val Lys Lys Gln Gln Ile Ile Thr Asp Ala
        35                  40                  45

Gln Val Asn Ile Asn Leu Ile Asn Lys Tyr Leu Asn Arg Asp Leu Glu
    50                  55                  60

Asn Cys Lys Glu Leu Thr Lys Thr Gly Ser Gly Asn Asn Tyr Glu Tyr
65                  70                  75                  80

Asn Ile Glu Met Pro Asp Asn Val Val Lys Tyr Glu Val Ser Ile Glu
                85                  90                  95

Thr Lys Lys Asn Thr Glu Val Tyr Ser Val Thr Arg Ile Gln Asn Asn
            100                 105                 110

Thr Ile Asp Thr Glu Asn Glu Val Arg Glu Ile Ile Tyr Asn Gln
        115                 120                 125

Pro Leu Val Gln Asn Asn Lys Glu Met Lys Glu Thr Pro Phe Lys Ile
    130                 135                 140

Glu Lys Gln Thr Gly Lys Ser Ile Tyr Thr Val Ser Ile Tyr Tyr Asn
145                 150                 155                 160

Glu Ser Val Gln Glu Ser His Lys Asn Ser Asn Leu Asn Asn Lys Thr
                165                 170                 175

Tyr Thr Phe Asp Val Met Ser Arg Ile Gly
            180                 185
```

<210> SEQ ID NO 79
<211> LENGTH: 186
<212> TYPE: PRT
<213> ORGANISM: Clostridium difficile

<400> SEQUENCE: 79

```
Met Tyr Lys Asn Asn Glu Lys Gly Leu Thr Leu Leu Glu Val Ile Ile
1               5                   10                  15

Ala Val Phe Ile Leu Thr Ile Val Leu Ser Ile Ser Tyr Lys Val Phe
            20                  25                  30

Asn Gly Ile Thr Ser Ala Val Lys Lys Gln Gln Ile Ile Thr Asp Ala
        35                  40                  45

Gln Val Asn Ile Asn Leu Ile Asn Lys Tyr Leu Asn Arg Asp Leu Glu
    50                  55                  60

Asn Cys Lys Glu Leu Thr Lys Thr Gly Ser Gly Asn Asn Tyr Glu Tyr
65                  70                  75                  80

Asn Ile Glu Met Pro Asp Asn Val Val Lys Tyr Glu Val Ser Ile Glu
                85                  90                  95

Thr Lys Lys Asn Thr Glu Val Tyr Ser Val Thr Arg Ile Gln Asn Asn
            100                 105                 110

Thr Ile Asp Thr Glu Asn Glu Val Arg Glu Ile Ile Tyr Asn Gln
        115                 120                 125

Pro Leu Val Gln Asn Asn Lys Glu Met Lys Glu Thr Pro Phe Lys Ile
    130                 135                 140

Glu Lys Arg Thr Gly Lys Ser Ile Tyr Thr Val Ser Ile Tyr Tyr Asn
145                 150                 155                 160

Glu Ser Val Gln Glu Ser His Lys Asn Ser Asn Leu Asn Asn Lys Thr
                165                 170                 175
```

Tyr Thr Phe Asp Val Met Ser Arg Ile Gly
            180                 185

<210> SEQ ID NO 80
<211> LENGTH: 567
<212> TYPE: DNA
<213> ORGANISM: Clostridium difficile

<400> SEQUENCE: 80
atgagtttgt acaaaaataa tgaaaaaggt cttaccttat agaagtaat aatagctgtt      60 tttatactga caatagtttt aagcatttct tataaggtgt ttaatggtat aacatcagca    120
gtaaaaaagc aacagattat tacagatgct caagtaaata ttaacctaat taataagtat    180
ctaaatagag atttggaaaa ctgtaaagag ctaactaaaa ctggttcagg tagtaattat    240
gaatataata tagagacgcc agataatatt gtaaatatg aagtttccat agaaactaaa     300
aaaaatacag aggtatattc tgtaacaaga atcgaaaaaa atacaattga tacagaaaat    360
gaagttagag aagagataat ctataatcaa ccactagttc aaaacaataa agaaatgaaa    420
gaaacaccat ttaaaataga aaagcaaact gataaatcta tttatactgt aagtatattc    480
tataatgaat cagttcaaga aggtcataaa aatagcaatt taaataacaa gacttataca    540
tttgatgtta tgtcgagaat aggataa                                        567

<210> SEQ ID NO 81
<211> LENGTH: 186
<212> TYPE: PRT
<213> ORGANISM: Clostridium difficile

<400> SEQUENCE: 81

Met Tyr Lys Asn Asn Glu Lys Gly Leu Thr Leu Leu Glu Val Ile Ile
1               5                   10                  15

Ala Val Phe Ile Leu Thr Ile Val Leu Ser Ile Ser Tyr Lys Val Phe
            20                  25                  30

Asn Gly Ile Thr Ser Ala Val Lys Lys Gln Gln Ile Ile Thr Asp Ala
        35                  40                  45

Gln Val Asn Ile Asn Leu Ile Asn Lys Tyr Leu Asn Arg Asp Leu Glu
    50                  55                  60

Asn Cys Lys Glu Leu Thr Lys Thr Gly Ser Gly Ser Asn Tyr Glu Tyr
65                  70                  75                  80

Asn Ile Glu Thr Pro Asp Asn Ile Val Lys Tyr Glu Val Ser Ile Glu
                85                  90                  95

Thr Lys Lys Asn Thr Glu Val Tyr Ser Val Thr Arg Ile Glu Lys Asn
            100                 105                 110

Thr Ile Asp Thr Glu Asn Glu Val Arg Glu Glu Ile Ile Tyr Asn Gln
        115                 120                 125

Pro Leu Val Gln Asn Asn Lys Glu Met Lys Glu Thr Pro Phe Lys Ile
    130                 135                 140

Glu Lys Gln Thr Asp Lys Ser Ile Tyr Thr Val Ser Ile Phe Tyr Asn
145                 150                 155                 160

Glu Ser Val Gln Glu Gly His Lys Asn Ser Asn Leu Asn Asn Lys Thr
                165                 170                 175

Tyr Thr Phe Asp Val Met Ser Arg Ile Gly
            180                 185

<210> SEQ ID NO 82
<211> LENGTH: 375

```
<212> TYPE: DNA
<213> ORGANISM: Clostridium difficile

<400> SEQUENCE: 82 ttgttttat tattgaaaat aagaaagagt ggttttatat caatcgaatg tataataagt      60
attgctatat tatatgtggc tgtttattta gtttctacat cattgtataa ttgttatagt     120
tttatcagta gaaatatatc tgacagagaa atgttaagta cagcaaaaaa atatatagaa    180
gatgagaagt atagaataca aaatagtaag tatgagttaa ttgaagataa gatagaaaaa    240
aattacataa atggatatga aattaacagt agaatagagc aaattttaga ttattatcaa    300
tgctatgaaa taaatataga gataaaaaat gaatttaaaa aactgaggtt taatagctat    360
gttactagaa aataa                                                      375

<210> SEQ ID NO 83
<211> LENGTH: 124
<212> TYPE: PRT
<213> ORGANISM: Clostridium difficile

<400> SEQUENCE: 83

Met Phe Leu Leu Leu Lys Ile Arg Lys Ser Gly Phe Ile Ser Ile Glu
1               5                   10                  15

Cys Ile Ile Ser Ile Ala Ile Leu Tyr Val Ala Val Tyr Leu Val Ser
                20                  25                  30

Thr Ser Leu Tyr Asn Cys Tyr Ser Phe Ile Ser Arg Asn Ile Ser Asp
            35                  40                  45

Arg Glu Met Leu Ser Thr Ala Lys Lys Tyr Ile Glu Asp Glu Lys Tyr
    50                  55                  60

Arg Ile Gln Asn Ser Lys Tyr Glu Leu Ile Glu Asp Lys Ile Glu Lys
65                  70                  75                  80

Asn Tyr Ile Asn Gly Tyr Glu Ile Asn Ser Arg Ile Glu Gln Ile Leu
                85                  90                  95

Asp Tyr Tyr Gln Cys Tyr Glu Ile Asn Ile Glu Ile Lys Asn Glu Phe
            100                 105                 110

Lys Lys Leu Arg Phe Asn Ser Tyr Val Thr Arg Lys
        115                 120

<210> SEQ ID NO 84
<211> LENGTH: 375
<212> TYPE: DNA
<213> ORGANISM: Clostridium difficile

<400> SEQUENCE: 84 ttgttttat tattgaaaat aagaaagagt ggttttatat caatcgaatg tataataagt      60
attgctatat tatatgtggc tgtttattta gtttctacat cattgtataa ttgttatagt     120
tttatcagta gaaatatatc tgacagagaa atgttaagta cagcaaaaaa atatatagaa    180
gatgagaagt atagaataca aaatagtaag tatgagttaa ttgaagataa gatagaaaaa    240
aattacataa atggatatga aattaacagt agaatagagc aaattttaga ttattatcaa    300
tgctatgaaa taaatataga gataaaaaat gaatttaaaa aactgaggtt taatagctat    360
gttactagaa aataa                                                      375

<210> SEQ ID NO 85
<211> LENGTH: 120
<212> TYPE: PRT
<213> ORGANISM: Clostridium difficile
```

<400> SEQUENCE: 85

Met Lys Ile Arg Lys Ser Gly Phe Ile Ser Ile Glu Cys Ile Ser
1               5                   10                  15

Ile Ala Ile Leu Tyr Val Ala Val Tyr Leu Val Ser Thr Ser Leu Tyr
            20                  25                  30

Asn Cys Tyr Ser Phe Ile Ser Arg Asn Ile Ser Asp Arg Glu Met Leu
        35                  40                  45

Ser Thr Ala Lys Lys Tyr Ile Glu Asp Glu Lys Tyr Arg Ile Gln Asn
50                  55                  60

Ser Lys Tyr Glu Leu Ile Glu Asp Lys Ile Glu Lys Asn Tyr Ile Asn
65                  70                  75                  80

Gly Tyr Glu Ile Asn Ser Arg Ile Glu Gln Ile Leu Asp Tyr Tyr Gln
                85                  90                  95

Cys Tyr Glu Ile Asn Ile Glu Ile Lys Asn Glu Phe Lys Lys Leu Arg
                100                 105                 110

Phe Asn Ser Tyr Val Thr Arg Lys
            115                 120

<210> SEQ ID NO 86
<211> LENGTH: 375
<212> TYPE: DNA
<213> ORGANISM: Clostridium difficile

<400> SEQUENCE: 86
ttgtttttat tattgaaaat aagaaagcgt ggttttatat caatcgaatg tgtaataagt     60
attgctatat tatatgtggc tgtttattta gtttctacat cattgtatag ttgttatagt    120
tttgtcagta gaaatatatc tgacagaaaa atgttaagta ctgcaaaaaa atatatagaa    180
gatgagaagt atagaataca aaatagtaag tatgagttaa ttgaaaataa gatagaaaaa    240
aattacataa atggatatga aattagcagt agagtagagc aaattttaga ttattatcaa    300
tgctatgaaa taaatataga gataaaaaat gaatttaaaa aattgaggtt taatagctat    360
gttactagaa aataa                                                    375

<210> SEQ ID NO 87
<211> LENGTH: 120
<212> TYPE: PRT
<213> ORGANISM: Clostridium difficile

<400> SEQUENCE: 87

Met Lys Ile Arg Lys Arg Gly Phe Ile Ser Ile Glu Cys Val Ile Ser
1               5                   10                  15

Ile Ala Ile Leu Tyr Val Ala Val Tyr Leu Val Ser Thr Ser Leu Tyr
            20                  25                  30

Ser Cys Tyr Ser Phe Val Ser Arg Asn Ile Ser Asp Arg Lys Met Leu
        35                  40                  45

Ser Thr Ala Lys Lys Tyr Ile Glu Asp Glu Lys Tyr Arg Ile Gln Asn
50                  55                  60

Ser Lys Tyr Glu Leu Ile Glu Asn Lys Ile Glu Lys Asn Tyr Ile Asn
65                  70                  75                  80

Gly Tyr Glu Ile Ser Ser Arg Val Glu Gln Ile Leu Asp Tyr Tyr Gln
                85                  90                  95

Cys Tyr Glu Ile Asn Ile Glu Ile Lys Asn Glu Phe Lys Lys Leu Arg
                100                 105                 110

Phe Asn Ser Tyr Val Thr Arg Lys
            115                 120

-continued

<210> SEQ ID NO 88
<211> LENGTH: 512
<212> TYPE: PRT
<213> ORGANISM: Clostridium difficile

<400> SEQUENCE: 88

```
Met Arg Lys Trp Asn Lys Phe Lys Ser Glu Arg Gly Ala Ala Leu Val
1               5                   10                  15

Leu Val Leu Ile Val Val Ala Leu Leu Ser Ile Val Gly Leu Ile Phe
            20                  25                  30

Ser Asn Gln Ile Ala Asn Arg Ile Lys Ser Thr Lys Thr Thr Asn Glu
        35                  40                  45

Gly Ile Gln Ala Lys Tyr Leu Ala Glu Thr Cys Val Glu Asn Ser Ile
    50                  55                  60

Asp Lys Ala Tyr Glu Lys Leu Tyr Asp Glu Leu Glu Lys Met Asp Asn
65                  70                  75                  80

Glu Phe Lys Ser Glu Asn Gln Glu Lys Ser Ile Ser Arg Ser Lys Leu
                85                  90                  95

Arg Asn Ile Ser Asp Glu Asp Phe Asn Asn Gln Asp Glu Lys Asn Ile
            100                 105                 110

Glu Ala Glu Arg Leu Gly Tyr Met Asn Asn Ile Asn Phe Tyr Leu Asn
        115                 120                 125

Lys Ala Ser Ser Asp Leu Glu Lys Ala Ser Met Glu Leu Lys Lys Leu
    130                 135                 140

Tyr Asp Leu Asp Met Leu Asp Tyr Arg Asp Ile Glu Tyr Val Asp Ala
145                 150                 155                 160

Asn Ile Ile Ser His Arg Asp Ser Ile Leu Glu Ile Cys Lys Asn Tyr
                165                 170                 175

Thr Ser Gly Asp Ile Ser Lys Ile Asn Glu Tyr Ile Leu Lys Glu Asp
            180                 185                 190

Ile Asp Ser Thr Thr Leu Ile Glu Ala Lys Leu Val Asn Asn Asp Ile
        195                 200                 205

Leu Leu Lys Met Phe Leu Glu Glu Asn Lys Ile Glu Asn Glu His Leu
    210                 215                 220

Asn Ser Ala Phe Ser His Thr Tyr Lys Ala Leu Asp Asn Ile Ser Leu
225                 230                 235                 240

Ala Met Gln Asn Met Ile Glu Tyr Arg His Thr Phe His Ile Asp Glu
                245                 250                 255

Pro Lys Val Glu Val Ser Asn Gly Ile Pro Asp Ser Gln Gln Tyr Tyr
            260                 265                 270

Glu Leu Ile Gln Asn Pro Ile Ile Asn Ser Met Glu Tyr Ile Trp Asn
        275                 280                 285

Ser Lys Trp Asp Thr Leu Glu Asn Leu Leu Glu Ile Leu Pro Asn Gln
    290                 295                 300

Thr Gln Gly Phe Asn Ser Leu Arg Val His Leu Arg Asn Asn Val Arg
305                 310                 315                 320

Lys Phe Glu Lys Leu Ser Asp Asn Ile Ser Ser Gly Lys Lys Asn Thr
                325                 330                 335

Ala Lys Asn Phe Leu Lys Tyr Lys Glu Leu Leu Tyr Glu Ile Ser Asp
            340                 345                 350

Gln Cys Asn Gln Leu Lys Ser Met Ser Tyr Glu Lys Ile Pro Val Lys
        355                 360                 365

Tyr Asp Asn Met Ala Leu Ile Thr Thr Phe Asp Tyr Ile Gln Asn Glu
```

```
Leu Leu Ala Glu Ile Lys Cys Arg Leu Lys Glu Leu Lys Pro Gln Glu
385                 390                 395                 400

Ile Asp Lys Thr Glu Gly Ile Thr Ile Lys Ile Pro Phe Tyr Lys Ala
                405                 410                 415

Asp Tyr Asp Met Thr Lys Glu Gly Trp Pro Lys Leu Lys Glu Asn Gly
            420                 425                 430

Ser Gly Ala Glu Leu Ser Leu Met Val Thr Gly Asp Lys Asp Gly Ile
        435                 440                 445

Lys Glu Val Glu Val Thr Asp Gly Lys Lys Asn Ile Ile Gly Leu Gly
    450                 455                 460

Val Glu Glu Asn Ser Asn Ser Lys Tyr Lys Val Asp Ala Ile Val Asn
465                 470                 475                 480

Phe Asn Leu Asn Ile Asp Thr Asn Val Val Gly Asn Tyr Asp Ile Lys
                485                 490                 495

Asp Lys Ile Leu Ile Asn His Asp Ile Ser Ser Tyr Lys Lys Val Asn
            500                 505                 510
```

<210> SEQ ID NO 89
<211> LENGTH: 174
<212> TYPE: PRT
<213> ORGANISM: Clostridium difficile

<400> SEQUENCE: 89

```
Met Lys His Lys Tyr Gly Tyr Leu Leu Leu Glu Ser Val Val Ser Leu
1               5                   10                  15

Ser Ser Met Val Ile Ile Ile Leu Val Leu Tyr Ser Ile Phe Leu Ser
                20                  25                  30

Thr Ile Asn Leu Lys Leu Lys Val Glu Asp Lys Ile Glu Leu Gln Gln
            35                  40                  45

Gln Ser Leu Glu Ile Ile Lys Ser Met Glu Gly Ile Ile Ser Asn Ser
        50                  55                  60

Met Gly Ile Met Asn Val Ser Asn Tyr Glu Glu Thr Phe Lys Lys Thr
65                  70                  75                  80

Thr Ser Ile Lys Cys Arg Tyr Val Asp Glu Asn Asn Glu Glu Ser
                85                  90                  95

Ile Ser Asn Lys Glu Ile Leu Asn Glu Arg Arg Asn Lys Leu Phe
            100                 105                 110

Val Asn Ser Leu Asn Gly Glu Ser Ser Gln Ala Gly Gly Tyr Glu Ile
        115                 120                 125

Gly Asp Tyr Val Asp Glu Met Tyr Val Leu Ile Thr Asn Asn Gly Gln
    130                 135                 140

Tyr Val Asn Ile Lys Leu Lys Leu Ser Lys Arg Ser Gln Lys Tyr Glu
145                 150                 155                 160

Thr Asp Phe Lys Ile Lys Val Trp Asn Phe Ser Glu Ser Ile
                165                 170
```

<210> SEQ ID NO 90
<211> LENGTH: 435
<212> TYPE: DNA
<213> ORGANISM: Artificial sequence
<220> FEATURE:
<223> OTHER INFORMATION: Synthetic polynucleotide

<400> SEQUENCE: 90
atggggaaca ccaacaacaa agctaacacc aaaaacgaca ccgacatcac ctctctgaac    60

```
tacgttcagt ctgaaatcga aaacctgcgt gaaaaaatca atctggtgaa attcgacttc    120
gactctctgg acaaactgga agacggtacc gttgtttacg aaaaactgat cgacaaatct    180
aaaaaagttg tttacgacaa agttctgtct gaaggtgacg tttctctgta cgacaccccg    240
tacgaaaaaa tcaccaccat caaagacgaa gacggtaacc tgatcgacaa aggtaacatc    300
accaacaaaa tcaaaccat cgttgaagac aaatctggtc agatctacaa aatcgctgtt     360
accggtaaat ctatgaacga ctactcttct aaaaaagaag ttaaaatcgt accgaaatc     420 ttcaaagaca aatga                                                      435
```

<210> SEQ ID NO 91
<211> LENGTH: 144
<212> TYPE: PRT
<213> ORGANISM: Artificial Sequence
<220> FEATURE:
<223> OTHER INFORMATION: Synthetic polypeptide

<400> SEQUENCE: 91

```
Met Gly Asn Thr Asn Asn Lys Ala Asn Thr Lys Asn Asp Thr Asp Ile
1               5                   10                  15
Thr Ser Leu Asn Tyr Val Gln Ser Glu Ile Glu Asn Leu Arg Glu Lys
            20                  25                  30
Ile Lys Ser Gly Glu Phe Asp Phe Asp Ser Leu Asp Lys Leu Glu Asp
        35                  40                  45
Gly Thr Val Val Tyr Glu Lys Leu Ile Asp Lys Ser Lys Lys Val Val
    50                  55                  60
Tyr Asp Lys Val Leu Ser Glu Gly Asp Val Ser Leu Tyr Asp Thr Pro
65                  70                  75                  80
Tyr Glu Lys Ile Thr Thr Ile Lys Asp Glu Asp Gly Asn Leu Ile Asp
                85                  90                  95
Lys Gly Asn Ile Thr Asn Lys Ile Lys Thr Ile Val Glu Asp Lys Ser
            100                 105                 110
Gly Gln Ile Tyr Lys Ile Ala Val Thr Gly Lys Ser Met Asn Asp Tyr
        115                 120                 125
Ser Ser Lys Lys Glu Val Lys Ile Val Thr Glu Ile Phe Lys Asp Lys
    130                 135                 140
```

<210> SEQ ID NO 92
<211> LENGTH: 450
<212> TYPE: DNA
<213> ORGANISM: Artificial Sequence
<220> FEATURE:
<223> OTHER INFORMATION: synthetic polynucleotide

<400> SEQUENCE: 92

```
atggggaaaa aacagcagat catcaccgac gctcaggtta acatcaacct gatcaacaaa     60
tacctgaacc gtgacctgga aaactgcaaa gaactgacca aaccggttc tggtaacaac    120 tacgaataca catcgaaat gccggacaac gttgttaaat acgaagtttc tatcgaaacc    180
aaaaaaaaca ccgaagttta ctctgttacc cgtatccaga caacaccat cgacaccgaa     240 aacgaagttc gtgaagaaat catctacaac cagccgctgg ttcagaacaa caaagaaatg    300
aaagaaaccc cgttcaaaat cgaaaaacag accggtaaat ctatctacac cgtttctatc    360
tactacaacg aatctgttca ggaatctcac aaaaactcta acctgaacaa caaaacctac    420
accttcgacg ttatgtctcg tatcggttga                                     450
```

<210> SEQ ID NO 93

```
<211> LENGTH: 193
<212> TYPE: PRT
<213> ORGANISM: Artificial Sequence
<220> FEATURE:
<223> OTHER INFORMATION: Synthetic polypeptide

<400> SEQUENCE: 93

Met His His His His His Ser Ser Gly Leu Val Pro Arg Gly Ser
1               5                   10                  15

Gly Met Lys Glu Thr Ala Ala Lys Phe Glu Arg Gln His Met Asp
            20                  25                  30

Ser Pro Asp Leu Gly Thr Asp Asp Asp Lys Ala Met Gly Lys Lys
        35                  40                  45

Gln Gln Ile Ile Thr Asp Ala Gln Val Asn Ile Asn Leu Ile Asn Lys
    50                  55                  60

Tyr Leu Asn Arg Asp Leu Glu Asn Cys Lys Glu Leu Thr Lys Thr Gly
65                  70                  75                  80

Ser Gly Asn Asn Tyr Glu Tyr Asn Ile Glu Met Pro Asp Asn Val Val
                85                  90                  95

Lys Tyr Glu Val Ser Ile Glu Thr Lys Lys Asn Thr Glu Val Tyr Ser
            100                 105                 110

Val Thr Arg Ile Gln Asn Asn Thr Ile Asp Thr Glu Asn Glu Val Arg
        115                 120                 125

Glu Glu Ile Ile Tyr Asn Gln Pro Leu Val Gln Asn Asn Lys Glu Met
    130                 135                 140

Lys Glu Thr Pro Phe Lys Ile Glu Lys Gln Thr Gly Lys Ser Ile Tyr
145                 150                 155                 160

Thr Val Ser Ile Tyr Tyr Asn Glu Ser Val Gln Glu Ser His Lys Asn
                165                 170                 175

Ser Asn Leu Asn Asn Lys Thr Tyr Thr Phe Asp Val Met Ser Arg Ile
            180                 185                 190

Gly

<210> SEQ ID NO 94
<211> LENGTH: 149
<212> TYPE: PRT
<213> ORGANISM: Artificial Sequence
<220> FEATURE:
<223> OTHER INFORMATION: Synthetic polypeptide

<400> SEQUENCE: 94

Met Gly Lys Lys Gln Gln Ile Ile Thr Asp Ala Gln Val Asn Ile Asn
1               5                   10                  15

Leu Ile Asn Lys Tyr Leu Asn Arg Asp Leu Glu Asn Cys Lys Glu Leu
            20                  25                  30

Thr Lys Thr Gly Ser Gly Asn Asn Tyr Glu Tyr Asn Ile Glu Met Pro
        35                  40                  45

Asp Asn Val Val Lys Tyr Glu Val Ser Ile Glu Thr Lys Lys Asn Thr
    50                  55                  60

Glu Val Tyr Ser Val Thr Arg Ile Gln Asn Asn Thr Ile Asp Thr Glu
65                  70                  75                  80

Asn Glu Val Arg Glu Glu Ile Ile Tyr Asn Gln Pro Leu Val Gln Asn
                85                  90                  95

Asn Lys Glu Met Lys Glu Thr Pro Phe Lys Ile Glu Lys Gln Thr Gly
            100                 105                 110

Lys Ser Ile Tyr Thr Val Ser Ile Tyr Tyr Asn Glu Ser Val Gln Glu
        115                 120                 125
```

Ser His Lys Asn Ser Asn Leu Asn Asn Lys Thr Tyr Thr Phe Asp Val
            130                 135                 140

Met Ser Arg Ile Gly
145

<210> SEQ ID NO 95
<211> LENGTH: 288
<212> TYPE: DNA
<213> ORGANISM: Artificial Sequence
<220> FEATURE:
<223> OTHER INFORMATION: Synthetic polynucleotide

<400> SEQUENCE: 95 atgggtcta cctctctgta caactgctac tctttcatct ctcgtaacat ctctgaccgt      60
gaaatgctgt ctaccgctaa aaatacatc gaagacgaaa ataccgtat ccagaactct     120 aaatacgaac tgatcgaaga caaaatcgaa aaaaactaca tcaacggtta cgaaatcaac     180
tctcgtatcg aacagatcct ggactactac cagtgctacg aaatcaacat cgaaatcaaa     240
aacgaattca aaaaactgcg tttcaactct acgttaccc gtaaatga                   288

<210> SEQ ID NO 96
<211> LENGTH: 139
<212> TYPE: PRT
<213> ORGANISM: Artificial Sequence
<220> FEATURE:
<223> OTHER INFORMATION: Synthetic polypeptide

<400> SEQUENCE: 96

Met His His His His His His Ser Ser Gly Leu Val Pro Arg Gly Ser
1               5                   10                  15

Gly Met Lys Glu Thr Ala Ala Ala Lys Phe Glu Arg Gln His Met Asp
            20                  25                  30

Ser Pro Asp Leu Gly Thr Asp Asp Asp Lys Ala Met Gly Ser Thr
        35                  40                  45

Ser Leu Tyr Asn Cys Tyr Ser Phe Ile Ser Arg Asn Ile Ser Asp Arg
    50                  55                  60

Glu Met Leu Ser Thr Ala Lys Lys Tyr Ile Glu Asp Glu Lys Tyr Arg
65                  70                  75                  80

Ile Gln Asn Ser Lys Tyr Glu Leu Ile Glu Asp Lys Ile Glu Lys Asn
                85                  90                  95

Tyr Ile Asn Gly Tyr Glu Ile Asn Ser Arg Ile Glu Gln Ile Leu Asp
            100                 105                 110

Tyr Tyr Gln Cys Tyr Glu Ile Asn Ile Glu Ile Lys Asn Glu Phe Lys
        115                 120                 125

Lys Leu Arg Phe Asn Ser Tyr Val Thr Arg Lys
    130                 135

<210> SEQ ID NO 97
<211> LENGTH: 95
<212> TYPE: PRT
<213> ORGANISM: Artificial Sequence
<220> FEATURE:
<223> OTHER INFORMATION: Synthetic polypeptide

<400> SEQUENCE: 97

Met Gly Ser Thr Ser Leu Tyr Asn Cys Tyr Ser Phe Ile Ser Arg Asn
1               5                   10                  15

Ile Ser Asp Arg Glu Met Leu Ser Thr Ala Lys Lys Tyr Ile Glu Asp
            20                  25                  30

Glu Lys Tyr Arg Ile Gln Asn Ser Lys Tyr Glu Leu Ile Glu Asp Lys
         35                  40                  45

Ile Glu Lys Asn Tyr Ile Asn Gly Tyr Glu Ile Asn Ser Arg Ile Glu
 50                  55                  60

Gln Ile Leu Asp Tyr Tyr Gln Cys Tyr Glu Ile Asn Glu Ile Lys
 65                  70                  75                  80

Asn Glu Phe Lys Lys Leu Arg Phe Asn Ser Tyr Val Thr Arg Lys
             85                  90                  95

<210> SEQ ID NO 98
<211> LENGTH: 444
<212> TYPE: DNA
<213> ORGANISM: Artificial Sequence
<220> FEATURE:
<223> OTHER INFORMATION: Synthetic polynucleotide

<400> SEQUENCE: 98
atggggtcta ccatcaacct gaaactgaaa gttgaagaca aaatcgaact gcagcagcag        60
tctctggaaa tcatcaaatc tatggaaggt atcatctcta actctatggg tatcatgaac       120
gtttctaact acgaagaaac cttcaaaaaa accacctcta tcaaatgccg ttacgttgac       180
gaaaacaaca cgaagaatc tatctctaac aaagaaatca tcctgaacga acgtcgtaac        240
aaactgttcg ttaactctct gaacggtgaa tcttctcagg ctggtggtta cgaaatcgtt       300
gactacgttg acgaaatgta cgttctgatc accaacaacg gtcagtacgt taacatcaaa       360
ctgaaactgt ctaaacgttc tcagaaatac gaaaccgact tcaaaatcaa agtttggaac       420
ttctctgaat ctatctgagg atcc                                              444

<210> SEQ ID NO 99
<211> LENGTH: 576
<212> TYPE: DNA
<213> ORGANISM: Artificial Sequence
<220> FEATURE:
<223> OTHER INFORMATION: Synthetic polynucleotide

<400> SEQUENCE: 99
atgcaccatc atcatcatca ttcttctggt ctggtgccac gcggttctgg tatgaaagaa        60
accgctgctg ctaaattcga acgccagcac atggacagcc cagatctggg taccgacgac       120
gacgacaagg ccatggggtc taccatcaac ctgaaactga agttgaaga caaaatcgaa        180 ctgcagcagc agtctctgga atcatcaaa tctatggaag gtatcatctc taactctatg        240
ggtatcatga acgtttctaa ctacgaagaa accttcaaaa aaccacctc tatcaaatgc        300 cgttacgttg acgaaaacaa caacgaagaa tctatctcta acaaagaaat catcctgaac       360
gaacgtcgta acaaactgtt cgttaactct ctgaacggtg aatcttctca ggctggtggt       420
tacgaaatcg gtgactacgt tgacgaaatg tacgttctga tcaccaacaa cggtcagtac       480
gttaacatca aactgaaact gtctaaacgt tctcagaaat acgaaaccga cttcaaaatc       540
aaagtttgga acttctctga atctatctga ggatcc                                 576

<210> SEQ ID NO 100
<211> LENGTH: 189
<212> TYPE: PRT
<213> ORGANISM: Artificial Sequence
<220> FEATURE:
<223> OTHER INFORMATION: Synthetic polypeptide

<400> SEQUENCE: 100

```
Met His His His His His Ser Ser Gly Leu Val Pro Arg Gly Ser
1               5                   10                  15

Gly Met Lys Glu Thr Ala Ala Lys Phe Glu Arg Gln His Met Asp
            20                  25                  30

Ser Pro Asp Leu Gly Thr Asp Asp Asp Lys Ala Met Gly Ser Thr
        35                  40                  45

Ile Asn Leu Lys Leu Lys Val Glu Asp Lys Ile Glu Leu Gln Gln Gln
50                  55                  60

Ser Leu Glu Ile Ile Lys Ser Met Glu Gly Ile Ile Ser Asn Ser Met
65                  70                  75                  80

Gly Ile Met Asn Val Ser Asn Tyr Glu Glu Thr Phe Lys Lys Thr Thr
                85                  90                  95

Ser Ile Lys Cys Arg Tyr Val Asp Glu Asn Asn Asn Glu Glu Ser Ile
            100                 105                 110

Ser Asn Lys Glu Ile Ile Leu Asn Glu Arg Arg Asn Lys Leu Phe Val
        115                 120                 125

Asn Ser Leu Asn Gly Glu Ser Ser Gln Ala Gly Gly Tyr Glu Ile Gly
    130                 135                 140

Asp Tyr Val Asp Glu Met Tyr Val Leu Ile Thr Asn Asn Gly Gln Tyr
145                 150                 155                 160

Val Asn Ile Lys Leu Lys Leu Ser Lys Arg Ser Gln Lys Tyr Glu Thr
                165                 170                 175

Asp Phe Lys Ile Lys Val Trp Asn Phe Ser Glu Ser Ile
                180                 185

<210> SEQ ID NO 101
<211> LENGTH: 145
<212> TYPE: PRT
<213> ORGANISM: Artificial Sequence
<220> FEATURE:
<223> OTHER INFORMATION: Synthetic polypeptide

<400> SEQUENCE: 101

Met Gly Ser Thr Ile Asn Leu Lys Leu Lys Val Glu Asp Lys Ile Glu
1               5                   10                  15

Leu Gln Gln Gln Ser Leu Glu Ile Ile Lys Ser Met Glu Gly Ile Ile
            20                  25                  30

Ser Asn Ser Met Gly Ile Met Asn Val Ser Asn Tyr Glu Glu Thr Phe
        35                  40                  45

Lys Lys Thr Thr Ser Ile Lys Cys Arg Tyr Val Asp Glu Asn Asn Asn
    50                  55                  60

Glu Glu Ser Ile Ser Asn Lys Glu Ile Ile Leu Asn Glu Arg Arg Asn
65                  70                  75                  80

Lys Leu Phe Val Asn Ser Leu Asn Gly Glu Ser Ser Gln Ala Gly Gly
                85                  90                  95

Tyr Glu Ile Gly Asp Tyr Val Asp Glu Met Tyr Val Leu Ile Thr Asn
            100                 105                 110

Asn Gly Gln Tyr Val Asn Ile Lys Leu Lys Leu Ser Lys Arg Ser Gln
        115                 120                 125

Lys Tyr Glu Thr Asp Phe Lys Ile Lys Val Trp Asn Phe Ser Glu Ser
    130                 135                 140

Ile
145

<210> SEQ ID NO 102
<211> LENGTH: 141
```

```
<212> TYPE: PRT
<213> ORGANISM: Artificial Sequence
<220> FEATURE:
<223> OTHER INFORMATION: Synthetic polypeptide

<400> SEQUENCE: 102

Met Gly Ser Asn Ile Asn Lys Ala Lys Val Ala Ser Val Glu Ser Asp
1               5                   10                  15

Tyr Ser Ser Ile Lys Ser Ala Ala Leu Ser Tyr Tyr Ser Asp Thr Asn
                20                  25                  30

Lys Ile Pro Val Thr Pro Asp Gly Gln Thr Gly Leu Asn Val Leu Glu
            35                  40                  45

Thr Tyr Met Glu Ser Leu Pro Asp Lys Ala Asp Ile Gly Gly Glu Tyr
50                  55                  60

Lys Leu Ile Lys Val Gly Asn Lys Leu Val Leu Gln Ile Gly Lys Asp
65                  70                  75                  80

Gly Glu Gly Val Thr Leu Thr Glu Ala Gln Ser Ala Lys Leu Leu Ser
                85                  90                  95

Asp Ile Gly Lys Asp Lys Ile Tyr Thr Gly Val Thr Gly Asp Asn Phe
            100                 105                 110

Gly Glu Gln Leu Lys Asp Thr Thr Lys Ile Asp Asn Lys Ala Leu Tyr
        115                 120                 125

Ile Val Leu Ile Asp Asn Thr Val Met Asp Ser Thr Lys
    130                 135                 140

<210> SEQ ID NO 103
<211> LENGTH: 83
<212> TYPE: PRT
<213> ORGANISM: Artificial Sequence
<220> FEATURE:
<223> OTHER INFORMATION: Synthetic polypeptide

<400> SEQUENCE: 103

Met Gly Gln Glu Ser Ala Lys Leu Asn Ala Asp Tyr Thr Asn Ala Ala
1               5                   10                  15

Asn Ile Val Thr Ala Ala Ser Met Ala Ile Asn Asp Asp Glu Lys Thr
                20                  25                  30

Ile Asp Ser Leu Ser Val Glu Thr Leu Lys Glu Lys Gly Tyr Leu Asn
            35                  40                  45

Thr Val Pro Val Pro Gln Ser Thr Ser Gly Lys Phe Glu Leu Val Ile
        50                  55                  60

Asn Asp Ser Gly Thr Asp Ile Ser Val Asn Ile Asn Ser Lys Gln Phe
65                  70                  75                  80

Tyr Pro Lys

<210> SEQ ID NO 104
<211> LENGTH: 238
<212> TYPE: PRT
<213> ORGANISM: Artificial Sequence
<220> FEATURE:
<223> OTHER INFORMATION: Synthetic polypeptide

<400> SEQUENCE: 104

Met Gly Asn Ile Glu Lys Ser Lys Ala Val Thr Cys Leu Ser Asn Arg
1               5                   10                  15

Glu Asn Ile Lys Thr Gln Ile Val Ile Ala Met Ala Glu Glu Ser Ser
                20                  25                  30

Lys Asp Lys Asn Glu Val Ile Lys Glu Val Leu Glu Asn Lys Asp Gly
            35                  40                  45
```

Lys Tyr Phe Glu Thr Glu Pro Lys Cys Lys Ser Gly Gly Ile Tyr Ser
 50                  55                  60

Ala Thr Phe Asp Asp Gly Tyr Asp Gly Ile Thr Gly Ile Glu Ser Ile
 65                  70                  75                  80

Ala Lys Val Tyr Val Thr Cys Thr Lys His Pro Asp Gly Ile Glu Met
                 85                  90                  95

Ala Arg Asp Ile His Gln Ser Met Lys Asp Leu Ile Ala Ser Phe Ala
            100                 105                 110

Gln Asp Pro Ser Ile Ile Pro Gly Ala Ser Lys Gly Asn Asp Asp Phe
        115                 120                 125

Arg Lys Tyr Leu Leu Asp Asn Lys Tyr Lys Asn Gly Trp Pro Thr Ile
130                 135                 140

Pro Asp Glu Phe Lys Ala Lys Tyr Gly Leu Ser Lys Asp Thr Leu Tyr
145                 150                 155                 160

Ile Gln Pro Tyr Ala Tyr Asn Pro Thr Lys Ser Asp Ala Thr Val Val
                165                 170                 175

Val Phe Ala Asn Asn Lys Thr Gly Gly Asn Trp Tyr Thr Ser Leu Val
            180                 185                 190

Tyr Asp Tyr Asp Glu Gly Arg Trp Tyr Lys Gly Lys Asn Gly Ile Ser
        195                 200                 205

Val Ala Gly Arg Ser Trp Asp Val Asp Thr Asp Ser Val Lys Ser Val
210                 215                 220

Lys Thr Glu Ile His Ser Lys Glu Gly Trp Gly Pro Leu Asn
225                 230                 235

<210> SEQ ID NO 105
<211> LENGTH: 1449
<212> TYPE: DNA
<213> ORGANISM: Artificial Sequence
<220> FEATURE:
<223> OTHER INFORMATION: Synthetic polynucleotide

<400> SEQUENCE: 105 atgggtcta accagatcgc taaccgtatc aaatctacca aaaccaccaa cgaaggtatc        60
caggctaaat acctggctga aacctgcgtt gaaaactcta tcgacaaagc ttacgaaaaa       120
ctgtacgacg aactggaaaa aatggacaac gaattcaaat ctgaaaacca ggaaaaatct       180
atctctcgtt ctaaactgcg taacatctct gacgaagact caacaaacca ggacgaaaaa       240
aacatcgaag ctgaacgtct gggttacatg aacaacatca acttctacct gaacaaagct       300
tcttctgacc tggaaaaagc ttctatggaa ctgaaaaaac tgtacgacct ggacatgctg       360
gactaccgtg acatcgaata cgttgacgct aacatcatct ctcaccgtga ctctatcctg       420
gaaatctgca aaaactacac ctctggtgac atctctaaaa tcaacgaata catcctgaaa       480
gaagacatcg actctaccac cctgatcgaa gctaaactgg ttaacaacga catcctgctg       540
aaaatgttcc tggaagaaaa caaaatcgaa acgaacaacc tgaactctgc tttctctcac       600
acctacaaag ctctggacaa catctctctg gctatgcaga catgatcga ataccgtcac        660 accttccaca tcgacgaacc gaaagttgaa gtttctaacg gtatcccgga ctctcagcag       720
tactacgaac tgatccagaa cccgatcatc aactctatgg aatacatctg gaactctaaa       780
tgggacaccc tggaaaacct gctggaaatc ctgccgaacc agacccaggg tttcaactct       840
ctgcgtgttc acctgcgtaa caacgttcgt aaattcgaaa aactgtctga acacatctct       900
tctggtaaaa aaacaccgc taaaaacttc ctgaaataca agaactgct gtacgaaatc        960

```
tctgaccagt gcaaccagct gaaatctatg tcttacgaaa aaatcccggt taaatacgac    1020
aacatggctc tgatcaccac cttcgactac atccagaacg aactgctggc tgaaatcaaa    1080
tgccgtctga agaactgaa accgcaggaa atcgacaaaa ccgaaggtat caccatcaaa    1140
atcccgttct acaaagctga ctacgacatg accaaagaag gttggccgaa actgaaagaa    1200
aacggttctg gtgctgaact gtctctgatg gttaccggtg acaaagacgg tatcaaagaa    1260
gttgaagtta ccgacggtaa aaaaaacatc atcggtctgg gtgttgaaga aaactctaac    1320
tctaaataca agttgacgc tatcgttaac ttcaacctga acatcgacac caacgttgtt    1380
ggtaactacg acatcaaaga caaaatcctg atcaaccacg acatctcttc ttacaaaaaa    1440
gttaactga                                                           1449
```

<210> SEQ ID NO 106
<211> LENGTH: 1581
<212> TYPE: DNA
<213> ORGANISM: Artificial Sequence
<220> FEATURE:
<223> OTHER INFORMATION: Synthetic polynucleotide

<400> SEQUENCE: 106

```
atgcaccatc atcatcatca ttcttctggt ctggtgccac gcggttctgg tatgaaagaa      60
accgctgctg ctaaattcga acgccagcac atggacagcc agatctgggg taccgacgac     120
gacgacaagg ccatggggtc taaccagatc gctaaccgta tcaaatctac caaaaccacc     180
aacgaaggta tccaggctaa ataccttggct gaaacctgcg ttgaaaactc tatcgacaaa     240
gcttacgaaa aactgtacga cgaactgaaa aaatggaca cgaattcaa atctgaaaac     300 caggaaaaat ctatctctcg ttctaaactg cgtaacatct ctgacgaaga cttcaacaac     360
caggacgaaa aaacatcga agctgaacgt ctgggttaca tgaacaacat caacttctac     420
ctgaacaaag cttcttctga cctggaaaaa gcttctatgg aactgaaaaa actgtacgac     480
ctggacatgc tggactaccg tgacatcgaa tacgttgacg ctaacatcat ctctcaccgt     540
gactctatcc tggaaatctg caaaaactac acctctggtg acatctctaa atcaacgaa     600 tacatcctga agaagacat cgactctacc ccctgatcg aagctaaaact ggttaacaac     660 gacatcctgc tgaaaatgtt cctggaagaa acaaaatcg aaaacgaaca cctgaactct     720
gctttctctc acacctacaa agctctggac aacatctctc tggctatgca gaacatgatc     780
gaataccgtc acaccttcca catcgacgaa ccgaaagttg aagtttctaa cggtatcccg     840
gactctcagc agtactacga actgatccag aacccgatca tcaactctat ggaatacatc     900
tggaactcta atgggacac cctggaaaac ctgctggaaa tcctgccgaa ccagacccag     960
ggtttcaact ctctgcgtgt tcacctgcgt aacaacgttc gtaaattcga aaactgtct    1020 gacaacatct cttctggtaa aaaaaacacc gctaaaaact tcctgaaata caagaactg    1080 ctgtacgaaa tctctgacca gtgcaaccag ctgaaatcta tgtcttacga aaaatcccg    1140 gttaaatacg acaacatggc tctgatcacc accttcgact acatccagaa cgaactgctg    1200
gctgaaatca atgccgtct gaaagaactg aaaccgcagg aaatcgacaa aaccgaaggt    1260
atcaccatca aatcccgtt ctacaaagct gactacgaca tgaccaaaga aggttggccg    1320
aaactgaaag aaaacggttc tggtgctgaa ctgtctctga tggttaccgg tgacaaagac    1380
ggtatcaaag aagttgaagt taccgacggt aaaaaaaaca tcatcggtct gggtgttgaa    1440
gaaaactcta actctaaata caagttgac gctatcgtta acttcaacct gaacatcgac    1500
accaacgttg ttggtaacta cgacatcaaa gacaaaatcc tgatcaacca cgacatctct    1560
```
tcttacaaaa aagttaactg a                                                    1581

<210> SEQ ID NO 107
<211> LENGTH: 526
<212> TYPE: PRT
<213> ORGANISM: Artificial Sequence
<220> FEATURE:
<223> OTHER INFORMATION: Synthetic polypeptide

<400> SEQUENCE: 107

Met His His His His His Ser Ser Gly Leu Val Pro Arg Gly Ser
1               5                   10                  15

Gly Met Lys Glu Thr Ala Ala Lys Phe Glu Arg Gln His Met Asp
            20                  25                  30

Ser Pro Asp Leu Gly Thr Asp Asp Asp Lys Ala Met Gly Ser Asn
        35                  40                  45

Gln Ile Ala Asn Arg Ile Lys Ser Thr Lys Thr Thr Asn Glu Gly Ile
    50                  55                  60

Gln Ala Lys Tyr Leu Ala Glu Thr Cys Val Glu Asn Ser Ile Asp Lys
65                  70                  75                  80

Ala Tyr Glu Lys Leu Tyr Asp Glu Leu Glu Lys Met Asp Asn Glu Phe
                85                  90                  95

Lys Ser Glu Asn Gln Glu Lys Ser Ile Ser Arg Ser Lys Leu Arg Asn
            100                 105                 110

Ile Ser Asp Glu Asp Phe Asn Asn Gln Asp Glu Lys Asn Ile Glu Ala
        115                 120                 125

Glu Arg Leu Gly Tyr Met Asn Asn Ile Asn Phe Tyr Leu Asn Lys Ala
    130                 135                 140

Ser Ser Asp Leu Glu Lys Ala Ser Met Glu Leu Lys Lys Leu Tyr Asp
145                 150                 155                 160

Leu Asp Met Leu Asp Tyr Arg Asp Ile Glu Tyr Val Asp Ala Asn Ile
                165                 170                 175

Ile Ser His Arg Asp Ser Ile Leu Glu Ile Cys Lys Asn Tyr Thr Ser
            180                 185                 190

Gly Asp Ile Ser Lys Ile Asn Glu Tyr Ile Leu Lys Glu Asp Ile Asp
        195                 200                 205

Ser Thr Thr Leu Ile Glu Ala Lys Leu Val Asn Asn Asp Ile Leu Leu
    210                 215                 220

Lys Met Phe Leu Glu Glu Asn Lys Ile Glu Asn Glu His Leu Asn Ser
225                 230                 235                 240

Ala Phe Ser His Thr Tyr Lys Ala Leu Asp Asn Ile Ser Leu Ala Met
                245                 250                 255

Gln Asn Met Ile Glu Tyr Arg His Thr Phe His Ile Asp Glu Pro Lys
            260                 265                 270

Val Glu Val Ser Asn Gly Ile Pro Asp Ser Gln Gln Tyr Tyr Glu Leu
        275                 280                 285

Ile Gln Asn Pro Ile Ile Asn Ser Met Glu Tyr Ile Trp Asn Ser Lys
    290                 295                 300

Trp Asp Thr Leu Glu Asn Leu Leu Glu Ile Leu Pro Asn Gln Thr Gln
305                 310                 315                 320

Gly Phe Asn Ser Leu Arg Val His Leu Arg Asn Asn Val Arg Lys Phe
                325                 330                 335

Glu Lys Leu Ser Asp Asn Ile Ser Ser Gly Lys Lys Asn Thr Ala Lys
            340                 345                 350

Asn Phe Leu Lys Tyr Lys Glu Leu Tyr Glu Ile Ser Asp Gln Cys
             355                 360                 365

Asn Gln Leu Lys Ser Met Ser Tyr Glu Lys Ile Pro Val Lys Tyr Asp
    370                 375                 380

Asn Met Ala Leu Ile Thr Thr Phe Asp Tyr Ile Gln Asn Glu Leu Leu
385                 390                 395                 400

Ala Glu Ile Lys Cys Arg Leu Lys Glu Leu Lys Pro Gln Glu Ile Asp
                405                 410                 415

Lys Thr Glu Gly Ile Thr Ile Lys Ile Pro Phe Tyr Lys Ala Asp Tyr
                420                 425                 430

Asp Met Thr Lys Glu Gly Trp Pro Lys Leu Lys Glu Asn Gly Ser Gly
            435                 440                 445

Ala Glu Leu Ser Leu Met Val Thr Gly Asp Lys Asp Gly Ile Lys Glu
    450                 455                 460

Val Glu Val Thr Asp Gly Lys Lys Asn Ile Ile Gly Leu Gly Val Glu
465                 470                 475                 480

Glu Asn Ser Asn Ser Lys Tyr Lys Val Asp Ala Ile Val Asn Phe Asn
                485                 490                 495

Leu Asn Ile Asp Thr Asn Val Val Gly Asn Tyr Asp Ile Lys Asp Lys
            500                 505                 510

Ile Leu Ile Asn His Asp Ile Ser Ser Tyr Lys Val Asn
        515                 520                 525

<210> SEQ ID NO 108
<211> LENGTH: 482
<212> TYPE: PRT
<213> ORGANISM: Artificial Sequence
<220> FEATURE:
<223> OTHER INFORMATION: Synthetic polypeptide

<400> SEQUENCE: 108

Met Gly Ser Asn Gln Ile Ala Asn Arg Ile Lys Ser Thr Lys Thr Thr
1               5                   10                  15

Asn Glu Gly Ile Gln Ala Lys Tyr Leu Ala Glu Thr Cys Val Glu Asn
            20                  25                  30

Ser Ile Asp Lys Ala Tyr Glu Lys Leu Tyr Asp Glu Leu Glu Lys Met
        35                  40                  45

Asp Asn Glu Phe Lys Ser Glu Asn Gln Glu Lys Ser Ile Ser Arg Ser
    50                  55                  60

Lys Leu Arg Asn Ile Ser Asp Glu Asp Phe Asn Asn Gln Asp Glu Lys
65                  70                  75                  80

Asn Ile Glu Ala Glu Arg Leu Gly Tyr Met Asn Asn Ile Asn Phe Tyr
                85                  90                  95

Leu Asn Lys Ala Ser Ser Asp Leu Glu Lys Ala Ser Met Glu Leu Lys
            100                 105                 110

Lys Leu Tyr Asp Leu Asp Met Leu Asp Tyr Arg Asp Ile Glu Tyr Val
        115                 120                 125

Asp Ala Asn Ile Ile Ser His Arg Asp Ser Ile Leu Glu Ile Cys Lys
    130                 135                 140

Asn Tyr Thr Ser Gly Asp Ile Ser Lys Ile Asn Glu Tyr Ile Leu Lys
145                 150                 155                 160

Glu Asp Ile Asp Ser Thr Thr Leu Ile Glu Ala Lys Leu Val Asn Asn
                165                 170                 175

Asp Ile Leu Leu Lys Met Phe Leu Glu Glu Asn Lys Ile Glu Asn Glu
            180                 185                 190

```
His Leu Asn Ser Ala Phe Ser His Thr Tyr Lys Ala Leu Asp Asn Ile
            195                 200                 205
Ser Leu Ala Met Gln Asn Met Ile Glu Tyr Arg His Thr Phe His Ile
210                 215                 220
Asp Glu Pro Lys Val Glu Val Ser Asn Gly Ile Pro Asp Ser Gln Gln
225                 230                 235                 240
Tyr Tyr Glu Leu Ile Gln Asn Pro Ile Ile Asn Ser Met Glu Tyr Ile
                245                 250                 255
Trp Asn Ser Lys Trp Asp Thr Leu Glu Asn Leu Leu Glu Ile Leu Pro
            260                 265                 270
Asn Gln Thr Gln Gly Phe Asn Ser Leu Arg Val His Leu Arg Asn Asn
            275                 280                 285
Val Arg Lys Phe Glu Lys Leu Ser Asp Asn Ile Ser Ser Gly Lys Lys
290                 295                 300
Asn Thr Ala Lys Asn Phe Leu Lys Tyr Lys Glu Leu Leu Tyr Glu Ile
305                 310                 315                 320
Ser Asp Gln Cys Asn Gln Leu Lys Ser Met Ser Tyr Glu Lys Ile Pro
                325                 330                 335
Val Lys Tyr Asp Asn Met Ala Leu Ile Thr Thr Phe Asp Tyr Ile Gln
                340                 345                 350
Asn Glu Leu Leu Ala Glu Ile Lys Cys Arg Leu Lys Glu Leu Lys Pro
            355                 360                 365
Gln Glu Ile Asp Lys Thr Glu Gly Ile Thr Ile Lys Ile Pro Phe Tyr
            370                 375                 380
Lys Ala Asp Tyr Asp Met Thr Lys Glu Gly Trp Pro Lys Leu Lys Glu
385                 390                 395                 400
Asn Gly Ser Gly Ala Glu Leu Ser Leu Met Val Thr Gly Asp Lys Asp
                405                 410                 415
Gly Ile Lys Glu Val Glu Val Thr Asp Gly Lys Lys Asn Ile Ile Gly
                420                 425                 430
Leu Gly Val Glu Glu Asn Ser Asn Ser Lys Tyr Lys Val Asp Ala Ile
            435                 440                 445
Val Asn Phe Asn Leu Asn Ile Asp Thr Asn Val Val Gly Asn Tyr Asp
450                 455                 460
Ile Lys Asp Lys Ile Leu Ile Asn His Asp Ile Ser Ser Tyr Lys Lys
465                 470                 475                 480
Val Asn

<210> SEQ ID NO 109
<211> LENGTH: 135
<212> TYPE: PRT
<213> ORGANISM: Artificial Sequence
<220> FEATURE:
<223> OTHER INFORMATION: Synthetic polypeptide

<400> SEQUENCE: 109

Met Gly Lys Asn Ile Glu Lys Ala Lys Ile Ala Lys Leu Glu Ala Asp
1               5                   10                  15
Ile Ser Ala Ile Lys Ser Ala Ser Leu Ser Tyr Tyr Ala Asp Glu Ser
                20                  25                  30
Lys Tyr Thr Asp Gly Gly Met Ile Ser Trp Val Lys Lys Asp Gly Lys
            35                  40                  45
Ile Ile Ile Asn Gly Gly Phe Lys Asp Pro Leu Ala Asp Lys Ile
        50                  55                  60
Glu Asn Leu Gly Met Pro Tyr Asn Gly Ser Tyr Leu Leu Met Ser Ser
```

```
                65                  70                  75                  80
Pro Gly His Glu Lys Tyr Leu Glu Leu Ser Ile Leu Pro Gly Glu
                    85                  90                  95

Ile Ser Lys Ser Gly Leu Asp Lys Leu Lys Asn Asp Tyr Gly Asn Leu
                100                 105                 110

Ile Asp Ile Thr Asn Asp Gln Asn Lys Ile Asn Ile Val Ile Lys Leu
            115                 120                 125

Leu Asn Asn Lys Ser Asn Thr
        130                 135

<210> SEQ ID NO 110
<211> LENGTH: 408
<212> TYPE: DNA
<213> ORGANISM: Artificial Sequence
<220> FEATURE:
<223> OTHER INFORMATION: Synthetic polynucleotide

<400> SEQUENCE: 110
atggggaaaa acatcgaaaa agctaaaatc gctaaactgg aagctgacat ctctgctatc      60
aaatctgctt ctctgtctta ctacgctgac gaatctaaat acaccgacgg tggtatgatc     120
tcttgggtta aaaagacgg taaaatcatc atcaacggtg gtttcaaaga cgacccgctg     180
gctgacaaaa tcgaaaacct gggtatgccg tacaacggtt cttacctgct gatgtcttct     240
ccgggtcacg aaaatacct ggaactgtct atcctgccgg aaggtgaaat ctctaaatct     300
ggtctggaca actgaaaaa cgactacggt aacctgatcg acatcaccaa cgaccagaac     360
aaaatcaaca tcgttatcaa actgctgaac aacaaatcta acacctga                 408

<210> SEQ ID NO 111
<211> LENGTH: 188
<212> TYPE: PRT
<213> ORGANISM: Artificial Sequence
<220> FEATURE:
<223> OTHER INFORMATION: Synthetic polypeptide

<400> SEQUENCE: 111

Met His His His His His Ser Ser Gly Leu Val Pro Arg Gly Ser
1               5                   10                  15

Gly Met Lys Glu Thr Ala Ala Ala Lys Phe Glu Arg Gln His Met Asp
                20                  25                  30

Ser Pro Asp Leu Gly Thr Asp Asp Asp Lys Ala Met Gly Asn Thr
            35                  40                  45

Asn Asn Lys Ala Asn Thr Lys Asn Asp Thr Asp Ile Thr Ser Leu Asn
        50                  55                  60

Tyr Val Gln Ser Glu Ile Glu Asn Leu Arg Glu Lys Ile Lys Ser Gly
65                  70                  75                  80

Glu Phe Asp Phe Asp Ser Leu Asp Lys Leu Glu Asp Gly Thr Val Val
                    85                  90                  95

Tyr Glu Lys Leu Ile Asp Lys Ser Lys Lys Val Val Tyr Asp Lys Val
                100                 105                 110

Leu Ser Glu Gly Asp Val Ser Leu Tyr Asp Thr Pro Tyr Glu Lys Ile
            115                 120                 125

Thr Thr Ile Lys Asp Glu Asp Gly Asn Leu Ile Asp Lys Gly Asn Ile
        130                 135                 140

Thr Asn Lys Ile Lys Thr Ile Val Glu Asp Lys Ser Gly Gln Ile Tyr
145                 150                 155                 160

Lys Ile Ala Val Thr Gly Lys Ser Met Asn Asp Tyr Ser Ser Lys Lys
```

```
                  165                 170                 175
Glu Val Lys Ile Val Thr Glu Ile Phe Lys Asp Lys
        180                 185

<210> SEQ ID NO 112
<211> LENGTH: 938
<212> TYPE: DNA
<213> ORGANISM: Clostridium difficile

<400> SEQUENCE: 112
atgggaatga ttattatgaa taaaaagggt tttacactaa ttgaattgtt agtagttata      60
tctataatag gcattttagt tatagtagct attccagcat tgtttagaaa tatagaaaaa     120
agtaaagcag ttacatgtct ttctaataga gaaaatataa agactcaaat tgttattgca     180
atggctgagg aatcaagtaa gggcaagaat gaagtcatga agaggtatt agaaaacaaa      240 gatggtaagt actttgaaac agaaccaaag tgtaagtcag gtggaatata ttcagcaacg     300
tttgatgatg gttatgatgg aataactgga atagaaagca ttgcaaaagt gtatgttact     360
tgtacaaaac atccagatgg tgttgaaatg ctagggata tacatcaaag tatgaaagat      420
ttgattgcat catttcaca agacccttct ataataccag gagcctcaaa gggtaatgat      480
gattttagaa atatttatt agacaataaa tataaaaatg ggtggcctac aattccagat      540
gaatttaagg caaatatgg attaagtaag gatacactat atatacaacc atatgcatat      600
agtcctacta atctgatgc tactgtagtt gtatttgcaa ataataagac tgggggtaat      660
tggtatactt ccctagttta cgattatgat gaaggtagat ggtataaagg taaaaatggt     720
atttctgttg caggtaggtc atgggatgtt gacacagata gtgttaagtc tgtaaaaaca     780
gagattcatt ctaaagaggg atggggtcct taaattaat atatcatgtt ttattaatct      840
ggtattgatt aaactataga aaagagcagt ttctatagat gacgaatacc agatttttcat     900 ttatatatat aattgagata tattaaaagt gtttatat                            938

<210> SEQ ID NO 113
<211> LENGTH: 938
<212> TYPE: DNA
<213> ORGANISM: Clostridium difficile

<400> SEQUENCE: 113
atgggaatga ttattatgaa taaaaagggt tttacattaa ttgaattgtt ggtagttata      60
tctataatag gaattttagt tatagtagct gttccagcgt tatttagaaa tatagaaaaa     120
agtaaggcag ttacatgtct ttctaataga gaaaatataa agactcaaat tgttattgca     180
atggctgagg aatcaagtaa agacaagaat gaagtcataa agaggtatt agaaaacaaa      240 gatggtaagt actttgaaac agaaccaaag tgtaagtcag gtggaatata ttcagcaacg     300
tttgatgatg gttatgatgg aataactgga atagaaagca ttgcaaaagt gtatgttact     360
tgtacaaaac atccagatgg tattgaaatg ctagggata tacatcaaag tatgaaagat      420
ttgattgcat catttgcaca agacccttct ataataccag gagcttcaaa gggcaatgat     480
gattttagaa atatttatt agacaataaa tataaaaatg ggtggcctac aattccagat      540
gaatttaagg caaatatgg attaagtaag gatacactat atatacaacc atatgcatat      600
aatcctacta atctgatgc tactgtagtt gtatttgcaa ataataagac tggaggtaat      660
tggtatactt ccctagttta cgattatgat gaaggtagat ggtataaagg taaaaatggt     720
atttctgttg caggtaggtc atgggatgtt gacacagata gtgttaagtc tgtaaaaaca     780
```

```
gagattcatt ctaaagaggg atggggtcct ttaaattaat atatcatgtt ttattaatct      840
ggtattgatt aaactataga aaagagcagt ttctatagat gacgaatacc agatttttcat     900 ttatatgtat aattaagata tattaaaagt atttatat                              938
```

```
<210> SEQ ID NO 114
<211> LENGTH: 941
<212> TYPE: DNA
<213> ORGANISM: Clostridium difficile

<400> SEQUENCE: 114
atgggaatga ttattatgaa taaaaagggt tttacactaa ttgaattgtt ggtagttata       60
tctataatag gaattttagt tatagtagct gttccagcgt tatttagaaa tatagaaaaa      120
agtaaggcgg ttacatgcct ttctaataga gaaaatataa agactcaaat tgttattgca      180
atggctgagg aaccaagtaa agataagaat aaagtcataa aagatgtact agaaaataaa      240
gatggtaagt actttgaaac agaaccaaag tgtaaatcag gtggaatata ttcagcaacg      300
tttgatgatg gttatgatgg aataactgga ggagaaagca ttgcaaaagt gtatgttact      360
tgtacagaac atccagacgg tgttgaaatg gctagggatg tacatcaaag tatgaaagat      420
ttgattgcat catttgcaca agacccttct ataataccag gagcttcaaa gagtaatgat      480
gattttagaa atatttatt agacaataaa tataaaaagg gatggcctac aattccagat      540
gaatttaaag caaatatgg attaagtaag gatacactat atatacaacc atatgcatat      600
aatcctacta aacctgatgc cactgtagtt gtatttgcaa ataataagac tggaggtaat      660
tggtacactt ccctagttta cgattatgat gaaggtagag ggtataaagg caaaaatggt      720
atttctgttg caggtaggtc atgggatgtt gatacagata gtgttaagtc tgtaaaaaca      780
gagattcatt ctaaagaggg atggggtcct ttaaattaat atataatgtt ttattaatct     840
ggtattgatt aaactataga aaagagcagt ttctatagat gacgaatacc agatttttat      900
ttatatgtat aattaatata tattaaaagt atttatattt t                         941
```

```
<210> SEQ ID NO 115
<211> LENGTH: 941
<212> TYPE: DNA
<213> ORGANISM: Clostridium difficile

<400> SEQUENCE: 115
atgggaatga ttattatgaa taaaaagggt tttacattaa ttgaattgtt ggtagttata       60
tctataatag gaattttagt tatagtagct gttccagcgt tatttagaaa tatagaaaaa      120
agtaaagcag ttacatgtct ttctaataga gaaaatataa agactcaaat tgttattgca      180
atggctgagg aatcaagtaa agacaagaat gaagtcataa aagaggtatt agaaaacaaa      240
gatggtaagt actttgaaac agaaccaaag tgtaagtcag gtggaatata ttcagcaacg      300
tttgatgatg gttatgatgg aataactgga atagaaagca ttgcaaaagt gtatgttact      360
tgtacaaaac atccagacgg tgttgaaatg gctagggatg tgcatcaaag tatgaaagat      420
ttgattgcat catttgcaca agacccttct ataataccag gagcttcaaa gggcaatgat      480
gattttagaa atatttatt agacaataaa tataaaaatg gtggcctac aattccagat      540 gaatttaagg caaatatgg attaagtaag gatacactat atatacaacc atatgcatat      600
aatcctacta aatctgatgc tactgtagtt gtatttgcaa ataataagac tggaggtaat      660
tggtatactt ccctagttta cgattatgat gaaggtagag ggtataaagg taaaaatggt      720
atttctgttg caggtaggtc atgggatgtt gacacagata gtgttaagtc tgtaaaaaca      780
```

```
gagattcatt ctaaagaggg atggggtcct ttaaattaat atatcatgtt ttattaatct    840
ggtattgatt aaactataga aaagagcagt ttctatagat gacgaatacc agattttcat    900
ttatatatat aattgagata tattaaaagt gtttatattt t                         941
```

<210> SEQ ID NO 116
<211> LENGTH: 941
<212> TYPE: DNA
<213> ORGANISM: Clostridium difficile

<400> SEQUENCE: 116

```
atgggaatga ttattatgaa taaaaagggt tttacattaa ttgaattgtt ggtagttata     60
tctataatag gaattttagt tatagtagct gttccagcgt tatttagaaa tatagaaaaa    120
agtaaggcag ttacatgtct ttctaataga gaaaatataa agactcaaat tgttattgca    180
atggctgagg aatcaagtaa agacaagaat gaagtcataa aagaggtatt agaaaacaaa    240
gatggtaagt actttgaaac agaaccaaag tgtaagtcag gtggaatata ttcagcaacg    300
tttgatgatg gttatgatgg aataactgga atagaaagca ttgcaaaagt gtatgttact    360
tgtacaaaac atccagatgg tattgaaatg gctagggata tacatcaaag tatgaaagat    420
ttgattgcat catttgcaca agacccttct ataataccag gagcttcaaa gggcaatgat    480
gattttagaa atatttatt agacaataaa tataaaaatg ggtggcctac aattccagat    540
gaatttaagg caaatatgg attaagtaag gatacactat atatacaacc atatgcatat    600
aatcctacta atctgatgc tactgtagtt gtatttgcaa ataataagac tggaggtaat    660
tggtatactt ccctagttta cgattatgat gaaggtagat ggtataaagg taaaaatggt    720
atttctgttg caggtaggtc atgggatgtt gacacagata gtgttaagtc tgtaaaaaca    780
gagattcatt ctaaagaggg atggggtcct ttaaattaat atatcatgtt ttattaatct    840
ggtattgatt aaactataga aaagagcagt ttctatagat gacgaatacc agattttcat    900
ttatatgtat aattaagata tattaaaagt atttatattt t                         941
```

<210> SEQ ID NO 117
<211> LENGTH: 267
<212> TYPE: PRT
<213> ORGANISM: Clostridium difficile

<400> SEQUENCE: 117

```
Met Asn Lys Lys Gly Phe Thr Leu Ile Glu Leu Leu Val Val Ile Ser
1               5                   10                  15

Ile Ile Gly Ile Leu Val Ile Val Ala Val Pro Ala Leu Phe Arg Asn
            20                  25                  30

Ile Glu Lys Ser Lys Ala Val Thr Cys Leu Ser Asn Arg Glu Asn Ile
        35                  40                  45

Lys Thr Gln Ile Val Ile Ala Met Ala Glu Glu Ser Ser Lys Asp Lys
    50                  55                  60

Asn Glu Val Ile Lys Glu Val Leu Glu Asn Lys Asp Gly Lys Tyr Phe
65                  70                  75                  80

Glu Thr Glu Pro Lys Cys Lys Ser Gly Gly Ile Tyr Ser Ala Thr Phe
                85                  90                  95

Asp Asp Gly Tyr Asp Gly Ile Thr Gly Ile Glu Ser Ile Ala Lys Val
            100                 105                 110

Tyr Val Thr Cys Thr Lys His Pro Asp Gly Ile Glu Met Ala Arg Asp
        115                 120                 125
```

-continued

```
Ile His Gln Ser Met Lys Asp Leu Ile Ala Ser Phe Ala Gln Asp Pro
    130             135                 140
Ser Ile Ile Pro Gly Ala Ser Lys Gly Asn Asp Asp Phe Arg Lys Tyr
145                 150                 155                 160
Leu Leu Asp Asn Lys Tyr Lys Asn Gly Trp Pro Thr Ile Pro Asp Glu
                165                 170                 175
Phe Lys Ala Lys Tyr Gly Leu Ser Lys Asp Thr Leu Tyr Ile Gln Pro
                180                 185                 190
Tyr Ala Tyr Asn Pro Thr Lys Ser Asp Ala Thr Val Val Val Phe Ala
            195                 200                 205
Asn Asn Lys Thr Gly Gly Asn Trp Tyr Thr Ser Leu Val Tyr Asp Tyr
    210                 215                 220
Asp Glu Gly Arg Trp Tyr Lys Gly Lys Asn Gly Ile Ser Val Ala Gly
225                 230                 235                 240
Arg Ser Trp Asp Val Asp Thr Asp Ser Val Lys Ser Val Lys Thr Glu
                245                 250                 255
Ile His Ser Lys Glu Gly Trp Gly Pro Leu Asn
                260                 265

<210> SEQ ID NO 118
<211> LENGTH: 376
<212> TYPE: DNA
<213> ORGANISM: Clostridium difficile

<400> SEQUENCE: 118
ttgtttttat tattgaaaat aagaaagagt ggtttatat caatcgaatg tataataagt        60
attgctatat tatatgtggc tgtttattta gtttctacat cattgtataa ttgttatagt      120
tttatcagta gaaatatatc tgacagagaa atgttaagta cagcaaaaaa aatatataga      180
agatgagaag tatagaatac aaaatagtaa gtatgagtta attgaagata agatagaaaa      240
aaattacata aatggatatg aaattaacag tagaatagag caaattttag attattatca      300
atgctatgaa ataaatatag agataaaaaa tgaatttaaa aaactgaggt ttaatagcta      360
tgttactaga aaataa                                                     376
```

ENGINEERED TYPE IV PILIN OF *CLOSTRIDIUM DIFFICILE*

CROSS REFERENCE TO RELATED APPLICATIONS

This application is a continuation-in-part of U.S. application Ser. No. 13/974,825, filed Aug. 23, 2013, which is a continuation of U.S. application Ser. No. 13/321,399, filed May 20, 2010, now U.S. Pat. No. 8,518,415, which issued Aug. 27, 2013, which is the U.S. National Stage under 35 U.S.C. §371 of International Application No. PCT/US2010/035664, filed May 20, 2010, which claims the benefit of U.S. Provisional Appl. No. 61/179,747, filed May 20, 2009. The content of the aforesaid applications is relied upon and incorporated by reference in its entirety.

STATEMENT OF FEDERALLY SPONSORED RESEARCH AND DEVELOPMENT

This invention was made with government support under Grant No. AI037606 awarded by the National Institutes of Health. The government has certain rights in the invention.

REFERENCE TO A SEQUENCE LISTING SUBMITTED ELECTRONICALLY VIA EFS-WEB

The content of the sequence listing (Name: sequence_listing_ST25.txt, Size: 166,371 bytes; and Date of Creation: Aug. 26, 2014) electronically submitted via EFS-Web is incorporated by reference in its entirety.

FIELD OF THE INVENTION

The present invention generally relates at least to the fields of molecular biology, immunology, infectious disease and medicine. In particular, the invention relates to a *Clostridium difficile* type IV pilin (tfp) gene which can serve as a diagnostic marker for identification of patients infected with *C. difficile* and as a vaccine for therapeutic interventions.

BACKGROUND OF THE INVENTION

*Clostridium difficile* associated disease (CDAD) is a dangerous emerging infection caused by an anaerobic, spore-forming *bacillus* that often threatens the health of elderly patients in various healthcare setting following antibiotic treatments of unrelated infections. CDAD symptoms range in severity from asymptomatic carriage, through mild diarrhea, to a more severe pseudomembranous colitis which can be fatal. The epidemiology of CDAD has been changing dramatically. Formerly found almost exclusively as a complication of antimicrobial therapy among the elderly and infirm in inpatient settings, CDAD has been reported increasingly in outpatients, among otherwise healthy individuals including children, and even in the absence of antimicrobial therapy. Deaths attributable to CDAD have quadrupled in the United States from 5.7 per million persons in 1999 to 23.7 per million in 2004. Redelings M D, Sorvillo F, Mascola L. Increase in *Clostridium difficile*-related mortality rates, United States, 1999-2004. *Emerg Infect Dis.* 2007; 13:1417-9. Estimates of the cost for treatment for CDAD in the United States have been dramatically revised upward from $1 billion in 2002 to $3.2 billion in 2007 due to a dramatic increase in the number of cases and increasing severity of the disease.

The mechanisms by which *C. difficile* colonizes the human colon are not established. A surface protein layer has been described which appears to play a role in binding to tissue culture cells in vitro, but its role in vivo has not been established. Calabi, E., Calabi, F., Phillips, A. D. & Fairweather, N. Binding of *Clostridium difficile* surface layer proteins to gastrointestinal tissues. *Infect Immun* (2002):70: 5770-5778. Enterotoxins A (TcdA) and B (TcdB) are the primary virulence factors of *C. difficile*. They are exoenzymes that monoglucosylate small Rho-like GTPases, ultimately leading to the disruption of the actin cytoskeleton of colonic intestinal epithelial cells, destruction of tight junction, and apoptosis. Release of cytokines from intoxicated target cells also leads to massive infiltration of neutrophils into damaged tissue regions, a hallmark of pseudomembranous colitis.

Although primary CDAD can usually be successfully treated with metronidazole or vancomycin, metronidazole resistance and refractory infections are becoming increasingly common. Furthermore, many patients suffer recurrent episodes of CDAD, which can be extremely distressing and difficult to manage. An effective vaccine against CDAD is urgently needed for primary and secondary (relapse) prevention. No licensed vaccine is currently available for CDAD. The approach to vaccination that has advanced furthest into clinical trials has targeted only the *C. difficile* enterotoxins. Toxoid preparations of toxin A and B have completed phase I trials, with both serum free and fecal antibody against both toxins being demonstrated. Kotloff K L, Wasserman S S, Losonsky G A, Thomas W, Jr., Nichols R, Edelman R, Bridwell M, Monath T P. Safety and immunogenicity of increasing doses of a *Clostridium difficile* toxoid vaccine administered to healthy adults. *Infect. Immun.* 2001 February; 69(2):988-95. The mechanisms by which serum antibody responses are effective against infection and disease caused by *C. difficile* are unclear, although it has been proposed that entry of IgG antitoxin from the blood into mucosal tissues of the large bowel or intestinal lumen may prevent toxin binding.

Type IV pili (Tfp) or fimbriae are hair-like surface appendages produced by many species of Gram negative bacteria including *Pseudomonas aeruginosa*, *Vibrio cholerae*, *Neisseria gonorrhoeae*, *N. meningitidis*, *Salmonella enterica* serovar *Typhi* (herein designated *S. typhi*), *Legionella pneumophila*, enteropathogenic and enterotoxigenic *Escherichia coli*. Tfp play numerous roles in diverse processes such as cellular adhesion, colonization, twitching motility, biofilm formation, and virulence. Tfp are composed exclusively of primarily of many copies of pilin protein, tightly packed in a helix so that the highly hydrophobic amino-terminus of the pilin is buried in the core of the pilus. Tfp pilins have been used successfully as subunit vaccines for the prevention of several diseases in animals. Lepper A W, Moore L J, Atwell J L, Tennent J M. The protective efficacy of pili from different strains of *Moraxella bovis* within the same serogroup against infectious bovine keratoconjunctivitis. *Vet. Microbiol.* 1992; 32:177-87. Lepper A W D, Atwell J L, Lehrbach P R, Schwartzkoff C L, Egerton J R, Tennent J M. The protective efficacy of cloned *Moraxella bovis* pili in monovalent and multivalent vaccine formulations against experimentally induced infectious bovine keratoconjunctivitis (IBK). *Vet. Microbiol.* 1995; 45:129-38. Stewart D J, Clark B L, Peterson J E, Emery D L, Smith E F, Griffiths D A, O'Donnell I J. The protection given by pilus and whole cell vaccines of *Bacteroides nodosus* strain 198 against ovine foot-rot induced by strains of different serogroups. *Aust. Vet. J.* 1985; 62:153-9. Egerton J R, Cox P T, Anderson B J, Kristo C, Norman M, Mattick J S. Protection of sheep against footrot with a recombinant DNA-based fimbrial vaccine. *Vet. Microbiol.* 1987; 14:393-409. Recently investigators have discovered that *Clostridium perfringens* has the genes for and can produce Tfp; similar genes are present in the *C. difficile* genome. Varga J J, Nguyen V, O'Brien D K, Rodgers K, Walker R A, Melville S B. Type IV pili-dependent gliding motility in the Gram-positive pathogen *Clostridium perfringens* and other Clostridia. *Mol. Microbiol.* 2006 November; 62(3):680-94.

There is a need for a multivalent *C. difficile* subunit vaccine and a diagnostic marker for identification of patients infected with *C. difficile*.

SUMMARY OF THE INVENTION

In one embodiment, the present invention relates to a method of inducing an immune response, comprising administering to a subject in need thereof an immunologically-effective amount of a vaccine comprising a *Clostridium difficile* type IV pilin or an antigenic fragment or variant thereof.

In another embodiment, the present invention relates to a method for overexpression of multiple *C. difficile* type IV pilins in gram negative bacteria including but not limited to *E. coli*. The type IV pili serve as colonization factors and vaccine targets.

In another embodiment, the present invention relates to a method for expressing and purifying high levels of *C. difficile* type IV pilins.

In another embodiment, the present invention relates to novel Type IV pilin proteins of *C. difficile* which exhibit high level expression in the bacteria *E. coli*.

In another embodiment, the present invention relates to novel vaccines for *C. difficile* comprising engineered recombinant *C. difficile* type IV pilins.

In another embodiment, the present invention relates to novel biomarkers for use in *C. difficile* detection in patients with *C. difficile* infections.

In another embodiment, the present invention relates to a method for prevention of *C. difficile* colonization and disease in a subject comprising administering a vaccine comprised of purified type IV pilin proteins to said subject.

In another embodiment, the present invention relates to a method for prevention of *C. difficile* spread among mammalian hosts, such as humans, comprising administering a vaccine comprised of purified type IV pilin proteins to said mammal.

BRIEF DESCRIPTION OF THE FIGURES

FIG. 5. NCBI COBALT multiple alignment of the full amino acid sequences for the seven pilin and pilin-like proteins from *C. difficile* strain R20291. The proteins share considerable amino acid similarity in the N-terminal hydrophobic regions, while they diverge in the C-terminal region. The black bar indicates the prepilin peptidase cleavage site.

DETAILED DESCRIPTION OF THE INVENTION

Figure 1:
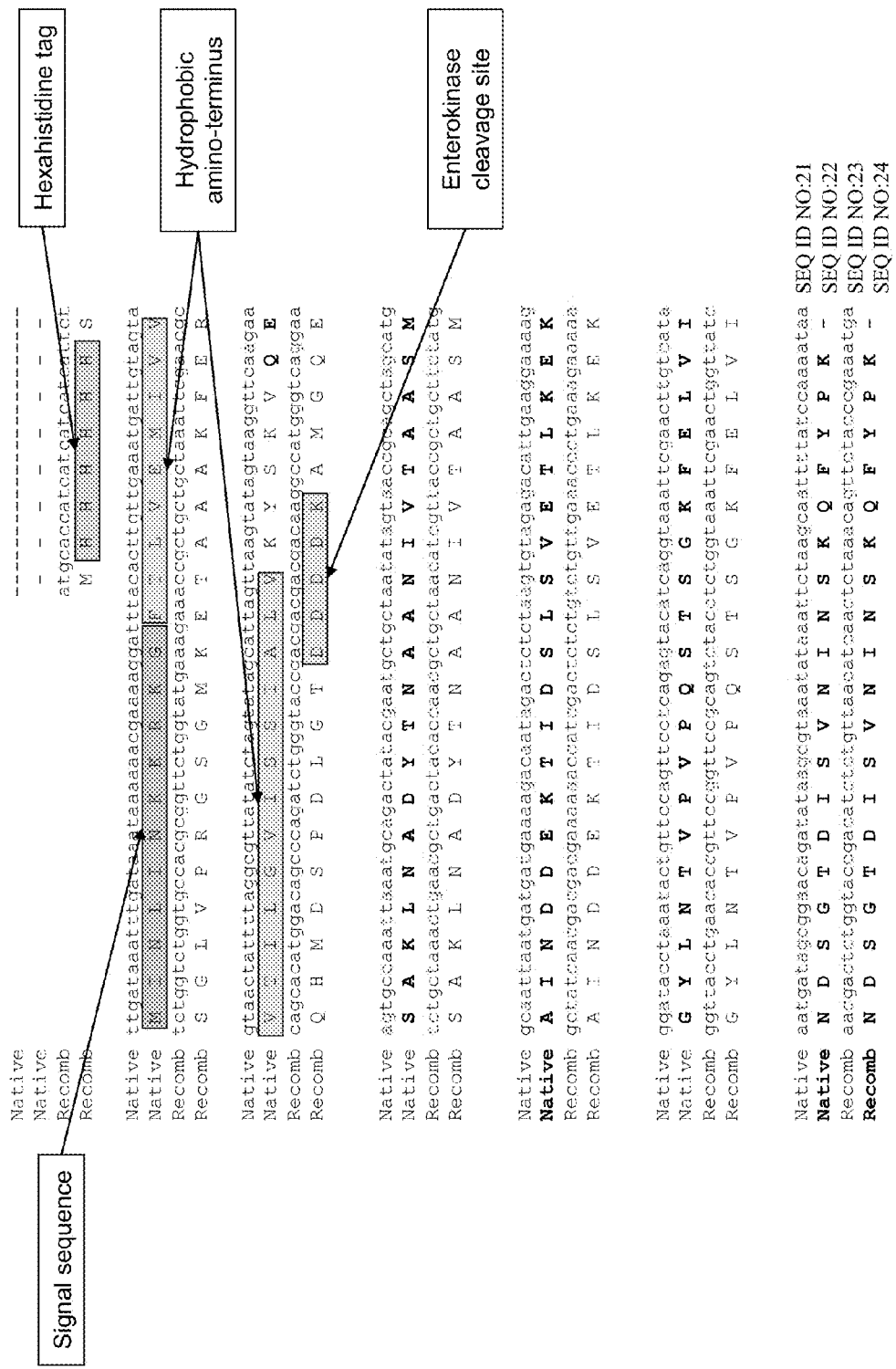
FIG. 1. Strategy for modification and purification of *C. difficile* PilA2 type IV pilin. The nucleotide and corresponding amino acid sequences of the native and recombinant pilA2 genes are aligned. The hexahistidine tag, enterokinase cleavage sequences of the recombinant protein, pre-pilin peptidase signal sequence and hydrophobic mature amino terminus of the native protein are boxed.

The Gram-positive anaerobe *Clostridium difficile* is the major cause of nosocomial diarrhea. Manifestations of infection include profuse diarrhea, pseudomembranous colitis, and death. Genes for type IV pili, a type of bacterial nanofiber often involved in colonization and until recently described only in Gram-negatives, are present in all members of the Clostridiales. Described herein are several pilin or pilin-like protein genes. The pilin or pilin-like proteins have relatively conserved N-terminal hydrophobic regions, but diverge widely at their C-termini. Eight of these genes are conserved across all sampled strains of *C. difficile*. Six identified pilin or pilin-like proteins were purified and used to immunize mice. Immunization of mice with each individual protein resulted in the generation of antibody responses that varied in titer and crossreactivity. These cross-reactive responses are notable given the low amino acid sequence identity among the antigens. Further studies in other small mammals mirrored results in mice. Results herein illuminate the components of the type IV pilus in *C. difficile* and identify targets for a vaccine directed against the bacterium.

Multiple Pilin Genes and Alleles Identified in Various Strains of *C. difficile*.

In one aspect, the present invention is directed to an engineered Type IV pilin gene of *C. difficile*.

In accordance with the claimed invention, the type IV pilin can come from any *C. difficile* strain. Examples of *C. difficile* strains include *C. difficile* CD196, *C. difficile* CIP 107932, *C. difficile* QCD-32g58, *C. difficile* QCD-37x79, *C. difficile* QCD-66c26, *C. difficile* QCD-76w55, *C. difficile* QCD-97b34, *C. difficile* R20291, *C. difficile* QCD-63q42, *C. difficile* QCD-23m63, *C. difficile* 630, *C. difficile* ATCC 43255, *C. difficile* 70-100-2010, *C. difficile* 050-P50-2011, *C. difficile* 002-P50-2011, *C. difficile* NAP08, *C. difficile* NAP07 and *C. difficile* BI1.

All of the strains listed above can have multiple genes that can be predicted to encode type IV pilin proteins. As used herein, these genes will be referred to as pilA1, pilA2, pilA3 (also referred to herein as pilW), pilA4 (also referred to herein as pilI), pilA5 (also referred to herein as pilU), pilA6 (also referred to herein as pilV), pilA7 (also referred to herein as pilX1), pilK and pilX2. The *C. difficile* strains can harbor allelic variants of the type IV pilins. Alleles of pilA1, as used herein, include pilA1.1, pilA1.2, pilA1.3, pilA1.4, pilA1.5, pilA1.6 and pilA1.7. Alleles of pilA2, as used herein, include pilA2.1, pilA2.2, pilA2.3 and pilA2.4. Alleles of pilA3 (pilW), as used herein, include pilA3.1 (pilW.1), pilA3.2 (pilW.2), pilA3.3 (pilW.3) and pilA3.4 (pilW.4). Alleles of pilA4 (pilI), as used herein, include pilA4.1 (pilJ.1), pilA4.2 (pilj.2), pilA4.3 (pilJ.3), pilA4.4 (pilJ.4), pilA4.5 (pilJ.5), pilA4.6 (pilJ.6), pilA4.7 (pilJ.7), pilA4.8 (pilJ.8) and pilA4.9 (pilJ.9). Alleles of pilA5 (pilU), as used herein, include pilA5.1 (pilU.1), pilA5.2 (pilU.2), pilA5.3 (pilU.3), pilA5.4 (pilU.4) and pilA5.5 (pilU.5). Alleles of pilA6 (pilV), as used herein, include pilA6.1 (pilV.1), pilA6.2 (pilV.2), pilA6.3 (pilV.3), pilA6.4 (pilV.4), pilA6.5 (pilV.5), pilA6.6 (pilV.6) and pilA6.7 (pilV.7). Alleles of pilA7 (pilX1), as used herein, include pilA7.1 (pilX1.1), pilA7.2 (pilX1.2) and pilA7.3 (pilX1.3).

Each of these genes is predicted to encode a protein composed of a short, positively charged signal peptide, a prepilin peptidase cleavage site and a hydrophobic mature amino-terminal domain characteristic of Type IVa pilins. Mature pilin proteins are naturally derived from pre-pilin proteins by the action of pre-pilin peptidase enzymes which cleave the signal peptide and N-methylate the mature amino terminus.

PilA1: The mature PilA1 protein is predicted to be 158-164 amino acids long. Nine strains are predicted to express identical PilA1 proteins (PilA1.1), while the PilA1 proteins of some of the other strains are predicted to be 75%, 89%, 91% and 93% identical to these nine.

PilA1.1 is found in *C. difficile* strains CD196, CIP 107932, QCD-32g58, QCD-37x79, QCD-66c26, QCD-76w55, QCD-97b34, R20291 and BI1. The native nucleotide sequence of PilA1.1 is SEQ ID NO:45 and the native amino acid sequence is SEQ ID NO:46.

PilA1.2 is found in *C. difficile* strain QCD-63q42. The native nucleotide sequence of PilA1.2 is SEQ ID NO:5 and the native amino acid sequence is SEQ ID NO:6.

PilA1.3 is found in *C. difficile* strains QCD-23m63, NAP08 and NAP07. The native nucleotide sequence of PilA1.3 is SEQ ID NO:9 and the native amino acid sequence is SEQ ID NO:10.

PilA1.4 is found in *C. difficile* strain 630. The native nucleotide sequence of PilA1.4 is SEQ ID NO:13 and the native amino acid sequence is SEQ ID NO:14.

PilA1.5 is found in *C. difficile* strain ATCC 43255. The native nucleotide sequence of PilA1.5 is SEQ ID NO:17 and the native amino acid sequence is SEQ ID NO:18.

PilA1.6 is found in *C. difficile* strain 70-100-2010. The native amino acid sequence is SEQ ID NO:47.

PilA1.7 is found in *C. difficile* strains 002-P50-2011 and 050-P50-2011. The native amino acid sequence is SEQ ID NO:48.

The first 9 amino acids of SEQ ID NOS: 6, 10, 14, 18, 46, 47 and 48 comprise pre-pilin leader sequence that is cleaved during processing in *C. difficile*.

PilA2: Eighteen strains are predicted to encode a 109-amino acid mature PilA2 protein. The predicted PilA2 protein is identical in 12 of these strains, and 95% identical in the other strains.

PilA2.1 is found in *C. difficile* strains CD196, CIP 107932, QCD-32g58, QCD-37x79, QCD-66c26, QCD-76w55, QCD-97b34, R20291, QCD63q42, 630, ATCC 43255 and BI1. The native nucleotide sequence of PilA2.1 is SEQ ID NO:21 (for strains CD196, CIP 107932, QCD-32g58, QCD-37x79, QCD-66c26, QCD-76w55, QCD-97b34, 820291, ATCC 43255 and BI1) and SEQ ID NO:49 (for strains QCD63q42 and 630) and the native amino acid sequence is SEQ ID NO:22. The first 11 amino acids of SEQ ID NO:22 comprise pre-pilin leader sequence that is cleaved during processing to yield the mature protein.

PilA2.2 is found in *C. difficile* strain QCD-23m63, NAP07 and NAP08. The native nucleotide sequence of PilA2.2 is SEQ ID NO:25 and the native amino acid sequence is SEQ ID NO:26. The first 8 amino acids of SEQ ID NO:26 comprise pre-pilin leader sequence that is cleaved during processing to yield the mature protein.

PilA2.3 is found in *C. difficile* strains 002-P50-2011 and 050-P50-2011. The native amino acid sequence is SEQ ID NO:50. The first 8 amino acids of SEQ ID NO:50 comprise pre-pilin leader sequence that is cleaved during processing to yield the mature protein.

PilA2.4 is found in *C. difficile* strain 70-100-2010. The native amino acid sequence is SEQ ID NO:51. The first 8 amino acids of SEQ ID NO:51 comprise pre-pilin leader sequence that is cleaved during processing to yield the mature protein.

PilA3 (also referred to as PilW): The pilA3 (pilW) gene is present in 13 strains and is predicted to encode a protein closely related at its amino terminus to PilA1. Forty-two of the first 57 amino acids of all PilA1 and PilA3 predicted mature proteins are identical. However, the sequence similarities between PilA1 and PilA3 end abruptly at that point. The predicted mature PilA3 proteins are 156-159 amino acids long. Nine strains are predicted to express identical PilA3 proteins, three additional strains are predicted to encode identical PilA3 proteins that are 76% identical to these nine and one strain is predicted to encode a PilA3 protein 95% identical to those of the majority.

PilA3.1 (PilW.1) is found in *C. difficile* strains CD196, CIP 107932, QCD-32g58, QCD-37x79, QCD-66c26, QCD-76w55, QCD-97b34, 820291 and BI1. The native nucleotide sequence of PilA3.1 is SEQ ID NO:29 and the native amino acid sequence is SEQ ID NO:30.

PilA3.2 (PilW.2) is found in *C. difficile* strain 630. The native nucleotide sequence of PilA3.2 is SEQ ID NO:33 and the native amino acid sequence is SEQ ID NO:34.

PilA3.3 (PilW.3) is found in *C. difficile* strains QCD-63q42 and ATCC 43255. The native nucleotide sequence of PilA3.3 is SEQ ID NO:37 and the native amino acid sequence is SEQ ID NO:38.

PilA3.4 (PilW.4) is found in *C. difficile* strain 70-100-2010. The native amino acid sequence is SEQ ID NO:52.

The first 6 amino acids of SEQ ID NOS:30, 34, 38 and 52 comprise pre-pilin leader sequence that is cleaved during processing to yield the mature proteins.

PilA4 (also referred to herein as PilI): The gene encoding the PilA4.1 protein is predicted to encode an identical 263 amino acid protein. PilA4.1 (PilJ.1) is found in *C. difficile* strains CD196 and R20291. The native nucleotide sequence of PilA4.1 is SEQ ID NO:41 and the native amino acid sequence is SEQ ID NO:42. The first 10 amino acids of SEQ ID NO:42 comprise pre-pilin leader sequence that is cleaved during processing to yield the mature protein.

PilA4.2 (PilJ.2) is found in *C. difficile* strain 630. The native amino acid sequence is SEQ ID NO:53.

PilA4.3 (PilJ.3) is found in *C. difficile* strains 050-P50-2011 and 002-P50-2011. The native amino acid sequence is SEQ ID NO:54.

PilA4.4 (PilJ.4) is found in *C. difficile* strain 70-100-2010. The native amino acid sequence is SEQ ID NO:55.

PilA4.5 (PilJ.5) is found in *C. difficile* strains NAP08 and NAP07. The native amino acid sequence is SEQ ID NO:56.

PilA4.6 (PilJ.6) is found in *C. difficile* strain QCD-63q42. The native amino acid sequence is SEQ ID NO:57.

PilA4.7 (PilJ.7) is found in *C. difficile* strains QCD-76w55, QCD-37x79, BI1, QCD-66c26, CIP 107932 and QCD-32g58. The native amino acid sequence is SEQ ID NO:58.

PilA4.8 (PilJ.8) is found in *C. difficile* strain ATCC 43255. The native amino acid sequence is SEQ ID NO:59.

PilA4.9 (PilJ.9) is found in *C. difficile* strain QCD-23m63. The native amino acid sequence is SEQ ID NO:60.

PilA5 (also referred to herein as PilU): The gene encoding the PilA5 protein is present in eighteen strains. PilA5.1 (PilU.1) is found in *C. difficile* strains CD196, 70-100-2010, QCD-63q42, QCD76w55, QCD-37x79, BI1, QCD-97b34, QCD-66c26, CIP 107932, R20291 and QCD-32g58. The native nucleotide sequence of PilA5.1 (strains CD196, 70-100-2010, QCD-76w55, QCD-37x79, BI1, QCD-97b34, QCD66c26, CIP 107932, 820291 and QCD-32g58) is SEQ ID NO:61 and SEQ ID NO:62 (strain QCD-63q42) and the native amino acid sequence is SEQ ID NO:63.

PilA5.2 (PilU.2) is found in *C. difficile* strains 630 and ATCC 43255. The native nucleotide sequence of PilA5.2 is SEQ ID NO:64 and the native amino acid sequence is SEQ ID NO:65.

PilA5.3 (PilU.3) is found in *C. difficile* strains 050-P50-2011 and 002-P50-2011. The native amino acid sequence is SEQ ID NO:66.

PilA5.4 (PilU.4) is found in *C. difficile* strains NAP08 and NAP07. The native amino acid sequence is SEQ ID NO:67.

PilA5.5 (PilU.5) is found in *C. difficile* strain QCD-23m63. The native nucleotide sequence of PilA5.5 is SEQ ID NO:68 and the native amino acid sequence is SEQ ID NO:69.

PilA6 (also referred to herein as PilV): The gene encoding the PilA6 protein is present in eighteen strains.

PilA6.1 (PilV.1) is found in *C. difficile* strains 820291, 70-100-2010 and CD196. The native nucleotide sequence of PilA6.1 is SEQ ID NO:70 and the native amino acid sequence is SEQ ID NO:71.

PilA6.2 (PilV.2) is found in *C. difficile* strain 630. The native nucleotide sequence of PilA6.2 is SEQ ID NO:72 and the native amino acid sequence is SEQ ID NO:73.

PilA6.3 (PilV.3) is found in *C. difficile* strain 050-P50-2011 and 002-P50-2011. The native amino acid sequence is SEQ ID NO:74.

PilA6.4 (PilV.4) is found in *C. difficile* strains NAP08 and NAP07. The native amino acid sequence is SEQ ID NO:75.

PilA6.5 (PilV.5) is found in *C. difficile* strains QCD-63q42, QCD-76w55, QCD-37x79, BI1, QCD-97b34, QCD-66c26, CIP 107932 and QCD-32g58. The native nucleotide sequence of PilA6.5 is SEQ ID NO:76 (for strains QCD-76w55, QCD-37x79, BI1, QCD-97b34, QCD-66c26, CIP 107932 and QCD-32g58) and is SEQ ID NO:77 (for strain QCD-63q42) and the native amino acid sequence is SEQ ID NO:78.

PilA6.6 (PilV.6) is found in *C. difficile* strain ATCC 43255. The native amino acid sequence is SEQ ID NO:79.

PilA6.7 (PilV.7) is found in *C. difficile* strain QCD-23m63. The native nucleotide sequence of PilA7.7 is SEQ ID NO:80 and the native amino acid sequence is SEQ ID NO:81.

PilA7 (also referred to herein as PilX1): The gene encoding the PilA7 protein is present in nine strains. PilA7.1 (PilX.1) is found in *C. difficile* strains R20291, 630 and CD196. The native nucleotide sequence of PilA7.1 is SEQ ID NO:82 and the native amino acid sequence is SEQ ID NO:83. PilA7.2 (PilX.2) is found in *C. difficile* strains QCD-63q42, QCD-76w55, QCD-37x79, ATCC 43255, BI1, QCD-97b34, QCD-66c26 and CIP 107932. The native nucleotide sequence of PilA7.2 is SEQ ID NO:84 and the native amino acid sequence is SEQ ID NO:85.

PilA7.3 (PilX.3) is found in *C. difficile* strain QCD-23m63. The native nucleotide sequence of PilA7.3 is SEQ ID NO:86 and the native amino acid sequence is SEQ ID NO:87.

PilK: The native amino acid sequence is SEQ ID NO:88.

PilX2: The native amino acid sequence is SEQ ID NO:89.

Nucleotide and amino acid sequences of native pilin genes from various strains are shown below.

```
PilA1 Nucleotide
>gi|260685375:c3986513-3985836 Clostridium
difficile R20291 chromosome, complete genome
(SEQ ID NO: 45)
ATGAAGTTAAAAAAGAATAAAAAAGGTTTCACTTTAGTGGAATTATTG
GTAGTAATTGCAATTATAGGTATATTAGCAGTAGTGGCAGTTCCAGCTT
TATTTAGTAATATAAACAAGGCTAAGGTAGCAAGTGTTGAGTCTGATTA
TAGTTCAGTTAAGAGTGCAGCATTATCTTATTATTCAGATACTAATAAG
ATACCAGTTACACCAGATGGTCAAACTGGTTTAAGTGTTTTAGAGACTT
ATATGGAGTCTCTGCCTGATAAAGCTGATATAGGTGGAAAATATAAAT
TGATTAAAGTTGGTAATAAATTGGTATTACAGATAGGTACAAATGATG
AAGGAGTTACATTAACAGAAGCACAATCAGCAAAATTATTGAGTGATA
TAGGTGAAAATAAAATATATACAAGTGTTACAGCAGATAATTTGGGAA
ATCCATTAACAAGTAATACAAAAGTAGATAATAAAGTTCTATATATAG
TACTTATAGATAATACTGTGATGGACTCAACAAAATAG >gi|126697566:c4105711-4105042 Clostridium
difficile 630, complete genome (SEQ ID NO: 13)
ATGAAGTTAAAAAAGAATAAAAAAGGTTTCACTTTAGTGGAATTATTG
GTAGTAATTGCAATTATAGGTATATTAGCAGTAGTGGCAGTTCCAGCTT
TATTTAGTAATATAAACAAGGCTAAGGTAGCAAGTGTTGAGTCTGATTA
TAGTTCAGTTAAGAGTGCAGCATTATCTTATTATTCAGATACTAATAAG
ATACCAGTTACACCAGATGGTCAAACTGGTTTAAGTGTTTTAGAGACTT
ATATGGAGTCTCTGCCTGATAAAGCTGATATAGGTGGAAAATATAAAT
TGATTAAAGTTGGTAATAAATTGGTATTACAGATAGGTACAAATACTG
AAGGAGTTACCTTAACAGAAGCACAATCAGCAAAATTATTGAGTGATA
TAGGTGAAAATAAAATATATACAAATGCAGCTCTTAGTGCTAAATTAA
CATCTACTACAAAGGTAAATAATGAAGCTTTATATATAGTTCTTATAGA
TAATATTGTAATGGA-TCAACAAGGAGCTTAA
```

>gi|260681769:c3905727-3905050 *Clostridium difficile* CD196 chromosome, complete genome
(SEQ ID NO: 45)
ATGAAGTTAAAAAAGAATAAAAAAGGTTTCACTTTAGTGGAATTATTG
GTAGTAATTGCAATTATAGGTATATTAGCAGTAGTGGCAGTTCCAGCTT
TATTTAGTAATATAAACAAGGCTAAGGTAGCAAGTGTTGAGTCTGATTA
TAGTTCAGTTAAGAGTGCAGCATTATCTTATTATTCAGATACTAATAAG
ATACCAGTTACACCAGATGGTCAAACTGGTTTAAGTGTTTTAGAGACTT
ATATGGAGTCTCTGCCTGATAAAGCTGATATAGGTGGAAAATATAAAT
TGATTAAAGTTGGTAATAAATTGGTATTACAGATAGGTACAAATGATG
AAGGAGTTACATTAACAGAAGCACAATCAGCAAAATTATTGAGTGATA
TAGGTGAAAATAAAATATATACAAGTGTTACAGCAGATAATTTGGGAA
ATCCATTAACAAGTAATACAAAAGTAGATAATAAAGTTCTATATATAG
TACTTATAGATAATACTGTGATGGACTCAACAAAATAG >gi|383843669:c3913747-3913070 *Clostridium difficile* BI1, complete genome (SEQ ID NO: 45)
ATGAAGTTAAAAAAGAATAAAAAAGGTTTCACTTTAGTGGAATTATTG
GTAGTAATTGCAATTATAGGTATATTAGCAGTAGTGGCAGTTCCAGCTT
TATTTAGTAATATAAACAAGGCTAAGGTAGCAAGTGTTGAGTCTGATTA
TAGTTCAGTTAAGAGTGCAGCATTATCTTATTATTCAGATACTAATAAG
ATACCAGTTACACCAGATGGTCAAACTGGTTTAAGTGTTTTAGAGACTT
ATATGGAGTCTCTGCCTGATAAAGCTGATATAGGTGGAAAATATAAAT
TGATTAAAGTTGGTAATAAATTGGTATTACAGATAGGTACAAATGATG
AAGGAGTTACATTAACAGAAGCACAATCAGCAAAATTATTGAGTGATA
TAGGTGAAAATAAAATATATACAAGTGTTACAGCAGATAATTTGGGAA
ATCCATTAACAAGTAATACAAAAGTAGATAATAAAGTTCTATATATAG
TACTTATAGATAATACTGTGATGGACTCAACAAAATAG >gi|224514682|ref|NZ_CM000659.1|:3806985-3807662 *Clostridium difficile* CIP
107932 chromosome, whole genome shotgun sequence_gi|221149347|gb|CM000659.1|
*Clostridium difficile* CIP 107932 chromosome,
whole genome shotgun sequence reverse complement
(SEQ ID NO: 45)
ATGAAGTTAAAAAAGAATAAAAAAGGTTTCACTTTAGTGGAATTATTG
GTAGTAATTGCAATTATAGGTATATTAGCAGTAGTGGCAGTTCCAGCTT
TATTTAGTAATATAAACAAGGCTAAGGTAGCAAGTGTTGAGTCTGATTA
TAGTTCAGTTAAGAGTGCAGCATTATCTTATTATTCAGATACTAATAAG
ATACCAGTTACACCAGATGGTCAAACTGGTTTAAGTGTTTTAGAGACTT
ATATGGAGTCTCTGCCTGATAAAGCTGATATAGGTGGAAAATATAAAT
TGATTAAAGTTGGTAATAAATTGGTATTACAGATAGGTACAAATGATG
AAGGAGTTACATTAACAGAAGCACAATCAGCAAAATTATTGAGTGATA
TAGGTGAAAATAAAATATATACAAGTGTTACAGCAGATAATTTGGGAA
ATCCATTAACAAGTAATACAAAAGTAGATAATAAAGTTCTATATATAG
TACTTATAGATAATACTGTGATGGACTCAACAAAATAG >gi|224514685|ref|NZ_CM000660.1|:3730901-3731577 *Clostridium difficile* QCD-23m63 chromosome,
whole genome shotgun sequence_gi|
221149428|gb|CM000660.1|*Clostridium difficile*
QCD-23m63 chromosome,
whole genome shotgun sequence reverse complement
(SEQ ID NO: 9)
ATGAAGTTAAAAAAGAATAAAAAAGGTTTCACTTTAGTGGAATT
ATTGGTAGTAATTGCAATTATAGGTATATTAGCAGTAGTGGCAGTTCCA
GCTTTATTTAGTAATATAAACAAGGCTAAGGTAGCAAGTGTTGAGTCTG
ATTATAGTTCAATTAAGAGTGCAGCATTATCTTATTATTCAGATACTAA
TAAAATACCAGTTACACCAGATGGTCAAACTGGTTTAAGTGTTTTAGAG
ACTTATATGGAATCTCTTCCTGATAAAGCTGATATAGGTGGAGAATATA
AATTGATTAAAGTTGGTAATAAATTAGTATTACAGATAGGTAAGATGG
TGAAGGAGTTACCTTAACAGAAGCGCAATCAGCAAAATTATTGAGTGA
TATAGGTGAAAATAAAATATATACAGGTGTTACAGGAGATAATTTTGG
AGAGCAATTAAAAGATACTACAAAAATAGATAATAAAGCTCTATATAT
AGTACTTATAGATAATACTGTGATGGATTCAACAAAATAG >gi|209401276|ref|NZ_CM000287.1|:3897532-3898209 *Clostridium difficile*
QCD-32g58 chromosome, whole genome shotgun
sequence_gi|145843961|gb|CM000287.4|
*Clostridium difficile* QCD-32g58 chromosome,
whole genome shotgun sequence reverse complement
(SEQ ID NO: 45)
ATGAAGTTAAAAAAGAATAAAAAAGGTTTCACTTTAGTGGAATTATTG
GTAGTAATTGCAATTATAGGTATATTAGCAGTAGTGGCAGTTCCAGCTT
TATTTAGTAATATAAACAAGGCTAAGGTAGCAAGTGTTGAGTCTGATTA
TAGTTCAGTTAAGAGTGCAGCATTATCTTATTATTCAGATACTAATAAG
ATACCAGTTACACCAGATGGTCAAACTGGTTTAAGTGTTTTAGAGACTT
ATATGGAGTCTCTGCCTGATAAAGCTGATATAGGTGGAAAATATAAAT
TGATTAAAGTTGGTAATAAATTGGTATTACAGATAGGTACAAATGATG
AAGGAGTTACATTAACAGAAGCACAATCAGCAAAATTATTGAGTGATA
TAGGTGAAAATAAAATATATACAAGTGTTACAGCAGATAATTTGGGAA
ATCCATTAACAAGTAATACAAAAGTAGATAATAAAGTTCTATATATAG
TACTTATAGATAATACTGTGATGGACTCAACAAAATAG >gi|224514680|ref|NZ_CM000658.1|:3881935-3882612
*Clostridium difficile* QCD-37x79 chromosome,
whole genome shotgun sequence_gi|
221149249|gb|CM000658.1|*Clostridium difficile*
QCD-37x79 chromosome,
whole genome shotgun sequence reverse complement
(SEQ ID NO: 45)
ATGAAGTTAAAAAAGAATAAAAAAGGTTTCACTTTAGTGGAATTATTG
GTAGTAATTGCAATTATAGGTATATTAGCAGTAGTGGCAGTTCCAGCTT
TATTTAGTAATATAAACAAGGCTAAGGTAGCAAGTGTTGAGTCTGATTA
TAGTTCAGTTAAGAGTGCAGCATTATCTTATTATTCAGATACTAATAAG
ATACCAGTTACACCAGATGGTCAAACTGGTTTAAGTGTTTTAGAGACTT
ATATGGAGTCTCTGCCTGATAAAGCTGATATAGGTGGAAAATATAAAT
TGATTAAAGTTGGTAATAAATTGGTATTACAGATAGGTACAAATGATG
AAGGAGTTACATTAACAGAAGCACAATCAGCAAAATTATTGAGTGATA
TAGGTGAAAATAAAATATATACAAGTGTTACAGCAGATAATTTGGGAA
ATCCATTAACAAGTAATACAAAAGTAGATAATAAAGTTCTATATATAG
TACTTATAGATAATACTGTGATGGACTCAACAAAATAG >gi|224514674|ref|NZ_CM000637.1|:3941893-3942571
*Clostridium difficile* QCD-63q42 chromosome, whole
genome shotgun sequence_gi|219819758|gb|CM000637.1|
*Clostridium difficile* QCD-63q42 chromosome,
whole genome shotgun sequence reverse complement
(SEQ ID NO: 5)
ATGAAGTTAAAAAAGAATAAAAAAGGTTTCACTTTAGTGGAAT
TATTGGTAGTAATTGCAATTATAGGTATATTAGCAGTAGTGGCAGTTCC
AGCTTTATTTAGTAATATAAACAAGGCTAAGGTAGCAAGTGTTGAGTCT
GATTATAGTTCAGTTAAGAGTGCTGCATTATCTTATTATTCAGATACTA
ATAAGATACCAGTTACACCAGATGGTCAAACTGGTTTAAGTGTTTTAGA
AACTTATATGGAGTCTCTTCCTGATAAAGCTGATATAGGTGGAGAATAT
AAATTGATTAAAGTTGGTAGTAAATTGGTATTACAGATAGGTACAAAT
ACTGAGGGAGTTACCTTAACAGAAGCACAATCAGCAAAATTATTGAGT
GATATAGGTGAAAAAAAAATATATACAAGCGCTACAACAAATAGTTTG
GGAGATCCATTAACAAGTAATACAAAAATAGATAATAAAGTTCTATAT
ATAGTACTTATAGATAATACTGTGATGGCACAACAAAATAG >gi|224531476|ref|NZ_CM000441.1|:3882382-3883059
*Clostridium difficile* QCD-66c26 chromosome,whole
genome shotgun sequence_gi|222154275|gb|CM000441.2|
*Clostridium difficile* QCD-66c26 chromosome,
whole genome shotgun sequence reverse complement
(SEQ ID NO: 45)
ATGAAGTTAAAAAAGAATAAAAAAGGTTTCACTTTAGTGGAAT
TATTGGTAGTAATTGCAATTATAGGTATATTAGCAGTAGTGGCAGTTCC
AGCTTTATTTAGTAATATAAACAAGGCTAAGGTAGCAAGTGTTGAGTCT
GATTATAGTTCAGTTAAGAGTGCAGCATTATCTTATTATTCAGATACTA
ATAAGATACCAGTTACACCAGATGGTCAAACTGGTTTAAGTGTTTTAGA
GACTTATATGGAGTCTCTGCCTGATAAAGCTGATATAGGTGGAAAATAT
AAATTGATTAAAGTTGGTAATAAATTGGTATTACAGATAGGTACAAAT
GATGAAGGAGTTACATTAACAGAAGCACAATCAGCAAAATTATTGAGT
GATATAGGTGAAAATAAAATATACAGGTTACAGCAGATAATTTG
GGAAATCCATTAACAAGTAATACAAAAGTAGATAATAAAGTTCTATAT
ATAGTACTTATAGATAATACTGTGATGGACTCAACAAAATAG >gi|224514686|ref|NZ_CM000661.1|:3867932-3868609
*Clostridium difficile* QCD-76w55 chromosome, whole
genome shotgun sequence_gi|221191950|gb|CM000661.1|
*Clostridium difficile* QCD-76w55 chromosome,
whole genome shotgun sequence reverse complement
(SEQ ID NO: 45)
ATGAAGTTAAAAAAGAATAAAAAAGGTTTCACTTTAGTGGAAT
TATTGGTAGTAATTGCAATTATAGGTATATTAGCAGTAGTGGCAGTTCC
AGCTTTATTTAGTAATATAAACAAGGCTAAGGTAGCAAGTGTTGAGTCT
GATTATAGTTCAGTTAAGAGTGCAGCATTATCTTATTATTCAGATACTA
ATAAGATACCAGTTACACCAGATGGTCAAACTGGTTTAAGTGTTTTAGA
GACTTATGGAGTCTCTGCCTGATAAAGCTGATATAGGTGGAAAATAT
AAATTGATTAAAGTTGGTAATAAATTGGTATTACAGATAGGTACAAAT
GATGAAGGAGTTACATTAACAGAAGCACAATCAGCAAAATTATTGAGT
GATATAGGTGAAAAAAAATATATACAAGTGTTACAGCAGATAATTTG
GGAAATCCATTAACAAGTAATACAAAAGTAGATAATAAAGTTCTATAT
ATAGTACTTATAGATAATACTGTGATGGACTCAACAAAATAG -continued >gi|224514679|ref|NZ_CM000657.1|:3790434-3791111
Clostridium difficile QCD-97b34 chromosome, whole
genome shotgun sequence_gi|221149047|gb|CM000657.1|
Clostridium difficile QCD-97b34 chromosome,
whole genome shotgun sequence reverse complement
(SEQ ID NO: 45)
ATGAAGTTAAAAAAGAATAAAAAAGGTTTCACTTTAGTGGAAT
TATTGGTAGTAATTGCAATTATAGGTATATTAGCAGTAGTGGCAGTTCC
AGCTTTATTTAGTAATATAAACAAGGCTAAGGTAGCAAGTGTTGAGTCT
GATTATAGTTCAGTTAAGAGTGCAGCATTATCTTATTATTCAGATACTA
ATAAGATACCAGTTACACCAGATGGTCAAACTGGTTTAAGTGTTTTAGA
GACTTATATGGAGTCTCTGCCTGATAAAGCTGATATAGGTGGAAATAT
AAATTGATTAAAGTTGGTAATAAATTGGTATTACAGATAGGTACAAAT
GATGAAGGAGTTACATTAACAGAAGCACAATCAGCAAAATTATTGAGT
GATATAGGTGAAAATAAAATATATACAAGTGTTACAGCAGATAATTTG
GGAAATCCATTAACAAGTAATACAAAAGTAGATAATAAAGTTCTATAT
ATAGTACTTATAGATAATACTGTGATGGACTCAACAAAATAG PilA1 Amino Acid
>gi|260688691|ref|YP_003219825.1|pilin
[Clostridium difficile R20291] (SEQ ID NO: 46)
MKLKKNKKGFTLVELLVVIAIIGILAVVAVPALFSNINKAKVASVESDYSS
VKSAALSYYSDTNKIPVTPDGQTGLSVLETYMESLPDKADIGGKYKLIKVG
NKLVLQIGTNDEGVTLTEAQSAKLLSDIGENKIYTSVTADNLGNPLTSNTK
VDNKVLYIVLIDNTVMDSTK >gi|126701137|ref|YP_001090034.1|pilin protein
[Clostridium difficile 630] (SEQ ID NO: 14)
MKLKKNKKGFTLVELLVVIAIIGILAVVAVPALFSNINKAKVASVESDYSS
VKSAALSYYSDTNKIPVTPDGQTGLSVLETYMESLPDKADIGGKYKLIKVG
NKLVLQIGTNTEGVTLTEAQSAKLLSDIGENKIYTNAALSAKLTSTTKVNN
EALYIVLIDNIVMDQQGA >gi|423087244|ref|ZP_17075633.1|putative
general secretion pathway protein G
[Clostridium difficile 050-P50-2011]
(SEQ ID NO: 48)
MKLKKNKKGFTLVELLVVIAIIGILAVVAVPALFSNINKAKVASVESDYSS
VKSAALSYYSDTNKIPVTPDGQTGLNVLETYMESLPDKADIGGKYKLIKVG
GNKLVLQIGKDGEGVTLTEAQSAKLLSDIGKDKIYTGVTGDNFGDQLKDT
TKIDNKALYIVLIDNTVMDSTK >gi|423080843|ref|ZP_17069460.1|putative
general secretion pathway protein G
[Clostridium difficile 002-P50-2011]
(SEQ ID NO: 48)
MKLKKNKKGFTLVELLVVIAIIGILAVVAVPALFSNINKAKVASVESDYSS
VKSAALSYYSDTNKIPVTPDGQTGLNVLETYMESLPDKADIGGKYKLIKV
GNKLVLQIGKDGEGVTLTEAQSAKLLSDIGKDKIYTGVTGDNFGDQLKDT
TKIDNKALYIVLIDNTVMDSTK >gi|423090613|ref|ZP_17078902.1|prepilin-type
cleavage/methylation protein
[Clostridium difficile 70-100-2010]
(SEQ ID NO: 47)
MKLKKNKKGFTLVELLVVIAIIGILAVVAVPALFSNINKAKVASVESDYSS
VKSAALSYYSDTNKIPVTPDGQTGLSVLETYMESLPDKADIGGKYKLIKVG
NKLVLQIGTNTEGVTLTEAQSAKLLSDIGENKIYTSTTTNSLGNPLTSNTK
IDNNVLYIVLIDNTVMDTTK >gi|296449065|ref|ZP_06890855.1|pilin protein
[Clostridium difficile NAP08] (SEQ ID NO: 10)
MKLKKNKKGFTLVELLVVIAIIGILAVVAVPALFSNINKAKVASVESDYSS
IKSAALSYYSDTNKIPVTPDGQTGLNVLETYMESLPDKADIGGEYKLIKVG
NKLVLQIGKDGEGVTLTEAQSAKLLSDIGKDKIYTGVTGDNFGEQLKDTTK
IDNKALYIVLIDNTVMDSTK >gi|296879888|ref|ZP_06903861.1|pilin protein
[Clostridium difficile NAP07] (SEQ ID NO: 10)
MKLKKNKKGFTLVELLVVIAIIGILAVVAVPALFSNINKAKVASVESDYSS
IKSAALSYYSDTNKIPVTPDGQTGLNVLETYMESLPDKADIGGEYKLIKVG
NKLVLQIGKDGEGVTLTEAQSAKLLSDIGKDKIYTGVTGDNFGEQLKDTTK
IDNKALYIVLIDNTVMDSTK >gi|260685033|ref|YP_003216318.1|pilin
[Clostridium difficile CD196] (SEQ ID NO: 46)
MKLKKNKKGFTLVELLVVIAIIGILAVVAVPALFSNINKAKVASVESDYSS
VKSAALSYYSDTNKIPVTPDGQTGLSVLETYMESLPDKADIGGKYKLIKVG
NKLVLQIGTNDEGVTLTEAQSAKLLSDIGENKIYTSVTADNLGNPLTSNTK
VDNKVLYIVLIDNTVMDSTK >gi|255102723|ref|ZP_05331700.1|pilin
[Clostridium difficile QCD-63q42] (SEQ ID NO: 6)
MKLKKNKKGFTLVELLVVIAIIGILAVVAVPALFSNINKAKVASVESDYSS
VKSAALSYYSDTNKIPVTPDGQTGLSVLETYMESLPDKADIGGEYKLIKVG
SKLVLQIGTNTEGVTLTEAQSAKLLSDIGEKKIYTSATTNSLGDPLTSNTK
IDNKVLYIVLIDNTVMDTTK >gi|255316218|ref|ZP_05357801.1|pilin
[Clostridium difficile QCD-76w55] (SEQ ID NO: 46)
MKLKKNKKGFTLVELLVVIAIIGILAVVAVPALFSNINKAKVASVESDYSS
VKSAALSYYSDTNKIPVTPDGQTGLSVLETYMESLPDKADIGGKYKLIKVG
NKLVLQIGTNDEGVTLTEAQSAKLLSDIGENKIYTSVTADNLGNPLTSNTK
VDNKVLYIVLIDNTVMDSTK >gi|255652059|ref|ZP_05398961.1|pilin
[Clostridium difficile QCD-37x79] (SEQ ID NO: 46)
MKLKKNKKGFTLVELLVVIAIIGILAVVAVPALFSNINKAKVASVESDYSS
VKSAALSYYSDTNKIPVTPDGQTGLSVLETYMESLPDKADIGGKYKLIKVG
NKLVLQIGTNDEGVTLTEAQSAKLLSDIGENKIYTSVTADNLGNPLTSNTK
VDNKVLYIVLIDNTVMDSTK >gi|255308544|ref|ZP_05352715.1|pilin
[Clostridium difficile ATCC 43255] (SEQ ID NO: 18)
MKLKKNKKGFTLVELLVVIAIIGILAVVAVPALFSNINKAKVASVESDYSS
IKSAALSYYSDTNKMPATTSNPVDLENLKTYMESLPDKADIGGEYQLLLVG
NKLVLQINDATLTGAQSTKLLSDLGNDKIYKTIGSDDKLTDLLTTNEKLDN
KVLYLVLIDNAEMDSTK >gi|384362707|ref|YP_006200559.1|pilin
[Clostridium difficile BI1] (SEQ ID NO: 46)
MKLKKNKKGFTLVELLVVIAIIGILAVVAVPALFSNINKAKVASVESDYSS
VKSAALSYYSDTNKIPVTPDGQTGLSVLETYMESLPDKADIGGKYKLIKVG
NKLVLQIGTNDEGVTLTEAQSAKLLSDIGENKIYTSVTADNLGNPLTSNTK
VDNKVLYIVLIDNTVMDSTK >gi|255518880|ref|ZP_05386556.1|pilin
[Clostridium difficile QCD-97b34] (SEQ ID NO: 46)
MKLKKNKKGFTLVELLVVIAIIGILAVVAVPALFSNINKAKVASVESDYSS
VKSAALSYYSDTNKIPVTPDGQTGLSVLETYMESLPDKADIGGKYKLIKVG
NKLVLQIGTNDEGVTLTEAQSAKLLSDIGENKIYTSVTADNLGNPLTSNTK
VDNKVLYIVLIDNTVMDSTK >gi|254977138|ref|ZP_05273610.1|pilin
[Clostridium difficile QCD-66c26] (SEQ ID NO: 46)
MKLKKNKKGFTLVELLVVIAIIGILAVVAVPALFSNINKAKVASVESDYSS
VKSAALSYYSDTNKIPVTPDGQTGLSVLETYMESLPDKADIGGKYKLIKVG
NKLVLQIGTNDEGVTLTEAQSAKLLSDIGENKIYTSVTADNLGNPLTSNTK
VDNKVLYIVLIDNTVMDSTK >gi|255094467|ref|ZP_05323945.1|pilin
[Clostridium difficile CIP 107932] (SEQ ID NO: 46)
MKLKKNKKGFTLVELLVVIAIIGILAVVAVPALFSNINKAKVASVESDYSS
VKSAALSYYSDTNKIPVTPDGQTGLSVLETYMESLPDKADIGGKYKLIKVG
NKLVLQIGTNDEGVTLTEAQSAKLLSDIGENKIYTSVTADNLGNPLTSNTK
VDNKVLYIVLIDNTVMDSTK >gi|306521795|ref|ZP_07408142.1|pilin
[Clostridium difficile QCD-32g58] (SEQ ID NO: 46)
MKLKKNKKGFTLVELLVVIAIIGILAVVAVPALFSNINKAKVASVESDYSS
VKSAALSYYSDTNKIPVTPDGQTGLSVLETYMESLPDKADIGGKYKLIKVG
NKLVLQIGTNDEGVTLTEAQSAKLLSDIGENKIYTSVTADNLGNPLTSNTK
VDNKVLYIVLIDNTVMDSTK >gi|255657470|ref|ZP_05402879.1|pilin
[Clostridium difficile QCD-23m63] (SEQ ID NO: 10)
MKLKKNKKGFTLVELLVVIAIIGILAVVAVPALFSNINKAKVASVESDYSS
IKSAALSYYSDTNKIPVTPDGQTGLNVLETYMESLPDKADIGGEYKLIKVG
NKLVLQIGKDGEGVTLTEAQSAKLLSDIGKDKIYTGVTGDNFGEQLKDTTK
IDNKALYIVLIDNTVMDSTK PilA2 Nucleotide
>gi|260685375:c3766496-3766029 Clostridium
difficile R20291 chromosome, complete genome
(SEQ ID NO: 21)
TTGATAAATTTGATAAATAAAAACGAAAAGGATTTACACTTGTTGAA
ATGATTGTAGTAGTAACTATTTTAGGCGTTATATCTAGTATAGCATTAG
TTAAGTATAGTAAGGTTCAAGAAAGTGCCAAATTAAATGCAGACTATA
CGAATGCTGCTAATATAGTAACTGCAGCTAGCATGGCAATTAATGATG ATGAAAAGACAATAGACTCTCTAAGTGTAGAAACATTGAAGGAAAAGG
GATACCTAAATACTGTTCCAGTTCCTCAGAGTACATCAGGTAAATTCGA
ACTTGTCATAAATGATAGCGGAACAGATATAAGCGTAAATATAAATTC
TAAACAATTTTATCCAAAATAA >gi|126697566|ref|NC_009089.1|:3856110-3856577
Clostridium difficile 630,
complete genome reverse complement (SEQ ID NO: 49)
TTGATAAATTTGATAAATAAAAAACGAAAAGGATTTACACTTGTTGAA
ATGATTGTAGTAGTAACTATTTTAGGCGTTATATCTAGTATAGCATTAG
TTAAGTATAGTAAGGTTCAAGAAAGTGCCAAATTAAATGCAGACTATA
CGAATGCTGCTAATATAGTAACCGCAGCTAGCATGGCAATTAATGATG
ATGAAAAGACAATAGACTCTCTAAGTGTAGAGACATTGAAGGAAAAGG
GATACCTAAATACTGTTCCAGTTCCTCAGAGTACATCAGGTAAATTCGA
ACTTGTCATAAATGATAGCGGAACAGATATAAGCGTAAATATAAATTC
TAAGCAATTTTATCCAAAATAA >gi|260681769|ref|NC_013315.1|:3685254-3685721
Clostridium difficile CD196
chromosome, complete genome reverse complement
(SEQ ID NO: 21)
TTGATAAATTTGATAAATAAAAAACGAAAAGGATTTACACTTGTTGAA
ATGATTGTAGTAGTAACTATTTTAGGCGTTATATCTAGTATAGCATTAG
TTAAGTATAGTAAGGTTCAAGAAAGTGCCAAATTAAATGCAGACTATA
CGAATGCTGCTAATATAGTAACTGCAGCTAGCATGGCAATTAATGATG
ATGAAAAGACAATAGACTCTCTAAGTGTAGAAACATTGAAGGAAAAGG
GATACCTAAATACTGTTCCAGTTCCTCAGAGTACATCAGGTAAATTCGA
ACTTGTCATAAATGATAGCGGAACAGATATAAGCGTAAATATAAATTC
TAAACAATTTTATCCAAAATAA >gi|383843669|ref|NC_017179.1|:3693274-3693741
Clostridium difficile BI1,
complete genome reverse complement (SEQ ID NO: 21)
TTGATAAATTTGATAAATAAAAAACGAAAAGGATTTACACTTGTTGAA
ATGATTGTAGTAGTAACTATTTTAGGCGTTATATCTAGTATAGCATTAG
TTAAGTATAGTAAGGTTCAAGAAAGTGCCAAATTAAATGCAGACTATA
CGAATGCTGCTAATATAGTAACTGCAGCTAGCATGGCAATTAATGATG
ATGAAAAGACAATAGACTCTCTAAGTGTAGAAACATTGAAGGAAAAGG
GATACCTAAATACTGTTCCAGTTCCTCAGAGTACATCAGGTAAATTCGA
ACTTGTCATAAATGATAGCGGAACAGATATAAGCGTAAATATAAATTC
TAAACAATTTTATCCAAAATAA >gi|224514682|ref|NZ_CM000659.1|:3608806-3609273
Clostridium difficile CIP 107932 chromosome,whole
genome shotgun sequence_gi|221149347|gb|CM000659.1|
Clostridium difficile CIP 107932 chromosome,
whole genome shotgun sequence reverse complement
(SEQ ID NO: 21)
TTGATAAATTTGATAAATAAAAAACGAAAAGGATTTACACTTGTTGAA
ATGATTGTAGTAGTAACTATTTTAGGCGTTATATCTAGTATAGCATTAG
TTAAGTATAGTAAGGTTCAAGAAAGTGCCAAATTAAATGCAGACTATA
CGAATGCTGCTAATATAGTAACTGCAGCTAGCATGGCAATTAATGATG
ATGAAAAGACAATAGACTCTCTAAGTGTAGAAACATTGAAGGAAAAGG
GATACCTAAATACTGTTCCAGTTCCTCAGAGTACATCAGGTAAATTCGA
ACTTGTCATAAATGATAGCGGAACAGATATAAGCGTAAATATAAATTC
TAAACAATTTTATCCAAAATAA >gi|224514685|ref|NZ_CM000660.1|:3489896-3490353
Clostridium difficile
QCD-23m63, whole genome shotgun
sequence_gi|221149428|gb|CM000660.1|
Clostridium diffcil eQCD-23m63 chromosome,
whole genome shotgun sequence reverse complement
(SEQ ID NO: 25)
TTGATAAATAAAAAACGAAAAGGATTTACACTTGTTGAAATGATTGTA
GTAGTAACTATTTTAGGAGTTATATCTAGTATAGCATTAGTTAAGTATA
GTAAGGTTCAAGAAAGTGCTAAATTAAATGCAGACTATACGAATGCTG
CTAATATAGTAACAGCAGCTAGTTGGCAATTAATGATGATGAAAATA
TAATAGACTCTCTAAGTGTAGAAGCATTGAAGGAAAAGGGATACCTAA
ATACTGTTCCAGTTCCTCAGAGTACATCAGGTAAATTCGAACTTGTTAT
AAATGATAACGGAACAGATATAAGCGTGAATATAAATTCTAAGCAATT
TTATCCAAAATAA >gi|209401276|ref|NZ_CM000287.1|:3675531-3675998
Clostridium difficile QCD-32g58 chromosome, whole
genome shotgun sequence_gi|145843961|gb|CM000287.4|
Clostridium difficile QCD-32g58 chromosome,
whole genome shotgun sequence reverse complement
(SEQ ID NO: 21)
TTGATAAATTTGATAAATAAAAAACGAAAAGGATTTACACTTGTTGAA
ATGATTGTAGTAGTAACTATTTTAGGCGTTATATCTAGTATAGCATTAG TTAAGTATAGTAAGGTTCAAGAAAGTGCCAAATTAAATGCAGACTATA
CGAATGCTGCTAATATAGTAACTGCAGCTAGCATGGCAATTAATGATG
ATGAAAAGACAATAGACTCTCTAAGTGTAGAAACATTGAAGGAAAAGG
GATACCTAAATACTGTTCCAGTTCCTCAGAGTACATCAGGTAAATTCGA
ACTTGTCATAAATGATAGCGGAACAGATATAAGCGTAAATATAAATTC
TAAACAATTTTATCCAAAATAA >gi|224514680|ref|NZ_CM000658.1|:3624778-3625245
Clostridium difficile QCD-37x79 chromosome, whole
genome shotgun sequence_gi|221149249|gb|CM000658.1|
Clostridium difficile QCD-37x79 chromosome,
whole genome shotgun sequence reverse complement
(SEQ ID NO: 21)
TTGATAAATTTGATAAATAAAAAACGAAAAGGATTTACACTTGTTGAA
ATGATTGTAGTAGTAACTATTTTAGGCGTTATATCTAGTATAGCATTAG
TTAAGTATAGTAAGGTTCAAGAAAGTGCCAAATTAAATGCAGACTATA
CGAATGCTGCTAATATAGTAACTGCAGCTAGCATGGCAATTAATGATG
ATGAAAAGACAATAGACTCTCTAAGTGTAGAAACATTGAAGGAAAAGG
GATACCTAAATACTGTTCCAGTTCCTCAGAGTACATCAGGTAAATTCGA
ACTTGTCATAAATGATAGCGGAACAGATATAAGCGTAAATATAAATTC
TAAACAATTTTATCCAAAATAA >gi|224514674|ref|NZ_CM000637.1|:3656335-3656802
Clostridium difficile QCD-63q42 chromosome, whole
genome shotgun sequence_gi|219819758|gb|CM000637.1|
Clostridium difficile QCD-63q42 chromosome,
whole genome shotgun sequence reverse complement
(SEQ ID NO: 49)
TTGATAAATTTGATAAATAAAAAACGAAAAGGATTTACACTTGTTGAA
ATGATTGTAGTAACTATTTTAGGCGTTATATCTAGTATAGCATTAG
TTAAGTATAGTAAGGTTCAAGAAAGTGCCAAATTAAATGCAGACTATA
CGAATGCTGCTAATATAGTAACCGCAGCTAGCATGGCAATTAATGATG
ATGAAAAGACAATAGACTCTCTAAGTGTAGAGACATTGAAGGAAAAGG
GATACCTAAATACTGTTCCAGTTCCTCAGAGTACATCAGGTAAATTCGA
ACTTGTCATAAATGATAGCGGAACAGATATAAGCGTAAATATAAATTC
TAAGCAATTTTATCCAAAATAA >gi|224531476|ref|NZ_CM000441.1|:3626011-3626478
Clostridium difficile QCD-66c26 chromosome, whole
genome shotgun sequence_gi|222154275|gb|CM000441.2|
Clostridium difficile QCD-66c26 chromosome,
whole genome shotgun sequence reverse complement
(SEQ ID NO: 21)
TTGATAAATTTGATAAATAAAAAACGAAAAGGATTTACACTTGTTGAA
ATGATTGTAGTAGTAACTATTTTAGGCGTTATATCTAGTATAGCATTAG
TTAAGTATAGTAAGGTTCAAGAAAGTGCCAAATTAAATGCAGACTATA
CGAATGCTGCTAATATAGTAACTGCAGCTAGCATGGCAATTAATGATG
ATGAAAAGACAATAGACTCTCTAAGTGTAGAAACATTGAAGGAAAAGG
GATACCTAAATACTGTTCCAGTTCCTCAGAGTACATCAGGTAAATTCGA
ACTTGTCATAAATGATAGCGGAACAGATATAAGCGTAAATATAAATTC
TAAACAATTTTATCCAAAATAA >gi|224514686|ref|NZ_CM000661.1|:3669441-3669908
Clostridium difficile QCD-76w55 chromosome, whole
genome shotgun sequence_gi|221191950|gb|CM000661.1|
Clostridium difficile QCD-76w55 chromosome,
whole genome shotgun sequence reverse complement
(SEQ ID NO: 21)
TTGATAAATTTGATAAATAAAAAACGAAAAGGATTTACACTTGTTGAA
ATGATTGTAGTAGTAACTATTTTAGGCGTTATATCTAGTATAGCATTAG
TTAAGTATAGTAAGGTTCAAGAAAGTGCCAAATTAAATGCAGACTATA
CGAATGCTGCTAATATAGTAACTGCAGCTAGCATGGCAATTAATGATG
ATGAAAAGACAATAGACTCTCTAAGTGTAGAAACATTGAAGGAAAAGG
GATACCTAAATACTGTTCCAGTTCCTCAGAGTACATCAGGTAAATTCGA
ACTTGTCATAAATGATAGCGGAACAGATATAAGCGTAAATATAAATTC
TAAACAATTTTATCCAAAATAA >gi|224514679|ref|NZ_CM000657.1|:3592135-3592602
Clostridium difficile QCD-97b34 chromosome, whole
genome shotgun sequence_gi|221149047|gb|CM000657.1|
Clostridium difficile QCD-97b34 chromosome,
whole genome shotgun sequence reverse complement
(SEQ ID NO: 21)
TTGATAAATTTGATAAATAAAAAACGAAAAGGATTTACACTTGTTGAA
ATGATTGTAGTAGTAACTATTTTAGGCGTTATATCTAGTATAGCATTAG
TTAAGTATAGTAAGGTTCAAGAAAGTGCCAAATTAAATGCAGACTATA
CGAATGCTGCTAATATAGTAACTGCAGCTAGCATGGCAATTAATGATG
ATGAAAAGACAATAGACTCTCTAAGTGTAGAAACATTGAAGGAAAAGG
GATACCTAAATACTGTTCCAGTTCCTCAGAGTACATCAGGTAAATTCGA
ACTTGTCATAAATGATAGCGGAACAGATATAAGCGTAAATATAAATTC
TAAACAATTTTATCCAAAATAA PilA2 Amino Acid
>gi|260688496|ref|YP_003219630.1|type IV pilin
[*Clostridium difficile* R20291]
MINLINKKRKGFTLVEMIVVVTILGVISSIALVKYSKVQESAKLNADYTNA
ANIVTAASMAINDDEKTIDSLSVETLKEKGYLNTVPVPQSTSGKFELVIND
SGTDISVNINSKQFYPK (SEQ ID NO: 22)

>gi|126700913|ref|YP_001089810.1|type IV pilin PilA
[*Clostridium difficile* 630] (SEQ ID NO: 22)
MINLINKKRKGFTLVEMIVVVTILGVISSIALVKYSKVQESAKLNADYTNA
ANIVTAASMAINDDEKTIDSLSVETLKEKGYLNTVPVPQSTSGKFELVIND
SGTDISVNINSKQFYPK >gi|423085901|ref|ZP_17074336.1|prepilin-type
cleavage/methylation protein
[*Clostridium difficile* 050-P50-2011]
(SEQ ID NO: 50)
MINKKRKGFTLVEMIVVVTILGVISSIALVKYSKVQESAKLNADYTNAANI
VTAASMAINDDEKIIDSLSVETLKEKGYLNTVPVPQSTSGKFELVINDNGT
DISVNINSKQFYPK >gi|423081802|ref|ZP_17070401.1|prepilin-type
cleavage/methylation protein
[*Clostridium difficile* 002-P50-2011]
(SEQ ID NO: 50)
MINKKRKGFTLVEMIVVVTILGVISSIALVKYSKVQESAKLNADYTNAANI
VTAASMAINDDEKIIDSLSVETLKEKGYLNTVPVPQSTSGKFELVINDNGT
DISVNINSKQFYPK >gi|423089396|ref|ZP_17077755.1|prepilin-type
cleavage/methylation protein
[*Clostridium difficile* 70-100-2010]
(SEQ ID NO: 51)
MINKKRKGFTLVEMIVVVTILGVISSIALVKYSKVQESAKLNADYTNAANI
VTAASMAINDDEKTIDSLSVETLKEKGYLNTVPVPQSTSGKFELVINDSGT
DISVNINSKQFYPK >gi|296451909|ref|ZP_06893625.1|probable type
IV pilin [*Clostridium difficile* NAP08]
(SEQ ID NO: 26)
MINKKRKGFTLVEMIVVVTILGVISSIALVKYSKVQESAKLNADYTNAANI
VTAASMAINDDENIIDSLSVEALKEKGYLNTVPVPQSTSGKFELVINDNGT
DISVNINSKQFYPK >gi|296879698|ref|ZP_06903673.1|probable type
IV pilin [*Clostridium difficile* NAP07]
(SEQ ID NO: 26)
MINKKRKGFTLVEMIVVVTILGVISSIALVKYSKVQESAKLNADYTNAANI
VTAASMAINDDENIIDSLSVEALKEKGYLNTVPVPQSTSGKFELVINDNGT
DISVNINSKQFYPK >gi|260684838|ref|YP_003216123.1|type IV pilin
[*Clostridium difficile* CD196] (SEQ ID NO: 22)
MINLINKKRKGFTLVEMIVVVTILGVISSIALVKYSKVQESAKLNADYTNA
ANIVTAASMAINDDEKTIDSLSVETLKEKGYLNTVPVPQSTSGKFELVIND
SGTDISVNINSKQFYPK >gi|255102461|ref|ZP_05331438.1|putative type
IV pilin [*Clostridium difficile* QCD-63q42]
(SEQ ID NO: 22)
MINLINKKRKGFTLVEMIVVVTILGVISSIALVKYSKVQESAKLNADYTNA
ANIVTAASMAINDDEKTIDSLSVETLKEKGYLNTVPVPQSTSGKFELVIND
SGTDISVNINSKQFYPK >gi|255316033|ref|ZP_05357616.1|putative type
IV pilin [*Clostridium difficile* QCD-76w55]
(SEQ ID NO: 22)
MINLINKKRKGFTLVEMIVVVTILGVISSIALVKYSKVQESAKLNADYTNA
ANIVTAASMAINDDEKTIDSLSVETLKEKGYLNTVPVPQSTSGKFELVIND
SGTDISVNINSKQFYPK >gi|255651812|ref|ZP_05398714.1|putative type
IV pilin [*Clostridium difficile* QCD-37x79]
(SEQ ID NO: 22)
MINLINKKRKGFTLVEMIVVVTILGVISSIALVKYSKVQESAKLNADYTNA
ANIVTAASMAINDDEKTIDSLSVETLKEKGYLNTVPVPQSTSGKFELVIND
SGTDISVNINSKQFYPK >gi|255308366|ref|ZP_05352537.1|putative type
IV pilin [*Clostridium difficile* ATCC 43255]
(SEQ ID NO: 22)
MINLINKKRKGFTLVEMIVVVTILGVISSIALVKYSKVQESAKLNADYTNA
ANIVTAASMAINDDEKTIDSLSVETLKEKGYLNTVPVPQSTSGKFELVIND
SGTDISVNINSKQFYPK >gi|384362508|ref|YP_006200360.1|type IV pilin
[*Clostridium difficile* BI1] (SEQ ID NO: 22)
MINLINKKRKGFTLVEMIVVVTILGVISSIALVKYSKVQESAKLNADYTNA
ANIVTAASMAINDDEKTIDSLSVETLKEKGYLNTVPVPQSTSGKFELVIND
SGTDISVNINSKQFYPK >gi|255518690|ref|ZP_05386366.1|putative type IV
pilin [*Clostridium difficile* QCD-97b34]
(SEQ ID NO: 22)
MINLINKKRKGFTLVEMIVVVTILGVISSIALVKYSKVQESAKLNADYTNA
ANIVTAASMAINDDEKTIDSLSVETLKEKGYLNTVPVPQSTSGKFELVIND
SGTDISVNINSKQFYPK >gi|254976893|ref|ZP_05273365.1|putative type
IV pilin [*Clostridium difficile* QCD-66c26]
(SEQ ID NO: 22)
MINLINKKRKGFTLVEMIVVVTILGVISSIALVKYSKVQESAKLNADYTNA
ANIVTAASMAINDDEKTIDSLSVETLKEKGYLNTVPVPQSTSGKFELVIND
SGTDISVNINSKQFYPK >gi|255094280|ref|ZP_05323758.1|putative type
IV pilin [*Clostridium difficile* CIP 107932]
(SEQ ID NO: 22)
MINLINKKRKGFTLVEMIVVVTILGVISSIALVKYSKVQESAKLNADYTNA
ANIVTAASMAINDDEKTIDSLSVETLKEKGYLNTVPVPQSTSGKFELVIND
SGTDISVNINSKQFYPK >gi|306521600|ref|ZP_07407947.1|putative type
IV pilin [*Clostridium difficile* QCD-32g58]
(SEQ ID NO: 22)
MINLINKKRKGFTLVEMIVVVTILGVISSIALVKYSKVQESAKLNADYTNA
ANIVTAASMAINDDEKTIDSLSVETLKEKGYLNTVPVPQSTSGKFELVIND
SGTDISVNINSKQFYPK >gi|255657252|ref|ZP_05402661.1|putative type
IV pilin [*Clostridium difficile* QCD-23m63]
(SEQ ID NO: 26)
MINKKRKGFTLVEMIVVVTILGVISSIALVKYSKVQESAKLNADYTNAANI
VTAASMAINDDENIIDSLSVEALKEKGYLNTVPVPQSTSGKFELVINDNGT
DISVNINSKQFYPK PilJ Nucleotide
>gi|260685375:847037-848101 *Clostridium difficile*
R20291 chromosome, complete genome (SEQ ID NO: 41)
ATGGGAATGATTATTATGAATAAAAAGGGTTTTACATTAATTGAATTGT
TGGTAGTTATATCTATAATAGGAATTTTAGTTATAGTAGCTGTTCCAGC
GTTATTTAGAAATATAGAAAAAAGTAAGGCAGTTACATGTCTTTCTAAT
AGAGAAAATATAAAGACTCAAATTGTTATTGCAATGGCTGAGGAATCA
AGTAAAGCAAGAATGAAGTCATAAAAGAGGTATTAGAAAACAAAGA
TGGTAAGTACTTTGAAACAGAACCAAAGTGTAAGTCAGGTGGAATATA
TTCAGCAACGTTTGATGATGGTTATGATGGAATAACTGGAATAGAAAG
CATTGCAAAAGTGTATGTTACTTGTACAAAACATCCAGATGGTATTGAA
ATGGCTAGGGATATACATCAAAGTATGAAAGATTTGATTGCATCATTTG
CACAAGACCCTTCTATAATACCAGGAGCTTCAAAGGGCAATGATGATT
TTAGAAAATATTTATTAGACAATAAATATAAAAATGGGTGGCCTACAA
TTCCAGATGAATTTAAGGCAAAATATGGATTAAGTAAGGATACACTAT
ATATACAACCATATGCATATAATCCTACTAAATCTGATGCTACTGTAGT
TGTATTTGCAAATAATAAGACTGGAGGTAATTGGTATACTTCCCTAGTT
TACGATTATGATGAAGGTAGATGGTATAAAGGTAAAAATGGTATTTCT
GTTGCAGGTAGGTCATGGGATGTTGACACAGATAGTGTTAAGTCTGTA
AAAACAGAGATTCATTCTAAAGAGGGATGGGGTCCTTTAAATTAATAT
ATCATGTTTTATTAATCTGGTATTGATTAAACTATAGAAAAGAGCAGTT
TCTATAGATGACGAATACCAGATTTTCATTTATATGTAATTAAGATA
TATTAAAAGTATTTATATTTT >gi|126697566:923152-924195 *Clostridium difficile*
630, complete genome (SEQ ID NO: 112)
ATGGGAATGATTATTATGAATAAAAAGGGTTTTACACTAATTGAATTGT
TAGTAGTTATATCTATAATAGGCATTTTAGTTATAGTAGCTATTCCAGC
ATTGTTTAGAAATATAGAAAAAAGTAAAGCAGTTACATGTCTTTCTAAT
AGAGAAAATATAAAGACTCAAATTGTTATTGCAATGGCTGAGGAATCA
AGTAAGGGCAAGAATGAAGTCATGAAAGAGGTATTAGAAAACAAAGA
TGGTAAGTACTTTGAAACAGAACCAAAGTGTAAGTCAGGTGGAATATA
TTCAGCAACGTTTGATGATGGTTATGATGGAATAACTGGAATAGAAAG -continued
CATTGCAAAAGTGTATGTTACTTGTACAAAACATCCAGATGGTGTTGAA
ATGGCTAGGGATATACATCAAAGTATGAAAGATTTGATTGCATCATTTT
CACAAGACCCTTCTATAATACCAGGAGCCTCAAAGGGTAATGATGATT
TTAGAAAATATTTATTAGACAATAAATATAAAAATGGGTGGCCTACAA
TTCCAGATGAATTTAAGGCAAAATATGGATTAAGTAAGGATACACTAT
ATATACAACCATATGCATATAGTCCTACTAAATCTGATGCTACTGTAGT
TGTATTTGCAAATAATAAGACTGGGGGTAATTGGTATACTTCCCTAGTT
TACGATTATGATGAAGGTAGATGGTATAAAGGTAAAAATGGTATTTCT
GTTGCAGGTAGGTCATGGGATGTTGACACAGATAGTGTTAAGTCTGTA
AAAACAGAGATTCATTCTAAAGAGGGATGGGGTCCTTTAAATTAATAT
ATCATGTTTTATTAATCTGGTATTGATTAAACTATAGAAAAGAGCAGTT
TCTATAGATGACGAATACCAGATTTTCATTTATATATAATTGAGATA
TATTAAAAGTGTTTATAT >gi|260681769:849422-850486 *Clostridium difficile*
CD196 chromosome, complete genome (SEQ ID NO: 41)
ATGGGAATGATTATTATGAATAAAAAGGGTTTTACATTAATTGAATTGT
TGGTAGTTATATCTATAATAGGAATTTTAGTTATAGTAGCTGTTCCAGC
GTTATTTAGAAATATAGAAAAAAGTAAGGCAGTTACATGTCTTTCTAAT
AGAGAAAATATAAAGACTCAAATTGTTATTGCAATGGCTGAGGAATCA
AGTAAAGACAAGAATGAAGTCATAAAAGAGGTTATTAGAAAACAAAGA
TGGTAAGTACTTTGAAACAGAACCAAAGTGTAAGTCAGGTGGAATATA
TTCAGCAACGTTTGATGATGGTTATGATGGAATAACTGGAATAGAAAG
CATTGCAAAAGTGTATGTTACTTGTACAAAACATCCAGATGGTATTGAA
ATGGCTAGGGATATACATCAAAGTATGAAAGATTTGATTGCATCATTTG
CACAAGACCCTTCTATAATACCAGGAGCTTCAAAGGGCAATGATGATT
TTAGAAAATATTTATTAGACAATAAATATAAAAATGGGTGGCCTACAA
TTCCAGATGAATTTAAGGCAAAATATGGATTAAGTAAGGATACACTAT
ATATACAACCATATGCATATAATCCTACTAAATCTGATGCTACTGTAGT
TGTATTTGCAAATAATAAGACTGGAGGTAATTGGTATACTTCCCTAGTT
TACGATTATGATGAAGGTAGATGGTATAAAGGTAAAAATGGTATTTCT
GTTGCAGGTAGGTCATGGGATGTTGACACAGATAGTGTTAAGTCTGTA
AAAACAGAGATTCATTCTAAAGAGGGATGGGGTCCTTTAAATTAATAT
ATCATGTTTTATTAATCTGGTATTGATTAAACTATAGAAAAGAGCAGTT
TCTATAGATGACGAATACCAGATTTTCATTTATATGTATAATTAAGATA
TATTAAAAGTATTTATATTTT >gi|383843669:859218-860261 *Clostridium difficile*
BI1, complete genome (SEQ ID NO: 113)
ATGGGAATGATTATTATGAATAAAAAGGGTTTTACATTAATTGAATTGT
TGGTAGTTATATCTATAATAGGAATTTTAGTTATAGTAGCTGTTCCAGC
GTTATTTAGAAATATAGAAAAAAGTAAGGCAGTTACATGTCTTTCTAAT
AGAGAAAATATAAAGACTCAAATTGTTATTGCAATGGCTGAGGAATCA
AGTAAAGACAAGAATGAAGTCATAAAAGAGGTTATTAGAAAACAAAGA
TGGTAAGTACTTTGAAACAGAACCAAAGTGTAAGTCAGGTGGAATATA
TTCAGCAACGTTTGATGATGGTTATGATGGAATAACTGGAATAGAAAG
CATTGCAAAAGTGTATGTTACTTGTACAAAACATCCAGATGGTATTGAA
ATGGCTAGGGATATACATCAAAGTATGAAAGATTTGATTGCATCATTTG
CACAAGACCCTTCTATAATACCAGGAGCTTCAAAGGGCAATGATGATT
TTAGAAAATATTTATTAGACAATAAATATAAAAATGGGTGGCCTACAA
TTCCAGATGAATTTAAGGCAAAATATGGATTAAGTAAGGATACACTAT
ATATACAACCATATGCATATAATCCTACTAAATCTGATGCTACTGTAGT
TGTATTTGCAAATAATAAGACTGGAGGTAATTGGTATACTTCCCTAGTT
TACGATTATGATGAAGGTAGATGGTATAAAGGTAAAAATGGTATTTCT
GTTGCAGGTAGGTCATGGGATGTTGACACAGATAGTGTTAAGTCTGTA
AAAACAGAGATTCATTCTAAAGAGGGATGGGGTCCTTTAAATTAATAT
ATCATGTTTTATTAATCTGGTATTGATTAAACTATAGAAAAGAGCAGTT
TCTATAGATGACGAATACCAGATTTTCATTTATATGTATAATTAAGATA
TATTAAAAGTATTTATAT >gi|224514682|ref|NZ_CM000659.1|:800966-802012
*Clostridium difficile* CIP 107932 chromosome, whole
genome shotgun sequence_gi|221149347|gb|CM000659.1|
*Clostridium difficile* CIP 107932 chromosome,
whole genome shotgun sequence (SEQ ID NO: 113)
ATGGGAATGATTATTATGAATAAAAAGGGTTTTACATTAATTGAATTGT
TGGTAGTTATATCTATAATAGGAATTTTAGTTATAGTAGCTGTTCCAGC
GTTATTTAGAAATATAGAAAAAAGTAAGGCAGTTACATGTCTTTCTAAT
AGAGAAAATATAAAGACTCAAATTGTTATTGCAATGGCTGAGGAATCA
AGTAAAGACAAGAATGAAGTCATAAAAGAGGTTATTAGAAAACAAAGA
TGGTAAGTACTTTGAAACAGAACCAAAGTGTAAGTCAGGTGGAATATA
TTCAGCAACGTTTGATGATGGTTATGATGGAATAACTGGAATAGAAAG
CATTGCAAAAGTGTATGTTACTTGTACAAAACATCCAGATGGTATTGAA
ATGGCTAGGGATATACATCAAAGTATGAAAGATTTGATTGCATCATTTG
CACAAGACCCTTCTATAATACCAGGAGCTTCAAAGGGCAATGATGATT
TTAGAAAATATTTATTAGACAATAAATATAAAAATGGGTGGCCTACAA
TTCCAGATGAATTTAAGGCAAAATATGGATTAAGTAAGGATACACTAT
ATATACAACCATATGCATATAATCCTACTAAATCTGATGCTACTGTAGT
TGTATTTGCAAATAATAAGACTGGAGGTAATTGGTATACTTCCCTAGTT
TACGATTATGATGAAGGTAGATGGTATAAAGGTAAAAATGGTATTTCT
GTTGCAGGTAGGTCATGGGATGTTGACACAGATAGTGTTAAGTCTGTA -continued
AAAACAGAGATTCATTCTAAAGAGGGATGGGGTCCTTTAAATTAATAT
ATCATGTTTTATTAATCTGGTATTGATTAAACTATAGAAAAGAGCAGTT
TCTATAGATGACGAATACCAGATTTTCATTTATATGTATAATTAAGATA
TATTAAAAGTATTTATATTTT >gi|224514685|ref|NZ_CM000660.1|:777898-778921
*Clostridium difficile* QCD-23m63 chromosome, whole
genome shotgun sequence_gi|221149428|gb|CM000660.1|
Q*Clostridium difficile* CD-23m63 chromosome,
whole genome shotgun sequence (SEQ ID NO: 114)
ATGGGAATGATTATTATGAATAAAAAGGGTTTTACACTAATTGAATTGT
TGGTAGTTATATCTATAATAGGAATTTTAGTTATAGTAGCTGTTCCAGC
GTTATTTAGAAATATAGAAAAAAGTAAGGCGGTTACATGCCTTTCTAAT
AGAGAAAATATAAAGACTCAAATTGTTATTGCAATGGCTGAGGAACCA
AGTAAAGATAAGAATAAAGTCATAAAAGATGTACTAGAAAATAAAGA
TGGTAAGTACTTTGAAACAGAACCAAAGTGTAAATCAGGTGGAATATA
TTCAGCAACGTTTGATGATGGTTATGATGGAATAACTGGAGGAGAAAG
CATTGCAAAAGTGTATGTTACTTGTACAGAACATCCAGACGGTGTTGAA
ATGGCTAGGGATGTACATCAAAGTATGAAAGATTTGATTGCATCATTTG
CACAAGACCCTTCTATAATACCAGGAGCTTCAAAGAGTAATGATGATT
TAGAAAATATTTATTAGACAATAAATATAAAAAGGGATGGCCTACAAT
TCCAGATGAATTTAAGGCAAAATATGGATTAAGTAAGGATACACTATA
TATACAACCATATGCATATAATCCTACTAAACCTGATGCCACTGTAGTT
GTATTTGCAAATAATAAGACTGGAGGTAATTGGTACACTTCCCTAGTTT
ACGATTATGATGAAGGTAGATGGTATAAAGGCAAAAATGGTATTTCTT
TGCAGGTAGGTCATGGGATGTTGATACAGATAGTGTTAAGTCTGTAA
AACAGAGATTCATTCTAAAGAGGGTGGGGTCCTTTAAATTAATATAT
AATGTTTTATTAATCTGGTATTGATTAAACTATAGAAAAGAGCAGTTTC
TATAGATGACGAATACCAGATTTTTATTTATATGTATAATTAATATATA
TTAAAAGTATTTATATTTT >gi|209401276|ref|NZ_CM000287.1|:818371-819417
*Clostridium difficile* QCD-32g58 chromosome, whole
genome shotgun sequence_gi|145843961|gb|CM000287.4|
*Clostridium difficile* QCD-32g58 chromosome,
whole genome shotgun sequence (SEQ ID NO: 113)
ATGGGAATGATTATTATGAATAAAAAGGGTTTTACATTAATTGAATTGT
TGGTAGTTATATCTATAATAGGAATTTTAGTTATAGTAGCTGTTCCAGC
GTTATTTAGAAATATAGAAAAAAGTAAGGCAGTTACATGTCTTTCTAAT
AGAGAAAATATAAAGACTCAAATTGTTATTGCAATGGCTGAGGAATCA
AGTAAAGACAAGAATGAAGTCATAAAAGAGGTTATTAGAAAACAAAGA
TGGTAAGTACTTTGAAACAGAACCAAAGTGTAAGTCAGGTGGAATATA
TTCAGCAACGTTTGATGATGGTTATGATGGAATAACTGGAATAGAAAG
CATTGCAAAAGTGTATGTTACTTGTACAAAACATCCAGATGGTATTGAA
ATGGCTAGGGATATACATCAAAGTATGAAAGATTTGATTGCATCATTTG
CACAAGACCCTTCTATAATACCAGGAGCTTCAAAGGGCAATGATGATT
TTAGAAAATATTTATTAGACAATAAATATAAAAATGGGTGGCCTACAA
TTCCAGATGAATTTAAGGCAAAATATGGATTAAGTAAGGATACACTAT
ATATACAACCATATGCATATAATCCTACTAAATCTGATGCTACTGTAGT
TGTATTTGCAAATAATAAGACTGGAGGTAATTGGTATACTTCCCTAGTT
TACGATTATGATGAAGGTAGATGGTATAAAGGTAAAAATGGTATTTCT
GTTGCAGGTAGGTCATGGGATGTTGACACAGATAGTGTTAAGTCTGTA
AAAACAGAGATTCATTCTAAAGAGGGATGGGGTCCTTTAAATTAATAT
ATCATGTTTTATTAATCTGGTATTGATTAAACTATAGAAAAGAGCAGTT
TCTATAGATGACGAATACCAGATTTTCATTTATATGTATAATTAAGATA
TATTAAAAGTATTTATATTTT >gi|224514680|ref|NZ_CM000658.1|:805580-806626
*Clostridium difficile* QCD-37x79 chromosome, whole
genome shotgun sequence_gi|221149249|gb|CM000658.1|
*Clostridium difficile* QCD-37x79 chromosome,
whole genome shotgun sequence (SEQ ID NO: 113)
ATGGGAATGATTATTATGAATAAAAAGGGTTTTACATTAATTGAATTGT
TGGTAGTTATATCTATAATAGGAATTTTAGTTATAGTAGCTGTTCCAGC
GTTATTTAGAAATATAGAAAAAAGTAAGGCAGTTACATGTCTTTCTAAT
AGAGAAAATATAAAGACTCAAATTGTTATTGCAATGGCTGAGGAATCA
AGTAAAGACAAGAATGAAGTCATAAAAGAGGTTATTAGAAAACAAAGA
TGGTAAGTACTTTGAAACAGAACCAAAGTGTAAGTCAGGTGGAATATA
TTCAGCAACGTTTGATGATGGTTATGATGGAATAACTGGAATAGAAAG
CATTGCAAAAGTGTATGTTACTTGTACAAAACATCCAGATGGTATTGAA
ATGGCTAGGGATATACATCAAAGTATGAAAGATTTGATTGCATCATTTG
CACAAGACCCTTCTATAATACCAGGAGCTTCAAAGGGCAATGATGATT
TTAGAAAATATTTATTAGACAATAAATATAAAAATGGGTGGCCTACAA
TTCCAGATGAATTTAAGGCAAAATATGGATTAAGTAAGGATACACTAT
ATATACAACCATATGCATATAATCCTACTAAATCTGATGCTACTGTAGT
TGTATTTGCAAATAATAAGACTGGAGGTAATTGGTATACTTCCCTAGTT
TACGATTATGATGAAGGTAGATGGTATAAAGGTAAAAATGGTATTTCT
GTTGCAGGTAGGTCATGGGATGTTGACACAGATAGTGTTAAGTCTGTA
AAAACAGAGATTCATTCTAAAGAGGGATGGGGTCCTTTAAATTAATAT -continued
```
ATCATGTTTTATTAATCTGGTATTGATTAAACTATAGAAAAGAGCAGTT
TCTATAGATGACGAATACCAGATTTTCATTTATATGTATAATTAAGATA
TATTAAAAGTATTTATATTTT
```

>gi|224514674|ref|NZ_CM000637.1|:800346-801392
*Clostridium difficile* QCD-63q42 chromosome, whole
genome shotgun sequence_gi|219819758|gb|CM000637.1|
*Clostridium difficile* QCD-63q42 chromosome,
whole genome shotgun sequence (SEQ ID NO: 115)
```
ATGGGAATGATTATTATGAATAAAAAGGGTTTTACATTAATTGAATTGT
TGGTAGTTATATCTATAATAGGAATTTTAGTTATAGTAGCTGTTCCAGC
GTTATTTAGAAATATAGAAAAAAGTAAAGCAGTTACATGTCTTTCTAAT
AGAGAAAATATAAAGACTCAAATTGTTATTGCAATGGCTGAGGAATCA
AGTAAAGACAAGAATGAAGTCATAAAAGAGGTATTAGAAAACAAAGA
TGGTAAGTACTTTGAAACAGAACCAAAGTGTAAGTCAGGTGGAATATA
TTCAGCAACGTTTGATGATGGTTATGATGGAATAACTGGAATAGAAAG
CATTGCAAAAGTGTATGTTACTTGTACAAAACATCCAGACGGTGTTGAA
ATGGCTAGGGATGTGCATCAAAGTATGAAAGATTTGATTGCATCATTTG
CACAAGACCCTTCTATAATACCAGGAGCTTCAAAGGGCAATGATGATT
TTAGAAAATATTTATTAGACAATAAATATAAAAATGGGTGGCCTACAA
TTCCAGATGAATTTAAGGCAAAATATGGATTAAGTAAGGATACACTAT
ATATACAACCATATGCATATAATCCTACTAAATCTGATGCTACTGTAGT
TGTATTTGCAAATAATAAGACTGGAGGTAATTGGTATACTTCCCTAGTT
TACGATTATGATGAAGGTAGATGGTATAAAGGTAAAATGGTATTTCT
GTTGCAGGTAGGTCATGGGATGTTGACACAGATAGTGTTAAGTCTGTA
AAAACAGAGATTCATTCTAAAGAGGGATGGGGTCCTTTAAATTAATAT
ATCATGTTTATTAATCTGGTATTGATTAAACTATAGAAAAGAGCAGTT
TCTATAGATGACGAATACCAGATTTTCATTTATATATATAATTGAGATA
TATTAAAAGTGTTTATATTTT
```

>gi|224531476|ref|NZ_CM000441.1|:800735-801781
*Clostridium difficile* QCD-66c26 chromosome, whole
genome shotgun sequence_gi|222154275|gb|CM000441.2|
*Clostridium difficile* QCD-66c26 chromosome, whole
genome shotgun sequence (SEQ ID NO: 113)
```
ATGGGAATGATTATTATGAATAAAAAGGGTTTTACATTAATTGAATTGT
TGGTAGTTATATCTATAATAGGAATTTTAGTTATAGTAGCTGTTCCAGC
GTTATTTAGAAATATAGAAAAAAGTAAGGCAGTTACATGTCTTTCTAAT
AGAGAAAATATAAAGACTCAAATTGTTATTGCAATGGCTGAGGAATCA
AGTAAAGACAAGAATGAAGTCATAAAAGAGGTATTAGAAAACAAAGA
TGGTAAGTACTTTGAAACAGAACCAAAGTGTAAGTCAGGTGGAATATA
TTCAGCAACGTTTGATGATGGTTATGATGGAATAACTGGAATAGAAAG
CATTGCAAAAGTGTATGTTACTTGTACAAAACATCCAGATGGTATTGAA
ATGGCTAGGGATATACATCAAAGTATGAAAGATTTGATTGCATCATTTG
CACAAGACCCTTCTATAATACCAGGAGCTTCAAAGGGCAATGATGATT
TTAGAAAATATTTATTAGACAATAAATATAAAAATGGGTGGCCTACAA
TTCCAGATGAATTTAAGGCAAAATATGGATTAAGTAAGGATACACTAT
ATATACAACCATATGCATATAATCCTACTAAATCTGATGCTACTGTAGT
TGTATTTGCAAATAATAAGACTGGAGGTAATTGGTATACTTCCCTAGTT
TACGATTATGATGAAGGTAGATGGTATAAAGGTAAAATGGTATTTCT
GTTGCAGGTAGGTCATGGGATGTTGACACAGATAGTGTTAAGTCTGTA
AAAACAGAGATTCATTCTAAAGAGGGATGGGGTCCTTTAAATTAATAT
ATCATGTTTTATTAATCTGGTATTGATTAAACTATAGAAAAGAGCAGTT
TCTATAGATGACGAATACCAGATTTTCATTTATATGTATAATTAAGATA
TATTAAAAGTATTTATATTTT
```

>gi|224514686|ref|NZ_CM000661.1|:854434-855480
*Clostridium difficile* QCD-76w55 chromosome, whole
genome shotgun sequence_gi|221191950|gb|CM000661.1|
*Clostridium difficile* QCD-76w55 chromosome,
whole genome shotgun sequence (SEQ ID NO: 113)
```
ATGGGAATGATTATTATGAATAAAAAGGGTTTTACATTAATTGAATTGT
TGGTAGTTATATCTATAATAGGAATTTTAGTTATAGTAGCTGTTCCAGC
GTTATTTAGAAATATAGAAAAAAGTAAGGCAGTTACATGTCTTTCTAAT
AGAGAAAATATAAAGACTCAAATTGTTATTGCAATGGCTGAGGAATCA
AGTAAAGACAAGAATGAAGTCATAAAAGAGGTATTAGAAAACAAAGA
TGGTAAGTACTTTGAAACAGAACCAAAGTGTAAGTCAGGTGGAATATA
TTCAGCAACGTTTGATGATGGTTATGATGGAATAACTGGAATAGAAAG
CATTGCAAAAGTGTATGTTACTTGTACAAAACATCCAGATGGTATTGAA
ATGGCTAGGGATATACATCAAAGTATGAAAGATTTGATTGCATCATTTG
CACAAGACCCTTCTATAATACCAGGAGCTTCAAAGGGCAATGATGATT
TTAGAAAATATTTATTAGACAATAAATATAAAAATGGGTGGCCTACAA
TTCCAGATGAATTTAAGGCAAAATATGGATTAAGTAAGGATACACTAT
ATATACAACCATATGCATATAATCCTACTAAATCTGATGCTACTGTAGT
TGTATTTGCAAATAATAAGACTGGAGGTAATTGGTATACTTCCCTAGTT
TACGATTATGATGAAGGTAGATGGTATAAAGGTAAAATGGTATTTCT
GTTGCAGGTAGGTCATGGGATGTTGACACAGATAGTGTTAAGTCTGTA
AAAACAGAGATTCATTCTAAAGAGGGATGGGGTCCTTTAAATTAATAT
ATCATGTTTTATTAATCTGGTATTGATTAAACTATAGAAAAGAGCAGTT
TCTATAGATGACGAATACCAGATTTTCATTTATATGTATAATTAAGATA
TATTAAAAGTATTTATATTTT
```

>gi|224514679|ref|NZ_CM000657.1|:797810-798856
*Clostridium difficile* QCD-97b34 chromosome, whole
genome shotgun sequence_gi|221149047|gb|CM000657.1|
*Clostridium difficile* QCD-97b34 chromosome,
whole genome shotgun sequence (SEQ ID NO: 116)
```
ATGGGAATGATTATTATGAATAAAAAGGGTTTTACATTAATTGAATTGT
TGGTAGTTATATCTATAATAGGAATTTTAGTTATAGTAGCTGTTCCAGC
GTTATTTAGAAATATAGAAAAAGTAAGGCAGTTACATGTCTTTCTAAT
AGAGAAAATATAAAGACTCAAATTGTTATTGCAATGGCTGAGGAATCA
AGTAAAGACAAGAATGAAGTCATAAAAGAGGTATTAGAAAACAAAGA
TGGTAAGTACTTTGAAACAGAACCAAAGTGTAAGTCAGGTGGAATATA
TTCAGCAACGTTTGATGATGGTTATGATGGAATAACTGGAATAGAAAG
CATTGCAAAAGTGTATGTTACTTGTACAAAACATCCAGATGGTATTGAA
ATGGCTAGGGATATACATCAAAGTATGAAAGATTTGATTGCATCATTTG
CACAAGACCCTTCTATAATACCAGGAGCTTCAAAGGGCAATGATGATT
TTAGAAAATATTTATTAGACAATAAATATAAAAATGGGTGGCCTACAA
TTCCAGATGAATTTAAGGCAAAATATGGATTAAGTAAGGATACACTAT
ATATACAACCATATGCATATAATCCTACTAAATCTGATGCTACTGTAGT
TGTATTTGCAAATAATAAGACTGGAGGTAATTGGTATACTTCCCTAGTT
TACGATTATGATGAAGGTAGATGGTATAAAGGTAAAATGGTATTTCT
GTTGCAGGTAGGTCATGGGATGTTGACACAGATAGTGTTAAGTCTGTA
AAAACAGAGATTCATTCTAAAGAGGGATGGGGTCCTTTAAATTAATAT
ATCATGTTTTATTAATCTGGTATTGATTAAACTATAGAAAAGAGCAGTT
TCTATAGATGACGAATACCAGATTTTCATTTATATGTATAATTAAGATA
TATTAAAAGTATTTATATTTT
```

PilJ Amino Acid
>gi|260686051|ref|YP_003217184.1|fimbrial
protein [*Clostridium difficile* R20291]
(SEQ ID NO: 42)
```
MGMIIMNKKGFTLIELLVVISIIGILVIVAVPALFRNIEKSKAVTCLSNRE
NIKTQIVIAMAEESSKDKNEVIKEVLENKDGKYFETEPKCKSGGIYSATFD
DGYDGITGIESIAKVYVTCTKHPDGIEMARDIHQSMKDLIASFAQDPSIIP
GASKGNDDFRKYLLDNKYKNGWPTIPDEFKAKYGLSKDTLYIQPYAYNPTK
SDATVVVFANNKTGGNWYTSLVYDYDEGRWYKGKNGISVAGRSWDVDTDSV
KSVKTEIHSKEGWGPLN
```

>gi|126698335|ref|YP_001087232.1|cell
surface protein [*Clostridium difficile* 630]
(SEQ ID NO: 53)
```
MNKKGFTLIELLVVISIIGILVIVAIPALFRNIEKSKAVTCLSNRENIKTQ
IVIAMAEESSKGKNEVMKEVLENKDGKYFETEPKCKSGGIYSATFDDGYDG
ITGIESIAKVYVTCTKHPDGVEMARDIHQSMKDLIASFSQDPSIIPGASKG
NDDFRKYLLDNKYKNGWPTIPDEFKAKYGLSKDTLYIQPYAYSPTKSDATV
VVFANNKTGGNWYTSLVYDYDEGRWYKGKNGISVAGRSWDVDTDSVKSVKT
EIHSKEGWGPLN
```

>gi|423085739|ref|ZP_17074178.1|prepilin-type
cleavage/methylation protein
[*Clostridium difficile* 050-P50-2011]
(SEQ ID NO: 54)
```
MGMIIMNKKGFTLIELLVVISIIGILVIVAVPALFRNIEKSKAVTCLSNRE
NIKTQIVIAMAEEQSKDKNEVIKEVLQNKDGKYFETEPKCKSGGIYSATFD
DGYDGITGIESIAKVYVTCTKHPDGVEMARDVHQSMKDLIASFAQDPSIIP
GASKGNDDFRKYLLDNKYKNGWPTIPDEFKAKYGLSKDTLYIQPYAYNPTK
SDATVVVFANNKTGGNWYTSLVYDYDEGRWYKGKNGISVAGRSWDVDTDSA
KSVKTEIHSKEGWGPLN
```

>gi|423082115|ref|ZP_17070710.1|prepilin-type
cleavage/methylation protein
[*Clostridium difficile* 002-P50-2011]
(SEQ ID NO: 54)
```
MGMIIMNKKGFTLIELLVVISIIGILVIVAVPALFRNIEKSKAVTCLSNRE
NIKTQIVIAMAEEQSKDKNEVIKEVLQNKDGKYFETEPKCKSGGIYSATFD
DGYDGITGIESIAKVYVTCTKHPDGVEMARDVHQSMKDLIASFAQDPSIIP
GASKGNDDFRKYLLDNKYKNGWPTIPDEFKAKYGLSKDTLYIQPYAYNPTK
SDATVVVFANNKTGGNWYTSLVYDYDEGRWYKGKNGISVAGRSWDVDTDSA
KSVKTEIHSKEGWGPLN
```

>gi|423090405|ref|ZP_17078704.1|prepilin-type
cleavage/methylation protein
[*Clostridium difficile* 70-100-2010]
(SEQ ID NO: 55)
```
MGMIIMNKKGFTLIELLVVISIIGILVIVAVPALFRNIEKSKAVTCLSNRE
NIKTQIVIAMAEESSKGKNEVMKEVLENKDGKYFETEPKCKSGGIYSATFD
DGYDGITGIESIAKVYVTCTKHPDGVEMARDIHQSMKDLIASFAQDPSIIP
GASKGNDDFRKYLLDNKYKNGWPTIPDEFKAKYGLSKDTLYIQPYAYSPTK
SDATVVVFANNKTGGNWYTSLVYDYDEGRWYKGKNGISVAGRSWDVDTDS
VKSVKTEIHSKEGWGPLN
```

>gi|296449548|ref|ZP_06891325.1|fimbrial protein
(pilin) [*Clostridium difficile* NAP08]
(SEQ ID NO: 56)
MGMIIMNKKGFTLIELLVVISIIGILVIVAVPALFRNIEKSKAVT
CLSNRENIKTQIVIAMAEEPSKDKNKVIKDVLENKDGKYFETEPKCKSGGI
YSATFDDGYDGITGGESIAKVYVTCTEHPDGVEMARDVHQSMKDLIASFAQ
DPSIIPGASKSNDDFRKYLLDNKYKKGWPTIPDEFKAKYGLSKDTLYIQPY
AYNPTKPDATVVVFANNKTGGNWYTSLVYDYDEGRWYKGKNGISVAGRSW
DVDTDSVKSVKTEIHSKEGWGPLN >gi|296878129|ref|ZP_06902144.1|fimbrial protein
(pilin) [*Clostridium difficile* NAP07]
(SEQ ID NO: 56)
MGMIIMNKKGFTLIELLVVISIIGILVIVAVPALFRNIEKSKAVTCLSNRE
NIKTQIVIAMAEEPSKDKNKVIKDVLENKDGKYFETEPKCKSGGIYSATFD
DGYDGITGGESIAKVYVTCTEHPDGVEMARDVHQSMKDLIASFAQDPSIIP
GASKSNDDFRKYLLDNKYKKGWPTIPDEFKAKYGLSKDTLYIQPYAYNPTK
PDATVVVFANNKTGGNWYTSLVYDYDEGRWYKGKNGISVAGRSWDVDTDS
VKSVKTEIHSKEGWGPLN >gi|260682452|ref|YP_003213737.1|fimbrial protein
[*Clostridium difficile* CD196] (SEQ ID NO: 42)
MGMIIMNKKGFTLIELLVVISIIGILVIVAVPALFRNIEKSKAVTCLSNRE
NIKTQIVIAMAEESSKDKNEVIKEVLENKDGKYFETEPKCKSGGIYSATFD
DGYDGITGIESIAKVYVTCTKHPDGIEMARDIHQSMKDLIASFAQDPSIIP
GASKGNDDFRKYLLDNKYKNGWPTIPDEFKAKYGLSKDTLYIQPYAYNPTK
SDATVVVFANNKTGGNWYTSLVYDYDEGRWYKGKNGISVAGRSWDVDTDSV
KSVKTEIHSKEGWGPLN >gi|255099871|ref|ZP_05328848.1|fimbrial protein
(pilin) [*Clostridium difficile* QCD-63q42]
(SEQ ID NO: 57)
MNKKGFTLIELLVVISIIGILVIVAVPALFRNIEKSKAVTCLSNRENIKTQ
IVIAMAEESSKDKNEVIKEVLENKDGKYFETEPKCKSGGIYSATFDDGYDG
ITGIESIAKVYVTCTKHPDGVEMARDVHQSMKDLIASFAQDPSIIPGASKG
NDDFRKYLLDNKYKNGWPTIPDEFKAKYGLSKDTLYIQPYAYNPTKSDATV
VVFANNKTGGNWYTSLVYDYDEGRWYKGKNGISVAGRSWDVDTDSVKSV
TEIHSKEGWGPLN >gi|255313497|ref|ZP_05355080.1|fimbrial protein
(pilin) [*Clostridium difficile* QCD-76w55]
(SEQ ID NO: 58)
MNKKGFTLIELLVVISIIGILVIVAVPALFRNIEKSKAVTCLSNRENIKTQ
IVIAMAEESSKDKNEVIKEVLENKDGKYFETEPKCKSGGIYSATFDDGYDG
ITGIESIAKVYVTCTKHPDGIEMARDIHQSMKDLIASFAQDPSIIPGASKG
NDDFRKYLLDNKYKNGWPTIPDEFKAKYGLSKDTLYIQPYAYNPTKSDATV
VVFANNKTGGNWYTSLVYDYDEGRWYKGKNGISVAGRSWDVDTDSVKSVKT
EIHSKEGWGPLN >gi|255649281|ref|ZP_05396183.1|fimbrial protein
(pilin) [*Clostridium difficile* QCD-37x79]
(SEQ ID NO: 58)
MNKKGFTLIELLVVISIIGILVIVAVPALFRNIEKSKAVTCLSNRENIKTQ
IVIAMAEESSKDKNEVIKEVLENKDGKYFETEPKCKSGGIYSATFDDGYDG
ITGIESIAKVYVTCTKHPDGIEMARDIHQSMKDLIASFAQDPSIIPGASKG
NDDFRKYLLDNKYKNGWPTIPDEFKAKYGLSKDTLYIQPYAYNPTKSDATV
VVFANNKTGGNWYTSLVYDYDEGRWYKGKNGISVAGRSWDVDTDSVKSVKT
EIHSKEGWGPLN >gi|255305759|ref|ZP_05349931.1|fimbrial protein
(pilin) [*Clostridium difficile* ATCC 43255]
(SEQ ID NO: 59)
MNKKGFTLIELLVVISIIGILVIVAVPALFRNIEKSKAVTCLSNRENIKTQ
IVIAMAEESSKDKNEVIKEVLENKDGKYFETEPKCKSGGIYSATFDDGYDG
ITGRESIAKVYVTCTKHPDGVEMARDVHQSMKDLIASFAQDPSIIPGASKG
NDDFRKYLLDNKYKNGWPTIPDEFKAKYGLSKDTLYIQPYAYNPTKSDATV
VVFANNKTGGNWYTSLVYDYDEGRWYKGKNGISVAGRSWDVDTDSVKSVK
TEIHSKEGWGPLN >gi|384360033|ref|YP_006197885.1|fimbrial protein
[*Clostridium difficile* BI1] (SEQ ID NO: 58)
MNKKGFTLIELLVVISIIGILVIVAVPALFRNIEKSKAVTCLSNRENIKTQ
IVIAMAEESSKDKNEVIKEVLENKDGKYFETEPKCKSGGIYSATFDDGYDG
ITGIESIAKVYVTCTKHPDGIEMARDIHQSMKDLIASFAQDPSIIPGASKG
NDDFRKYLLDNKYKNGWPTIPDEFKAKYGLSKDTLYIQPYAYNPTKSDATV
VVFANNKTGGNWYTSLVYDYDEGRWYKGKNGISVAGRSWDVDTDSVKSVKT
EIHSKEGWGPLN >gi|255516185|ref|ZP_05383861.1|fimbrial protein
(pilin) [*Clostridium difficile* QCD-97b34]
(SEQ ID NO: 117)
MNKKGFTLIELLVVISIIGILVIVAVPALFRNIEKSKAVTCLSNRENIKTQ
IVIAMAEESSKDKNEVIKEVLENKDGKYFETEPKCKSGGIYSATFDDGYDG
ITGIESIAKVYVTCTKHPDGIEMARDIHQSMKDLIASFAQDPSIIPGASKG
NDDFRKYLLDNKYKNGWPTIPDEFKAKYGLSKDTLYIQPYAYNPTKSDATV
VVFANNKTGGNWYTSLVYDYDEGRWYKGKNGISVAGRSWDVDTDSVKSVKT
EIHSKEGWGPLN >gi|254974373|ref|ZP_05270845.1|fimbrial protein
(pilin) [*Clostridium difficile* QCD-66c26]
(SEQ ID NO: 58)
MNKKGFTLIELLVVISIIGILVIVAVPALFRNIEKSKAVTCLSNRENIKTQ
IVIAMAEESSKDKNEVIKEVLENKDGKYFETEPKCKSGGIYSATFDDGYDG
ITGIESIAKVYVTCTKHPDGIEMARDIHQSMKDLIASFAQDPSIIPGASKG
NDDFRKYLLDNKYKNGWPTIPDEFKAKYGLSKDTLYIQPYAYNPTKSDATV
VVFANNKTGGNWYTSLVYDYDEGRWYKGKNGISVAGRSWDVDTDSVKSVKT
EIHSKEGWGPLN >gi|255091767|ref|ZP_05321245.1|fimbrial protein
(pilin) [*Clostridium difficile* CIP 107932]
(SEQ ID NO: 58)
MNKKGFTLIELLVVISIIGILVIVAVPALFRNIEKSKAVTCLSNRENIKTQ
IVIAMAEESSKDKNEVIKEVLENKDGKYFETEPKCKSGGIYSATFDDGYDG
ITGIESIAKVYVTCTKHPDGIEMARDIHQSMKDLIASFAQDPSIIPGASKG
NDDFRKYLLDNKYKNGWPTIPDEFKAKYGLSKDTLYIQPYAYNPTKSDATV
VVFANNKTGGNWYTSLVYDYDEGRWYKGKNGISVAGRSWDVDTDSVKSVKT
EIHSKEGWGPLN >gi|306519381|ref|ZP_07405728.1|fimbrial protein
(pilin) [*Clostridium difficile* QCD-32g58]
(SEQ ID NO: 58)
MNKKGFTLIELLVVISIIGILVIVAVPALFRNIEKSKAVTCLSNRENIKTQ
IVIAMAEESSKDKNEVIKEVLENKDGKYFETEPKCKSGGIYSATFDDGYDG
ITGIESIAKVYVTCTKHPDGIEMARDIHQSMKDLIASFAQDPSIIPGASKG
NDDFRKYLLDNKYKNGWPTIPDEFKAKYGLSKDTLYIQPYAYNPTKSDATV
VVFANNKTGGNWYTSLVYDYDEGRWYKGKNGISVAGRSWDVDTDSVKSVKT
EIHSKEGWGPLN >gi|255654804|ref|ZP_05400213.1|fimbrial protein
(pilin) [*Clostridium difficile* QCD-23m63]
(SEQ ID NO: 60)
MNKKGFTLIELLVVISIIGILVIVAVPALFRNIEKSKAVTCLSNRENIKTQ
IVIAMAEESSKDKNKVIKDVLENKDGKYFETEPKCKSGGIYSATFDDGYDG
ITGGESIAKVYVTCTEHPDGVEMARDVHQSMKDLIASFAQDPSIIPGASKS
NDDFRKYLLDNKYKKGWPTIPDEFKAKYGLSKDTLYIQPYAYNPTKPDATV
VVFANNKTGGNWYTSLVYDYDEGRWYKGKNGISVAGRSWDVDTDSVKSV
KTEIHSKEGWGPLN PilU Nucleotide
>gi|260685375:c3979688-3979003 *Clostridium
difficile* R20291 chromosome,complete genome
(SEQ ID NO: 61)
ATGAGTAAAAAGAATAGTGAAAGAGGATTTTCCTTAATTGAAGTGTTA
GTAGCTATGGCTATTATGGGAATTGTACTATTTGCATTTTTAATATTAT
CAATACTAATAACAAAGCAAACACTAAAAATGACACAGATATAACTTC
CTTAAACTATGTCCAAAGTGAAATAGAAAATCTAAGAGAAAAGATAAA
AAGTGGAGAATTTGATTTTGATAGTTTAGATAAACTAGAAGATGGAAC
TGTCGTATATGAAAAATTAATAGATAAATCAAAAAAAGTTGTATATGA
TAAAGTTCTTAGTGAAGGTGACGTGAGCTTATATGATACTCCATATGAA
AAGATTACAACAATAAAGATGAAGATGGTAATTTAATCGACAAAGGA
AATATTACAAATAAGATAAAGACTATTGTAGAAGATAAAAGTGGTCAG
ATATATAAAGTGTAACTGGAAAAAGCATGAATGACTATTCAAGT
AAAAAAGAGGTTAAAATTGTAACTGAAATATTTAAAGATAAATAA >gi|126697566|ref|NC_009089.1|:4098233-4098915
*Clostridium difficile* 630,
complete genome reverse complement (SEQ ID NO: 64)
ATGAGTAAAAAGAATAGTGAAAGAGGATTTTCCTTAATTGAAGTGTTA
GTAGCTATGGCTATTATGGGAATTGTACTATTTGCATTTTTAATATTAT
CAATACTAATAACAAAGCAAACACTAAAAATGACACAGATATAACTTC
CTTAAACTATGTCCAAAGTGAAATAGAAAATCTAAGAGAAAAGATAAA
AAGTGGAGAATTTGATTTTGATAGTTTAGATAAACTAGAAGATGGAAC
TGTCGTATATGAAAAATTAATAGATAAATCAAAAAAAGTTGTATATGA
TAAAGTTCTTAGTGAAGGTGATGTGAGCTTATATGATACTCCATATGAA
AAGATTACAACAATAAAGATGAAGATGGTAATTTAATCGACAAAGGA
AATATTACAAATAAGATAAAGACTATTGTAGAAGATAAAAGTGGTCAG
ATATATAAAACTGTAACTGGAAAAAGCATGAATGACTATTCAAGT
AAAAAAGAGGTTAAAATTGTAACTGAAATATTTAAAGATAAATAA -continued \>gi|260681769|ref|NC_013315.1|:3898217-3898902
Clostridium difficile CD196
chromosome, complete genome reverse complement
(SEQ ID NO: 61)
ATGAGTAAAAAGAATAGTGAAAGAGGATTTTCCTTAATTGAAGTGTTA
GTAGCTATGGCTATTATGGGAATTGTACTATTTGCATTTTTTAATATTAT
CAATACTAATAACAAAGCAAACACTAAAAATGACACAGATATAACTTC
CTTAAACTATGTCCAAAGTGAAATAGAAATCTAAGAGAAAAGATAAA
AAGTGGAGAATTTGATTTTGATAGTTTAGATAAACTAGAAGATGGAAC
TGTCGTATATGAAAAATTAATAGATAAATCAAAAAAAGTTGTATATGA
TAAAGTTCTTAGTGAAGGTGACGTGAGCTTATATGATACTCCATATGAA
AAGATTACAACAATAAAAGATGAAGATGGTAATTTAATCGACAAAGGA
AATATTACAAATAAGATAAAGACTATTGTAGAAGATAAAAGTGGTCAG
ATATATAAAATAGCTGTAACTGGGAAAAGCATGAATGACTATTCAAGT
AAAAAAGAGGTTAAAATTGTAACTGAAATATTTAAAGATAAATAA \>gi|383843669|ref|NC_017179.1|:3906237-3906922
Clostridium difficile BI1,
complete genome reverse complement (SEQ ID NO: 61)
ATGAGTAAAAAGAATAGTGAAAGAGGATTTTCCTTAATTGAAGTGTTA
GTAGCTATGGCTATTATGGGAATTGTACTATTTGCATTTTTTAATATTAT
CAATACTAATAACAAAGCAAACACTAAAAATGACACAGATATAACTTC
CTTAAACTATGTCCAAAGTGAAATAGAAATCTAAGAGAAAAGATAAA
AAGTGGAGAATTTGATTTTGATAGTTTAGATAAACTAGAAGATGGAAC
TGTCGTATATGAAAAATTAATAGATAAATCAAAAAAAGTTGTATATGA
TAAAGTTCTTAGTGAAGGTGACGTGAGCTTATATGATACTCCATATGAA
AAGATTACAACAATAAAAGATGAAGATGGTAATTTAATCGACAAAGGA
AATATTACAAATAAGATAAAGACTATTGTAGAAGATAAAAGTGGTCAG
ATATATAAAATAGCTGTAACTGGGAAAAGCATGAATGACTATTCAAGT
AAAAAAGAGGTTAAAATTGTAACTGAAATATTTAAAGATAAATAA \>gi|224514682|ref|NZ_CM000659.1|:3800152-3800837
Clostridium difficile CIP 107932 chromosome,whole
genome shotgun sequence_gi|221149347|gb|CM000659.1|
Clostridium difficile CIP 107932 chromosome,
whole genome shotgun sequence reverse complement
(SEQ ID NO: 61)
ATGAGTAAAAAGAATAGTGAAAGAGGATTTTCCTTAATTGAAGTGTTA
GTAGCTATGGCTATTATGGGAATTGTACTATTTGCATTTTTTAATATTAT
CAATACTAATAACAAAGCAAACACTAAAAATGACACAGATATAACTTC
CTTAAACTATGTCCAAAGTGAAATAGAAATCTAAGAGAAAAGATAAA
AAGTGGAGAATTTGATTTTGATAGTTTAGATAAACTAGAAGATGGAAC
TGTCGTATATGAAAAATTAATAGATAAATCAAAAAAAGTTGTATATGA
TAAAGTTCTTAGTGAAGGTGACGTGAGCTTATATGATACTCCATATGAA
AAGATTACAACAATAAAAGATGAAGATGGTAATTTAATCGACAAAGGA
AATATTACAAATAAGATAAAGACTATTGTAGAAGATAAAAGTGGTCAG
ATATATAAAATAGCTGTAACTGGGAAAAGCATGAATGACTATTCAAGT
AAAAAAGAGGTTAAAATTGTAACTGAAATATTTAAAGATAAATAA \>gi|224514685|ref|NZ_CM000660.1|:3724075-3724753
Clostridium difficile QCD-23m63 chromosome, whole
genome shotgun sequence_gi|221149428|gb|CM000660.1|
Clostridium difficile QCD-23m63 chromosome,
whole genome shotgun sequence reverse complement
(SEQ ID NO: 68)
ATGAGTAAAAAGAATAGTGAAAGAGGATTTTCCTTAATTGAAGTGTTA
GTAGCTATGGCTATTATGGGAATTATACTATTTGCGTTTTTTAATATTAT
CAATACTAATAATAAAGCAAATATTAAAAATGACACAGATATAAATTC
CTTAAACTATGTCCAAAGTGAAATAGAAATCTAAGAGAGAAAGATAAA
AAGTGGAGAATTTGATTTTGATAGTTTAGATAAAATGGAAGATGGGAC
TGTCGTATATGAAAAATTAATAGATAAGTCAAAAAAAATTGTATATGA
TAAAGTTCTTAGTGAGGGTAACGTGAGCTTATATGATACTCCATATGAA
AAGATTACAACAATAAAAGATGAAGATGGTAATTTAATCGATAAAGAA
AATATTACAAATAAGATAAAGACTATTGTAGAAGATAAAAGTGGTCAG
ATATATAAAATAGCTGTAACTGGGAAAAGCATGAATGACTATTCAAGT
AAAAAAGAAGTTAAGATTGTAACTGAAATATTTAAAGATAAATAA \>gi|209401276|ref|NZ_CM000287.1|:3890698-3891383
Clostridium difficile QCD-32g58 chromosome, whole
genome shotgun sequence_gi|145843961|gb|CM000287.4|
Clostridium difficile QCD-32g58 chromosome,
whole genome shotgun sequence reverse complement
(SEQ ID NO: 61)
ATGAGTAAAAAGAATAGTGAAAGAGGATTTTCCTTAATTGAAGTGTTA
GTAGCTATGGCTATTATGGGAATTGTACTATTTGCATTTTTTAATATTAT
CAATACTAATAACAAAGCAAACACTAAAAATGACACAGATATAACTTC
CTTAAACTATGTCCAAAGTGAAATAGAAATCTAAGAGAAAAGATAAA
AAGTGGAGAATTTGATTTTGATAGTTTAGATAAACTAGAAGATGGAAC
TGTCGTATATGAAAAATTAATAGATAAATCAAAAAAAGTTGTATATGA
TAAAGTTCTTAGTGAAGGTGACGTGAGCTTATATGATACTCCATATGAA
AAGATTACAACAATAAAAGATGAAGATGGTAATTTAATCGACAAAGGA -continued AATATTACAAATAAGATAAAGACTATTGTAGAAGATAAAAGTGGTCAG
ATATATAAAATAGCTGTAACTGGGAAAAGCATGAATGACTATTCAAGT
AAAAAAGAGGTTAAAATTGTAACTGAAATATTTAAAGATAAATAA \>gi|224514680|ref|NZ_CM000658.1|:3875102-3875787
Clostridium difficile QCD-37x79 chromosome, whole
genome shotgun sequence_gi|221149249|gb|CM000658.1|
Clostridium difficile QCD-37x79 chromosome,
whole genome shotgun sequence reverse complement
(SEQ ID NO: 61)
ATGAGTAAAAAGAATAGTGAAAGAGGATTTTCCTTAATTGAAGTGTTA
GTAGCTATGGCTATTATGGGAATTGTACTATTTGCATTTTTTAATATTAT
CAATACTAATAACAAAGCAAACACTAAAAATGACACAGATATAACTTC
CTTAAACTATGTCCAAAGTGAAATAGAAATCTAAGAGAAAAGATAAA
AAGTGGAGAATTTGATTTTGATAGTTTAGATAAACTAGAAGATGGAAC
TGTCGTATATGAAAAATTAATAGATAAATCAAAAAAAGTTGTATATGA
TAAAGTTCTTAGTGAAGGTGACGTGAGCTTATATGATACTCCATATGAA
AAGATTACAACAATAAAAGATGAAGATGGTAATTTAATCGACAAAGGA
AATATTACAAATAAGATAAAGACTATTGTAGAAGATAAAAGTGGTCAG
ATATATAAAATAGCTGTAACTGGGAAAAGCATGAATGACTATTCAAGT
AAAAAAGAGGTTAAAATTGTAACTGAAATATTTAAAGATAAATAA \>gi|224514674|ref|NZ_CM000637.1|:3935063-3935745
Clostridium difficile QCD-63q42 chromosome, whole
genome shotgun sequence_gi|219819758|gb|CM000637.1|
Clostridium difficile QCD-63q42 chromosome,
whole genome shotgun sequence reverse complement
(SEQ ID NO: 62)
ATGAGTAAAAAGAATAGTGAAAGAGGATTTTCCTTAATTGAAGTGTTA
GTAGCTATGGCTATTATGGGAATTGTACTATTTGCATTTTTTAATATTAT
CAATACTAATAACAAAGCAAACACTAAAAATGACACAGATATAACTTC
CTTAAACTATGTTCAAAGTGAAATAGAAATCTAAGAGAAAAGATAAA
AAGTGGAGAATTTGATTTTGATAGTTTAGATAAACTAGAAGATGGAAC
TGTCGTATATGAAAAATTAATAGATAAATCAAAAAAAGTTGTATATGA
TAAAGTTCTTAGTGAAGGTGATGTGAGCTTATATGATACTCCATATGAA
AAGATTACAACAATAAAAGATGAAGATGGTAATTTAATCGACAAAGGA
AATATTACAAATAAGATAAAGACTATTGTAGAAGATAAAAGTGGTCAG
ATATATAAAATAGCTGTAACTGGGAAAAGCATGAATGACTATTCAAGT
AAAAAAGAGGTTAAAATTGTAACTGAAATATTTAAAGATAAATAA \>gi|224531476|ref|NZ_CM000441.1|:3875549-3876234
Clostridium difficile QCD-66c26 chromosome, whole
genome shotgun sequence_gi|222154275|gb|CM000441.2|
Clostridium difficile QCD-66c26 chromosome,
whole genome shotgun sequence reverse complement
(SEQ ID NO: 61)
ATGAGTAAAAAGAATAGTGAAAGAGGATTTTCCTTAATTGAAGTGTTA
GTAGCTATGGCTATTATGGGAATTGTACTATTTGCATTTTTTAATATTAT
CAATACTAATAACAAAGCAAACACTAAAAATGACACAGATATAACTTC
CTTAAACTATGTCCAAAGTGAAATAGAAATCTAAGAGAAAAGATAAA
AAGTGGAGAATTTGATTTTGATAGTTTAGATAAACTAGAAGATGGAAC
TGTCGTATATGAAAAATTAATAGATAAATCAAAAAAAGTTGTATATGA
TAAAGTTCTTAGTGAAGGTGACGTGAGCTTATATGATACTCCATATGAA
AAGATTACAACAATAAAAGATGAAGATGGTAATTTAATCGACAAAGGA
AATATTACAAATAAGATAAAGACTATTGTAGAAGATAAAAGTGGTCAG
ATATATAAAATAGCTGTAACTGGGAAAAGCATGAATGACTATTCAAGT
AAAAAAGAGGTTAAAATTGTAACTGAAATATTTAAAGATAAATAA \>gi|224514686|ref|NZ_CM000661.1|:3861099-3861784
Clostridium difficile QCD-76w55 chromosome, whole
genome shotgun sequence_gi|221191950|gb|CM000661.1|
Clostridium difficile QCD-76w55 chromosome,
whole genome shotgun sequence reverse complement
(SEQ ID NO: 61)
ATGAGTAAAAAGAATAGTGAAAGAGGATTTTCCTTAATTGAA
GTGTTAGTAGCTATGGCTATTATGGGAATTGTACTATTTGCATTTTTTAA
TATTATCAATACTAATAACAAAGCAAACACTAAAAATGACACAGATAT
AACTTCCTTAAACTATGTCCAAAGTGAAATAGAAATCTAAGAGAAAA
GATAAAAAGTGGAATTTGATTTTGATAGTTTAGATAAACTAGAAGA
TGGAACTGTCGTATATGAAAAATTAATAGATAAATCAAAAAAAGTTGT
ATATGATAAAGTTCTTAGTGAAGGTGACGTGAGCTTATATGATACTCCA
TATGAAAAGATTACAACAATAAAAGATGAAGATGGTAATTTAATCGAC
AAAGGAAATATTACAAATAAGATAAAGACTATTGTAGAAGATAAAAGT
GGTCAGATATATAAAATAGCTGTAACTGGGAAAAGCATGAATGACTAT
TCAAGTAAAAAAGAGGTTAAAATTGTAACTGAAATATTTAAAGATAAA
TAA >gi|224514679|ref|NZ_CM000657.1|:3783601-3784286
*Clostridium difficile* QCD-97b34 chromosome, whole
genome shotgun sequence_gi|221149047|gb|CM000657.1|
*Clostridium difficile* QCD-97b34 chromosome,
whole genome shotgun sequence reverse complement
(SEQ ID NO: 61)
ATGAGTAAAAAGAATAGTGAAAGAGGATTTTCCTTAATTGAAGTGTTA
GTAGCTATGGCTATTATGGGAATTGTACTATTTGCATTTTTTAATATTAT
CAATACTAATAACAAAGCAAACACTAAAAATGACACAGATATAACTTC
CTTAAACTATGTCCAAAGTGAAATAGAAAATCTAAGAGAAAAGATAAA
AAGTGGAGAATTTGATTTTGATAGTTTAGATAAACTAGAAGATGGAAC
TGTCGTATATGAAAAATTAATAGATAAATCAAAAAAAGTTGTATATGA
TAAAGTTCTTAGTGAAGGTGACGTGAGCTTATATGATACTCCATATGAA
AAGATTACAACAATAAAAGATGAAGATGGTAATTTAATCGACAAAGGA
AATATTACAAATAAG PilU Amino Acid
>gi|260688685|ref|YP_003219819.1|type IV pilin
[*Clostridium difficile* R20291] (SEQ ID NO: 63)
MSKKNSERGFSLIEVLVAMAIMGIVLFAFFNIINTNNKANTKNDTDITSLN
YVQSEIENLREKIKSGEFDFDSLDKLEDGTVVYEKLIDKSKKVVYDKVLSE
GDVSLYDTPYEKITTIKDEDGNLIDKGNITNKIKTIVEDKSGQIYKIAVTG
KSMNDYSSKKEVKIVTEIFKDK >gi|126701131|ref|YP_001090028.1|type IV pilin
[*Clostridium difficile* 630] (SEQ ID NO: 65)
MSKKNSERGFSLIEVLVAMAIMGIVLFAFFNIINTNNKANTKNDTDITSLN
YVQSEIENLREKIKSGEFDFDSLDKLEDGTVVYEKLIDKSKKVVYDKVLSE
GDVSLYDTPYEKITTIKDEDGNLIDKGNITNKIKTIVEDKSGQIYKITVTG
KSMNDYS SKKEVKIVTEIFKDK >gi|423087238|ref|ZP_17075627.1|prepilin-type
cleavage/methylation protein
[*Clostridium difficile* 050-P50-2011]
(SEQ ID NO: 66)
MSKKNSERGFSLIEVLVAMAIMGIVLFAFFNIINTNNKANTKNDTDITSLN
YVQSEIENLREKIKSGEFDFDSLDKLEDGTVVYEKLIDKSKKVVYDKVLSE
SDVSLYDIPYEKITTIKDEDGNLIDKENITNKIKTIVEDKSGQIYKVAVTG
KSMNDYSSKKEVKIVTEIFKDK >gi|423080837|ref|ZP_17069454.1|prepilin-type
cleavage/methylation protein
[*Clostridium difficile* 002-P50-2011]
(SEQ ID NO: 66)
MSKKNSERGFSLIEVLVAMAIMGIVLFAFFNIINTNNKANTKNDTDITSLN
YVQSEIENLREKIKSGEFDFDSLDKLEDGTVVYEKLIDKSKKVVYDKVLSE
SDVSLYDIPYEKITTIKDEDGNLIDKENITNKIKTIVEDKSGQIYKVAVTG
KSMNDYSSKKEVKIVTEIFKDK >gi|423090607|ref|ZP_17078896.1|prepilin-type
cleavage/methylation protein
[*Clostridium difficile* 70-100-2010]
(SEQ ID NO: 71)
MSKKNSERGFSLIEVLVAMAIMGIVLFAFFNIINTNNKANTKNDTDITSLN
YVQSEIENLREKIKSGEFDFDSLDKLEDGTVVYEKLIDKSKKVVYDKVLSE
GDVSLYDTPYEKITTIKDEDGNLIDKGNITNKIKTIVEDKSGQIYKIAVTG
KSMNDYSSKKEVKIVTEIFKDK >gi|296449059|ref|ZP_06890849.1|probable type
IV pilin [*Clostridium difficile* NAP08]
(SEQ ID NO: 67)
MSKKNSKRGFSLIEVLVAMAIMGIILFAFFNIINTNNKANIKNDTDINSLN
YVQSEIENLREKIKSGEFDFDSLDKMEDGTVVYEKLIDKSKKIVYDKVLSE
GNVSLYDTPYEKITTIKDEDGNLIDKENITNKIKTIVEDKSGQIYKIAVTG
KSMNDYSSKKEVKIVTEIFKDK >gi|296879882|ref|ZP_06903855.1|probable type
IV pilin [*Clostridium difficile* NAP07]
(SEQ ID NO: 67)
MSKKNSKRGFSLIEVLVAMAIMGIILFAFFNIINTNNKANIKNDTDINSLN
YVQSEIENLREKIKSGEFDFDSLDKMEDGTVVYEKLIDKSKKIVYDKVLSE
GNVSLYDTPYEKITTIKDEDGNLIDKENITNKIKTIVEDKSGQIYKIAVTG
KSMNDYSSKKEVKIVTEIFKDK >gi|260685027|ref|YP_003216312.1|type IV
pilin [*Clostridium difficile* CD196]
(SEQ ID NO: 63)
MSKKNSERGFSLIEVLVAMAIMGIVLFAFFNIINTNNKANTKNDTDITSLN
YVQSEIENLREKIKSGEFDFDSLDKLEDGTVVYEKLIDKSKKVVYDKVLSE
GDVSLYDTPYEKITTIKDEDGNLIDKGNITNKIKTIVEDKSGQIYKIAVTG
KSMNDYSSKKEVKIVTEIFKDK >gi|255102717|ref|ZP_05331694.1|putative type IV
pilin [*Clostridium difficile* QCD-63q42]
(SEQ ID NO: 63)
MSKKNSERGFSLIEVLVAMAIMGIVLFAFFNIINTNNKANTKNDTDITSLN
YVQSEIENLREKIKSGEFDFDSLDKLEDGTVVYEKLIDKSKKVVYDKVLSE
GDVSLYDTPYEKITTIKDEDGNLIDKGNITNKIKTIVEDKSGQIYKIAVTG
KSMNDYSSKKEVKIVTEIFKDK >gi|255316212|ref|ZP_05357795.1|putative type IV
pilin [*Clostridium difficile* QCD-76w55]
(SEQ ID NO: 63)
MSKKNSERGFSLIEVLVAMAIMGIVLFAFFNIINTNNKANTKNDTDITSLN
YVQSEIENLREKIKSGEFDFDSLDKLEDGTVVYEKLIDKSKKVVYDKVLSE
GDVSLYDTPYEKITTIKDEDGNLIDKGNITNKIKTIVEDKSGQIYKIAVTG
KSMNDYSSKKEVKIVTEIFKDK >gi|255652053|ref|ZP_05398955.1|putative type IV
pilin [*Clostridium difficile* QCD-37x79]
(SEQ ID NO: 63)
MSKKNSERGFSLIEVLVAMAIMGIVLFAFFNIINTNNKANTKNDTDITSLN
YVQSEIENLREKIKSGEFDFDSLDKLEDGTVVYEKLIDKSKKVVYDKVLSE
GDVSLYDTPYEKITTIKDEDGNLIDKGNITNKIKTIVEDKSGQIYKIAVTG
KSMNDYSSKKEVKIVTEIFKDK >gi|255308538|ref|ZP_05352709.1|putative type
IV pilin [*Clostridium difficile* ATCC 43255]
(SEQ ID NO: 65)
MSKKNSERGFSLIEVLVAMAIMGIVLFAFFNIINTNNKANTKNDTDITSLN
YVQSEIENLREKIKSGEFDFDSLDKLEDGTVVYEKLIDKSKKVVYDKVLSE
GDVSLYDTPYEKITTIKDEDGNLIDKGNITNKIKTIVEDKSGQIYKITVTG
KSMNDYSSKKEVKIVTEIFKDK >gi|384362701|ref|YP_006200553.1|type IV pilin +
8 *Clostridium difficile* BI1] (SEQ ID NO: 63)
MSKKNSERGFSLIEVLVAMAIMGIVLFAFFNIINTNNKANTKNDTDITSLN
YVQSEIENLREKIKSGEFDFDSLDKLEDGTVVYEKLIDKSKKVVYDKVLSE
GDVSLYDTPYEKITTIKDEDGNLIDKGNITNKIKTIVEDKSGQIYKIAVTG
KSMNDYSSKKEVKIVTEIFKDK >gi|255518874|ref|ZP_05386550.1|putative type
IV pilin [*Clostridium difficile* QCD-97b34]
(SEQ ID NO: 63)
MSKKNSERGFSLIEVLVAMAIMGIVLFAFFNIINTNNKANTKNDTDITSLN
YVQSEIENLREKIKSGEFDFDSLDKLEDGTVVYEKLIDKSKKVVYDKVLSE
GDVSLYDTPYEKITTIKDEDGNLIDKGNITNKIKTIVEDKSGQIYKIAVTG
KSMNDYSSKKEVKIVTEIFKDK >gi|254977132|ref|ZP_05273604.1|putative type
IV pilin [*Clostridium difficile* QCD-66c26]
(SEQ ID NO: 63)
MSKKNSERGFSLIEVLVAMAIMGIVLFAFFNIINTNNKANTKNDTDITSLN
YVQSEIENLREKIKSGEFDFDSLDKLEDGTVVYEKLIDKSKKVVYDKVLSE
GDVSLYDTPYEKITTIKDEDGNLIDKGNITNKIKTIVEDKSGQIYKIAVTG
KSMNDYSSKKEVKIVTEIFKDK >gi|255094461|ref|ZP_05323939.1|putative type
IV pilin [*Clostridium difficile* CIP 107932]
(SEQ ID NO: 63)
MSKKNSERGFSLIEVLVAMAIMGIVLFAFFNIINTNNKANTKNDTDITSLN
YVQSEIENLREKIKSGEFDFDSLDKLEDGTVVYEKLIDKSKKVVYDKVLSE
GDVSLYDTPYEKITTIKDEDGNLIDKGNITNKIKTIVEDKSGQIYKIAVTG
KSMNDYSSKKEVKIVTEIFKDK >gi|306521790|ref|ZP_07408137.1|putative type
IV pilin [*Clostridium difficile* QCD-32g58]
(SEQ ID NO: 63)
MSKKNSERGFSLIEVLVAMAIMGIVLFAFFNIINTNNKANTKNDTDITSLN
YVQSEIENLREKIKSGEFDFDSLDKLEDGTVVYEKLIDKSKKVVYDKVLSE
GDVSLYDTPYEKITTIKDEDGNLIDKGNITNKIKTIVEDKSGQIYKIAVTG
KSMNDYSSKKEVKIVTEIFKDK >gi|255657464|ref|ZP_05402873.1|putative type
IV pilin [*Clostridium difficile* QCD-23m63]
(SEQ ID NO: 69)
MSKKNSKRGFSLIEVLVAMAIMGIILFAFFNIINTNNKANIKNDTDINSLN
YVQSEIENLREKIKSGEFDFDSLDKMEDGTVVYEKLIDKSKKIVYDKVLSE
GNVSLYDTPYEKITTIKDEDGNLIDKENITNKIKTIVEDKSGQIYKIAVTG
KSMNDYSSKKEVKIVTEIFKDK PilX1 Nucleotide
>gi|260685375:1303160-1303646 Clostridium difficile
R20291 chromosome, complete genome (SEQ ID NO: 82)
TTGTTTTTATTATTGAAAATAAGAAAGAGTGGTTTTATATCAATCGAAT
GTATAATAAGTATTGCTATATTATATGTGGCTGTTTATTTAGTTTCTACA
TCATTGTATAATTGTTATAGTTTTATCAGTAGAAATATATCTGACAGAG
AAATGTTAAGTACAGCAAAAAAATATATAGAAGATGAGAAGTATAGA
ATACAAAATAGTAAGTATGAGTTAATTGAAGATAAGATAGAAAAAAT
TACATAAATGGATATGAAATTAACAGTAGAATAGAGCAAATTTTAGAT
TATTATCAATGCTATGAAATAAATATAGAGATAAAAAATGAATTTAAA
AAACTGAGGTTTAATAGCTATGTTACTAGAAAATAA >gi|126697566|ref|NC_009089.1|:1445237-1445723
Clostridium difficile 630,complete genome
(SEQ ID NO: 82)
TTGTTTTTATTATTGAAAATAAGAAAGAGTGGTTTTATATCAATCGAAT
GTATAATAAGTATTGCTATATTATATGTGGCTGTTTATTTAGTTTCTACA
TCATTGTATAATTGTTATAGTTTTATCAGTAGAAATATATCTGACAGAG
AAATGTTAAGTACAGCAAAAAAATATATAGAAGATGAGAAGTATAGA
ATACAAAATAGTAAGTATGAGTTAATTGAAGATAAGATAGAAAAAAT
TACATAAATGGATATGAAATTAACAGTAGAATAGAGCAAATTTTAGAT
TATTATCAATGCTATGAAATAAATATAGAGATAAAAAATGAATTTAAA
AAACTGAGGTTTAATAGCTATGTTACTAGAAAATAA >gi|260681769|ref|NC_013315.1|:1305539-1306025
Clostridium difficile CD196 chromosome,
complete genome (SEQ ID NO: 82)
TTGTTTTTATTATTGAAAATAAGAAAGAGTGGTTTTATATCAATCGAAT
GTATAATAAGTATTGCTATATTATATGTGGCTGTTTATTTAGTTTCTACA
TCATTGTATAATTGTTATAGTTTTATCAGTAGAAATATATCTGACAGAG
AAATGTTAAGTACAGCAAAAAAATATATAGAAGATGAGAAGTATAGA
ATACAAAATAGTAAGTATGAGTTAATTGAAGATAAGATAGAAAAAAT
TACATAAATGGATATGAAATTAACAGTAGAATAGAGCAAATTTTAGAT
TATTATCAATGCTATGAAATAAATATAGAGATAAAAAATGAATTTAAA
AAACTGAGGTTTAATAGCTATGTTACTAGAAAATAA >gi|383843669|ref|NC_017179.1|:1315316-1315802
Clostridium difficile BI1, complete genome
(SEQ ID NO: 84)
TTGTTTTTATTATTGAAAATAAGAAAGAGTGGTTTTATATCAATCGAAT
GTATAATAAGTATTGCTATATTATATGTGGCTGTTTATTTAGTTTCTACA
TCATTGTATAATTGTTATAGTTTTATCAGTAGAAATATATCTGACAGAG
AAATGTTAAGTACAGCAAAAAAATATATAGAAGATGAGAAGTATAGA
ATACAAAATAGTAAGTATGAGTTAATTGAAGATAAGATAGAAAAAAT
TACATAAATGGATATGAAATTAACAGTAGAATAGAGCAAATTTTAGAT
TATTATCAATGCTATGAAATAAATATAGAGATAAAAAATGAATTTAAA
AAACTGAGGTTTAATAGCTATGTTACTAGAAAATAA >gi|224514682|ref|NZ_CM000659.1|:1243126-1243612
Clostridium difficile CIP 107932 chromosome,
whole genome shotgun sequence_gi|
221149347|gb|CM000659.1|Clostridium difficile
CIP 107932 chromosome, whole genome shotgun
sequence (SEQ ID NO: 84)
TTGTTTTTATTATTGAAAATAAGAAAGAGTGGTTTTATATCAATCGAAT
GTATAATAAGTATTGCTATATTATATGTGGCTGTTTATTTAGTTTCTACA
TCATTGTATAATTGTTATAGTTTTATCAGTAGAAATATATCTGACAGAG
AAATGTTAAGTACAGCAAAAAAATATATAGAAGATGAGAAGTATAGA
ATACAAAATAGTAAGTATGAGTTAATTGAAGATAAGATAGAAAAAAT
TACATAAATGGATATGAAATTAACAGTAGAATAGAGCAAATTTTAGAT
TATTATCAATGCTATGAAATAAATATAGAGATAAAAAATGAATTTAAA
AAACTGAGGTTTAATAGCTATGTTACTAGAAAATAA >gi|224514685|ref|NZ_CM000660.1|:1242911-1243392
Clostridium difficile QCD-23m63 chromosome, whole
genome shotgun sequence_gi|221149428|gb|CM000660.1|
Clostridium difficile QCD-23m63 chromosome,
whole genome shotgun sequence (SEQ ID NO: 86)
TTGTTTTTATTATTGAAAATAAGAAAGCGTGGTTTTATATCAATCGAAT
GTGTAATAAGTATTGCTATATTATATGTGGCTGTTTATTTAGTTTCTACA
TCATTGTATAGTTGTTATAGTTTTGTCAGTAGAAATATATCTGACAGAA
AAATGTTAAGTACTGCAAAAAAATATATAGAAGATGAGAAGTATAGA
TACAAAATAGTAAGTATGAGTTAATTGAAAATAAGATAGAAAAAAATT
ACATAAATGGATATGAAATTAGCAGTAGAGTAGAGCAAATTTTAGATT
ATTATCAATGCTATGAAATAAATATAGAGATAAAAAATGAATTTAAA
AATTGAGGTTTAATAGCTATGTTACTAGAAAATAA >gi|209401276|ref|NZ_CM000287.1|:1320445-1320932
Clostridium difficile QCD-32g58 chromosome, whole
genome shotgun sequence_gi|145843961|gb|CM000287.4|
Clostridium difficile QCD-32g58 chromosome,
whole genome shotgun sequence (SEQ ID NO: 118)
TTGTTTTTATTATTGAAAATAAGAAAGAGTGGTTTTATATCAATCGAAT
GTATAATAAGTATTGCTATATTATATGTGGCTGTTTATTTAGTTTCTACA
TCATTGTATAATTGTTATAGTTTTATCAGTAGAAATATATCTGACAGAG
AAATGTTAAGTACAGCAAAAAAATATATAGAAGATGAGAAGTATAGA
AATACAAAATAGTAAGTATGAGTTAATTGAAGATAAGATAGAAAAAAA
TTACATAAATGGATATGAAATTAACAGTAGAATAGAGCAAATTTTAGA
TTATTATCAATGCTATGAAATAAATATAGAGATAAAAAATGAATTTAA
AAAACTGAGGTTTAATAGCTATGTTACTAGAAAATAA >gi|224514680|ref|NZ_CM000658.1|:1255164-1255650
Clostridium difficile QCD-37x79 chromosome, whole
genome shotgun sequence_gi|221149249|gb|CM000658.1|
Clostridium difficile QCD-37x79 chromosome,
whole genome shotgun sequence (SEQ ID NO: 84)
TTGTTTTTATTATTGAAAATAAGAAAGAGTGGTTTTATATCAATCGAAT
GTATAATAAGTATTGCTATATTATATGTGGCTGTTTATTTAGTTTCTACA
TCATTGTATAATTGTTATAGTTTTATCAGTAGAAATATATCTGACAGAG
AAATGTTAAGTACAGCAAAAAAATATATAGAAGATGAGAAGTATAGA
ATACAAAATAGTAAGTATGAGTTAATTGAAGATAAGATAGAAAAAAT
TACATAAATGGATATGAAATTAACAGTAGAATAGAGCAAATTTTAGAT
TATTATCAATGCTATGAAATAAATATAGAGATAAAAAATGAATTTAAA
AAACTGAGGTTTAATAGCTATGTTACTAGAAAATAA >gi|224514674|ref|NZ_CM000637.1|:1221271-1221757
Clostridium difficile QCD-63q42 chromosome, whole
genome shotgun sequence_gi|219819758|gb|CM000637.1|
Clostridium difficile QCD-63q42 chromosome,
whole genome shotgun sequence (SEQ ID NO: 84)
TTGTTTTTATTATTGAAAATAAGAAAGAGTGGTTTTATATCAATCGAAT
GTATAATAAGTATTGCTATATTATATGTGGCTGTTTATTTAGTTTCTACA
TCATTGTATAATTGTTATAGTTTTATCAGTAGAAATATATCTGACAGAG
AAATGTTAAGTACAGCAAAAAAATATATAGAAGATGAGAAGTATAGA
ATACAAAATAGTAAGTATGAGTTAATTGAAGATAAGATAGAAAAAAT
TACATAAATGGATATGAAATTAACAGTAGAATAGAGCAAATTTTAGAT
TATTATCAATGCTATGAAATAAATATAGAGATAAAAAATGAATTTAAA
AAACTGAGGTTTAATAGCTATGTTACTAGAAAATAA >gi|224531476|ref|NZ_CM000441.1|:1249688-1250174
Clostridium difficile QCD-66c26 chromosome, whole
genome shotgun sequence_gi|222154275|gb|CM000441.2|
Clostridium difficile QCD-66c26 chromosome,
whole genome shotgun sequence (SEQ ID NO: 84)
TTGTTTTTATTATTGAAAATAAGAAAGAGTGGTTTTATATCAATCGAAT
GTATAATAAGTATTGCTATATTATATGTGGCTGTTTATTTAGTTTCTACA
TCATTGTATAATTGTTATAGTTTTATCAGTAGAAATATATCTGACAGAG
AAATGTTAAGTACAGCAAAAAAATATATAGAAGATGAGAAGTATAGA
ATACAAAATAGTAAGTATGAGTTAATTGAAGATAAGATAGAAAAAAT
TACATAAATGGATATGAAATTAACAGTAGAATAGAGCAAATTTTAGAT
TATTATCAATGCTATGAAATAAATATAGAGATAAAAAATGAATTTAAA
AAACTGAGGTTTAATAGCTATGTTACTAGAAAATAA >gi|224514686|ref|NZ_CM000661.1|:1299288-1299774
Clostridium difficile QCD-76w55 chromosome, whole
genome shotgun sequence_gi|221191950|gb|CM000661.1|
Clostridium difficile QCD-76w55 chromosome,
whole genome shotgun sequence (SEQ ID NO: 84)
TTGTTTTTATTATTGAAAATAAGAAAGAGTGGTTTTATATCAATCGAAT
GTATAATAAGTATTGCTATATTATATGTGGCTGTTTATTTAGTTTCTACA
TCATTGTATAATTGTTATAGTTTTATCAGTAGAAATATATCTGACAGAG
AAATGTTAAGTACAGCAAAAAAATATATAGAAGATGAGAAGTATAGA
ATACAAAATAGTAAGTATGAGTTAATTGAAGATAAGATAGAAAAAAT
TACATAAATGGATATGAAATTAACAGTAGAATAGAGCAAATTTTAGAT
TATTATCAATGCTATGAAATAAATATAGAGATAAAAAATGAATTTAAA
AAACTGAGGTTTAATAGCTATGTTACTAGAAAATAA >gi|224514679|ref|NZ_CM000657.1|:1235923-1236409
Clostridium difficile QCD-97b34 chromosome, whole
genome shotgun sequence_gi|221149047|gb|CM000657.1|
Clostridium difficile QCD-97b34 chromosome,
whole genome shotgun sequence (SEQ ID NO: 84)
TTGTTTTTATTATTGAAAATAAGAAAGAGTGGTTTTATATCAATCGAAT
GTATAATAAGTATTGCTATATTATATGTGGCTGTTTATTTAGTTTCTACA
TCATTGTATAATTGTTATAGTTTTATCAGTAGAAATATATCTGACAGAG
AAATGTTAAGTACAGCAAAAAAATATATAGAAGATGAGAAGTATAGA -continued
ATACAAAATAGTAAGTATGAGTTAATTGAAGATAAGATAGAAAAAAT
TACATAAATGGATATGAAATTAACAGTAGAATAGAGCAAATTTTAGAT
TATTATCAATGCTATGAAATAAATATAGAGATAAAAAATGAATTTAAA
AAACTGAGGTTTAATAGCTATGTTACTAGAAAATAA PilX1 Amino Acid
>gi|260686446|ref|YP_003217579.1|hypothetical
protein CDR20291_1081
[*Clostridium difficile* R20291] (SEQ ID NO: 83)
MFLLLKIRKSGFISIECIISIAILYVAVYLVSTSLYNCYSFISRNISDREM
LSTAKKYIEDEKYRIQNSKYELIEDKIEKNYINGYEINSRIEQILDYYQCY
EINIEIKNEFKKLRFNSYVTRK >gi|126698838|ref|YP_001087735.1|hypothetical
protein CD630_12420
[*Clostridium difficile* 630] (SEQ ID NO: 83)
MFLLLKIRKSGFISIECIISIAILYVAVYLVSTSLYNCYSFISRNISDREM
LSTAKKYIEDEKYRIQNSKYELIEDKIEKNYINGYEINSRIEQILDYYQCY
EINIEIKNEFKKLRFNSYVTRK >gi|260682848|ref|YP_003214133.1|hypothetical
protein CD196_1103
[*Clostridium difficile* CD196] (SEQ ID NO: 83)
MFLLLKIRKSGFISIECIISIAILYVAVYLVSTSLYNCYSFISRNISDREM
LSTAKKYIEDEKYRIQNSKYELIEDKIEKNYINGYEINSRIEQILDYYQCY
EINIEIKNEFKKLRFNSYVTRK >gi|255100258|ref|ZP_05329235.1|hypothetical
protein CdifQCD-6_05582
[*Clostridium difficile* QCD-63q42] (SEQ ID NO: 85)
MKIRKSGFISIECIISIAILYVAVYLVSTSLYNCYSFISRNISDREMLSTA
KKYIEDEKYRIQNSKYELIEDKIEKNYINGYEINSRIEQILDYYQCYEINI
EIKNEFKKLRFNSYVTRK >gi|255313913|ref|ZP_05355496.1|hypothetical
protein CdifQCD-7_06170
[*Clostridium difficile* QCD-76w55] (SEQ ID NO: 85)
MKIRKSGFISIECIISIAILYVAVYLVSTSLYNCYSFISRNISDREMLSTA
KKYIEDEKYRIQNSKYELIEDKIEKNYINGYEINSRIEQILDYYQCYEINI
EIKNEFKKLRFNSYVTRK >gi|255649692|ref|ZP_05396594.1|hypothetical
protein CdifQCD_05844
[*Clostridium difficile* QCD-37x79] (SEQ ID NO: 85)
MKIRKSGFISIECIISIAILYVAVYLVSTSLYNCYSFISRNISDREMLSTA
KKYIEDEKYRIQNSKYELIEDKIEKNYINGYEINSRIEQILDYYQCYEINI
EIKNEFKKLRFNSYVTRK >gi|255306198|ref|ZP_05350370.1|hypothetical
protein CdifA_06370
[*Clostridium difficile* ATCC 43255] (SEQ ID NO: 85)
MKIRKSGFISIECIISIAILYVAVYLVSTSLYNCYSFISRNISDREMLSTA
KKYIEDEKYRIQNSKYELIEDKIEKNYINGYEINSRIEQILDYYQCYEINI
EIKNEFKKLRFNSYVTRK >gi|384360437|ref|YP_006198289.1|hypothetical
protein CDBI1_05655
[*Clostridium difficile* BI1] (SEQ ID NO: 85)
MKIRKSGFISIECIISIAILYVAVYLVSTSLYNCYSFISRNISDREMLSTA
KKYIEDEKYRIQNSKYELIEDKIEKNYINGYEINSRIEQILDYYQCYEINI
EIKNEFKKLRFNSYVTRK >gi|255516592|ref|ZP_05384268.1|hypothetical
protein CdifQCD-_05729
[*Clostridium difficile* QCD-97b34] (SEQ ID NO: 85)
MKIRKSGFISIECIISIAILYVAVYLVSTSLYNCYSFISRNISDREMLSTA
KKYIEDEKYRIQNSKYELIEDKIEKNYINGYEINSRIEQILDYYQCYEINI
EIKNEFKKLRFNSYVTRK >gi|254974786|ref|ZP_05271258.1|hypothetical
protein CdifQC_05710
[*Clostridium difficile* QCD-66c26] (SEQ ID NO: 85)
MKIRKSGFISIECIISIAILYVAVYLVSTSLYNCYSFISRNISDREMLSTA
KKYIEDEKYRIQNSKYELIEDKIEKNYINGYEINSRIEQILDYYQCYEINI
EIKNEFKKLRFNSYVTRK >gi|255092174|ref|ZP_05321652.1|hypothetical
protein CdifC_05887
[*Clostridium difficile* CIP 107932] (SEQ ID NO: 85)
MKIRKSGFISIECIISIAILYVAVYLVSTSLYNCYSFISRNISDREMLSTA
KKYIEDEKYRIQNSKYELIEDKIEKNYINGYEINSRIEQILDYYQCYEINI
EIKNEFKKLRFNSYVTRK >gi|255655252|ref|ZP_05400661.1|hypothetical
protein CdifQCD-2_06035
[*Clostridium difficile* QCD-23m63] (SEQ ID NO: 87)
MKIRKRGFISIECVISIAILYVAVYLVSTSLYSCYSFVSRNISDRKMLSTA
KKYIEDEKYRIQNSKYELIENKIEKNYINGYEISSRVEQILDYYQCYEINI
EIKNEFKKLRFNSYVTRK PilV Nucleotide
>gi|260685375:c3980297-3979561 *Clostridium
difficile* R20291 chromosome, complete genome
(SEQ ID NO: 70)
ATGAGTTTGTACAAAAATAATGAAAAGGTCTTACTTTATTAGAAGTA
ATAATAGCTGTTTTTATACTGACAATAGTTTTAAGTATTTCTTATAAAGT
GTTCAATGGTATAACATCAGCAGTAAAAAAGCAACAGATTATTACAGA
TGCTCAAGTAAATATTAATCTAATTAATAAGTATCTAAATAGAGATTTG
GAAAACTGTAAAGAGCTAACTAAAACTGGTTCAGGTAATAATTATGAA
TACAATATAGAGATGCCAGATAATGTTGTAAAATATGAAGTTTCTATAG
AAACTAAAAAAATACAGAGGTATATTCTGTAACGAGAATCCAAAACA
ATACAATTGATACAGAAAATGAAGTTAGAGAAGAGATAATCTATAATC
AACCACTAGTTCAAAACAATAAAGAAATGAAGGAAACACCCATTTAAA
TAGAAAAGCAAACTGGTAAATCTATTTATACTGTAAGTATATACTATAA
TGAATCAGTGCAAGAAAGTCATAAAAATAGCAATTTAAATAACAAAAC
TTATACATTTGATGTTATGTCAAGAATAGGGTAA >gi|126697566|ref|NC_009089.1|:4098788-4099524
*Clostridium difficile* 630,
complete genome reverse complement (SEQ ID NO: 72)
ATGAGTTTGTACAAAAATAATGAAAAGGTCTTACTTTATTAGAAGTA
ATAATAGCTGTTTTTATACTGACAATAGTTTTAAGTATTTCTTATAAAGT
GTTCAATGGTATAACATCAGCAGTAAAAAAGCAACAGATTATTACAGA
TGCTCAAGTAAATATTAATCTAATTAATAAGTATCTAAATAGAGATTTG
GAAAACTGTAAAGAACTAACTAAAACTGGTTCAGGTAATAATTATGAA
TACAATATAGAGATGCCAGATAATGTTGTAAAATATGAAGTTTCTATAG
AAACTAAAAAAATACAGAGGTATATTCTGTAACGAGAATCCAAAACA
ATACAATTGATACAGAAAATGAAGTTAGAGAAGAGATAATCTACAATC
AACCACTAGTTCAAAACAATAAAGAAATGAAGGAAACACCCATTTAAA
TAGAAAAGCAAACTGGTAAATCTATTTATACTGTAAGTATATACTATAA
TGAATCAGTGCAAGAAAGTCATAAAAATAGCAATTTAAATAACAAAAC
TTATACATTTGATGTTATGTCAAGAATAGGGTAA >gi|260681769|ref|NC_013315.1|:3898775-3899511
*Clostridium difficile* CD196
chromosome, complete genome reverse complement
(SEQ ID NO: 70)
ATGAGTTTGTACAAAAATAATGAAAAGGTCTTACTTTATTAGAAGTA
ATAATAGCTGTTTTTATACTGACAATAGTTTTAAGTATTTCTTATAAAGT
GTTCAATGGTATAACATCAGCAGTAAAAAAGCAACAGATTATTACAGA
TGCTCAAGTAAATATTAATCTAATTAATAAGTATCTAAATAGAGATTTG
GAAAACTGTAAAGAGCTAACTAAAACTGGTTCAGGTAATAATTATGAA
TACAATATAGAGATGCCAGATAATGTTGTAAAATATGAAGTTTCTATAG
AAACTAAAAAAATACAGAGGTATATTCTGTAACGAGAATCCAAAACA
ATACAATTGATACAGAAAATGAAGTTAGAGAAGAGATAATCTATAATC
AACCACTAGTTCAAAACAATAAAGAAATGAAGGAAACACCCATTTAAA
TAGAAAAGCAAACTGGTAAATCTATTTATACTGTAAGTATATACTATAA
TGAATCAGTGCAAGAAAGTCATAAAAATAGCAATTTAAATAACAAAAC
TTATACATTTGATGTTATGTCAAGAATAGGGTAA >gi|383843669|ref|NC_017179.1|:3906795-3907531
*Clostridium difficile* BI1,
complete genome reverse complement (SEQ ID NO: 76)
ATGAGTTTGTACAAAAATAATGAAAAGGTCTTACTTTATTAGAAGTA
ATAATAGCTGTTTTTATACTGACAATAGTTTTAAGTATTTCTTATAAAGT
GTTCAATGGTATAACATCAGCAGTAAAAAAGCAACAGATTATTACAGA
TGCTCAAGTAAATATTAATCTAATTAATAAGTATCTAAATAGAGATTTG
GAAAACTGTAAAGAGCTAACTAAAACTGGTTCAGGTAATAATTATGAA
TACAATATAGAGATGCCAGATAATGTTGTAAAATATGAAGTTTCTATAG
AAACTAAAAAAATACAGAGGTATATTCTGTAACGAGAATCCAAAACA
ATACAATTGATACAGAAAATGAAGTTAGAGAAGAGATAATCTATAATC
AACCACTAGTTCAAAACAATAAAGAAATGAAGGAAACACCCATTTAAA
TAGAAAAGCAAACTGGTAAATCTATTTATACTGTAAGTATATACTATAA
TGAATCAGTGCAAGAAAGTCATAAAAATAGCAATTTAAATAACAAAAC
TTATACATTTGATGTTATGTCAAGAATAGGGTAA >gi|224514682|ref|NZ_CM000659.1|:3800710-3801446
Clostridium difficile CIP
107932 chromosome, whole genome shotgun
sequence_gi|221149347|gb|CM000659.1|
Clostridium difficile CIP 107932 chromosome,
whole genome shotgun sequence reverse complement
(SEQ ID NO: 76)
ATGAGTTTGTACAAAAATAATGAAAAAGGTCTTACTTTATTAGAAGTA
ATAATAGCTGTTTTTATACTGACAATAGTTTTAAGTATTTCTTATAAAGT
GTTCAATGGTATAACATCAGCAGTAAAAAAGCAACAGATTATTACAGA
TGCTCAAGTAAATATTAATCTAATTAATAAGTATCTAAATAGAGATTTG
GAAAACTGTAAAGAGCTAACTAAAACTGGTTCAGGTAATAATTATGAA
TACAATATAGAGATGCCAGATAATGTTGTAAAATATGAAGTTTCTATAG
AAACTAAAAAAAATACAGAGGTATATTCTGTAACGAGAATCCAAAACA
ATACAATTGATACAGAAAATGAAGTTAGAGAAGAGATAATCTATAATC
AACCCACTAGTTCAAAACAATAAAGAAATGAAGGAAACACCATTTAAAA
TAGAAAAGCAAACTGGTAAATCTATTTATACTGTAAGTATATACTATAA
TGAATCAGTGCAAGAAAGTCATAAAAATAGCAATTTAAATAACAAAAC
TTATACATTTGATGTTATGTCAAGAATAGGGTAA >gi|224514685|ref|NZ_CM000660.1|:3724627-3725362
Clostridium difficile
QCD-23m63 chromosome, whole genome shotgun
sequence_gi|221149428|gb|CM000660.1|
Clostridium difficile QCD-23m63 chromosome,
whole genome shotgun sequence reverse complement
(SEQ ID NO: 80)
ATGAGTTTGTACAAAAATAATGAAAAAGGTCTTACCTTATTAGAAGTA
ATAATAGCTGTTTTTATACTGACAATAGTTTTAAGCATTTCTTATAAGGT
GTTTAATGGTATAACATCAGCAGTAAAAAAGCAACAGATTATTACAGA
TGCTCAAGTAAATATTAACCTAATTAATAAGTATCTAAATAGAGATTTG
GAAAACTGTAAAGAGCTAACTAAAACTGGTTCAGGTAGTAATTATGAA
TATAATATAGAGACGCCAGATAATATTGTAAAATATGAAGTTTCCATA
GAAACTAAAAAAAATACAGAGGTATATTCTGTAACAAGAATCGAAAAA
AATACAATTGATACAGAAAATGAAGTTAGAGAAGAGATAATCTATAAT
CAACCACTAGTTCAAAACAATAAAGAAATGAAAGAAACACCATTTAAA
ATAGAAAAGCAAACTGATAAATCTATTTATACTGTAAGTATATTCTATA
ATGAATCAGTTCAAGAAGGTCATAAAAATAGCAATTTAAATAACAAGA
CTTATACATTTGATGTTATGTCGAGAATAGGATAA >gi|209401276|ref|NZ_CM000287.1|:3891256-3891992
Clostridium difficile QCD-32g58 chromosome, whole
genome shotgun sequence_gi|145843961|gb|CM000287.4|
Clostridium difficile QCD-32g58 chromosome,
whole genome shotgun sequence reverse complement
(SEQ ID NO: 76)
ATGAGTTTGTACAAAAATAATGAAAAAGGTCTTACTTTATTAGAAGTA
ATAATAGCTGTTTTTATACTGACAATAGTTTTAAGTATTTCTTATAAAGT
GTTCAATGGTATAACATCAGCAGTAAAAAAGCAACAGATTATTACAGA
TGCTCAAGTAAATATTAATCTAATTAATAAGTATCTAAATAGAGATTTG
GAAAACTGTAAAGAGCTAACTAAAACTGGTTCAGGTAATAATTATGAA
TACAATATAGAGATGCCAGATAATGTTGTAAAATATGAAGTTTCTATAG
AAACTAAAAAAAATACAGAGGTATATTCTGTAACGAGAATCCAAAACA
ATACAATTGATACAGAAAATGAAGTTAGAGAAGAGATAATCTATAATC
AACCCACTAGTTCAAAACAATAAAGAAATGAAGGAAACACCATTTAAAA
TAGAAAAGCAAACTGGTAAATCTATTTATACTGTAAGTATATACTATAA
TGAATCAGTGCAAGAAAGTCATAAAAATAGCAATTTAAATAACAAAAC
TTATACATTTGATGTTATGTCAAGAATAGGGTAA >gi|224514680|ref|NZ_CM000658.1|:3875660-3876396
Clostridium difficile QCD-37x79 chromosome, whole
genome shotgun sequence_gi|221149249|gb|CM000658.1|
Clostridium difficile QCD-37x79 chromosome,
whole genome shotgun sequence reverse complement
(SEQ ID NO: 76)
ATGAGTTTGTACAAAAATAATGAAAAAGGTCTTACTTTATTAGAAGTA
ATAATAGCTGTTTTTATACTGACAATAGTTTTAAGTATTTCTTATAAAGT
GTTCAATGGTATAACATCAGCAGTAAAAAAGCAACAGATTATTACAGA
TGCTCAAGTAAATATTAATCTAATTAATAAGTATCTAAATAGAGATTTG
GAAAACTGTAAAGAGCTAACTAAAACTGGTTCAGGTAATAATTATGAA
TACAATATAGAGATGCCAGATAATGTTGTAAAATATGAAGTTTCTATAG
AAACTAAAAAAAATACAGAGGTATATTCTGTAACGAGAATCCAAAACA
ATACAATTGATACAGAAAATGAAGTTAGAGAAGAGATAATCTATAATC
AACCCACTAGTTCAAAACAATAAAGAAATGAAGGAAACACCATTTAAAA
TAGAAAAGCAAACTGGTAAATCTATTTATACTGTAAGTATATACTATAA
TGAATCAGTGCAAGAAAGTCATAAAAATAGCAATTTAAATAACAAAAC
TTATACATTTGATGTTATGTCAAGAATAGGGTAA >gi|224514674|ref|NZ_CM000637.1|:3935618-3936354
Clostridium difficile QCD-63q42 chromosome, whole
genome shotgun sequence_gi|219819758|gb|CM000637.1|
Clostridium difficile QCD-63q42 chromosome,
whole genome shotgun sequence reverse complement
(SEQ ID NO: 77)
ATGAGTTTGTACAAAAATAATGAAAAAGGTCTTACTTTATTAGAAGTA
ATAATAGCTGTTTTTATACTGACAATAGTTTTAAGTATTTCTTATAAAGT
GTTCAATGGTATAACATCAGCAGTAAAAAAGCAACAGATTATTACAGA
TGCTCAAGTAAATATTAATCTAATTAATAAGTATCTAAATAGAGATTTG
GAAAACTGTAAAGAACTAACTAAAACTGGTTCAGGTAATAATTATGAA
TACAATATAGAGATGCCAGATAATGTTGTAAAATATGAAGTTTCTATAG
AAACTAAAAAAATACAGAGGTATATTCTGTAACGAGAATCCAAAACA
ATACAATTGATACAGAAAATGAAGTTAGAGAAGAAATAATCTATAATC
AACCACTAGTTCAAAACAATAAAGAAATGAAGGAAACACCATTTAAAA
TAGAAAAGCAAACTGGTAAATCTATTTATACTGTAAGTATATACTATAA
TGAATCAGTGCAAGAAAGTCATAAAAATAGCAATTTAAATAACAAAAC
TTATACATTTGATGTTATGTCAAGAATAGGGTAA >gi|224531476|ref|NZ_CM000441.1|:3876193-3876759
Clostridium difficile QCD-66c26 chromosome, whole
genome shotgun sequence_gi|222154275|gb|CM000441.2|
Clostridium difficile QCD-66c26 chromosome,
whole genome shotgun sequence reverse complement
(SEQ ID NO: 76)
ATGAGTTTGTACAAAAATAATGAAAAAGGTCTTACTTTATTAGAAGTA
ATAATAGCTGTTTTTATACTGACAATAGTTTTAAGTATTTCTTATAAAGT
GTTCAATGGTATAACATCAGCAGTAAAAAAGCAACAGATTATTACAGA
TGCTCAAGTAAATATTAATCTAATTAATAAGTATCTAAATAGAGATTTG
GAAAACTGTAAAGAGCTAACTAAAACTGGTTCAGGTAATAATTATGAA
TACAATATAGAGATGCCAGATAATGTTGTAAAATATGAAGTTTCTATAG
AAACTAAAAAAAATACAGAGGTATATTCTGTAACGAGAATCCAAAACA
ATACAATTGATACAGAAAATGAAGTTAGAGAAGAGATAATCTATAATC
AACCACTAGTTCAAAACAATAAAGAAATGAAGGAAACACCATTTAAAA
TAGAAAAGCAAACTGGTAAATCTATTTATACTGTAAGTATATACTATAA
TGAATCAGTGCAAGAAAGTCATAAAAATAGCAATTTAAATAACAAAAC
TTATACATTTGATGTTATGTCAAGAATAGGGTAA >gi|224514686|ref|NZ_CM000661.1|:3861743-3862309
Clostridium difficile QCD-76w55 chromosome, whole
genome shotgun sequence_gi|221191950|gb|CM000661.1|
Clostridium difficile QCD-76w55 chromosome,
whole genome shotgun sequence reverse complement
(SEQ ID NO: 76)
ATGAGTTTGTACAAAAATAATGAAAAAGGTCTTACTTTATTAGAAGTA
ATAATAGCTGTTTTTATACTGACAATAGTTTTAAGTATTTCTTATAAAGT
GTTCAATGGTATAACATCAGCAGTAAAAAAGCAACAGATTATTACAGA
TGCTCAAGTAAATATTAATCTAATTAATAAGTATCTAAATAGAGATTTG
GAAAACTGTAAAGAGCTAACTAAAACTGGTTCAGGTAATAATTATGAA
TACAATATAGAGATGCCAGATAATGTTGTAAAATATGAAGTTTCTATAG
AAACTAAAAAAAATACAGAGGTATATTCTGTAACGAGAATCCAAAACA
ATACAATTGATACAGAAAATGAAGTTAGAGAAGAGATAATCTATAATC
AACCACTAGTTCAAAACAATAAAGAAATGAAGGAAACACCATTTAAAA
TAGAAAAGCAAACTGGTAAATCTATTTATACTGTAAGTATATACTATAA
TGAATCAGTGCAAGAAAGTCATAAAAATAGCAATTTAAATAACAAAAC
TTATACATTTGATGTTATGTCAAGAATAGGGTAA >gi|224514679|ref|NZ_CM000657.1|:3784159-3784895
Clostridium difficile QCD-97b34 chromosome, whole
genome shotgun sequence_gi|221149047|gb|CM000657.1|
Clostridium difficile QCD-97b34 chromosome,
whole genome shotgun sequence reverse complement
(SEQ ID NO: 76)
ATGAGTTTGTACAAAAATAATGAAAAAGGTCTTACTTTATTAGAAGTA
ATAATAGCTGTTTTTATACTGACAATAGTTTTAAGTATTTCTTATAAAGT
GTTCAATGGTATAACATCAGCAGTAAAAAAGCAACAGATTATTACAGA
TGCTCAAGTAAATATTAATCTAATTAATAAGTATCTAAATAGAGATTTG
GAAAACTGTAAAGAGCTAACTAAAACTGGTTCAGGTAATAATTATGAA
TACAATATAGAGATGCCAGATAATGTTGTAAAATATGAAGTTTCTATAG
AAACTAAAAAAAATACAGAGGTATATTCTGTAACGAGAATCCAAAACA
ATACAATTGATACAGAAAATGAAGTTAGAGAAGAGATAATCTATAATC
AACCACTAGTTCAAAACAATAAAGAAATGAAGGAAACACCATTTAAAA
TAGAAAAGCAAACTGGTAAATCTATTTATACTGTAAGTATATACTATAA
TGAATCAGTGCAAGAAAGTCATAAAAATAGCAATTTAAATAACAAAAC
TTATACATTTGATGTTATGTCAAGAATAGGGTAA -continued PilV Amino Acid
>gi|260688686|ref|YP_003219820.1|
type IV pilin [Clostridium difficile R20291]
(SEQ ID NO: 71)
MSLYKNNEKGLTLLEVIIAVFILTIVLSISYKVFNGITSAVKKQQIITDAQ
VNINLINKYLNRDLENCKELTKTGSGNNYEYNIEMPDNVVKYEVSIETKKN
TEVYSVTRIQNNTIDTENEVREEIIYNQPLVQNNKEMKETPFKIEKQTGKS
IYTVSIYYNESVQESHKNSNLNNKTYTFDVMSRIG >gi|126701132|ref|YP_001090029.1|
type IV pilin [Clostridium difficile 630]
(SEQ ID NO: 73)
MMSLYKNNEKGLTLLEVIIAVFILTIVLSISYKVFNGITSAVKKQQIITDA
QVNINLINKYLNRDLENCKELTKTGSGNNYEYNIEMPDNVVKYEVSIETKK
NTEVYSVTRIQNNTIDTENEVREEIIYNQPLVQNNKEMKETPFKIEKQTGK
SIYTVSIYYNESVQESHKNSNLNNKTYTFDVMSRIG >gi|423087239|ref|ZP_17075628.1|
prepilin-type cleavage/methylation protein
[Clostridium difficile 050-P50-2011]
(SEQ ID NO: 74)
MSLYKNNEKGLTLLEVIIAVFILTIVLSISYKVFNGITSAVKRQQIITDAQ
VNINLINKYLNRDLENCKELTKTGSGNNYEYNIEMPDNVVKYEVSIETKKH
TEVYSVTRIQKNTIDTENEVREEIIYNQPLVQNNKEMKETPFKIEKQTGKS
IYTVSIYYNESVQESHKNINLNNKTYTFDVMSRIG >gi|423080838|ref|ZP_17069455.1|
prepilin-type cleavage/methylation protein
[Clostridium difficile 002-P50-2011]
(SEQ ID NO: 74)
MSLYKNNEKGLTLLEVIIAVFILTIVLSISYKVFNGITSAVKRQQIITDAQ
VNINLINKYLNRDLENCKELTKTGSGNNYEYNIEMPDNVVKYEVSIETKKH
TEVYSVTRIQKNTIDTENEVREEIIYNQPLVQNNKEMKETPFKIEKQTGKS
IYTVSIYYNESVQESHKNINLNNKTYTFDVMSRIG >gi|423090608|ref|ZP_17078897.1|
prepilin-type cleavage/methylation protein
[Clostridium difficile 70-100-2010]
(SEQ ID NO: 71)
MSLYKNNEKGLTLLEVIIAVFILTIVLSISYKVFNGITSAVKKQQIITDAQ
VNINLINKYLNRDLENCKELTKTGSGNNYEYNIEMPDNVVKYEVSIETKKN
TEVYSVTRIQNNTIDTENEVREEIIYNQPLVQNNKEMKETPFKIEKQTGKS
IYTVSIYYNESVQESHKNSNLNNKTYTFDVMSRIG >gi|296449060|ref|ZP_06890850.1|
probable type IV pilin [Clostridium difficile
NAP08] (SEQ ID NO: 75)
MSLYKNNEKGLTLLEVIIAVFILTIVLSISYKVFNGITSAVKKQQIITDAQ
VNINLINKYLNRDLENCKELTKTGSGSNYEYNIETPDNIVKYEVSIETKKN
TEVYSVTRIEKNTIDTENEVREEIIYNQPLVQNNKEMKETPFKIEKQTDKS
IYTVSIFYNESVQEGHKNSNLNNKTYTFDVMSRIG >gi|296879883|ref|ZP_06903856.1|
probable type IV pilin [Clostridium difficile
NAP07] (SEQ ID NO: 75)
MSLYKNNEKGLTLLEVIIAVFILTIVLSISYKVFNGITSAVKKQQIITDAQ
VNINLINKYLNRDLENCKELTKTGSGSNYEYNIETPDNIVKYEVSIETKKN
TEVYSVTRIEKNTIDTENEVREEIIYNQPLVQNNKEMKETPFKIEKQTDKS
IYTVSIFYNESVQEGHKNSNLNNKTYTFDVMSRIG >gi|260685028|ref|YP_003216313.1|
type IV pilin [Clostridium difficile CD196]
(SEQ ID NO: 71)
MSLYKNNEKGLTLLEVIIAVFILTIVLSISYKVFNGITSAVKKQQIITDAQ
VNINLINKYLNRDLENCKELTKTGSGNNYEYNIEMPDNVVKYEVSIETKKN
TEVYSVTRIQNNTIDTENEVREEIIYNQPLVQNNKEMKETPFKIEKQTGKS
IYTVSIYYNESVQESHKNSNLNNKTYTFDVMSRIG >gi|255102718|ref|ZP_05331695.1|
putative type IV pilin [Clostridium difficile
QCD-63q42] (SEQ ID NO: 78)
MYKNNEKGLTLLEVIIAVFILTIVLSISYKVFNGITSAVKKQQIITDAQVN
INLINKYLNRDLENCKELTKTGSGNNYEYNIEMPDNVVKYEVSIETKKNTE
VYSVTRIQNNTIDTENEVREEIIYNQPLVQNNKEMKETPFKIEKQTGKSIY
TVSIYYNESVQESHKNSNLNNKTYTFDVMSRIG >gi|255316213|ref|ZP_05357796.1|
putative type IV pilin [Clostridium difficile
QCD-76w55] (SEQ ID NO: 78)
MYKNNEKGLTLLEVIIAVFILTIVLSISYKVFNGITSAVKKQQIITDAQVN
INLINKYLNRDLENCKELTKTGSGNNYEYNIEMPDNVVKYEVSIETKKNTE
VYSVTRIQNNTIDTENEVREEIIYNQPLVQNNKEMKETPFKIEKQTGKSIY
TVSIYYNESVQESHKNSNLNNKTYTFDVMSRIG >gi|255652054|ref|ZP_05398956.1|
putative type IV pilin [Clostridium difficile
QCD-37x79] (SEQ ID NO: 78)
MYKNNEKGLTLLEVIIAVFILTIVLSISYKVFNGITSAVKKQQIITDAQVN
INLINKYLNRDLENCKELTKTGSGNNYEYNIEMPDNVVKYEVSIETKKNTE
VYSVTRIQNNTIDTENEVREEIIYNQPLVQNNKEMKETPFKIEKQTGKSIY
TVSIYYNESVQESHKNSNLNNKTYTFDVMSRIG >gi|255308539|ref|ZP_05352710.1|
putative type IV pilin [Clostridium difficile
ATCC 43255] (SEQ ID NO: 79)
MYKNNEKGLTLLEVIIAVFILTIVLSISYKVFNGITSAVKKQQIITDAQVN
INLINKYLNRDLENCKELTKTGSGNNYEYNIEMPDNVVKYEVSIETKKNTE
VYSVTRIQNNTIDTENEVREEIIYNQPLVQNNKEMKETPFKIEKRTGKSIY
TVSIYYNESVQESHKNSNLNNKTYTFDVMSRIG >gi|384362702|ref|YP_006200554.1|
type IV pilin [Clostridium difficile BI1]
(SEQ ID NO: 78)
MYKNNEKGLTLLEVIIAVFILTIVLSISYKVFNGITSAVKKQQIITDAQVN
INLINKYLNRDLENCKELTKTGSGNNYEYNIEMPDNVVKYEVSIETKKNTE
VYSVTRIQNNTIDTENEVREEIIYNQPLVQNNKEMKETPFKIEKQTGKSIY
TVSIYYNESVQESHKNSNLNNKTYTFDVMSRIG >gi|255518875|ref|ZP_05386551.1|
putative type IV pilin [Clostridium difficile
QCD-97b34] (SEQ ID NO: 78)
MYKNNEKGLTLLEVIIAVFILTIVLSISYKVFNGITSAVKKQQIITDAQVN
INLINKYLNRDLENCKELTKTGSGNNYEYNIEMPDNVVKYEVSIETKKNTE
VYSVTRIQNNTIDTENEVREEIIYNQPLVQNNKEMKETPFKIEKQTGKSIY
TVSIYYNESVQESHKNSNLNNKTYTFDVMSRIG >gi|254977133|ref|ZP_05273605.1|
putative type IV pilin [Clostridium difficile
QCD-66c26] (SEQ ID NO: 78)
MYKNNEKGLTLLEVIIAVFILTIVLSISYKVFNGITSAVKKQQIITDAQVN
INLINKYLNRDLENCKELTKTGSGNNYEYNIEMPDNVVKYEVSIETKKNTE
VYSVTRIQNNTIDTENEVREEIIYNQPLVQNNKEMKETPFKIEKQTGKSIY
TVSIYYNESVQESHKNSNLNNKTYTFDVMSRIG >gi|255094462|ref|ZP_05323940.1|
putative type IV pilin [Clostridium difficile
CIP 107932] (SEQ ID NO: 78)
MYKNNEKGLTLLEVIIAVFILTIVLSISYKVFNGITSAVKKQQIITDAQVN
INLINKYLNRDLENCKELTKTGSGNNYEYNIEMPDNVVKYEVSIETKKNTE
VYSVTRIQNNTIDTENEVREEIIYNQPLVQNNKEMKETPFKIEKQTGKSIY
TVSIYYNESVQESHKNSNLNNKTYTFDVMSRIG >gi|306521791|ref|ZP_07408138.1|
putative type IV pilin [Clostridium difficile
QCD-32g58] (SEQ ID NO: 78)
MYKNNEKGLTLLEVIIAVFILTIVLSISYKVFNGITSAVKKQQIITDAQVN
INLINKYLNRDLENCKELTKTGSGNNYEYNIEMPDNVVKYEVSIETKKNTE
VYSVTRIQNNTIDTENEVREEIIYNQPLVQNNKEMKETPFKIEKQTGKSIY
TVSIYYNESVQESHKNSNLNNKTYTFDVMSRIG >gi|255657465|ref|ZP_05402874.1|
putative type IV pilin [Clostridium difficile
QCD-23m63] (SEQ ID NO: 81)
MYKNNEKGLTLLEVIIAVFILTIVLSISYKVFNGITSAVKKQQIITDAQVN
INLINKYLNRDLENCKELTKTGSGSNYEYNIETPDNIVKYEVSIETKKNTE
VYSVTRIEKNTIDTENEVREEIIYNQPLVQNNKEMKETPFKIEKQTDKSIY
TVSIFYNESVQEGHKNSNLNNKTYTFDVMSRIG PilW Nucleotide
>gi|260685375:2578173-2578815 Clostridium difficile
R20291 chromosome, complete genome (SEQ ID NO: 29)
ATGAAAAATAAAAAAGGATTTACTCTAGTGGAATTATTAGTAGTAATT
GCTATAATAGGAATTTGGCAATAATAGCACTTCCAGCATTATTTAAAA
ATATAGAAAAAGCAAAGATAGCTAAACTTGAAGCTGATATAAGTGCAA
TAAAAAGTGCATCTCTTAGTTACTATGCTGATGAATCCAAGTATACTGA
TGGAGGAATGATATCATGGGTAAAGAAAGATGGAAAAATAATAATAA
ATGGGGGTTTTAAAGATGACCCATTAGCAGATAAAATAGAAAATTTAG
GGATGCCTTATAATGGTTCATATCTGTTAATGTCATCTCCTGGTCATGA
AAAAATATCTAGAATTAAGCATACTTCCAGAAGGAGAAATAAGCAAAG
TGGTCTAGATAAATTAAAAAATGATTATGGAAATTTAATAGACATAAC
GAACGATCAAAATAAAATAAATATTGTAATAAAACTTTTAAATAATAA
ATCGAATACTTAA >gi|126697566|ref|NC_009089.1|:2669120-2669761
*Clostridium difficile* 630,
complete genome (SEQ ID NO: 33)
ATGAAAAATAAAAAAGGATTTACTCTAGTGGAATTATTAGTAGTAATT
GCTATAATAGGAATATTGGCAATAGTAGCACTTCCAGCATTATTTAAAA
ATATAGAAAAAGCAAAGATAGCTAAACTTGAAGCTGATATAAGTGCAA
TAAAAAGTGCGTCTCTTAGCTACTATGCAGATGAATCAAAATATACTGA
TGGAGGAATGATATCATGGGTAAAGAAAGATGGAAAAATAATAATAA
ATGGTGGCTTTAAAGATGACCCATTAGCAGATAAAATAGAAAATTTAG
GTATGCCTTATAATGGTTCATATCTATTAATGTCATCTCCTGGTCATGAA
AAATATCTAGAATTAAGTATACTTCCAGAAGGAGAAATAAGCAAAGT
GGTCTAGATAAATTAAAAAGTGATTATGGAAGTTCAATAGACATAAAG
AACGATCAAAACAAAATAGATATTGTAATAAAACTTTTAAATGATAAA
TCGAATACTTAA >gi|260681769|ref|NC_013315.1|:2497692-2498186
*Clostridium difficile* CD196
chromosome, complete genome (SEQ ID NO: 29)
ATGAAAAATAAAAAAGGATTTACTCTAGTGGAATTATTAGTAGTAATT
GCTATAATAGGAATATTGGCAATAATAGCACTTCCAGCATTATTTAAAA
ATATAGAAAAAGCAAAGATAGCTAAACTTGAAGCTGATATAAGTGCAA
TAAAAAGTGCATCTCTTAGTTACTATGCTGATGAATCCAAGTATACTGA
TGGAGGAATGATATCATGGGTAAAGAAAGATGGAAAAATAATAATAA
ATGGGGGTTTTAAAGATGACCCATTAGCAGATAAAATAGAAAATTTAG
GGATGCCTTATAATGGTTCATATCTGTTAATGTCATCTCCTGGTCATGA
AAAATATCTAGAATTAAGCATACTTCCAGAAGGAGAAATAAGCAAAAG
TGGTCTAGATAAATTAAAAAATGATTATGGAAATTTAATAGACATAAC
GAACGATCAAAATAAAATAAATATTGTAATAAAACTTTTAAATAATAA
ATCGAATACTTAA >gi|383843669|ref|NC_017179.1|:2505704-2506198
*Clostridium difficile* BI1,
complete genome (SEQ ID NO: 29)
ATGAAAAATAAAAAAGGATTTACTCTAGTGGAATTATTAGTAGTAATT
GCTATAATAGGAATATTGGCAATAATAGCACTTCCAGCATTATTTAAAA
ATATAGAAAAAGCAAAGATAGCTAAACTTGAAGCTGATATAAGTGCAA
TAAAAAGTGCATCTCTTAGTTACTATGCTGATGAATCCAAGTATACTGA
TGGAGGAATGATATCATGGGTAAAGAAAGATGGAAAAATAATAATAA
ATGGGGGTTTTAAAGATGACCCATTAGCAGATAAAATAGAAAATTTAG
GGATGCCTTATAATGGTTCATATCTGTTAATGTCATCTCCTGGTCATGA
AAAATATCTAGAATTAAGCATACTTCCAGAAGGAGAAATAAGCAAAAG
TGGTCTAGATAAATTAAAAAATGATTATGGAAATTTAATAGACATAAC
GAACGATCAAAATAAAATAAATATTGTAATAAAACTTTTAAATAATAA
ATCGAATACTTAA >gi|224514682|ref|NZ_CM000659.1|:2432746-2433388
*Clostridium difficile* CIP
107932 chromosome, whole genome shotgun
sequence_gi|221149347|gb|CM000659.1|
*Clostridium difficile* CIP 107932 chromosome,
whole genome shotgun sequence (SEQ ID NO: 29)
ATGAAAAATAAAAAAGGATTTACTCTAGTGGAATTATTAGTAGTAATT
GCTATAATAGGAATATTGGCAATAATAGCACTTCCAGCATTATTTAAAA
ATATAGAAAAAGCAAAGATAGCTAAACTTGAAGCTGATATAAGTGCAA
TAAAAAGTGCATCTCTTAGTTACTATGCTGATGAATCCAAGTATACTGA
TGGAGGAATGATATCATGGGTAAAGAAAGATGGAAAAATAATAATAA
ATGGGGGTTTTAAAGATGACCCATTAGCAGATAAAATAGAAAATTTAG
GGATGCCTTATAATGGTTCATATCTGTTAATGTCATCTCCTGGTCATGA
AAAATATCTAGAATTAAGCATACTTCCAGAAGGAGAAATAAGCAAAAG
TGGTCTAGATAAATTAAAAAATGATTATGGAAATTTAATAGACATAAC
GAACGATCAAAATAAAATAAATATTGTAATAAAACTTTTAAATAATAA
ATCGAATACTTAA >gi|209401276|ref|NZ_CM000287.1|:2490934-2491576
*Clostridium difficile* QCD-32g58 chromosome, whole
genome shotgun sequence_gi|145843961|gb|CM000287.4|
*Clostridium difficile* QCD-32g58 chromosome,
whole genome shotgun sequence (SEQ ID NO: 29)
ATGAAAAATAAAAAAGGATTTACTCTAGTGGAATTATTAGTAGTAATT
GCTATAATAGGAATATTGGCAATAATAGCACTTCCAGCATTATTTAAAA
ATATAGAAAAAGCAAAGATAGCTAAACTTGAAGCTGATATAAGTGCAA
TAAAAAGTGCATCTCTTAGTTACTATGCTGATGAATCCAAGTATACTGA
TGGAGGAATGATATCATGGGTAAAGAAAGATGGAAAAATAATAATAA
ATGGGGGTTTTAAAGATGACCCATTAGCAGATAAAATAGAAAATTTAG
GGATGCCTTATAATGGTTCATATCTGTTAATGTCATCTCCTGGTCATGA
AAAATATCTAGAATTAAGCATACTTCCAGAAGGAGAAATAAGCAAAAG
TGGTCTAGATAAATTAAAAAATGATTATGGAAATTTAATAGACATAAC
GAACGATCAAAATAAAATAAATATTGTAATAAAACTTTTAAATAATAA
ATCGAATACTTAA >gi|224514680|ref|NZ_CM000658.1|:2444282-2444924
*Clostridium difficile* QCD-37x79 chromosome, whole
genome shotgun sequence_gi|221149249|gb|CM000658.1|
*Clostridium difficile* QCD-37x79 chromosome,
whole genome shotgun sequence (SEQ ID NO: 29)
ATGAAAAATAAAAAAGGATTTACTCTAGTGGAATTATTAGTAGTAATT
GCTATAATAGGAATATTGGCAATAATAGCACTTCCAGCATTATTTAAAA
ATATAGAAAAAGCAAAGATAGCTAAACTTGAAGCTGATATAAGTGCAA
TAAAAAGTGCATCTCTTAGTTACTATGCTGATGAATCCAAGTATACTGA
TGGAGGAATGATATCATGGGTAAAGAAAGATGGAAAAATAATAATAA
ATGGGGGTTTTAAAGATGACCCATTAGCAGATAAAATAGAAAATTTAG
GGATGCCTTATAATGGTTCATATCTGTTAATGTCATCTCCTGGTCATGA
AAAATATCTAGAATTAAGCATACTTCCAGAAGGAGAAATAAGCAAAAG
TGGTCTAGATAAATTAAAAAATGATTATGGAAATTTAATAGACATAAC
GAACGATCAAAATAAAATAAATATTGTAATAAAACTTTTAAATAATAA
ATCGAATACTTAA >gi|224514674|ref|NZ_CM000637.1|:2483568-2484018
*Clostridium difficile* QCD-63q42 chromosome, whole
genome shotgun sequence_gi|219819758|gb|CM000637.1|
*Clostridium difficile* QCD-63q42 chromosome,
whole genome shotgun sequence (SEQ ID NO: 37)
ATGAAAAATAAAAAAGGATTTACTCTAGTGGAATTATTAGTAGTAATT
GCTATAATAGGAATATTGGCAATAGTAGCACTTCCAGCATTATTTAAAA
ATATAGAAAAAGCAAAGATAGCTAAACTTGAAGCTGATATAAGTGCAA
TAAAAAGTGCGTCTCTTAGCTACTATGCAGATGAATCAAAATATACTGA
AGGAAACATATATGGTGGACTAAAAAAGATGGAAAAATAACAGTAA
ACTCTGGTATTGGTGATGAAGACCCTTTGGCACATAAAATAGAAAATTT
AGGCATGCCTTATAATGGTTCGTACACTTTAGTGTCATCTAATGGTAGT
GAAGAATACTTAGAATTAAACATAATTATAGATGGAGAAATAAGTAAA
AGTGGTCTAGATAAATTAGAAGAAGATTATGGTAGTTCAATAACAATA
CCAAATGATAAAAATA >gi|224531476|ref|NZ_CM000441.1|:2438544-2439186
*Clostridium difficile* QCD-66c26 chromosome, whole
genome shotgun sequence_gi|222154275|gb|CM000441.2|
*Clostridium difficile* QCD-66c26 chromosome,
whole genome shotgun sequence (SEQ ID NO: 29)
ATGAAAAATAAAAAAGGATTTACTCTAGTGGAATTATTAGTAGTAATT
GCTATAATAGGAATATTGGCAATAATAGCACTTCCAGCATTATTTAAAA
ATATAGAAAAAGCAAAGATAGCTAAACTTGAAGCTGATATAAGTGCAA
TAAAAAGTGCATCTCTTAGTTACTATGCTGATGAATCCAAGTATACTGA
TGGAGGAATGATATCATGGGTAAAGAAAGATGGAAAAATAATAATAA
ATGGGGGTTTTAAAGATGACCCATTAGCAGATAAAATAGAAAATTTAG
GGATGCCTTATAATGGTTCATATCTGTTAATGTCATCTCCTGGTCATGA
AAAATATCTAGAATTAAGCATACTTCCAGAAGGAGAAATAAGCAAAAG
TGGTCTAGATAAATTAAAAAATGATTATGGAAATTTAATAGACATAAC
GAACGATCAAAATAAAATAAATATTGTAATAAAACTTTTAAATAATAA
ATCGAATACTTAA >gi|224514686|ref|NZ_CM000661.1|:2487075-2487717
*Clostridium difficile* QCD-76w55 chromosome, whole
genome shotgun sequence_gi|221191950|gb|CM000661.1|
*Clostridium difficile* QCD-76w55 chromosome,
whole genome shotgun sequence (SEQ ID NO: 29)
ATGAAAAATAAAAAAGGATTTACTCTAGTGGAATTATTAGTAGTAATT
GCTATAATAGGAATATTGGCAATAATAGCACTTCCAGCATTATTTAAAA
ATATAGAAAAAGCAAAGATAGCTAAACTTGAAGCTGATATAAGTGCAA
TAAAAAGTGCATCTCTTAGTTACTATGCTGATGAATCCAAGTATACTGA
TGGAGGAATGATATCATGGGTAAAGAAAGATGGAAAAATAATAATAA
ATGGGGGTTTTAAAGATGACCCATTAGCAGATAAAATAGAAAATTTAG
GGATGCCTTATAATGGTTCATATCTGTTAATGTCATCTCCTGGTCATGA
AAAATATCTAGAATTAAGCATACTTCCAGAAGGAGAAATAAGCAAAAG
TGGTCTAGATAAATTAAAAAATGATTATGGAAATTTAATAGACATAAC
GAACGATCAAAATAAAATAAATATTGTAATAAAACTTTTAAATAATAA
ATCGAATACTTAA >gi|224514679|ref|NZ_CM000657.1|:2420211-2420853
*Clostridium difficile* QCD-97b34 chromosome, whole
genome shotgun sequence_gi|221149047|gb|CM000657.1|
*Clostridium difficile* QCD-97b34 chromosome,
whole genome shotgun sequence (SEQ ID NO: 29)
ATGAAAAATAAAAAAGGATTTACTCTAGTGGAATTATTAGTAGTAATT
GCTATAATAGGAATATTGGCAATAATAGCACTTCCAGCATTATTTAAAA
ATATAGAAAAAGCAAAGATAGCTAAACTTGAAGCTGATATAAGTGCAA
TAAAAAGTGCATCTCTTAGTTACTATGCTGATGAATCCAAGTATACTGA
TGGAGGAATGATATCATGGGTAAAGAAAGATGGAAAAATAATAATAA
ATGGGGGTTTTAAAGATGACCCATTAGCAGATAAAATAGAAAATTTAG
GGATGCCTTATAATGGTTCATATCTGTTAATGTCATCTCCTGGTCATGA -continued
```
AAAATATCTAGAATTAAGCATACTTCCAGAAGGAGAAATAAGCAAAAG
TGGTCTAGATAAATTAAAAAATGATTATGGAAATTTAATAGACATAAC
GAACGATCAAAATAAAATAAATATTGTAATAAAACTTTTAAATAATAA
ATCGAATACTTAA PilW Amino Acid
>gi|260687543|ref|YP_003218677.1|
pilin protein [Clostridium difficile R20291]
(SEQ ID NO: 30)
MKNKKGFTLVELLVVIAIIGILAIIALPALFKNIEKAKIAKLEADISAIKS
ASLSYYADESKYTDGGMISWVKKDGKIIINGGFKDDPLADKIENLGMPYNG
SYLLMSSPGHEKYLELSILPEGEISKSGLDKLKNDYGNLIDITNDQNKINI
VIKLLNNKSNT >gi|126699922|ref|YP_001088819.1|
pilin protein [Clostridium difficile 630]
(SEQ ID NO: 34)
MKNKKGFTLVELLVVIAIIGILAIVALPALFKNIEKAKIAKLEADISAIKS
ASLSYYADESKYTDGGMISWVKKDGKIIINGGFKDDPLADKIENLGMPYNG
SYLLMSSPGHEKYLELSILPEGEISKSGLDKLKSDYGSSIDIKNDQNKIDI
VIKLLNDKSNT >gi|423092327|ref|ZP_17080131.1|
prepilin-type cleavage/methylation protein
[Clostridium difficile 70-100-2010] (SEQ ID NO: 52)
MKNKKGFTLVELLVVIAIIGILAIVALPALFKNIEKAKIAKLEADISAIKS
ASLSYYADESKYTEGNIIWWTKKDGKITVNSGIGDEDPLAHKIENLGMPYN
GSYTLVSSNGSEEYLELNIIIDGEISKSGLDKLEEDYGSSIKIPNDKNMII
TFLSNKSDN >gi|260683883|ref|YP_003215168.1|
pilin [Clostridium difficile CD196] (SEQ ID NO: 30)
MKNKKGFTLVELLVVIAIIGILAIIALPALFKNIEKAKIAKLEADISAIKS
ASLSYYADESKYTDGGMISWVKKDGKIIINGGFKDDPLADKIENLGMPYNG
SYLLMSSPGHEKYLELSILPEGEISKSGLDKLKNDYGNLIDITNDQNKINI
VIKLLNNKSNT >gi|255101452|ref|ZP_05330429.1|
putative pilin protein [Clostridium difficile
QCD-63q42] (SEQ ID NO: 38)
MKNKKGFTLVELLVVIAIIGILAIVALPALFKNIEKAKIAKLEADISAIKS
ASLSYYADESKYTEGNIIWWTKKDGKITVNSGIGDEDPLAHKIENLGMPYN
GSYTLVSSNGSEEYLELNIIIDGEISKSGLDKLEEDYGSSITIPNDKNMII
TFLSNKSDN >gi|255315015|ref|ZP_05356598.1|
putative pilin protein [Clostridium difficile
QCD-76w55] (SEQ ID NO: 30)
MKNKKGFTLVELLVVIAIIGILAIIALPALFKNIEKAKIAKLEADISAIKS
ASLSYYADESKYTDGGMISWVKKDGKIIINGGFKDDPLADKIENLGMPYNG
SYLLMSSPGHEKYLELSILPEGEISKSGLDKLKNDYGNLIDITNDQNKINI
VIKLLNNKSNT >gi|255650800|ref|ZP_05397702.1|
putative pilin protein [Clostridium difficile
QCD-37x79] (SEQ ID NO: 30)
MKNKKGFTLVELLVVIAIIGILAIIALPALFKNIEKAKIAKLEADISAIKS
ASLSYYADESKYTDGGMISWVKKDGKIIINGGFKDDPLADKIENLGMPYNG
SYLLMSSPGHEKYLELSILPEGEISKSGLDKLKNDYGNLIDITNDQNKTNI
VIKLLNNKSNT >gi|255307325|ref|ZP_05351496.1|
putative pilin protein [Clostridium difficile
ATCC 43255] (SEQ ID NO: 38)
MKNKKGFTLVELLVVIAIIGILAIVALPALFKNIEKAKIAKLEADISAIKS
ASLSYYADESKYTEGNIIWWTKKDGKITVNSGIGDEDPLAHKIENLGMPYN
GSYTLVSSNGSEEYLELNIIIDGEISKSGLDKLEEDYGSSITIPNDKNMII
TFLSNKSDN >gi|384361517|ref|YP_006199369.1|
pilin protein [Clostridium difficile BI1]
(SEQ ID NO: 30)
MKNKKGFTLVELLVVIAIIGILAIIALPALFKNIEKAKIAKLEADISAIKS
ASLSYYADESKYTDGGMISWVKKDGKIIINGGFKDDPLADKIENLGMPYNG
SYLLMSSPGHEKYLELSILPEGEISKSGLDKLKNDYGNLIDITNDQNKINI
VIKLLNNKSNT >gi|255517690|ref|ZP_05385366.1|
putative pilin protein [Clostridium difficile
QCD-97b34] (SEQ ID NO: 30)
MKNKKGFTLVELLVVIAIIGILAIIALPALFKNIEKAKIAKLEADISAIKS
ASLSYYADESKYTDGGMISWVKKDGKIIINGGFKDDPLADKIENLGMPYNG
SYLLMSSPGHEKYLELSILPEGEISKSGLDKLKNDYGNLIDITNDQNKINI
VIKLLNNKSNT >gi|254975886|ref|ZP_05272358.1|
putative pilin protein [Clostridium difficile
QCD-66c26] (SEQ ID NO: 30)
MKNKKGFTLVELLVVIAIIGILAIIALPALFKNIEKAKIAKLEADISAIKS
ASLSYYADESKYTDGGMISWVKKDGKIIINGGFKDDPLADKIENLGMPYNG
SYLLMSSPGHEKYLELSILPEGEISKSGLDKLKNDYGNLIDITNDQNKINI
VIKLLNNKSNT >gi|255093273|ref|ZP_05322751.1|
putative pilin protein [Clostridium difficile CIP
107932] (SEQ ID NO: 30)
MKNKKGFTLVELLVVIAIIGILAIIALPALFKNIEKAKIAKLEADISAIKS
ASLSYYADESKYTDGGMISWVKKDGKIIINGGFKDDPLADKIENLGMPYNG
SYLLMSSPGHEKYLELSILPEGEISKSGLDKLKNDYGNLIDITNDQNKINI
VIKLLNNKSNT >gi|306520701|ref|ZP_07407048.1|putative
pilin protein [Clostridium difficile
QCD-32g58] (SEQ ID NO: 30)
MKNKKGFTLVELLVVIAIIGILAIIALPALFKNIEKAKIAKLEADISAIK
SASLSYYADESKYTDGGMISWVKKDGKIIINGGFKDDPLADKIENLGMPY
NGSYLLMSSPGHEKYLELSILPEGEISKSGLDKLKNDYGNLIDITNDQNK
INIVIKLLNNKSNT PilK Amino Acid
PilK (CDR20291 3343) (SEQ ID NO: 88)
MRKWNKFKSERGAALVLVLIVVALLSIVGLIFSNQIANRIKSTKTTNEGIQ
AKYLAETCVENSIDKAYEKLYDELEKMDNEFKSENQEKSISRSKLRNISDE
DFNNQDEKNIEAERLGYMNNINFYLNKASSDLEKASMELKKLYDLDMLDY
RDIEYVDANIISHRDSILEICKNYTSGDISKINEYILKEDIDSTTLIEAKL
VNNDILLKMFLEENKIENEHLNSAFSHTYKALDNISLAMQNMIEYRHTFHI
DEPKVEVSNGIPDSQQYYELIQNPIINSMEYIWNSKWDTLENLLEILPNQT
QGFNSLRVHLRNNVRKFEKLSDNISSGKKNTAKNFLKYKELLYEISDQCNQ
LKSMSYEKIPVKYDNMALITTFDYIQNELLAEIKCRLKELKPQEIDKTEGI
TIKIPFYKADYDMTKEGWPKLKENGSGAELSLMVTGDKDGIKEVEVTDGKK
NIIGLGVEENSNSKYKVDAIVNFNLNIDTNVVGNYDIKDKILINHDISSYK
KVN PilX2 Amino Acid
PilX2 (CDR20291 1084) (SEQ ID NO: 89)
MKHKYGYLLLESVVSLSSMVIIILVLYSIFLSTINLKLKVEDKIELQQ
QSLEIIKSMEGIISNSMGIMNVSNYEETFKKTTSIKCRYVDENNNEESISN
KEIILNERRNKLFVNSLNGESSQAGGYEIGDYVDEMYVLITNNGQYVNIKL
KLSKRSQKYETDFKIKVWNFSESI
```

Vectors, Host Cells, Recombinant Expression, Polypeptides, Antigenic Fragments and Variants.

In some embodiments, the present invention relates to vectors that comprise a type IV pilin polynucleotide from C. difficile, host cells which are genetically engineered to express type IV pilins and the production of polypeptides of the invention by recombinant techniques. Cell-free translation systems can also be employed to produce such proteins using RNAs derived from the DNA constructs of the invention.

When a polynucleotide encoding a type IV pilin of C. difficile is used for the recombinant production of a polypeptide, the polynucleotide may include the coding sequence for the full-length polypeptide or an antigenic fragment thereof, by itself; the coding sequence for the full-length polypeptide or fragment in reading frame with other coding sequences, such as those encoding a leader or secretory sequence, a pre-, or pro or prepro-protein sequence, or other fusion peptide portions. For example, a marker sequence that facilitates purification of the fused polypeptide can be encoded. In certain embodiments of this aspect of the invention, the marker sequence is a hexahistidine peptide, for example, as provided in the pQE vector (Qiagen, Inc.) and described in Gentz et al., *Proc Natl Acad Sci USA* 86:821-824 (1989), or it may be the HA tag, which corresponds to an epitope derived from the influenza hemagglutinin protein (Wilson, I., et al., *Cell* 37:767, 1984). The polynucleotide may also contain non-coding 5' and 3' sequences, such as transcribed, non-translated sequences, ribosome binding sites and sequences that stabilize mRNA.

Representative examples of appropriate hosts include bacterial cells, such as streptococci, staphylococci, *E. coli, Streptomyces, Bacillus subtilis*, and *Salmonella enterica typhi* cells; fungal cells, such as yeast cells and *Aspergillus* cells. In some embodiments, gram negative bacteria are the host cells. A great variety of expression systems can be used, including DNA or RNA vectors. In other embodiments, the invention provides an isolated nucleic acid molecule comprising a type IV pilin operably linked to a heterologous promoter. In some embodiments, the invention further provides an isolated nucleic acid molecule comprising a type IV pilin operably linked to a heterologous promoter, wherein said isolated nucleic acid molecule is capable of expressing a type IV pilin polypeptide when used to transform an appropriate host cell.

In some embodiments, the invention relates to an isolated nucleic acid molecule encoding an antigenic fragment of type IV pilin linked to an affinity tag sequence and enzymatic cleavage sequence to facilitate purification. In some embodiments, the affinity tag is a 6×-Histidine tag and the cleavage sequence is recognized by enterokinase. In some embodiments, the nucleic acid molecules are optimized to increase expression in *E. coli* without altering the amino acid sequence using preferred codons in *E. coli*.

In some embodiments, the present invention is directed to purified polypeptides, variants and antigenic fragments of a type IV pilin of *C. difficile*. In some embodiments, the type IV pilin is engineered to lack the native leader sequence and amino terminal hydrophobic domain.

In some embodiments, the type IV pilin is engineered as follows: the amino acid sequence of the pilin gene is inspected to identify the prepilin peptidase cleavage site, usually found approximately 5-15 amino acids from the amino terminus. The cleavage site is preceded by a glycine residue and followed by five amino acids: a phenylalanine, tyrosine, leucine or alanine; a threonine or serine; a leucine; a valine a leucine or an isoleucine; and a glutamic acid. Additional minor variations on these residues sometimes occur. Next, a stretch of hydrophobic amino acids immediately following these five residues is identified using a conventional internet secondary structure prediction algorithm. This sequence is inspected to identify a hydrophilic amino acid (serine, glutamine, asparigine, lysine) approximately 25 (range 20-30) amino acids from the cleavage site. In some embodiments, the expression construct begins with the codon for this amino acid and continues to the stop codon.

In some embodiments, the amino acid sequence to be expressed is then reverse translated for codon optimization in *E. coli* using a commercial tool and synthesized along with flanking restriction sites. In some embodiments, the synthetic gene is cloned into an expression vector, such as pET30B to add an N-terminal hexahistidine tag and protease cleavage site.

In some embodiments, the type IV pilin polypeptides of the present invention include the polypeptides of SEQ ID NO:2, SEQ ID NO:6, SEQ ID NO:10, SEQ ID NO:14, SEQ ID NO:18, SEQ ID NO:22, SEQ ID NO:26, SEQ ID NO:30, SEQ ID NO:34, SEQ ID NO:38, SEQ ID NO:42, SEQ ID NO:46, SEQ ID NO:47, SEQ ID NO:48, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:63, SEQ ID NO:65, SEQ ID NO:66, SEQ ID NO:67, SEQ ID NO:69, SEQ ID NO:71, SEQ ID NO:73, SEQ ID NO:74, SEQ ID NO:75, SEQ ID NO:78, SEQ ID NO:79, SEQ ID NO:81, SEQ ID NO:83, SEQ ID NO:85, SEQ ID NO:87, SEQ ID NO:88 and SEQ ID NO:89 as well as antigenic fragments and variants which have at least 90% identity thereto. In some embodiments, the polypeptides have at least 96%, 97% or 98% identity to the polypeptides of SEQ ID NO:2, SEQ ID NO:6, SEQ ID NO:10, SEQ ID NO:14, SEQ ID NO:18, SEQ ID NO:22, SEQ ID NO:26, SEQ ID NO:30, SEQ ID NO:34, SEQ ID NO:38, SEQ ID NO:42, SEQ ID NO:46, SEQ ID NO:47, SEQ ID NO:48, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:63, SEQ ID NO:65, SEQ ID NO:66, SEQ ID NO:67, SEQ ID NO:69, SEQ ID NO:71, SEQ ID NO:73, SEQ ID NO:74, SEQ ID NO:75, SEQ ID NO:78, SEQ ID NO:79, SEQ ID NO:81, SEQ ID NO:83, SEQ ID NO:85, SEQ ID NO:87, SEQ ID NO:88, SEQ ID NO:89 and antigenic fragments thereof. In some embodiments, the polypeptides have at least 91%, 92%, 93%, 94%, 95%, 96%, 97%, 98%, 99%, or 100% identity to the polypeptide of SEQ ID NO:2, SEQ ID NO:6, SEQ ID NO:10, SEQ ID NO:14, SEQ ID NO:18, SEQ ID NO:22, SEQ ID NO:26, SEQ ID NO:30, SEQ ID NO:34, SEQ ID NO:38, SEQ ID NO:42, SEQ ID NO:46, SEQ ID NO:47, SEQ ID NO:48, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:63, SEQ ID NO:65, SEQ ID NO:66, SEQ ID NO:67, SEQ ID NO:69, SEQ ID NO:71, SEQ ID NO:73, SEQ ID NO:74, SEQ ID NO:75, SEQ ID NO:78, SEQ ID NO:79, SEQ ID NO:81, SEQ ID NO:83, SEQ ID NO:85, SEQ ID NO:87, SEQ ID NO:88, SEQ ID NO:89 and antigenic fragments thereof.

In some embodiments, the variant polypeptides, including those which have 90% or more identity to the type IV pilins described herein or antigenic fragments thereof, are recognized by an antibody that binds a polypeptide selected from the group consisting of SEQ ID NO:2, SEQ ID NO:6, SEQ ID NO:10, SEQ ID NO:14, SEQ ID NO:18, SEQ ID NO:22, SEQ ID NO:26, SEQ ID NO:30, SEQ ID NO:34, SEQ ID NO:38, SEQ ID NO:42, SEQ ID NO:46, SEQ ID NO:47, SEQ ID NO:48, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:63, SEQ ID NO:65, SEQ ID NO:66, SEQ ID NO:67, SEQ ID NO:69, SEQ ID NO:71, SEQ ID NO:73, SEQ ID NO:74, SEQ ID NO:75, SEQ ID NO:78, SEQ ID NO:79, SEQ ID NO:81, SEQ ID NO:83, SEQ ID NO:85, SEQ ID NO:87, SEQ ID NO:88 and SEQ ID NO:89 and antigenic fragments thereof. In some embodiments, the invention is directed to a variant having 90%, 91%, 92%, 93%, 94%, 95%, 96%, 97%, 98%, 99% or more identity to a type IV pilin described herein and is recognized by an antibody that binds a type IV pilin antigenic fragment selected from the group consisting of amino acids 35-173 of SEQ ID NO:2, amino acids 35-173 of SEQ ID NO:6, amino acids 35-173 of SEQ ID NO:10, amino acids 35-171 of SEQ ID NO:14, amino acids 35-170 of SEQ ID NO:18, amino acids 34-119 of SEQ ID NO:22, amino acids 31-116 of SEQ ID NO:26, amino acids 32-164 of SEQ ID NO:30, amino acids 32-164 of SEQ ID NO:34, amino acids 32-162 of SEQ ID NO:38, amino acids 36-272 of SEQ ID NO:42, amino acids 35-173 of SEQ ID NO:46, amino acids 35-173 of SEQ ID NO:47, amino acids 35-173 of SEQ ID NO:48, amino acids 31-116 of SEQ ID NO:50, amino acids 31-116 of SEQ ID NO:51, amino acids 32-162 of SEQ ID NO:52, amino acids 31-267 of SEQ ID NO:53, amino acids 36-272 of SEQ ID NO:54, amino acids 36-272 of SEQ ID NO:55, amino acids 36-272 of SEQ ID NO:56, amino acids 31-267 of SEQ ID NO:57, amino acids 31-267 of SEQ ID NO:58, amino acids 31-267 of SEQ ID NO:59 and amino acids 31-267 of SEQ ID NO:60, amino acids 34-175 of SEQ ID NO: 63, amino acids 34-175 of SEQ ID NO: 65, amino acids 34-175 of SEQ ID NO: 66, amino acids 34-175 of SEQ ID NO: 67, amino acids 34-175 of SEQ ID NO: 69, amino acids 42-188 of SEQ ID NO: 71, amino acids 43-189 of SEQ ID NO: 73, amino acids 42-188 of SEQ ID NO:74, amino acids 42-188 of SEQ ID NO:75, amino acids 40-186 of SEQ ID NO:78, amino acids 40-186 of SEQ ID NO:79, amino acids 40-186 of SEQ ID NO:81, amino acids 32-124 of SEQ ID NO:83, amino acids 28-120 of SEQ ID NO:85, amino acids 28-120 of SEQ ID NO:87, amino acids 33-512 of SEQ ID NO:88 and amino acids 32-174 of SEQ ID NO:89. In some embodiments, the type IV pilin polypeptides, variants or antigenic fragments are part of a larger protein such as a fusion protein. It is often advantageous to include additional amino acid sequence which contains secretory or leader sequences, pro-sequences, sequences which aid in purification such as multiple histidine residues, or additional sequence for stability during recombinant production.

An antigenic fragment is a polypeptide having an amino acid sequence that entirely is the same as part but not all of the amino acid sequence of one of the aforementioned type IV pilin polypeptides. The antigenic fragment can be "free-standing," or comprised within a larger polypeptide of which they form a part or region, most preferably as a single continuous region.

In some embodiments, the antigenic fragments include, for example, truncation polypeptides having the amino acid sequence of the type IV pilin polypeptides, except for deletion of a continuous series of residues that includes the amino terminus, or a continuous series of residues that includes the carboxyl terminus or deletion of two continuous series of residues, one including the amino terminus and one including the carboxyl terminus. In some embodiments, fragments are characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, and high antigenic index regions.

The antigenic fragment can be of any size. In some embodiments the fragment is capable of inducing an immune response in a subject or be recognized by a specific antibody. In some embodiments, the fragment corresponds to an amino-terminal truncation mutant. In some embodiments, the number of amino terminal amino acids missing from the fragment ranges from 1-100 amino acids. In some embodiments, it ranges from 1-75 amino acids, 1-50 amino acids, 1-40 amino acids, 1-30 amino acids, 1-25 amino acids, 1-20 amino acids, 1-15 amino acids, 1-10 amino acids and 1-5 amino acids.

In some embodiments, the fragment corresponds to carboxyl-terminal truncation mutant. In some embodiments, the number of carboxyl terminal amino acids missing from the fragment ranges from 1-100 amino acids. In some embodiments, it ranges from 1-75 amino acids, 1-50 amino acids, 1-40 amino acids, 1-30 amino acids, 1-25 amino acids, 1-20 amino acids, 1-15 amino acids, 1-10 amino acids and 1-5 amino acids.

In some embodiments, the fragment corresponds to an internal fragment that lacks both the amino and carboxyl terminal amino acids. In some embodiments, the fragment is 7-200 amino acid residues in length. In some embodiments, the fragment is 10-100 amino acid residues, 15-85 amino acid residues, 25-65 amino acid residues or 30-50 amino acid residues in length. In some embodiments, the fragment is 7 amino acids, 10 amino acids, 12 amino acids, 15 amino acids, 20 amino acids, 25 amino acids, 30 amino acids, 35 amino acids, 40 amino acids, 45 amino acids, 50 amino acids 55 amino acids, 60 amino acids, 80 amino acids or 100 amino acids in length.

Of course larger antigenic fragments are also useful according to the present invention, as are fragments corresponding to most, if not all, of the amino acid sequence of SEQ ID NO:2, SEQ ID NO:6, SEQ ID NO:10, SEQ ID NO:14, SEQ ID NO:18, SEQ ID NO:22, SEQ ID NO:26, SEQ ID NO:30, SEQ ID NO:34, SEQ ID NO:38, SEQ ID NO:42, SEQ ID NO:46, SEQ ID NO:47, SEQ ID NO:48, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:63, SEQ ID NO:65, SEQ ID NO:66, SEQ ID NO:67, SEQ ID NO:69, SEQ ID NO:71, SEQ ID NO:73, SEQ ID NO:74, SEQ ID NO:75, SEQ ID NO:78, SEQ ID NO:79, SEQ ID NO:81, SEQ ID NO:83, SEQ ID NO:85, SEQ ID NO:87, SEQ ID NO:88 and SEQ ID NO:89.

In some embodiments, the antigenic fragment is selected from the group consisting of a peptide comprising amino acids 35-173 of SEQ ID NO:2, amino acids 35-173 of SEQ ID NO:6, amino acids 35-173 of SEQ ID NO:10, amino acids 35-171 of SEQ ID NO:14, amino acids 35-170 of SEQ ID NO:18, amino acids 34-119 of SEQ ID NO:22, amino acids 31-116 of SEQ ID NO:26, amino acids 32-164 of SEQ ID NO:30, amino acids 32-164 of SEQ ID NO:34, amino acids 32-162 of SEQ ID NO:38, amino acids 36-272 of SEQ ID NO:42, amino acids 35-173 of SEQ ID NO:46, amino acids 35-173 of SEQ ID NO:47, amino acids 35-173 of SEQ ID NO:48, amino acids 31-116 of SEQ ID NO:50, amino acids 31-116 of SEQ ID NO:51, amino acids 32-162 of SEQ ID NO:52, amino acids 31-267 of SEQ ID NO:53, amino acids 36-272 of SEQ ID NO:54, amino acids 36-272 of SEQ ID NO:55, amino acids 36-272 of SEQ ID NO:56, amino acids 31-267 of SEQ ID NO:57, amino acids 31-267 of SEQ ID NO:58, amino acids 31-267 of SEQ ID NO:59 and amino acids 31-267 of SEQ ID NO:60, amino acids 34-175 of SEQ ID NO: 63, amino acids 34-175 of SEQ ID NO: 65, amino acids 34-175 of SEQ ID NO: 66, amino acids 34-175 of SEQ ID NO: 67, amino acids 34-175 of SEQ ID NO: 69, amino acids 42-188 of SEQ ID NO: 71, amino acids 42-188 of SEQ ID NO:74, amino acids 43-189 of SEQ ID NO: 72, amino acids 42-188 of acids 32-174 SEQ ID NO:75, amino acids 40-186 of SEQ ID NO:78, amino acids 40-186 of SEQ ID NO:79, amino acids 40-186 of SEQ ID NO:81, amino acids 32-124 of SEQ ID NO:83, amino acids 28-120 of SEQ ID NO:85, amino acids 28-120 of SEQ ID NO:87, amino acids 33-512 of SEQ ID NO:88 and amino acids 32-174 of SEQ ID NO:89.

Thus, the polypeptides of the invention include polypeptides having an amino acid sequence at least 90% identical to that of SEQ ID NO:2, SEQ ID NO:6, SEQ ID NO:10, SEQ ID NO:14, SEQ ID NO:18, SEQ ID NO:22, SEQ ID NO:26, SEQ ID NO:30, SEQ ID NO:34, SEQ ID NO:38, SEQ ID NO:42, SEQ ID NO:46, SEQ ID NO:47, SEQ ID NO:48, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:63, SEQ ID NO:65, SEQ ID NO:66, SEQ ID NO:67, SEQ ID NO:69, SEQ ID NO:71, SEQ ID NO:73, SEQ ID NO:74, SEQ ID NO:75, SEQ ID NO:78, SEQ ID NO:79, SEQ ID NO:81, SEQ ID NO:83, SEQ ID NO:85, SEQ ID NO:87, SEQ ID NO:88, SEQ ID NO:89 or antigenic fragments thereof. In some embodiments, the variants are those that vary from the reference by conservative amino acid substitutions, i.e., those that substitute a residue with another of like characteristics. Typical substitutions are among Ala, Val, Leu and Ile; among Ser and Thr; among the acidic residues Asp and Glu; among Asn and Gln; and among the basic residues Lys and Arg, or aromatic residues Phe and Tyr. In some embodiments, the polypeptides are variants in which several, 5 to 10, 1 to 5, or 1 to 2 amino acids are substituted, deleted, or added in any combination.

The type IV pilin polypeptides, variants and antigenic fragments of the invention can be prepared in any suitable manner. Such polypeptides include isolated naturally occurring polypeptides, recombinantly produced polypeptides, synthetically produced polypeptides, or polypeptides produced by a combination of these methods.

In some embodiments, the invention is directed to engineered type IV pilin which is optimized for high level expression in *E. coli* using codons that are preferred in *E. coli*. In some embodiments, the invention is directed to engineered antigenic fragments of type IV pilin of *C. difficile* (nucleic acid and amino acid sequences), which are optimized for expression in *E. coli*, and harbor a histidine tag and enterokinase cleavage site to facilitate purification of the protein. In some embodiments, the fragments lack the prepilin leader sequence and hydrophobic domain found in the native proteins.

In some embodiments, the codons are optimized for high level expression in *E. coli*. As used herein, a codon that is "optimized for high level expression in *E. coli*" refers to a codon that is relatively more abundant in *E. coli* in comparison with all other codons corresponding to the same amino acid. In some embodiments, at least 40% of the codons are optimized for high level expression in *E. coli*. In some embodiments, at least 50%, at least 60%, at least 70%, at least 80%, at least 85%, at least 90%, at least 95%, or at least 99% of the codons are optimized for high level expression in *E. coli*.

The following sequences are optimized for expression in *E. coli* and also are fused to histidine tags and enterokinase cleavage sites.

SEQ ID NO:3 is a nucleotide sequence comprising an antigenic fragment encoding amino acids 35-173 of PilA1.1. The amino acid sequence encoded by SEQ ID NO:3 is SEQ ID NO:4. The amino acid sequence of the final translated sequence is SEQ ID NO:102.

SEQ ID NO:7 is a nucleotide sequence comprising an antigenic fragment encoding amino acids 35-173 of PilA1.2. The amino acid sequence encoded by SEQ ID NO:7 is SEQ ID NO:8.

SEQ ID NO:11 is a nucleotide sequence comprising an antigenic fragment encoding amino acids 35-173 of PilA1.3. The amino acid sequence encoded by SEQ ID NO:11 is SEQ ID NO:12.

SEQ ID NO:15 is a nucleotide sequence comprising an antigenic fragment encoding amino acids 35-171 of PilA1.4. The amino acid sequence encoded by SEQ ID NO:15 is SEQ ID NO:16.

SEQ ID NO:19 is a nucleotide sequence comprising an antigenic fragment encoding amino acids 35-170 of PilA1.5. The amino acid sequence encoded by SEQ ID NO:19 is SEQ ID NO:20.

SEQ ID NO:23 is a nucleotide sequence comprising an antigenic fragment encoding amino acids 34-119 of PilA2.1. The amino acid sequence encoded by SEQ ID NO:23 is SEQ ID NO:24. The amino acid sequence of the final translated sequence is SEQ ID NO:103.

SEQ ID NO:27 is a nucleotide sequence comprising an antigenic fragment encoding amino acids 31-116 of PilA2.2. The amino acid sequence encoded by SEQ ID NO:27 is SEQ ID NO:28.

SEQ ID NOS:31 and 110 are nucleotide sequences comprising an antigenic fragment encoding amino acids 32-164 of PilA3.1. The amino acid sequence encoded by SEQ ID NO:31 is SEQ ID NO:32. The amino acid sequence of the final translated sequence is SEQ ID NO:109.

SEQ ID NO:35 is a nucleotide sequence comprising an antigenic fragment encoding amino acids 32-164 of PilA3.2. The amino acid sequence encoded by SEQ ID NO:35 is SEQ ID NO:36.

SEQ ID NO:39 is a nucleotide sequence comprising an antigenic fragment encoding amino acids 32-162 of PilA3.3. The amino acid sequence encoded by SEQ ID NO:39 is SEQ ID NO:40.

SEQ ID NO:43 is a nucleotide sequence comprising an antigenic fragment encoding amino acids 36-272 of PilA4.1. The amino acid sequence encoded by SEQ ID NO:43 is SEQ ID NO:44. The amino acid sequence of the final translated sequence is SEQ ID NO:104.

SEQ ID NO:90 is a nucleotide sequence comprising an antigenic fragment encoding amino acids 34-175 of PilA5 (PilU). The amino acid sequence encoded by SEQ ID NO:90 is SEQ ID NO:91. The amino acid sequence of the histidine tagged sequence is SEQ ID NO:111.

SEQ ID NO:92 is a nucleotide sequence comprising an antigenic fragment encoding amino acids 42-188 of PilA6 (PilV). The amino acid sequence encoded by SEQ ID NO:92 is SEQ ID NO:94. The amino acid sequence of the histidine tagged sequence is SEQ ID NO:93.

SEQ ID NO:95 is a nucleotide sequence comprising an antigenic fragment encoding amino acids 32-124 of PilA7 (PilX1). The amino acid sequence encoded by SEQ ID NO:95 is SEQ ID NO:97. The amino acid sequence of the histidine tagged sequence is SEQ ID NO:96.

SEQ ID NO:105 is a nucleotide sequence comprising an antigenic fragment encoding amino acids 33-512 of PilK. SEQ ID NO:106 comprises PilK sequence in pET30B expression vector. The amino acid sequence encoded by SEQ ID NO:106 is SEQ ID NO:107. The amino acid sequence of the final translated sequence is SEQ ID NO:108.

SEQ ID NO:98 is a nucleotide sequence comprising an antigenic fragment encoding amino acids acids 32-174 of PilX2. SEQ ID NO:99 comprises PilX2 sequence in pET30B expression vector. The amino acid sequence encoded by SEQ ID NO:99 is SEQ ID NO:100. The amino acid sequence of the final translated sequence is SEQ ID NO:101.

In accordance with the invention, such polypeptides and fragments are useful as immunogens and also as diagnostic tools to aid in the detection of antibodies that react with type IV pilin of *C. difficile* from a biological sample from a subject suspected of being infected, or at risk for infection, previously infected or immunized with a type IV pilin immunogen.

Methods of Inducing an Immune Response.

The present invention also includes methods of inducing an immune response comprising administering to a subject in need thereof an immunologically-effective amount of a vaccine comprising *Clostridium difficile* type IV pilin or an antigenic fragment or variant thereof.

In certain aspects of the invention, the vaccine is administered alone in a single dose or administered in sequential doses.

In some embodiments, a combination of *C. difficile* type IV pilins or antigenic fragments or variants thereof is administered, to provide protection against a broad spectrum of *C. difficile* strains, or particular strains that are more prevalent. The combination that can be administered is not limiting. In some embodiments, the combination is administered as a single, multivalent vaccine composition. In other embodiments, the type IV pilins or antigenic fragments or variants thereof are administered in more than one vaccine composition.

In some embodiments, one of the following combinations is administered: a combination comprising one or more PilA1, one or more PilA2, one or more PilA3 and one or more PilA4 proteins, variants or antigenic fragment thereof, a combination comprising one or more PilA1, one or more PilA2, one or more PilA3 proteins, variants or antigenic fragments thereof, a combination comprising one or more PilA1, one or more PilA2, one or more PilA4 proteins, variants or antigenic fragments thereof, a combination comprising one or more PilA1, one or more PilA3, one or more PilA4 proteins, variants or antigenic fragments thereof, a combination comprising one or more PilA2, one or more PilA3, one or more PilA4 proteins, variants or antigenic fragments thereof, a combination comprising one or more PilA1 and one or more PilA2 proteins, variants or antigenic fragments thereof, a combination comprising one or more PilA1 and one or more PilA3 proteins, variants or antigenic fragments thereof, a combination comprising one or more PilA1 and one or more PilA4 proteins, variants or antigenic fragments thereof, a combination comprising one or more PilA2 and one or more PilA3 proteins, variants or antigenic fragments thereof, a combination comprising one or more PilA2 and one or more PilA4 proteins, variants or antigenic fragments thereof, and a combination comprising one or more PilA3 and one or more PilA4 proteins, variants or antigenic fragments thereof, a combination comprising one or more PilA1 (pilA1.1, pilA1.2, pilA1.3, pilA1.4, pilA1.5, pilA1.6 and pilA1.7), one or more PilA2 (pilA2.1, pilA2.2, pilA2.3 and pilA2.4), one or more PilA3 (pilW) (pilA3.1 (pilW.1), pilA3.2 (pilW.2), pilA3.3 (pilW.3) and pilA3.4 (pilW.4)), one or more PilA4 (pilI) (pilA4.1 (pilJ.1), pilA4.2 (pilJ.2), pilA4.3 (pilJ.3), pilA4.4 (pilJ.4), pilA4.5 (pilJ.5), pilA4.6 (pilj.6), pilA4.7 (pilJ.7), pilA4.8 (pilJ.8) and pilA4.9 (pilJ.9)), one or more PilA5 (pilU) (pilA5.1 (pilU.1), pilA5.2 (pilU.2), pilA5.3 (pilU.3), pilA5.4 (pilU.4) and pilA5.5 (pilU.5)), one or more PilA6 (pili) (pilA6.1 (pilV.1), pilA6.2 (pilV.2), pilA6.3 (pilV.3), pilA6.4 (pilV.4), pilA6.5 (pilV.5), pilA6.6 (pilV.6) and pilA6.7 (pilV.7)), one or more PilA7 (pilX1)(pilA7.1 (pilX1.1), pilA7.2 (pilX1.2) and pilA7.3 (pilX1.3)), one or more PilK and/or one or more PilX2 proteins, variants or antigenic fragment thereof. The PilA1, PilA2, PilA3 (PilW), PilA4 (PilI), PilA5 (PilU), PilA6 (PilV), PilA7 (PilX1), PilK and PilX2 can be from any strain. In some embodiments, they are from strain R20291

In some embodiments, one or more PilA1, one or more PilA7 (PilX1), one or more PilA4 (PilJ), or one or more PilA2 is administered. In some embodiments, one or more PilA1 and one or more PilA7 (PilX1) is administered. In some embodiments, one or more PilA1 and one or more PilA4 (PilJ) is administered. In some embodiments, one or more PilA7 (PilX1) and one or more PilA4 (PilJ) is administered. In some embodiments, one or more PilA1 and one or more PilA2 is administered. In some embodiments, one or more PilA7 (PilX1) and one or more PilA2 is administered. In some embodiments, one or more PilA4 (PilJ) and one or more PilA2 is administered. In some embodiments, one or more PilA1, one or more PilA4 (PilJ) and one or more PilA2 is administered. In some embodiments, one or more PilA1, one or more PilA7 (PilX1) and one or more PilA2 is administered. In some embodiments, one or more PilA4 (PilJ), one or more PilA7 (PilX1) and one or more PilA2 is administered. In some embodiments, the PilA1, PilA2, PilA7 (PilX1), and PilA4 (PilJ) is from strain 820291.

In some embodiments, a combination comprising one or more PilA1, one or more PilA7 (PilX1) and one or more PilA4 (PilI) is administered. In some embodiments, a combination comprising one or more PilA1, one or more PilA2, one or more PilA7 (PilX1) and one or more PilA4 (PilI) is administered. In some embodiments, the PilA1, PilA2, PilA7 (PilX1), and PilA4 (PilI) is from strain R20291.

In some embodiments, PilA1 comprises a peptide selected from the group consisting of a PilA1.1 antigenic fragment (amino acids amino acids 35-173 of SEQ ID NO:46), a PilA1.2 antigenic fragment (amino acids amino acids 35-173 of SEQ ID NO:6), a PilA1.3 antigenic fragment (amino acids amino acids 35-173 of SEQ ID NO:10), a PilA1.4 antigenic fragment (amino acids 35-171 of SEQ ID NO:14), a PilA1.5 antigenic fragment (amino acids 35-170 of SEQ ID NO:18), a PilA1.6 antigenic fragment (amino acids 35-173 of SEQ ID NO:47, a PilA1.7 antigenic fragment (amino acids 35-173 of SEQ ID NO:48) and combinations thereof. In some embodiments, PilA1 includes all the PilA1 allele fragments listed above.

In some embodiments, PilA2 comprises a peptide selected from the group consisting of a PilA2.1 antigenic fragment (amino acids 34-119 of SEQ ID NO: 22), a PilA2.2 antigenic fragment (amino acids 31-116 of SEQ ID NO:26), a PilA2.3 antigenic fragment (amino acids 31-116 of SEQ ID NO:50), a PilA2.4 antigenic fragment amino acids 31-116 of SEQ ID NO:51 and combinations thereof. In some embodiments, PilA2 includes all the PilA2 allele fragments listed above.

In some embodiments, PilA3 (PilW) comprises a peptide selected from the group consisting of a PilA3.1 antigenic fragment (amino acids 32-164 of SEQ ID NO: 30), a PilA3.2 antigenic fragment (amino acids 32-164 of SEQ ID NO:34), a PilA3.3 antigenic fragment (amino acids 32-162 of SEQ ID NO:38), a PilA3.4 antigenic fragment (amino acids 32-162 of SEQ ID NO:52) and combinations thereof. In some embodiments, PilA3 includes all the PilA3 allele fragments listed above.

In some embodiments, PilA4 (PilI) comprises a peptide selected from the group consisting of a PilA4.1 antigenic fragment (amino acids 36-272 of SEQ ID NO: 42), a PilA4.2 antigenic fragment (amino acids 31-267 of SEQ ID NO:53), a PilA4.3 antigenic fragment (amino acids 36-272 of SEQ ID NO:54), a PilA4.4 antigenic fragment (amino acids 36-272 of SEQ ID NO:55), a PilA4.5 antigenic fragment (amino acids 36-272 of SEQ ID NO:56), a PilA4.6 antigenic fragment (amino acids 31-267 of SEQ ID NO:57), a PilA4.7 antigenic fragment (amino acids 31-267 of SEQ ID NO:58), a PilA4.8 antigenic fragment (amino acids 31-267 of SEQ ID NO:59), a PilA4.9 antigenic fragment (amino acids 31-267 of SEQ ID NO:60) and combinations thereof. In some embodiments, PilA4 includes all the PilA4 allele fragments listed above.

In some embodiments, PilA5 (PilU) comprises a peptide selected from the group consisting of a PilA5.1 antigenic fragment (amino acids 34-175 of SEQ ID NO: 63), a PilA5.2 antigenic fragment (amino acids 34-175 of SEQ ID NO: 65), a PilA5.3 antigenic fragment (amino acids 34-175 of SEQ ID NO: 66), a PilA5.4 antigenic fragment (amino acids 34-175 of SEQ ID NO: 67), a PilA5.5 antigenic fragment (amino acids 34-175 of SEQ ID NO: 69) and combinations thereof. In some embodiments, PilA5 includes all the PilA5 allele fragments listed above.

In some embodiments, PilA6 (PilV) comprises a peptide selected from the group consisting of a PilA6.1 antigenic fragment (amino acids 42-188 of SEQ ID NO: 71), a PilA6.2 antigenic fragment (amino acids 43-189 of SEQ ID NO: 73), a PilA6.3 antigenic fragment (amino acids 42-188 of SEQ ID NO:74), a PilA6.4 antigenic fragment (amino acids 42-188 of SEQ ID NO:75), a PilA6.5 antigenic fragment (amino acids 40-186 of SEQ ID NO:78), a PilA6.6 antigenic fragment (amino acids 40-186 of SEQ ID NO:79), a PilA6.7 antigenic fragment (amino acids 40-186 of SEQ ID NO:81) and combinations thereof. In some embodiments, PilA6 includes all the PilA6 allele fragments listed above.

In some embodiments, PilA7 (PilX1) comprises a peptide selected from the group consisting of a PilA7.1 antigenic fragment (amino acids 32-124 of SEQ ID NO:83), a PilA7.2 antigenic fragment (amino acids 28-120 of SEQ ID NO:85), a PilA7.3 antigenic fragment (amino acids 28-120 of SEQ ID NO:87) and combinations thereof. In some embodiments, PilA7 includes all the PilA7 allele fragments listed above.

In some embodiments, the type IV pilin is from a *C. difficile* strain selected from the group consisting of *C. difficile* CD196, *C. difficile* CIP 107932, *C. difficile* QCD-32g58, *C. difficile* QCD-37x79, *C. difficile* QCD-66c26, *C. difficile* QCD-76w55, *C. difficile* QCD-97b34, *C. difficile* R20291, *C. difficile* QCD-63q42, *C. difficile* QCD-23m63, *C. difficile* 630, *C. difficile* ATCC 43255, *C. difficile* 70-100-2010, *C. difficile* 050-P50-2011, *C. difficile* 002-P50-2011, *C. difficile* NAP08, *C. difficile* NAP07 and *C. difficile* BI1 and combinations thereof.

In some embodiments, the type IV pilin is selected from the group consisting of SEQ ID NO:2; SEQ ID NO:6; SEQ ID NO:10; SEQ ID NO:14; SEQ ID NO:18; SEQ ID NO:22; SEQ ID NO:26; SEQ ID NO:30; SEQ ID NO:34; SEQ ID NO:38; SEQ ID NO:42, SEQ ID NO:46, SEQ ID NO:47, SEQ ID NO:48, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:63, SEQ ID NO:65, SEQ ID NO:66, SEQ ID NO:67, SEQ ID NO:69, SEQ ID NO:71, SEQ ID NO:73, SEQ ID NO:74, SEQ ID NO:75, SEQ ID NO:78, SEQ ID NO:79, SEQ ID NO:81, SEQ ID NO:83, SEQ ID NO:85, SEQ ID NO:87, SEQ ID NO:88, SEQ ID NO:89, variants thereof, antigenic fragments thereof, and combinations thereof.

In some embodiments, a combination of PilA1 type IV pilin is administered. In some embodiments, one of the following combinations is administered: a combination comprising SEQ ID NO:46, variants or antigenic fragments thereof; a combination comprising SEQ ID NO:6, variants or antigenic fragments thereof a combination comprising SEQ ID NO:10, variants or antigenic fragments thereof a combination comprising SEQ ID NO:14, variants or antigenic fragments thereof and a combination comprising SEQ ID NO:18, variants or antigenic fragments thereof.

In some embodiments, a combination of SEQ ID NO:46, SEQ ID NO:6, SEQ ID NO:10, SEQ ID NO:14 and SEQ ID NO:18, variants or antigenic fragments thereof is administered.

In some embodiments, the combination comprises at least four type IV pilins. In some embodiments, the type IV pilins are PilA1 alleles, variants or antigenic fragments thereof. In some embodiments, one of the following combinations is administered: a combination of SEQ ID NO:46, SEQ ID NO:6, SEQ ID NO:10 and SEQ ID NO:18 or variants or antigenic fragments thereof a combination of SEQ ID NO:46, SEQ ID NO:6, SEQ ID NO:10 and SEQ ID NO:14, or variants or antigenic fragments thereof a combination of SEQ ID NO:46, SEQ ID NO:10, SEQ ID NO:14 and SEQ ID NO:18 or variants or antigenic fragments thereof a combination of SEQ ID NO:46, SEQ ID NO:6, SEQ ID NO:14 and SEQ ID NO:18 or variants or antigenic fragments thereof and a combination of SEQ ID NO:6, SEQ ID NO:10, SEQ ID NO:14 and SEQ ID NO:18 or variants or antigenic fragments thereof.

In some embodiments, the combination comprises at least three type IV pilins. In some embodiments, the type IV pilins are PilA1 alleles, variants or antigenic fragments thereof. In some embodiments, one of the following combinations is administered: a combination of SEQ ID NO:46, SEQ ID NO:6 and SEQ ID NO:10, or variants or antigenic fragments thereof; a combination of SEQ ID NO:46, SEQ ID NO:6 and SEQ ID NO:14, or variants or antigenic fragments thereof; a combination of SEQ ID NO:46, SEQ ID NO:6 and SEQ ID NO:18, or variants or antigenic fragments thereof; a combination of SEQ ID NO:46, SEQ ID NO:10 and SEQ ID NO:14, or variants or antigenic fragments thereof; a combination of SEQ ID NO:46, SEQ ID NO:10 and SEQ ID NO:18, or variants or antigenic fragments thereof; a combination of SEQ ID NO:46, SEQ ID NO:14 and SEQ ID NO:18, or variants or antigenic fragments thereof; a combination of SEQ ID NO:6, SEQ ID NO:10 and SEQ ID NO:14, or variants or antigenic fragments thereof; a combination of SEQ ID NO:6, SEQ ID NO:10 and SEQ ID NO:18, or variants or antigenic fragments thereof; a combination of SEQ ID NO:6, SEQ ID NO:14 and SEQ ID NO:18, or variants or antigenic fragments thereof; and a combination of SEQ ID NO:10, SEQ ID NO:14 and SEQ ID NO:18, or variants or antigenic fragments thereof.

In some embodiments, the combination comprises at least three type IV pilins that are PilA3 alleles, variants or antigenic fragments thereof. In some embodiments, a combination of SEQ ID NO:30, SEQ ID NO:34 and SEQ ID NO:38, or variants or antigenic fragments thereof is administered. In some embodiments, the combination comprises at least two type IV pilins.

In some embodiments, the type IV pilins are PilA1 alleles, variants or antigenic fragments thereof. In some embodiments, one of the following combinations is administered: a combination of SEQ ID NO:46 and SEQ ID NO:6, or variants or antigenic fragments thereof; a combination of SEQ ID NO:46 and SEQ ID NO:10, or variants or antigenic fragments thereof; a combination of SEQ ID NO:46 and SEQ ID NO:14, or variants or antigenic fragments thereof; a combination of SEQ ID NO:46 and SEQ ID NO:18, or variants or antigenic fragments thereof; a combination of SEQ ID NO:6 and SEQ ID NO:10, or variants or antigenic fragments thereof; a combination of SEQ ID NO:6 and SEQ ID NO:14, or variants or antigenic fragments thereof; a combination of SEQ ID NO:6 and SEQ ID NO:18, or variants or antigenic fragments thereof; a combination of SEQ ID NO:10 and SEQ ID NO:14, or variants or antigenic fragments thereof; a combination of SEQ ID NO:10 and SEQ ID NO:18, or variants or antigenic fragments thereof; and a combination of SEQ ID NO:14 and SEQ ID NO:18, or variants or antigenic fragments thereof.

In some embodiments, the combination comprises at least two type IV pilins that are PilA2 alleles, variants or antigenic fragments thereof. In some embodiments, a combination of SEQ ID NO:22 and SEQ ID NO:26 or variants or antigenic fragments thereof is administered.

In some embodiments, the combination comprises at least two type IV pilins that are PilA3 alleles, variants or antigenic fragments thereof. In some embodiments, one of the following combinations is administered: a combination of SEQ ID NO:30 and SEQ ID NO:34 or variants or antigenic fragments thereof; a combination of SEQ ID NO:30 and SEQ ID NO:38, or variants or antigenic fragments thereof; and a combination of SEQ ID NO:34 and SEQ ID NO:38 or variants or antigenic fragments thereof.

In some embodiments, a combination comprising a PilA1, PilA2, PilA3 and PilA4 protein, variant or antigenic fragment thereof is administered.

In some embodiments, the antigenic fragment of the PilA1 protein comprises a peptide selected from the group consisting of: amino acids 35-173 of SEQ ID NO:46; amino acids 35-173 of SEQ ID NO:6; amino acids 35-173 of SEQ ID NO:10; amino acids 35-171 of SEQ ID NO:14; amino acids 35-170 of SEQ ID NO:18 and combinations thereof.

In some embodiments, the antigenic fragment of the PilA2 protein comprises a peptide selected from the group consisting of: amino acids 34-119 of SEQ ID NO:22; amino acids 31-116 of SEQ ID NO:26 and combinations thereof.

In some embodiments, the antigenic fragment of the PilA3 protein comprises a peptide selected from the group consisting of: amino acids 32-164 of SEQ ID NO:30; amino acids 32-164 of SEQ ID NO:34; amino acids 32-162 of SEQ ID NO:38; and combinations thereof.

In some embodiments, the antigenic fragment of the Pil4A4 protein comprises amino acids 36-272 of SEQ ID NO:42.

In some embodiments, the type IV pilins, variants or antigenic fragments thereof for use in the methods of the invention are recombinantly produced. In some embodiments, the type IV pilins, variants or antigenic fragments thereof are produced in *E. coli* using genetically engineered nucleic acids optimized for high level expression using preferred *E. coli* codons.

In some embodiments, a type IV pilin or antigenic fragment or variant thereof is conjugated, either genetically or chemically to one or more type IV pilins or antigenic fragments or variants thereof, another *C. difficile* antigen, a bacterial antigen, toxin or the like, and administered as a conjugate vaccine.

As used herein, an immunologically-effective amount is an amount sufficient to induce an immune response in the subject.

As used herein, an "immune response" is the physiological response of the subject's immune system to an immunizing composition. An immune response may include an innate immune response, an adaptive immune response, or both. In some embodiments of the present invention, the immune response is a protective immune response. A protective immune response confers immunological cellular memory upon the subject, with the effect that a secondary exposure to the same or a similar antigen is characterized by one or more of the following characteristics: shorter lag phase than the lag phase resulting from exposure to the selected antigen in the absence of prior exposure to the immunizing composition; production of antibody which continues for a longer period than production of antibody resulting from exposure to the selected antigen in the absence of prior exposure to the immunizing composition; a change in the type and quality of antibody produced in comparison to the type and quality of antibody produced upon exposure to the selected antigen in the absence of prior exposure to the immunizing composition; a shift in class response, with IgG antibodies appearing in higher concentrations and with greater persistence than IgM, than occurs in response to exposure to the selected antigen in the absence of prior exposure to the immunizing composition; an increased average affinity (binding constant) of the antibodies for the antigen in comparison with the average affinity of antibodies for the antigen resulting from exposure to the selected antigen in the absence of prior exposure to the immunizing composition; and/or other characteristics known in the art to characterize a secondary immune response.

In some embodiments, the vaccines of the invention are administered with a pharmaceutically acceptable carrier, such that it provides host immunity against an infection.

The term "carrier" denotes an organic or inorganic ingredient, natural or synthetic, with which the active ingredient is combined to facilitate the application of the vaccine. The characteristics of the carrier depend on the nature of the vaccine and the route of administration. Physiologically and pharmaceutically-acceptable carriers include diluents, fillers, salts, buffers, stabilizers, solubilizers, and other materials. The term "pharmaceutically acceptable" is used to refer to a non-toxic material that is compatible with a biological system such as a cell, cell culture, tissue, or organism.

In practicing immunization protocols for treatment and/or prevention, an immunologically-effective amount of type IV pilin or a variant or antigenic fragment thereof is administered to a subject. The particular dosage depends upon the age, weight, sex and medical condition of the subject to be treated, as well as on the method of administration.

The vaccines of the invention can be administered by either single or multiple dosages of an effective amount. In some embodiments, an effective amount of the type IV pilin of the invention can vary from 0.01-5,000 µg/ml per dose. In other embodiments, an effective amount of the type IV pilin can vary from 0.1-500 µg/ml per dose, and in other embodiments, it can vary from 10-300 µg/ml per dose. In one embodiment, the dosage of type IV pilin will range from about 10 µg to about 1000 µg. In another embodiment, the amount administered will be between about 20 µg and about 500 µg. In some embodiments, the amount administered will be between about 75 µg and 250 µg. Greater doses may be administered on the basis of body weight. The exact dosage can be determined by routine dose/response protocols known to one of ordinary skill in the art. In some embodiments, the amount of the type IV pilin that provides an immunologically-effective amount for vaccination against infection is from about 1 µg or less to about 5000 µg or more. In some embodiments, it is from about 2, 3, 4, 5, 6, 7, 8, 9, 10, 15, 20, 25, 30, 35, 40, 45 or 50 µg to about 55, 60, 65, 70, 75, 80, 85, 90, or 95 µg per kg body weight. In one embodiment, the immunologically-effective amount for vaccination against bacterial infection is from 10 µg to 1000 µg.

The term "subject" as used herein, refers to animals, such as mammals. For example, mammals contemplated include humans, primates, dogs, cats, sheep, cattle, goats, pigs, horses, chickens, mice, rats, rabbits, guinea pigs, and the like. The terms "subject", "patient", and "host" are used interchangeably. In some embodiments, the subject is a human. In some embodiments, the subjects are patients who are at high risk of *C. difficile* infections. In some embodiments, the subjects are selected from the group consisting of elderly patients in healthcare or nursing care settings, patients who have undergone antibiotic treatment of unrelated infections, are currently undergoing antibiotic treatment or are about to undergo antibiotic treatment, patients in healthcare settings, patients who have previously been infected with *C. difficile* or who have experienced CDAD symptoms. In some embodiments, the subjects are outpatients. In some embodiments, the subjects are healthy individuals. In some embodiments, the subjects are at risk of *C. difficile* infection because of their close contact with an infected individual or exposure to surroundings that might be infected with *C. difficile* or infection causing spores thereof.

In some embodiments, the subjects include patients that have received broad spectrum antibiotics, such as hospitalized elderly patients, nursing home residents, chronically ill patients, cancer patients, AIDS patients, patients in intensive care units, and patients receiving dialysis treatment.

The vaccine of the present invention may confer resistance to *Clostridium difficile* by either passive immunization or active immunization. In one embodiment of passive immunization, the vaccine is provided to a subject (i.e. a human or mammal), and the elicited antisera is recovered and directly provided to a recipient suspected of having an infection caused by *C. difficile*.

In some embodiments of passive immunization, the *C. difficile* immune globulin is administered in amounts ranging from 100 µg/kg-100 mg/kg, or 1-50 mg/kg, for example, about 15 mg/kg, depending on donor titer. The immune globulin can be administered in, e.g., one or two doses. an initial dose can be administered for treatment and a second dose can be administered to prevent relapse.

The administration of the vaccine (or the antisera which it elicits) may be for either a "prophylactic" or "therapeutic" purpose. When provided prophylactically, the vaccine is provided in advance of any symptom of *C. difficile* infection. The prophylactic administration of the vaccine serves to prevent or attenuate any subsequent infection. When provided therapeutically, the vaccine is provided upon the detection of a symptom of actual infection. The therapeutic administration of the vaccine serves to attenuate any actual infection. In some embodiments, administration of the vaccine of the invention attenuates *C. difficile* colonization and disease in the subject. In some embodiments, administration of the vaccine of the invention prevents *C. difficile* colonization and disease in the subject.

The vaccines (or antisera which it elicits) can be provided either prior to the onset of infection (so as to prevent or attenuate an anticipated infection) or after the initiation of an actual infection.

In some embodiments, the vaccines are administered with other vaccines targeting other components of *C. difficile*. In some embodiments, the vaccines are administered in conjunction with vaccines comprising toxoid preparations of enterotoxins A (TcdA) and B (TcdB) of *C. difficile*.

In some embodiments, the subject is co-administered with agents used to treat *C. difficile* infection, such as metronidazole and/or vancomycin in conjunction with methods as described herein.

The invention also provides a method for inducing an immune response which comprises administering to a subject, suspected of being at risk for infection caused by *C. difficile*, an immunologically-effective amount of an antisera elicited from the exposure of a second individual to a vaccine of the invention, such that it provides host immunity to the infection.

The vaccine of the invention can be administered to mammals of any age. In some embodiments, the vaccines can be administered as a single dose or in a series including one or more boosters. In some embodiments, the time interval between the first and second vaccinations is one week, two weeks, three weeks, 1 month, 2 months, 3 months, 4 months, 5 months, 6 months, 7 months, 8 months, 9 months, 10 months, 11 months, one year, 1.5 years and two years. In some embodiments, two sequential booster immunizations are administered.

In some embodiments, the immunization schedule would involve a primary series of three immunizations with a spacing of 1-2 months between the doses. In some embodiments, a booster dose could be administered ~6-12 months later.

Conjugate Vaccines

In one aspect, the present invention is further directed to a conjugate vaccine comprising a *C. difficile* type IV pilin, an antigenic fragment or a variant thereof.

The conjugation can be either through chemical or genetic means. The genetic or chemical conjugation encompasses coupling the type IV pilin either through gene fusion or chemically to another entity, for example, using cross-linkers, to increase the immune response. Standard techniques and methods can be employed to make the conjugate vaccines of the invention.

In some embodiments, the *C. difficile* type IV pilin, antigenic fragment or variant thereof is conjugated to another *C. difficile* type IV pilin, antigenic fragment or variant thereof. In some embodiments, conjugation is to a bacterial toxin. In some embodiments, it is conjugated to a nontoxic variant of a bacterial toxin. In some embodiments, it is conjugated to a nontoxic variant of enterotoxin A (TcdA) or B (TcdB). Other toxins include tetanospasmin, alpha toxin, enterotoxin, botox diphtheria toxin, anthrax toxin, listeriolysin O, streptolysin, leukocidin (Panton-Valentine leukocidin), *Staphylococcus aureus* alpha/beta/delta, exfoliatin, toxic shock syndrome toxin, SEB), cord factor, diphtheria toxin, shiga toxin, verotoxin/shiga-like toxin (*E. coli*), *E. coli* heat-stable enterotoxin/enterotoxin, cholera toxin, pertussis toxin, *Pseudomonas* exotoxinextracellular adenylate cyclase, type I (Superantigen), type II (Pore forming toxins), type III (AB toxin/AB5), lipopolysaccharide (Lipid A), *Bacillus thuringiensis* delta endotoxin, clumping factor A, and fibronectin binding protein A.

In some embodiments, the *C. difficile* type IV pilin, antigenic fragment or variant thereof conjugated to a bacterial toxin is selected from the group consisting of PilA1, PilA2, PilA3 (PilW), PilA4 (PilI), PilA5 (PilU), PilA6 (PilV), PilA7 (PilX1), PilK and PilX2. In some embodiments, the *C. difficile* type IV pilin, antigenic fragment or variant thereof conjugated to a bacterial toxin is PilA2.

In some embodiments, a *C. difficile* type IV pilin, antigenic fragment or variant thereof is conjugated to a polysaccharide, using techniques known in the art.

A multivalent vaccine may also be prepared by mixing the *C. difficile* type IV pilin conjugate with other antigens, including other *C. difficile* type IV pilins and conjugates thereof, other *C. difficile* antigens and conjugates thereof, antigens against other organisms and conjugates thereof, bacterial toxins as discussed above and conjugates thereof, and/or other polysaccharides and conjugates thereof, using techniques known in the art. In some embodiments, the invention is directed to a multivalent vaccine comprising a mixture of *C. difficile* type IV pilin conjugates derived from various *C. difficile* strains, each conjugate comprising a type IV pilin characteristic of the strain.

Methods for making conjugate vaccines are described in, for example, US Patent Application Publication No. 20090028889. Techniques to conjugate a type IV pilin include, in part, coupling through available functional groups (such as amino, carboxyl, thio and aldehyde groups). See, e.g., Hermanson, Bioconjugate Techniques (Academic Press; 1992); Aslam and Dent, eds. Bioconjugation: Protein coupling Techniques for the Biomedical Sciences (MacMillan: 1998); S. S. Wong, *Chemistry of Protein Conjugate and Crosslinking CRC Press* (1991), and Brenkeley et al., Brief Survey of Methods for Preparing Protein Conjugates With Dyes, Haptens and Cross-Linking Agents, *Bioconjugate Chemistry* 3 #1 (January 1992); Jacob, C. O, et al., *Eur. J. Immunol.* 16:1057-1062 (1986); Parker, J. M. R. et al., In: *Modern Approaches to Vaccines*, Chanock, R. M. et al., eds, pp. 133-138, Cold Spring Harbor Laboratory, Cold Spring Harbor, N.Y. (1983); Zurawski, V. R, et al., *J. Immunol.* 121:122-129 (1978); Klipstein, F. A, et al., *Infect. Immun.* 37:550-557 (1982); Bessler, W. G, *Immunobiol.* 170:239-244 (1985); Posnett, D. N, et al., *J. Biol. Chem.* 263:1719-1725 (1988); Ghose, A. C, et al., *Molec. Immunol.* 25:223-230 (1988); all of which disclosures are incorporated herein by reference). An example of a conjugate vaccine was developed against *Haemophilus influenzae* (Anderson, P, Infec. and Immunology 39:223-238 (1983); Chu, C, et al., *Infect. Immun.* 40:245-256 (1983); Lepow, M, Pediat. *Infect. Dis. J.* 6:804-807 (1987), which disclosures are incorporated herein by reference), Additional methods for producing such a conjugate vaccine are disclosed by European Patent Publication 245,045; U.S. Pat. Nos. 4,673,574 and 4,761,283; U.S. Pat. No. 4,789,735; European Patent Publication No. 206,852; U.S. Pat. No. 4,619,828; U.S. Pat. No. 4,284,537; U.S. Pat. No. 5,192,540; U.S. Pat. No. 5,370,872; U.S. Pat. No. 5,302,386; and U.S. Pat. No. 5,576,002 all of which disclosures are incorporated herein by reference.

In some embodiments, the conjugate vaccine comprises a type IV pilin, antigenic fragment or a variant thereof selected from the group consisting of PilA1, PilA2, PilA3 (PilW), PilA4 (PilJ), PilA5 (PilU), PilA6 (PilV), PilA7 (PilX1), PilK and PilX2.

In some embodiments, the conjugate vaccine comprises a combination of type IV pilins, antigenic fragments or variants thereof as described herein. In some embodiments, the conjugate vaccine comprises multiple alleles of a type IV pilin, antigenic fragment or variant thereof in any combination. In some embodiments, the conjugate vaccine comprises one or more pilA1 (pilA1.1, pilA1.2, pilA1.3, pilA1.4, pilA1.5, pilA1.6 and pilA1.7), one or more pilA2 (pilA2.1, pilA2.2, pilA2.3 and pilA2.4), one or more pilA3 (pilW) (pilA3.1 (pilW.1), pilA3.2 (pilW.2), pilA3.3 (pilW.3) and pilA3.4 (pilW.4)), one or more pilA4 (pilJ) (pilA4.1 (pilJ.1), pilA4.2 (pilJ.2), pilA4.3 (pilJ.3), pilA4.4 (pilJ.4), pilA4.5 (pilJ.5), pilA4.6 (pilJ.6), pilA4.7 (pilJ.7), pilA4.8 (pilJ.8) and pilA4.9 (pilJ.9)), one or more pilA5 (pilU) (pilA5.1 (pilU.1), pilA5.2 (pilU.2), pilA5.3 (pilU.3), pilA5.4 (pilU.4) and pilA5.5 (pilU.5)), one or more pilA6 (pilV) (pilA6.1 (pilV.1), pilA6.2 (pilV.2), pilA6.3 (pilV.3), pilA6.4 (pilV.4), pilA6.5 (pilV.5), pilA6.6 (pilV.6) and pilA6.7 (pilV.7)), one or more pilA7 (pilX1) (pilA7.1 (pilX1.1), pilA7.2 (pilX1.2) and pilA7.3 (pilX1.3)), one or more pilK and/or one or more pilX2.

For example, in some embodiments, multiple alleles are genetically conjugated to each other to make a fusion protein. In some embodiments, the conjugate vaccine comprises PilA1.1, PilA1.2, PilA1.3, PilA1.4 and PilA1.5 or antigenic fragments or variants thereof. In some embodiments, the conjugate vaccine comprises PilA2.1 and PilA2.2 or antigenic fragments or variants thereof. In some embodiments, the conjugate vaccine comprises PilA3.1, PilA3.2 and PilA3.3 or antigenic fragments or variants thereof.

Vaccine Compositions

As would be understood by one of ordinary skill in the art, when the *C. difficile* type IV pilin of the present invention is provided to a subject, it may be in a composition which may contain salts, buffers, adjuvants, or other substances which are desirable for improving the efficacy of the composition. Adjuvants are substances that can be used to specifically augment a specific immune response. Normally, the adjuvant and the composition are mixed prior to presentation to the immune system, or presented separately, but into the same site of the animal being immunized. Adjuvants can be loosely divided into several groups based upon their composition. These groups include oil adjuvants (for example, Freund's complete and incomplete), mineral salts (for example, $AlK(SO_4)_2$, $AlNa(SO_4)_2$, $AlNH_4(SO_4)$, silica, kaolin, and carbon), polynucleotides (for example, poly IC and poly AU acids), and certain natural substances (for example, wax D from *Mycobacterium tuberculosis*, as well as substances found in *Corynebacterium parvum*, or *Bordetella pertussis*, and members of the genus *Brucella*. Adjuvants are described by Warren et al. (*Ann. Rev. Biochem.*, 4:369-388, 1986), the entire disclosure of which is hereby incorporated by reference.

In some embodiments of the invention, conventional adjuvants can be administered together with the type IV pilin. In some embodiments, the adjuvants are saponins such as, for example, Quil A. (Superfos A/S, Denmark). In some embodiments, monophosphoryl lipid A plus trehalose dimycolate (Ribi-700; Ribi Immunochemical Research, Hamilton, Mont.) is used as an adjuvant.

In some embodiments, the composition comprises one or more adjuvants selected from polymers, co-polymers such as polyoxyethylene-polyoxypropylene co-polymers, including block co-polymers, polymer P1005, monotide ISA72, sorbitan monooleate, squalene, CRL-8300 adjuvant, QS 21, trehalose, bacterial extracts, including mycobacterial extracts, detoxified endotoxins, membrane lipids, Freund's complete adjuvant, Freund's incomplete adjuvant, lipopolysaccharide, monophosphoryl lipid A, muramyl dipeptide, liposomes containing lipid A, alum, muramyl tripeptide-phosphatidylethanoloamine, keyhole and limpet hemocyanin, modified lipid A, modified lipooligosaccharide(s) (LOS) consisting of core regions of LPS and lipid A molecules, a TLR4 agonist, double mutant labeled enterotoxin (see Norton et al., *Clinical Vaccine Immunology* 18(4):546-551 (2011)), IL-2, IL-6, IL-12, RANTES, GM-CSF, TNF-α, or IFN-γ, one or more growth factors, such as GM-CSF or G-CSF; one or more molecules such as OX-40L or 41 BBL, or combinations of thereof. See, for example, Salgaller et al., 1998, *J. Surg. Oncol.* 68(2):122-38; Lotze et al., 2000, *Cancer J. Sci. Am.* 6(Suppl 1):561-6; Cao et al., 1998, *Stem Cells* 16(Suppl 1):251-60; Kuiper et al., 2000, *Adv. Exp. Med. Biol.* 465:381-90).

The vaccines can be formulated into liquid preparations for, e.g., nasal, rectal, buccal, vaginal, peroral, intragastric, mucosal, perlinqual, alveolar, gingival, olfactory, or respiratory mucosa administration. Suitable forms for such administration include solutions, suspensions, emulsions, syrups, and elixirs. The vaccines can also be formulated for parenteral, subcutaneous, intradermal, intramuscular, intraperitoneal or intravenous administration, injectable administration, sustained release from implants, or administration by eye drops. Suitable forms for such administration include sterile suspensions and emulsions. Such vaccines can be in admixture with a suitable carrier, diluent, or excipient such as sterile water, physiological saline, glucose, and the like. The vaccines can also be lyophilized. The vaccines can contain auxiliary substances such as wetting or emulsifying agents, pH buffering agents, gelling or viscosity enhancing additives, preservatives, flavoring agents, colors, and the like, depending upon the route of administration and the preparation desired. Texts, such as *Remington: The Science and Practice of Pharmacy*, Lippincott Williams & Wilkins; 20th edition (Jun. 1, 2003) and *Remington's Pharmaceutical Sciences*, Mack Pub. Co.; $18^{th}$ and $19^{th}$ editions (December 1985, and June 1990, respectively), incorporated herein by reference in their entirety, can be consulted to prepare suitable preparations. Such preparations can include complexing agents, metal ions, polymeric compounds such as polyacetic acid, polyglycolic acid, hydrogels, dextran, and the like, liposomes, microemulsions, micelles, unilamellar or multilamellar vesicles, erythrocyte ghosts or spheroblasts. Suitable lipids for liposomal formulation include, without limitation, monoglycerides, diglycerides, sulfatides, lysolecithin, phospholipids, saponin, bile acids, and the like. The presence of such additional components can influence the physical state, solubility, stability, rate of in vivo release, and rate of in vivo clearance, and are thus chosen according to the intended application, such that the characteristics of the carrier are tailored to the selected route of administration.

In some embodiments, the vaccine of the invention is administered parenterally. Parenteral vehicles include phosphate buffered saline, sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. In some embodiments, the vaccines for parenteral administration may be in the form of a sterile injectable preparation, such as a sterile injectable aqueous or nonaqueous solutions, suspensions, and emulsions. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Suspensions may be formulated according to methods well known in the art using suitable dispersing or wetting agents and suspending agents. The sterile injectable preparation may also be a sterile injectable solution or suspension in a parenterally acceptable diluent or solvent, such as a solution in 1,3-butanediol. Suitable diluents include, for example, water, Ringer's solution and isotonic sodium chloride solution. In addition, sterile fixed oils may be employed conventionally as a solvent or suspending medium. For this purpose, any bland fixed oil may be employed including synthetic mono- or diglycerides. In addition, fatty acids such as oleic acid may likewise be used in the preparation of injectable preparations.

Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents.

In some embodiments, the vaccines are provided as liquid suspensions or as freeze-dried products. Suitable liquid preparations include, e.g., isotonic aqueous solutions, suspensions, emulsions, or viscous compositions that are buffered to a selected pH. Transdermal preparations include lotions, gels, sprays, ointments or other suitable techniques. If nasal or respiratory (mucosal) administration is desired (e.g., aerosol inhalation or insufflation), compositions can be in a form and dispensed by a squeeze spray dispenser, pump dispenser or aerosol dispenser. Aerosols are usually under pressure by means of a hydrocarbon. Pump dispensers can preferably dispense a metered dose or a dose having a particular particle size, as discussed below.

When in the form of solutions, suspensions and gels, in some embodiments, the formulations contain a major amount of water (preferably purified water) in addition to the active ingredient. Minor amounts of other ingredients such as pH adjusters, emulsifiers, dispersing agents, buffering agents, preservatives, wetting agents, jelling agents, colors, and the like can also be present.

In some embodiments, the compositions are isotonic with the blood or other body fluid of the recipient. In some embodiments, the isotonicity of the compositions can be attained using sodium tartrate, propylene glycol or other inorganic or organic solutes. In some embodiments, sodium chloride is used. In some embodiments, buffering agents can be employed, such as acetic acid and salts, citric acid and salts, boric acid and salts, and phosphoric acid and salts. In some embodiments of the invention, phosphate buffered saline is used for suspension.

In some embodiments, the viscosity of the compositions can be maintained at the selected level using a pharmaceutically acceptable thickening agent. In some embodiments, methylcellulose is used because it is readily and economically available and is easy to work with. Other suitable thickening agents include, for example, xanthan gum, carboxymethyl cellulose, hydroxypropyl cellulose, carbomer, and the like. The concentration of the thickener can depend upon the agent selected. In some embodiments, viscous compositions are prepared from solutions by the addition of such thickening agents.

In some embodiments, a pharmaceutically acceptable preservative can be employed to increase the shelf life of the compositions. Benzyl alcohol can be suitable, although a variety of preservatives including, for example, parabens, thimerosal, chlorobutanol, or benzalkonium chloride can also be employed. A suitable concentration of the preservative can be from 0.02% to 2% based on the total weight although there can be appreciable variation depending upon the agent selected.

In some embodiments, pulmonary delivery of the vaccine can also be employed. In some embodiments, the vaccine is delivered to the lungs of a mammal while inhaling and traverses across the lung epithelial lining to the blood stream. A wide range of mechanical devices designed for pulmonary delivery of therapeutic products can be employed, including but not limited to nebulizers, metered dose inhalers, and powder inhalers, all of which are familiar to those skilled in the art. These devices employ formulations suitable for the dispensing of the conjugate. Typically, each formulation is specific to the type of device employed and can involve the use of an appropriate propellant material, in addition to diluents, adjuvants and/or carriers useful in therapy.

In embodiments where the vaccine is prepared for pulmonary delivery in particulate form, it has an average particle size of from 0.1 μm or less to 10 μm or more. In some embodiments, it has an average particle size of from about 0.2, 0.3, 0.4, 0.5, 0.6, 0.7, 0.8, or 0.9 μm to about 1.0, 1.5, 2.0, 2.5, 3.0, 3.5, 4.0, 4.5, 5.0, 5.5, 6.0, 6.5, 7.0, 7.5, 8.0, 8.5, 9.0, or 9.5 μm for pulmonary delivery. Pharmaceutically acceptable carriers for pulmonary delivery of the vaccine include carbohydrates such as trehalose, mannitol, xylitol, sucrose, lactose, and sorbitol. Other ingredients for use in formulations can include DPPC, DOPE, DSPC and DOPC. Natural or synthetic surfactants can be used, including polyethylene glycol and dextrans, such as cyclodextran and other related enhancers, as well as cellulose and cellulose derivatives, and amino acids can also be used. Liposomes, microcapsules, microspheres, inclusion complexes, and other types of carriers can also be employed.

Formulations suitable for use with a nebulizer, either jet or ultrasonic, typically comprise the peptide dissolved or suspended in water at a concentration of about 0.01 or less to 100 mg or more of peptide per mL of solution, preferably from about 0.1, 1, 2, 3, 4, 5, 6, 7, 8, 9, or 10 mg to about 15, 20, 25, 30, 35, 40, 45, 50, 55, 60, 65, 70, 75, 80, 85, or 90 mg of peptide per mL of solution. The formulation can also include a buffer and a simple sugar (e.g., for protein stabilization and regulation of osmotic pressure). The nebulizer formulation can also contain a surfactant, to reduce or prevent surface induced aggregation of the conjugate caused by atomization of the solution in forming the aerosol.

Formulations for use with a metered-dose inhaler device generally comprise a finely divided powder containing the inventive compound suspended in a propellant with the aid of a surfactant. The propellant can include conventional propellants, such chlorofluorocarbon, a hydrochlorofluorocarbons, hydrofluorocarbons, and hydrocarbons, such as trichlorofluoromethane, dichlorodifluoromethane, dichlorotetrafluoroethanol, and 1,1,1,2-tetrafluoroethane, and combinations thereof. Suitable surfactants include sorbitan trioleate, soya lecithin, and oleic acid.

Formulations for dispensing from a powder inhaler device typically comprise a finely divided dry powder containing the peptide, optionally including a bulking agent, such as lactose, sorbitol, sucrose, mannitol, trehalose, or xylitol in an amount that facilitates dispersal of the powder from the device, typically from about 1 wt. % or less to 99 wt. % or more of the formulation, preferably from about 5, 10, 15, 20, 25, 30, 35, 40, 45, or 50 wt. % to about 55, 60, 65, 70, 75, 80, 85, or 90 wt. % of the formulation.

Diagnostic Methods

In some embodiments, the invention relates to type IV pilin polynucleotides, proteins or antibodies reactive specifically against the type IV pilins for use as diagnostic reagents. Detection of DNA, mRNA (or cDNA), protein levels, or antibodies directed against type IV pilins will provide a diagnostic tool that can add to or define a diagnosis of infection or susceptibility to infection. In some embodiments, the detection of one or more type IV pilins will direct the medical practitioner to set an appropriate course of treatment for the patient.

Nucleic acids for diagnosis may be obtained, for example, from a subject's bodily sample, such as, for example, the stool. Nucleic acid levels (DNA, mRNA, cDNA) can be assayed by comparison to a standard or control level from an uninfected and/or infected individual. The nucleic acids can be used directly for detection or can amplified enzymatically by using PCR or other amplification techniques prior to analysis.

In some embodiments, expression is measured at the RNA level using any of the methods well known in the art for the quantitation of polynucleotides; for example, RT-PCR, RNase protection, Northern blotting, array analysis, and other hybridization methods may be utilized. Assay techniques that may be used to determine the level of a type IV pilin protein in a sample derived from a host include radioimmunoassays, competitive-binding assays, Western blot analysis and ELISA assays.

In some embodiments, the invention is directed to methods for detecting *C. difficile* infection in a subject. In some embodiments, the method comprises obtaining a bodily sample from the subject; and analyzing the sample for the presence of a type IV pilin from *C. difficile* or an antibody that binds thereto. In some embodiments, the sample is a stool sample, a blood sample, a serum sample, a urine sample, and a saliva sample.

In some embodiments, the type IV pilin nucleic acid is detected. In some embodiments, type IV pilin protein is detected. In some embodiments, an antibody binding to type IV pilin is detected.

Other *C. difficile* markers, such as enterotoxins A (TcdA) and B (TcdB), can also be simultaneously assayed, in accordance with the methods of the present invention.

Type IV Pilin Antibodies

The type IV pilins of the invention or their antigenic fragments or variants thereof, or cells expressing them may also be used as immunogens to produce antibodies immunospecific for the type IV pilin.

Antibodies generated against the type IV pilin polypeptides can be obtained by administering the polypeptides or antigenic fragments, variants or cells to an animal using routine protocols. In some embodiments, antisera against type IV pilin are generated in a subject for use in passive immunotherapy. For preparation of monoclonal antibodies, any technique which provides antibodies produced by continuous cell line cultures can be used. Examples include the hybridoma technique (Kohler, G. and Milstein, C., *Nature* 256:495-497 (1975)), the trioma technique, the human B-cell hybridoma technique (Kozbor, et al., *Immunology Today* 4:72 (1983)) and the EBV-hybridoma technique (Cole et al., *Monoclonal Antibodies and Cancer Therapy*, pp. 77-96, Alan R. Liss, Inc., (1985)).

Techniques for the production of single chain antibodies (U.S. Pat. No. 4,946,778) may also be adapted to produce single chain antibodies to polypeptides of this invention. Also, transgenic mice, or other organisms including other mammals, may be used to express humanized antibodies. In some embodiments, the antibodies are humanized.

In some embodiments, the above-described antibodies or antisera is employed to detect a type IV pilin, for use in passive immunotherapy, or to purify a type IV pilin by affinity chromatography.

The present invention is further illustrated by the following Examples. These Examples are provided to aid in the understanding of the invention and are not to be construed as a limitation thereof.

Example 1

Expression and purification of the type IV pilins from *C. difficile*. We used the following novel strategy to express and purify high levels of recombinant *C. difficile* type IV pilins. This method involves identification of insoluble and soluble domains of the proteins, engineering of codon optimized synthetic pilin genes which do not exist in nature but which result in expression of pilin domains identical to those found in nature, optimal expression of pilin proteins, and purification to homogeneity. This method has been successful using two different pilin gene sequences.

We used our understanding of type IV pilin protein structure to identify the pre-pilin peptidase cleavage sites and hydrophobic mature amino-termini of each pilin gene. For the pilA2 gene found in *C. difficile* strain 630 and 10 other sequenced strains, we omitted from the recombinant construct the codons for the signal sequence and the first 27 residues of the mature protein (FIG. 1). In type IV pilus biogenesis the former domain is removed prior to pilus assembly and the latter domain is highly hydrophobic, buried in the core of the pilus, and interferes with pilin solubility and purification. Antibodies directed against this domain are not protective against infection since they do not bind to epitopes expressed on the pilus surface.

Figure 2:
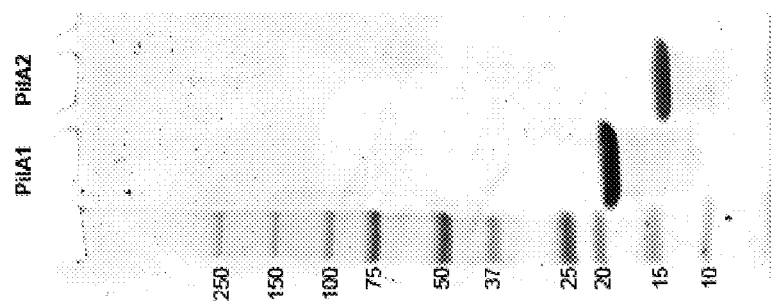
FIG. 2. Coomassie stained gel of purified *C. difficile* PilA1 and PilA2 proteins. M, molecular size standards are shown in the first lane.

Next, using oligonucleotide assembly polymerase chain reaction, we synthesized the remaining part of the pilA2 gene using codons optimized for *E. coli* to avoid translation limitations imposed by the differences in codon preference between these unrelated species. This procedure resulted in alteration of 73% of the codons without changing any of the natural amino acid sequence. This sequence is entirely novel and does not occur in nature. We then cloned the truncated optimized pilA2 gene into the pET30 T7 expression plasmid (Novagen) in frame with a hexahistidine tag (facilitating purification) and an enterokinase cleavage site (for potential removal of the tag, if required). After transformation and induction in *E. coli* strain BL21, we achieved extraordinarily robust levels of expression of a protein with the expected molecular mass of 13.8 kDa (FIG. 2). We were able to obtain more than 70 mg of pure protein from two liters of culture after one-step affinity purification on a nickel-nitrilotriacetic acid column.

Similarly, we engineered, synthesized and subcloned a recombinant pilA1 expression plasmid using the sequence from *C. difficile* strain 630 as a guide and following the identical strategy of domain omission, codon optimization, and vector and strain selection used for pilA2. We were similarly successful in high yield, high purity expression of recombinant PilA1 protein (FIG. 2). In the sequence listing we present the sequence of novel recombinant vectors for expression of each variant of PilA1, PilA2, PilA3, and PilA4. In some embodiments, the invention relates to identifying, engineering and producing recombinant synthetic *C. difficile* pilin genes of any type for pilin protein purification and use in vaccines and for diagnosis.

Example 2

Figure 3:
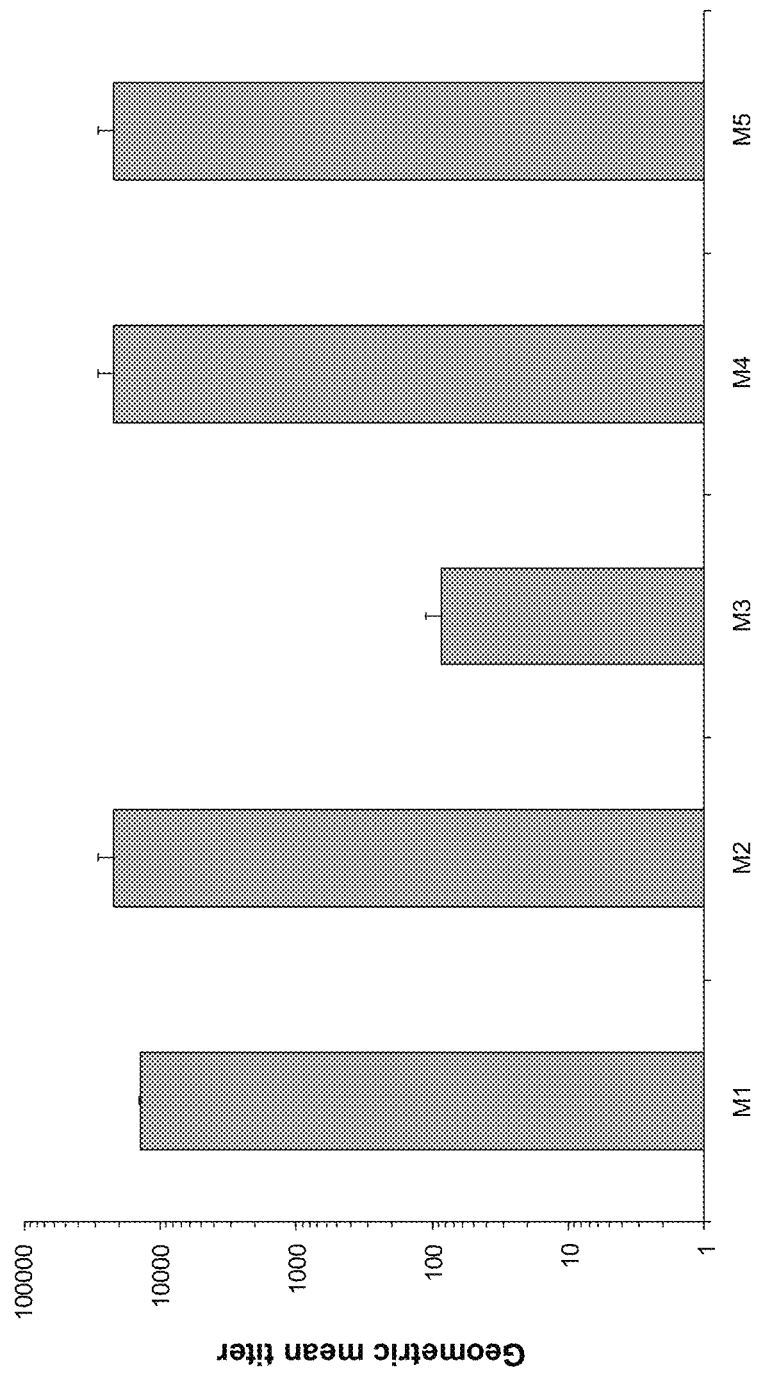
FIG. 3. PilA1 is immunogenic in mice. Geometric mean titers for five mice immunized as described in the text. Data are geometric means and standard errors of triplicate samples from three independent ELISA assays.

Generation of polyclonal antisera against recombinant *C. difficile* PilA1. We immunized 5 mice each with purified PilA1 and PilA2 pilin proteins using a standard regimen consisting of primary subcutaneous injection with Freund's complete adjuvant followed by two booster immunizations with incomplete adjuvant. Using the purified pilin proteins as antigens, we were able to demonstrate in 4 of 5 mice a significant immune response against PilA1 (FIG. 3). However, PilA2 was not immunogenic using this protocol.

Example 3

The efficacy of passive immunization with antibodies to PilA1 in prevention of *C. difficile* colonization and disease in a murine model. We will determine the efficacy of passive immunization using a recently reported murine model of experimental *C. difficile* colitis. Chen et al. *Gastroenterol.* 135(6):1984-92 (2008). Female nine-week-old C57BL6 mice will be treated for 3 days with an antibiotic cocktail of kanamycin (0.4 mg/ml), gentamicin (0.035 mg/ml), colistin (850 U/ml), metronidazole (0.215 mg/ml), and vancomycin (0.045 mg/ml), administered in the drinking water. After this treatment, mice will be switched over to regular drinking water for another 3 days. Finally, on day 7, a single dose of clindamycin (10 mg/kg) will be administered by the intraperitoneal route 24 hrs prior to orogastric challenge with *C. difficile* strain 630. One group of 14 mice will receive twice the $LD_{50}$ ($1\times10^4$ CFU) of *C. difficile* strain 630 pre-mixed with normal mouse sera and the other will receive the same dose pre-mixed with pooled immune sera from the four mice with titers against PilA1 greater than 1:10,000.

Mice will be weighed daily, scored for the development of diarrhea, and followed until they recover, die or require euthanasia. CDAD will be defined as any of the following: diarrhea, loss of 5% of pre-challenge body weight, or death. The experiment will be repeated once. With 28 mice in each group there is an 80% chance of detecting a reduction in CDAD, the primary endpoint, from 60% to 20% with a P value<0.05. In addition to monitoring CDAD, we will measure the effect of passive immunization on colonization and excretion of the organism, which will be highly relevant to control of *C. difficile* in health care settings.

Example 4

The efficacy of immunization with purified pilin in prevention of *C. difficile* colonization and disease in a murine model. We will establish the immunogenicity and protective efficacy of immunization with PilA1 and PilA2 in the murine model. Groups of six mice each will receive subcutaneous injections of PBS, PilA1 or PilA2. Fourteen days after completion of the immunization schedule, mice will be treated with antimicrobials and challenged with twice the $LD_{50}$ ($1\times10^4$ CFU) of *C. difficile* strain 630 as described in section above. Mice will be weighed daily, scored for the development of diarrhea, and followed until they recover, die or require euthanasia. CDAD will be defined as any of the following: diarrhea, loss of 5% of pre-challenge body weight, or death. The experiment will be repeated three times for a total of 24 mice in each group. In addition to monitoring CDAD, we will measure the effect of passive immunization on colonization and excretion of the organism.

Example 5

T4P Pilin Gene Sequences, Analysis, and Nomenclature

The *C. difficile* R20291 genome encodes at least nine putative pilin or pilin-like proteins (Table 1).

TABLE 1

Nomenclature and size of seven pilin genes in C. difficile R20291

| NCBI gene identifier | NCBI protein accession number | Mature Protein Designation | Mature pilin predicted length (aa) | Mature pilin predicted size (kDa) |
|---|---|---|---|---|
| CDR20291_3350[a] | YP_003219825 | PilA1 | 164 | 17.5 |
| CDR20291_3155[a] | YP_003219630 | PilA2 | 108 | 11.7 |
| CDR20291_0683 | YP_003217184 | PilJ | 262 | 29.2 |
| CDR20291_3344[a] | YP_003219819 | PilU | 166 | 18.8 |
| CDR20291_3345 | YP_003219820 | PilV | 178 | 20.6 |
| CDR20291_2191 | YP_003218677 | PilW | 158 | 17.3 |
| CDR20291_1081 | YP_003217579 | PilX | 113 | 13.7 |

[a]indicates gene was previously identified in strain 630 (Varga, 2006).

Figure 4:
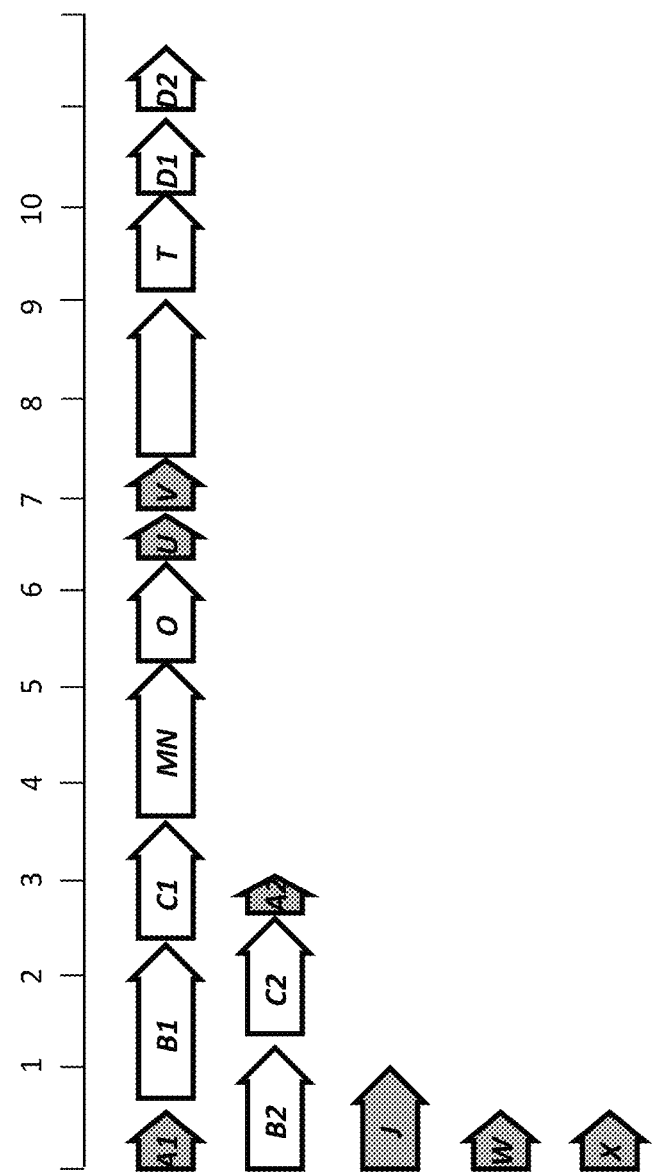
FIG. 4. Clusters of *C. difficile* R20291 T4P genes. Predicted functions of genes are as follows: PilB1, PilB2: assembly ATPase; PilC1,PilC2: polytopic membrane protein; PilMN: bitopic membrane protein homologous to both PilM and PilN; Pil0: bitopic membrane protein with cytoplasmic domain; PilT: refraction ATPase; PilD1, PilD2: prepilin peptidase. Predicted pilin proteins are shaded and pilin-like proteins are shaded.

Pilins were identified by BLAST searches based on the pilin genes previously identified in strain 630 (Varga, J. J., V. Nguyen, D. K. O'Brien, K. Rodgers, R. A. Walker, and S. B. Melville. 2006. Type IV pili-dependent gliding motility in the Gram-positive pathogen Clostridium perfringens and other Clostridia. Mol. Microbiol. 62:680-694.) and by using PilFind (Imam, S., Z. Chen, D. S. Roos, and M. Pohlschröder. 2011. Identification of surprisingly diverse type IV pili, across a broad range of gram-positive bacteria. PLoS. ONE. 6:e28919). Four of these genes are located in the main T4P gene cluster, one is located in a smaller T4P cluster, two are located near one another, and the remaining three are scattered throughout the genome (FIG. 4—organization of genes in cluster). We have named each pilin in accordance with prior T4P nomenclature as well as its predicted function.

Figure 5:
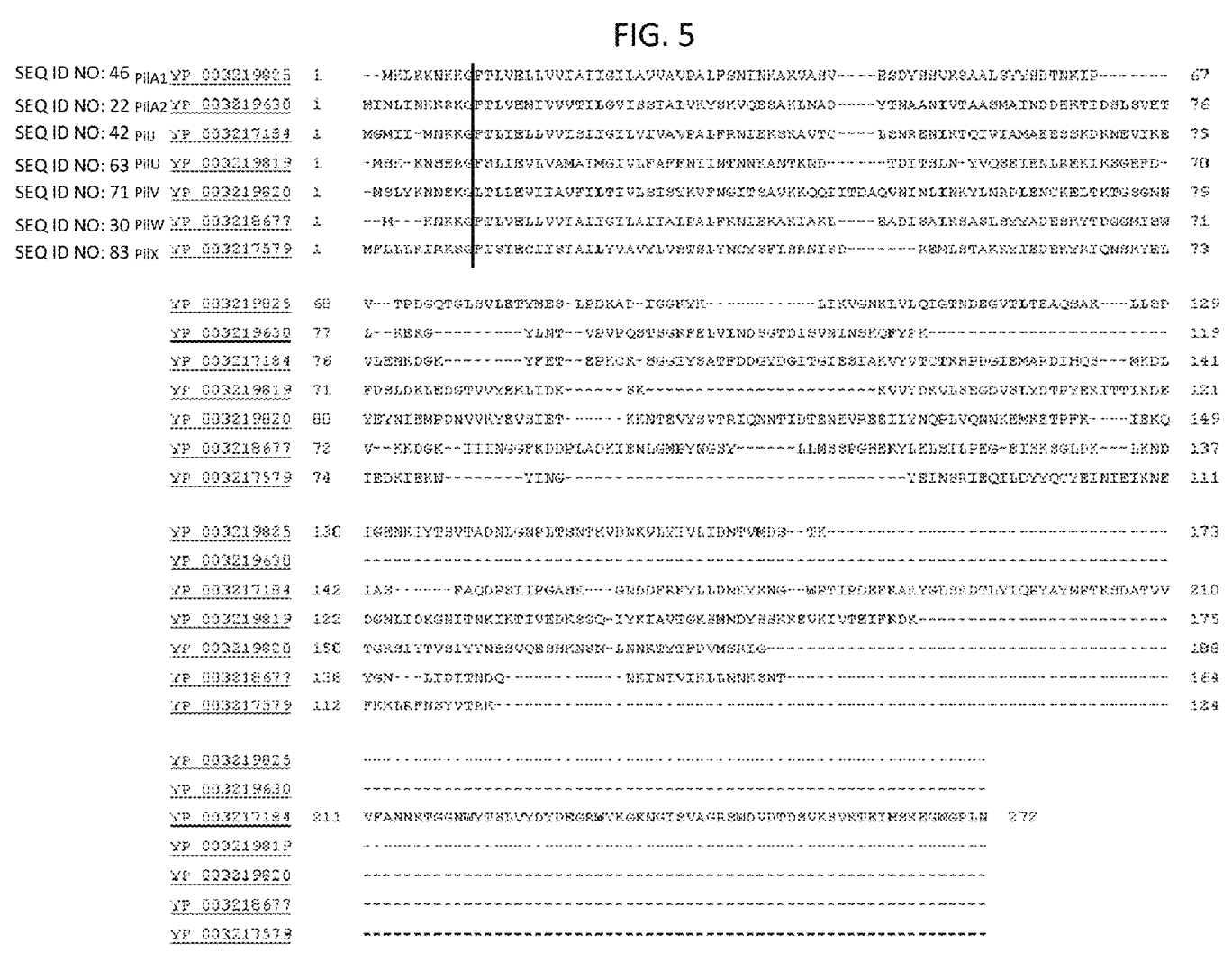

Although each predicted pilin proteins is relatively well conserved across strains, the seven pilins diverge from each other. All the predicted prepilin proteins share the N-terminal prepilin peptidase cleavage site and a hydrophobic N-terminal domain, but their amino acid sequences differ significantly after this region (Table 1, FIG. 5). The prepilins are predicted to range from 119 to 272 amino acids in length, and 13 to 30 kDa in mass. Of the nine pilins, six are present in all 18 C. difficile genomes annotated with protein sequences available in the NCBI genome database. All strains analyzed are capable of producing both toxin A and toxin B. The three not present in every strain are each found in eleven or twelve of the eighteen strains analyzed (Table 2).

TABLE 2

Comparison of R20291 pilin amino acid sequences with corresponding sequences in publically available protein-annotated genomes

| Strain | Ribotype[a] | PFGE type | Percent identity with R20291 pilin amino acid sequence | | | | | | |
|---|---|---|---|---|---|---|---|---|---|
| | | | PilA1 | PilA2 | PilJ | PilU | PilV | PilW | PilX |
| R20291 | 027 | NAP1 | 100% | 100% | 100% | 100% | 100% | 100% | 100% |
| 050-P50-2011 | NA | NA | 91% | 97% | 98% | 98% | 98% | —[b] | — |
| 002-P50-2011 | NA | NA | 91% | 97% | 98% | 98% | 98% | — | — |
| 70-100-2010 | NA | NA | 95% | 99% | 99% | 100% | 100% | 77% | — |
| QCD-63G42 | NA | NAP2 | 94% | 100% | 99% | 100% | 99% | 77% | 99% |
| 630 | 012 | NA | 91% | 100% | 98% | 99% | 100% | 96% | 100% |
| CD196 | 027 | NA | 100% | 100% | 100% | 100% | 100% | 100% | 100% |
| QCD-76W55 | 027 | NAP1 | 100% | 100% | 100% | 100% | 99% | 100% | 99% |
| QCD-32G58 | 027 | NAP1 | 100% | 100% | 100% | 100% | 99% | 100% | — |
| BI1 | 027 | NAP1 | 100% | 100% | 100% | 100% | 99% | 100% | 99% |
| QCD-66C26 | 027 | NAP1 | 100% | 100% | 100% | 100% | 99% | 100% | 99% |
| QCD-37X79 | NA | NAP1 | 100% | 100% | 100% | 100% | 99% | 100% | 99% |
| CIP 107932 | NA | NAP1 | 100% | 100% | 100% | 100% | 99% | 100% | 99% |
| QCD-97B34 | NA | NAP1 | 100% | 100% | 100% | 100% | 99% | 100% | 99% |
| NAP08 | 078 | NA | 90% | 96% | 96% | 95% | 96% | — | — |
| NAP07 | 078 | NAP7 | 90% | 96% | 96% | 95% | 96% | — | — |
| QCD-23M63 | 078 | NAP7 | 90% | 96% | 96% | 95% | 95% | — | 93% |
| ATCC 43255 | 087 | NA | 76% | 100% | 99% | 99% | 99% | 77% | 99% |
| Average percent identity | | | 95% | 99% | 99% | 99% | 98% | 93% | 99% |
| Minimum percent identity | | | 76% | 96% | 96% | 95% | 95% | 77% | 93% |

[a]NA, not available in NCBI database
[b]Indicates pilin is not present in that strain Although the number of strains is small, the absence of at least one of the pilins appears to correlate with non-ribotype 027, non PFGE NAP1 status (Table 2, p=0.049, Fisher's exact test). Amino acid sequences of each of the nine pilins are well conserved across strains; minimum and average percent identity for each pilin range from 76% to 96% and 93% to 99% (relative to the gene in 820291) respectively, across the eighteen strains (Table 2).

The gene CDR20291_3350 is the first open reading frame in the main T4P gene cluster, and shows the greatest polymorphism across all *C. difficile* strains. For these and other reasons (see discussion), it is our hypothesis that this protein is the major pilin of the *C. difficile* T4P, and thus propose pilA1 as the gene designation and PilA1 the name of the mature protein. In other T4P systems, the 'A' designation indicates the major pilin, as in TcpA of *V. cholerae* and PilA of *P. aeruginosa*.

The gene CDR20291_3155 is predicted to encode a small pilin located in the small T4P gene cluster. The presence of two or more accessory genes in that cluster may indicate the potential to make distinct pili. Therefore, we propose pilA2 as the gene designation and PilA2 as the name for the mature protein encoded by CDR20291_3155.

Gene CDR20291_0683 is predicted to encode a large pilin. It is present in every strain examined, although it is not part of either the large or small T4P gene clusters. It also is one of the less diverse pilins across the 18 genomes. Structural analysis (Piepenbrink et al, unpublished/in press) indicates the protein encoded by CDR20291_0683 contains two globular C-terminal pilin domains, rather than the single domain typical of pilins in Gram-negative bacteria (Craig, L., M. E. Pique, and J. A. Tainer. 2004. Type IV pilus structure and bacterial pathogenicity. *Nat. Rev. Microbiol.* 2:363-378.). Molecular modeling indicates that pili composed primarily of the product of this gene would be wider than any observed indicating that pili composed entirely of this protein are unlikely. Given its size, low sequence diversity, and location outside of the gene cluster, it likely encodes a minor pilin. We propose pilJ as the gene designation and PilJ as the mature protein identifiers for gene CDR20291_0683, with T indicating 'Janus' for the two C-terminal pilin domains. Precedent for this designation exists in the EPEC bundle-forming pilus, where one of the minor pilins is termed BfpJ and the T2S minor pseudopilin GspJ (Stone, K. D., H.-Z. Zhang, L. K. Carlson, and M. S. Donnenberg. 1996. A cluster of fourteen genes from enteropathogenic *Escherichia coli* is sufficient for biogenesis of a type IV pilus. *Mol. Microbiol.* 20:325-337).

Genes CDR20291_3344 and CDR20291_3345 are located adjacent to one another in the T4P gene cluster, and their predicted products share a relatively high degree of amino acid sequence similarity with each other (Tables 2, 3). Their amino acid sequences have low variability across strains, leading us to believe they are minor pilins. Following the model of *Neisseria* and *Pseudomonas* minor pilins (Winther-Larsen et al *PNAS* 2001 for *Neisseria* PilV; Alm & Mattick *J Bacteriology* 1996 for *Pseudomonas* FimU), we propose pilU and pilV, and PilU and PilV as the gene and mature protein identifiers for CDR20291_3344 and CDR20291_3345, respectively.

Immediately downstream of pilV in the main T4P cluster lies the CDR__ open reading frame, predicted to encode a protein with similarities to pilin-like proteins including a possible prepilin peptidase cleavage site. However, this unusually large potential prepilin-like protein lacks the conserved glutamic acid at position +5. We propose pilK for this gene and PilK for the mature protein as the GspK proteins of T2S systems are also large and lack the conserved glutamic acid.

Given that genes CDR20291_2191, CDR20291_ and 1081 are of low variability and not present in every strain, we believe that they encode minor pilins as well; again following the nomenclature of *Pseudomonas* minor pilins (Alm, R. A., J. P. Hallinan, A. A. Watson, and J. S. Mattick. 1996. Fimbrial biogenesis genes of *Pseudomonas aeruginosa*: PilW and pilX increase the similarity of type 4 fimbriae to the GSP protein-secretion systems and pilY1 encodes a gonococcal PilC homologue. *Mol. Microbiol.* 22:161-173), we propose PilW and PilX1 and PilX2, respectively, as their designations.

Given our observations regarding the pilin amino acid sequence diversity across strains, we decided to investigate how the diversity in pilin amino acid sequences across different strains was reflected in their nucleotide sequences, and thus undertook an analysis of rates of synonymous and nonsynonymous mutations in the coding sequences for each pilin. For the majority of the pilins, rates of both synonymous and nonsynonymous substitutions were low. Those nonsynonymous substitutions that did occur tended to cluster neat the C-termini of the proteins (data not shown). As the N-termini are buried inside the pilus and play a critical role in pilin-pilin interactions, the relative paucity of substitutions there is consistent with the results of similar analyses conducted in other T4P pilin genes. PilA1 and, surprisingly, PilW have the greatest number of sites with substitutions, while PilU, PilV, and PilX have relatively few.

The ratio of nonsynonymous substitutions per site to synonymous substitutions per site, called dN/dS or ω, is a standard measure of selective pressure. Values of w for the full-length nucleotide sequences were generally close to 0, congruent with the theory that most sites in a protein are subject to purifying selection (with a resulting low ω) due to functional constraints. While PilX has an overall ω value above 1, we believe this can be attributed to the low overall

TABLE 3

Pilin amino acid sequence percent identity and maximum identity within *C. difficile* R20291, as determined by NCBI BLAST Query Sequence

| | PilA1 | | PilA2 | | PilJ | | PilU | | PilV | | PilW | | PilX | |
|---|---|---|---|---|---|---|---|---|---|---|---|---|---|---|
| | Percent coverage | Maximum identity | Percent coverage | Maximum identity | Percent coverage | Maximum identity | Percent coverage | Maximum identity | Percent coverage | Maximum identity | Percent coverage | Maximum identity | Percent coverage | Maximum identity |
| PilA1 | — | — | 56 | 29 | 28 | 63 | 21 | 48 | 24 | 38 | 43 | 74 | 19 | 30 |
| PilA2 | 79 | 29 | — | — | 94 | 29 | 15 | 37 | 15 | 100 | 63 | 37 | 10 | 33 |
| PilJ | 18 | 63 | 41 | 29 | — | — | 45 | 48 | 18 | 40 | 21 | 58 | 23 | 50 |
| PilU | 32 | 46 | 10 | 37 | 49 | 50 | — | — | 52 | 67 | 10 | 83 | 90 | 27 |
| PilV | 22 | 38 | 9 | 100 | 26 | 40 | 74 | 67 | — | — | 15 | 50 | 6 | 46 |
| PilW | 37 | 74 | 45 | 35 | 45 | 52 | 45 | 48 | 18 | 40 | — | — | 17 | 28 |
| PilX | 26 | 30 | 9 | 33 | 56 | 50 | 91 | 27 | 10 | 46 | 9 | 33 | — | — | number of substitutions in this gene (2 synonymous and 8 nonsynonymous substitutions total in the twelve sequences analyzed).

TABLE 4

Calculation of ω and identification of sites under positive selection

| Pilin | dn/ds | 2ΔL | Reject null model | Sites under positive selection |
|---|---|---|---|---|
| PilA1 | 0.41186 | 13.36 | Yes | 113 D, 142 D, 146 N, 150 S |
| PilA2 | 0.08367 | 2E−05 | No | — |
| PilJ | 0.10553 | −2E−06 | No | — |
| PilU | 0.14692 | 0.924 | No | — |
| PilV | 0.09817 | −3.8E−05 | No | — |
| PilW | 0.17345 | 3.94 | No | — |
| PilX | 1.43702 | 0.124 | No | — |

Bold text indicates significance with 99% confidence, plain text indicates significance at 95% confidence It is unlikely that entire genes will be subject to positive selection; rather, individual codons undergo selection. These sites of positive selection can be identified by statistical methods, such as the likelihood-ratio test (LRT) tests for the presence of positively selected sites. If the LRT is positive, a Bayes empirical Bayes (BEB) approach can determine which sites are under positive selection (Yang et al 2005). Of the seven pilins, only PilA1 had a positive LRT. The BEB analysis identified four codons under positive selection, all of which were clustered in the C-terminal region of the pilin involved, which is likely to be exposed to the environment rather than buried in the body of the pilus.

Example 6

Pilin Purification, Immunogenicity and Cross-Reactivity in Animals.

Figure 6:
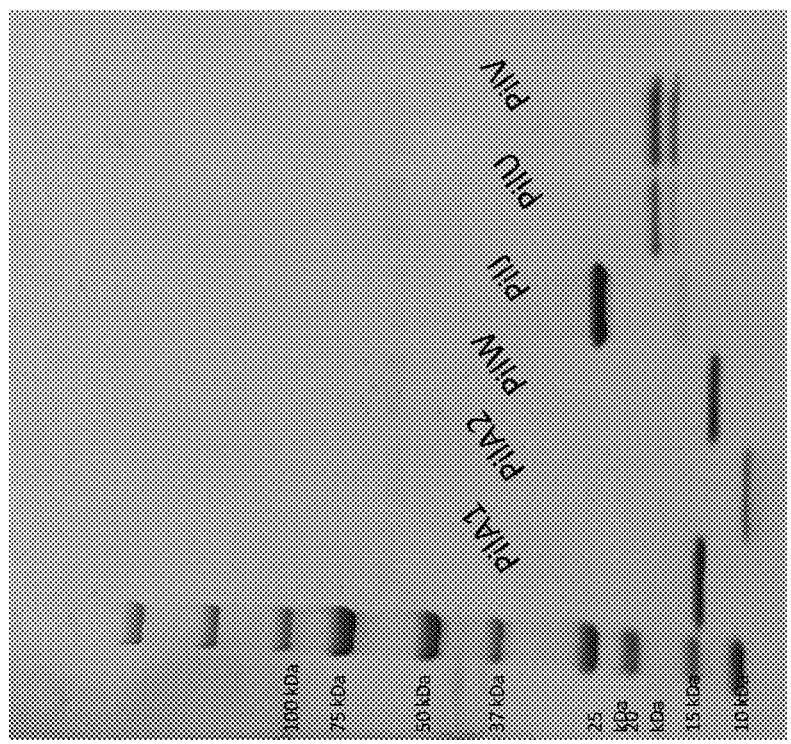
FIG. 6. Coomassie stained gel of purified pilin and pilin-like proteins after removal of hexa-histidine tags. Lane 1, PilA1 (molecular masse 15.1 kDa); lane 2, PilA2 (9.0 kDa); lane 3, PilW (15.0 kDa); lane 4, PilI (26.6 kDa); lane 5, PilU (16.4 kDa); lane six, PilV (17.1 kDa). The sizes of molecular mass markers are indicated to the left.

Artificial genes with codons optimized for *E. coli* expression and lacking the signal sequence and conserved N-terminal hydrophobic domain were synthesized for seven pilin proteins. Six of seven proteins were soluble and successfully purified (FIG. 6); only PilX proved insoluble and difficult to purify.

To test the immunogenicity of the six purified pilin and pilin-like proteins, mice were immunized intradermally with purified protein and adjuvant and boosted subcutaneously at 1 and 2 weeks after the initial injection. Terminal bleeds were collected 59 days after the initial injection. Preimmune and terminal serum from each mouse was tested by ELISA for antibody response against the homologous protein. Although all pilin and pilin-like proteins induced a detectable antibody response, those responses varied by pilin. Immunization with PilW, PilU, or PilV led to a higher titer homologous antibody response than immunization with any of the other three proteins, while PilA1 generated the weakest responses of any pilin, and was the only pilin to which an immunized mouse produced no detectable antibody (FIG. 7).

Figure 7:
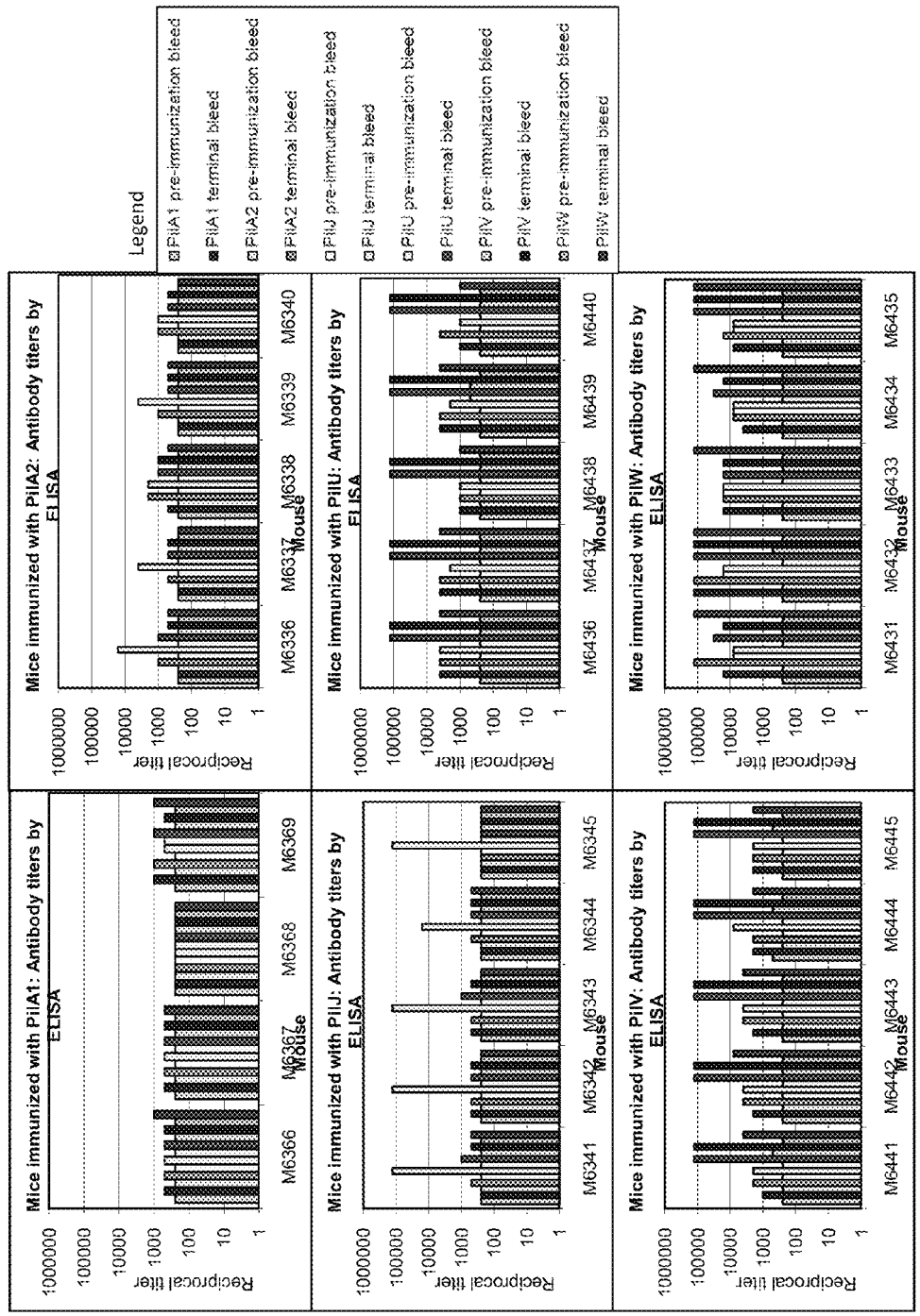
FIG. 7. Pilin immunogenicity and anti-pilin antibody crossreactivity determined by ELISA. The designations on the X-axis indicate the number of each mouse immunized with the pilin specified in the graph title. The different bar colors are the pilin antigens with which the particular mouse serum, specified in the X axis, from pre-immunization (pale colors) and terminal bleeds (dark colors) were tested. Red indicates PilA1, orange indicates PilA2, yellow indicates PilI, green indicates PilU, blue indicates PilV, and violet indicates PilW.

After determining the titer of antibodies against the immunizing pilin or pilin-like protein, we next measured the antibody titer against the five heterologous proteins (FIG. 7). Notably, the highly conserved N-terminus of each protein was excluded from the purified soluble protein antigens, and thus all cross-reactive responses are due to epitopes present in less conserved regions of the proteins. Antibodies raised against PilJ were almost completely specific to their immunizing antigen. In contrast, the antibody response to PilW proved pan-reactive, but was the most variable by mouse. Antibodies raised against PilU reacted strongly to both PilU and PilV, and vice versa, suggesting strong epitope conservation between these proteins. Interestingly, antibodies raised against PilA2 proved more reactive to PilJ than to PilA2.

Figure 8A:
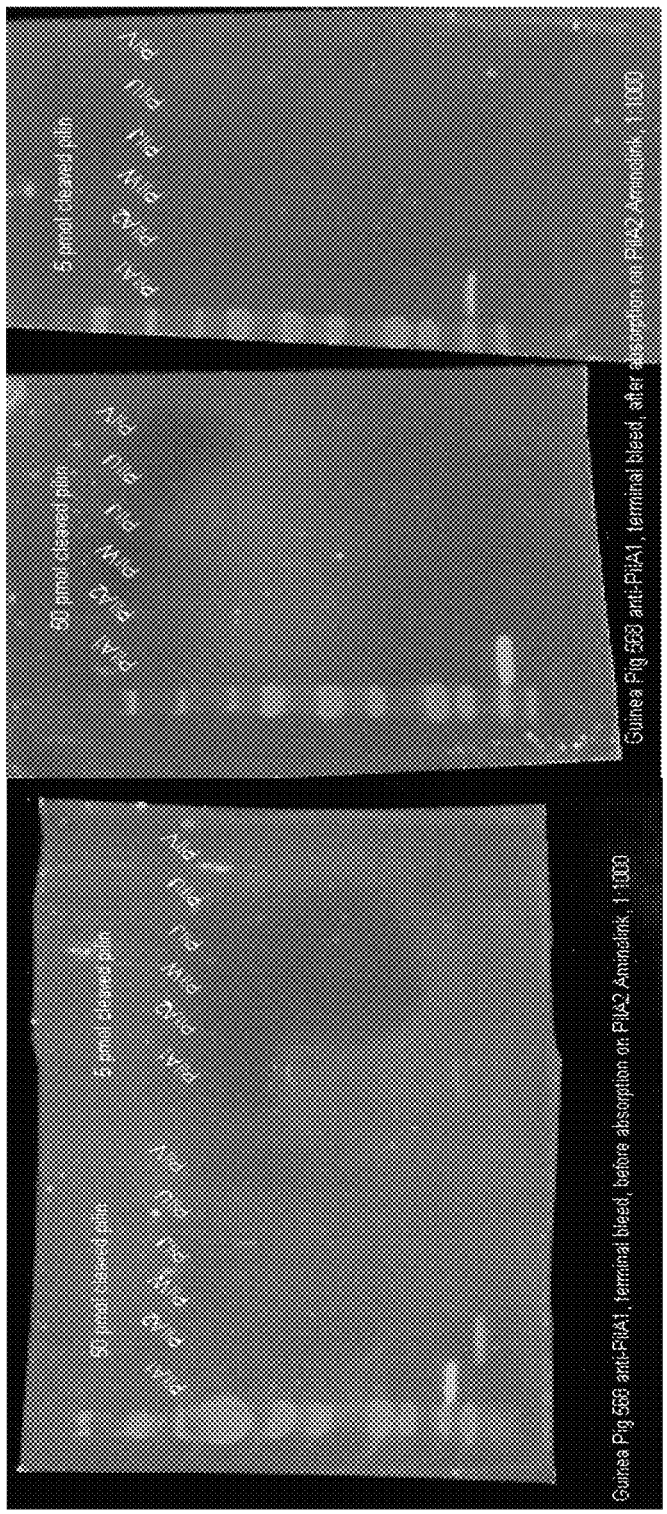
FIG. 8. Antibodies raised in small mammals recognize untagged pilin proteins. All lane assignments as follows: Lane 1: PilA1, 50 pmol; lane 2: PilA2, 50 pmol; lane 3: PilW, 50 pmol; lane 4: PilI, 50 pmol; lane 5: PilU, 50 pmol; lane 6: PilV, 50 pmol. (The sizes of molecular mass markers are indicated to the left. A) Antibody raised in rabbit against PilI demonstrated strong and specific response to PilI. (B) Antibody raised in guinea pig against PilA1, before (left) and after (right) immunoabsorption on PilA2 Aminolink column. (C) Antibody raised in two different rats against PilA2, demonstrating that one reacted only to PilA2 (left), and one only to PilI (right).
Figure 8B:
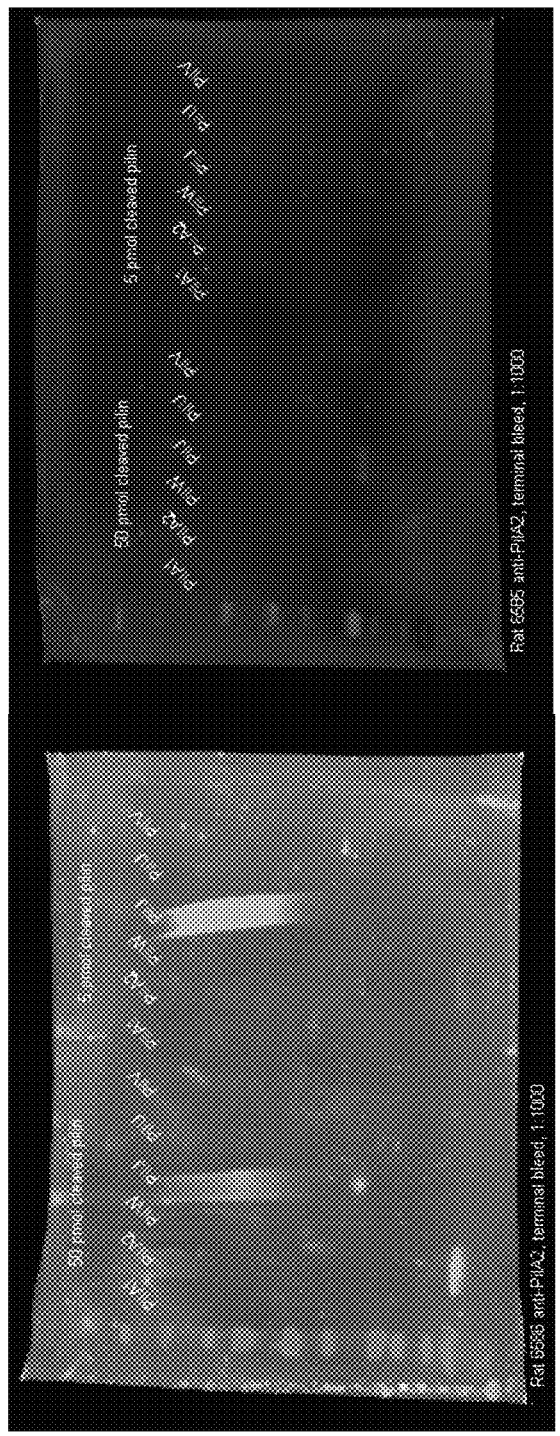
Figure 8C:
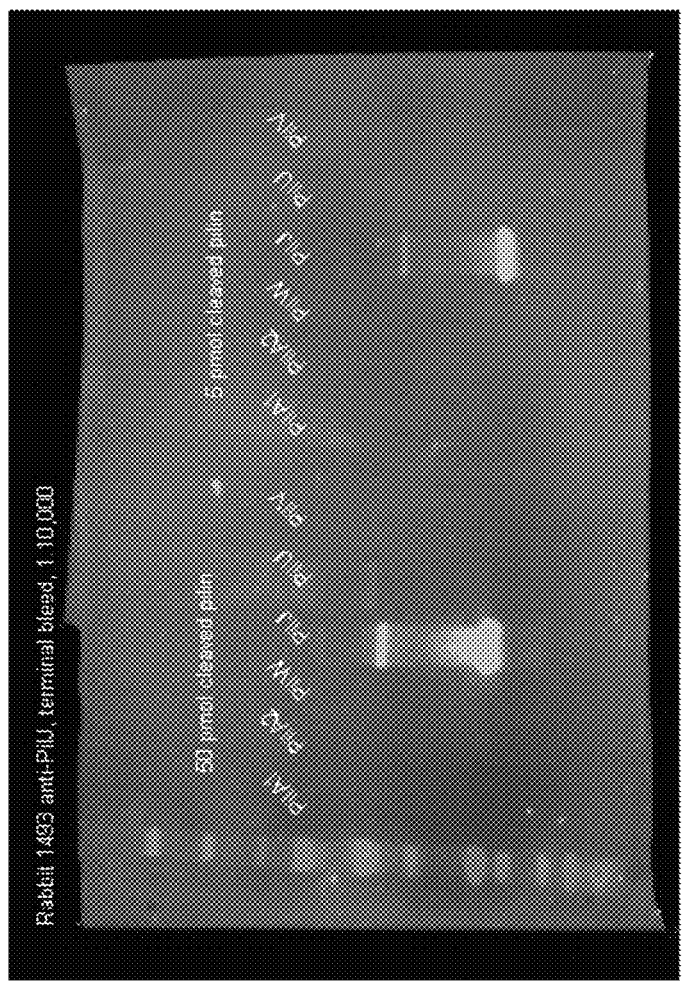

To produce greater volumes of sera for future experiments, we immunized additional species of small mammals with selected pilins. Our results with these species mirror our experiences in mice. As in mice, immunization with PilJ produced a specific and robust response in rabbits (FIG. 8A). In contrast, guinea pigs immunized with PilA1 required several boosts to generate significant responses; these antibodies also cross-reacted with PilA2, and immunoadsorption was necessary to select for antibodies specific for PilA1 (FIG. 8B). This experience is reminiscent of the poor immunogenicity of PilA1 in mice. Of three rats immunized with PilA2, two responded only to PilJ on Western blot; the third responded specifically to PilA2 (FIG. 8C). The ability to generate antibodies crossreactive with PilJ was also a feature of PilA2 immunization in mice.

Methods

Pilin Gene Identification

Three *C. difficile* pilin genes (pilA1, pilA2, and pilU were previously identified in strain 630 (Varga, J. J., V. Nguyen, D. K. O'Brien, K. Rodgers, R. A. Walker, and S. B. Melville. 2006. Type IV pili-dependent gliding motility in the Gram-positive pathogen *Clostridium perfringens* and other Clostridia. *Mol. Microbiol.* 62:680-694). The presence of those pilins in 820291, a BI/NAP1/027 strain isolated in 2006 from the Stoke Mandeville hospital outbreak in Buckinghamshire, United Kingdom, was confirmed by BLAST search. The additional pilins were identified by BLAST search of the R20291 genome using amino-terminal sequences from the previously identified pilins, and by use of PilFind (Imam, S., Z. Chen, D. S. Roos, and M. Pohlschröder. 2011. Identification of surprisingly diverse type IV pili, across a broad range of gram-positive bacteria. *PLoS. ONE.* 6:e28919).

Analysis of Pilin Nucleotide Sequences

Nucleotide sequences for each pilin were obtained from GenBank/NCBI for the twelve genomes with fully assembled contigs. Those that were unassembled (NAP08, NAP07, ATCC 9689, 70-100-2010, 050-P50-2011, and 050-P50-2011) were excluded from further analysis. Sequences were aligned in Clustal Omega and manually edited. Rates of synonymous and nonsynonymous substitutions were calculated with SNAP. Calculation of w, tests for positive selection, and identification of positively-selected sites was completed using CodeML from PAML version 4.7. Maximum-likelihood phylogenetic trees for use in CodeML were assembled in MEGA 5.2.

Protein Expression and Purification

DNA sequences of each pilin lacking the signal peptide and codons for the N-terminal hydrophobic domain were codon-optimized for expression in *E. coli*, commercially synthesized (Genscript), cloned into the pET30b vector downstream of the hexa-histidine tag sequence, and transformed into *Escherichia coli* BL21(DE3) cells (Invitrogen). The precise sequence for each plasmid is available on request. After inoculation of 1 L Luria broth+kanamycin with 20 mL turbid overnight culture, cells were grown to OD600=0.5 at 30° C. and induced with 1.0 mM Isopropyl β-D-1-thiogalactopyranoside. After a set induction time for each pilin determined in pilot studies, cultures were pelleted by centrifugation at 5000×g for 10 minutes at 4° C. (Beckman Coulter); pellets were stored at −20° C. Cell pellets were resuspended in 50 mM NaH$_2$PO$_4$, 300 mM NaCl, 20 mM imidazole, pH8.0 with protease inhibitors (Roche) and lysed in a French press at 1200 psi (Sim Aminco); lysates were centrifuged at 35000×g for 30 min. Supernatants containing each fusion protein were applied to nickel-nitrilotriacetic acid agarose (Qiagen) and incubated, with rotation, at 4° C. for 1 hr. After washing, protein was eluted from the resin with increasing concentrations of imidazole in 50 mM NaH$_2$PO$_4$, 300 mM NaCl, pH 8.0. If necessary, column fractions were further purified by size-exclusion chromatography using a Sephacryl S-100 column. For ELISA assays, immunoblotting and immunoabsorption, the N-terminal purification tag was cleaved from each purified pilin protein with recombinant enterokinase (Novagen) and removed by incubation with Ni-NTA resin.

Antibody Generation

Purified tagged pilin protein samples were sent to Rockland Immunochemicals, where they were used to immunize mice. Pre-immunization bleeds were taken 1 day prior to intradermal immunization with purified pilin plus Freund's complete adjuvant. Mice were boosted with antigen and incomplete Freund's adjuvant subcutaneously at 7 and 14 days post-immunization. Terminal bleeds were taken 59 days after immunization. Polyclonal antibodies to untagged PilA1 were raised in guinea pigs, antibodies to untagged PilA2 were raised in rats, and antibodies to untagged PilJ were raised in rabbits (Rockland Immunochemicals). Briefly, animals were immunized intradermally with purified untagged protein and complete Freund's adjuvant, and boosted on days 7, 14, and 28 with protein and incomplete Freund's adjuvant. Test bleeds were taken on day 38. Terminal bleeds for rabbits and one rat were taken on day 59. The guinea pigs and remaining rats were boosted again, and terminal bleeds taken on day 80.

ELISA

Unless otherwise noted, all solutions were used at 50 μl/well. Nunc Maxisorp 96-well plates were coated overnight with purified cleaved pilin or pilin-like protein, brought to 10 μg/mL in phosphate-buffered saline with 0.05% Tween-20 (PBST) 50 μl/well. Blank wells were coated with plain PBST. After coating, plates were blocked with 5% bovine serum albumin (Sigma) in PBST for 1 hr at 37° C., 100 μL/well. Serum samples diluted 1:500 in PBST were added and serially diluted with one volume PBST in plate to a final volume of 50 μL/well. All sera were run in triplicate. Normal mouse serum (KPL) was loaded at 1:500 in PBST. Blank wells were loaded with PBST. Samples were incubated on plate for 2 hours at room temperature. Peroxidase-tagged goat anti-mouse-IgG (H+L) (KPL) was added at a 1:1000 dilution and incubated for 30 minutes at 37° C. Plates were developed with Sureblue Safestain (KPL) for 30 minutes at room temperature. Optical density at 655 nm (OD655) was read with a microplate reader (BioRad model 680). Blanks were averaged and subtracted from sample/standard wells. Normal mouse serum (KPL) was used to provide a standard against which experimental serum could be judged. The average plus two standard deviations of the OD655 with normal mouse serum was taken as the nonspecific normal mouse background OD. For experimental samples, triplicate wells were averaged; the highest dilution with an OD655 greater than normal mouse background was taken as the antibody titer.

Immunoabsorbance and Immunoblotting

Upon terminal bleed, guinea pig antibodies to PilA1 were found to cross-react with PilA2. This crossreactivity to PilA2 was eliminated by PilA2 immobilized on Aminolink columns (Thermo Scientific). Columns were prepared according to kit protocols. Briefly, tagged PilA2 in 0.1M NaH$_2$PO$_4$ was incubated with resin and 50 mM NaCNBH$_3$ at 4° C. overnight with end-over-end rotation. Unbound PilA2 was washed from resin with additional 0.1M NaH$_2$PO$_4$ buffer. For immunoabsorption, guinea pig anti-PilA1 was diluted 1:1 in 0.1M NaH$_2$PO$_4$ and incubated with resin at 4° C. for 1 hour with rotation. Unbound antibody was washed from column and concentrated back to original volume. Purified untagged pilins were boiled for 10 minutes in Laemmli buffer and applied to precast 4-15% gradient Mini-PROTEAN TGX polyacrylamide gels (Bio-Rad). Proteins were transferred to polyvinylidene difluoride (PVDF) membranes, blocked for 1 hour with 5% non-fat dry milk, then incubated at 4° C. overnight with polyclonal rabbit anti-PilJ at a 1:10,000 dilution, polyclonal rat anti-PilA2 at 1:1000 dilution, or polyclonal guinea pig anti-PilA1 at 1:1000 dilution. Membranes were washed in PBST, incubated with IRDye 800CW donkey anti-rabbit IgG H+L, donkey anti-guinea pig IgG H+L, or goat anti-rat IgG H+L (Li-Cor Biosciences) as appropriate for 1 hour, and infrared signals were detected and quantified using the Odyssey imaging system (Li-Cor Biosciences).

What is claimed is:

1. A pharmaceutical composition comprising an isolated polypeptide comprising
   i) a *Clostridium difficile* type IV pilin or an antigenic fragment or variant thereof, wherein the variant is recognized by an antibody that binds the *C. difficile* type IV pilin, wherein the isolated *C. difficile* type IV pilin or antigenic fragment or variant thereof is recombinantly produced, wherein the variant has at least 90% sequence identity to the type IV pilin, wherein the type IV pilin is selected from the group consisting of:
   a. SEQ ID NO:46;
   b. SEQ ID NO: 47;
   c. SEQ ID NO:48;
   d. SEQ ID NO:50;
   e. SEQ ID NO:51;
   f. SEQ ID NO:52;
   g. SEQ ID NO:63;
   h. SEQ ID NO:65;
   i. SEQ ID NO: 66;
   j. SEQ ID NO: 67;
   k. SEQ ID NO:69;
   l. SEQ ID NO: 71;
   m. SEQ ID NO:73;
   n. SEQ ID NO:74;
   o. SEQ ID NO: 75;
   p. SEQ ID NO:78;
   q. SEQ ID NO:79;
   r. SEQ ID NO: 81;
   s. SEQ ID NO:83;
   t. SEQ ID NO:85;
   u. SEQ ID NO: 87;
   v. SEQ ID NO:88; and
   w. SEQ ID NO:89;
   wherein the antigenic fragment is selected from the group consisting of:
   i. an amino-terminal truncation mutant of the type IV pilin, wherein the number of amino terminal amino acids missing from the fragment ranges from 1-100 amino acids;
   ii. a carboxyl-terminal truncation mutant of the type IV pilin, wherein the number of carboxyl terminal amino acids missing from the fragment ranges from 1-100 amino acids; and
   iii. an internal fragment of the type IV pilin lacking both the amino and carboxyl terminal amino acids and being 10-100 amino acid residues in length; and
   ii) an affinity tag s 2. The pharmaceutical composition of claim 1, comprising a combination of isolated polypeptides of claim 1.

3. The pharmaceutical composition of claim 2, wherein said isolated polypeptides are conjugated.

4. The pharmaceutical composition of claim 2, wherein said isolated polypeptides are encoded by nucleic acids that are conjugated genetically.

5. The pharmaceutical composition of claim 1, wherein said isolated polypeptide comprises the *C. difficile* type IV pilin antigenic fragment.

6. The pharmaceutical composition of claim 1, wherein the antigenic fragment is produced in *E. coli*.

7. The pharmaceutical composition claim 6, wherein the antigenic fragment is encoded by a nucleic acid sequence optimized to increase expression in *E. coli*.

8. The pharmaceutical composition claim 7, wherein the nucleic acid sequence is selected from the group consisting of:
   a. SEQ ID NO:110;
   b. SEQ ID NO:90;
   c. SEQ ID NO:92;
   d. SEQ ID NO:95;
   e. SEQ ID NO:105; and
   f. SEQ ID NO:98.

9. The pharmaceutical composition of claim 1, wherein the type IV pilin is from a strain selected from the group consisting of *C. difficile* CD196, *C. difficile* CIP 107932, *C. difficile* QCD-32g58, *C. difficile* QCD-37x79, *C. difficile* QCD-66c26, *C. difficile* QCD-76w55, *C. difficile* QCD-97b34, *C. difficile* 820291, *C. difficile* QCD-63q42, *C. difficile* QCD-23m63, *C. difficile* 630, *C. difficile* ATCC 43255, *C. difficile* 70-100-2010, *C. difficile* 050-P50-2011, *C. difficile* 002-P50-2011, *C. difficile* NAP08, *C. difficile* NAP07, *C. difficile* BI1 and combinations thereof.

10. The composition of claim 6, wherein the isolated polypeptide further comprises an enzymatic cleavage sequence.

11. A pharmaceutical composition for inducing an immune response against *Clostridium difficile* comprising at least one isolated polypeptide comprising
   i) a *C. difficile* type IV pilin or an antigenic fragment or variant thereof, wherein the variant is recognized by an antibody that binds the *C. difficile* type IV pilin, wherein the isolated *C. difficile* type IV pilin or antigenic fragment or variant thereof is recombinantly produced, wherein the variant has at least 90% sequence identity to the type IV pilin, wherein the type IV pilin is selected from the group consisting of:
   a. SEQ ID NO:46;
   b. SEQ ID NO: 47;
   c. SEQ ID NO:48;
   d. SEQ ID NO:50;
   e. SEQ ID NO:51;
   f. SEQ ID NO:52;
   g. SEQ ID NO:53;
   h. SEQ ID NO: 54;
   i. SEQ ID NO:55;
   j. SEQ ID NO:56;
   k. SEQ ID NO: 57;
   l. SEQ ID NO:58;
   m. SEQ ID NO:59;
   n. SEQ ID NO: 60;
   o. SEQ ID NO:63;
   p. SEQ ID NO:65;
   q. SEQ ID NO: 66;
   r. SEQ ID NO:67;
   s. SEQ ID NO:69;
   t. SEQ ID NO: 71;
   u. SEQ ID NO:73;
   v. SEQ ID NO:74;
   w. SEQ ID NO: 75;
   x. SEQ ID NO:78;
   y. SEQ ID NO:79;
   z. SEQ ID NO: 81;
   aa. SEQ ID NO:83;
   bb. SEQ ID NO:85;
   cc. SEQ ID NO: 87;
   dd. SEQ ID NO:88; and
   ee. SEQ ID NO:89;
   wherein the antigenic fragment is selected from the group consisting of:
   i. an amino-terminal truncation mutant of the type IV pilin, wherein the number of amino terminal amino acids missing from the fragment ranges from 1-100 amino acids;
   ii. a carboxyl-terminal truncation mutant of the type IV pilin, wherein the number of carboxyl terminal amino acids missing from the fragment ranges from 1-100 amino acids; and
   iii. an internal fragment of the type IV pilin lacking both the amino and carboxyl terminal amino acids and being 10-100 amino acid residues in length;
   ii) an affinity tag sequence to facilitate purification; and
   iii) an enzymatic cleavage sequence.

12. The pharmaceutical composition of claim 11, comprising a combination of isolated polypeptides of claim 11.

13. The pharmaceutical composition of claim 11, wherein said isolated polypeptide comprises a *C. difficile* type IV pilin antigenic fragment that comprises a peptide selected from the group consisting of:
   a. amino acids 35-173 of SEQ ID NO:46;
   b. amino acids 35-173 of SEQ ID NO:47;
   c. amino acids 35-173 of SEQ ID NO:48;
   d. amino acids 31-116 of SEQ ID NO:50;
   e. amino acids 31-116 of SEQ ID NO:51;
   f. amino acids 32-162 of SEQ ID NO:52;
   g. amino acids 31-267 of SEQ ID NO:53;
   h. amino acids 36-272 of SEQ ID NO:54;
   i. amino acids 36-272 of SEQ ID NO:55;
   j. amino acids 36-272 of SEQ ID NO:56;
   k. amino acids 31-267 of SEQ ID NO:57;
   l. amino acids 31-267 of SEQ ID NO:58;
   m. amino acids 31-267 of SEQ ID NO:59;
   n. amino acids 31-267 of SEQ ID NO:60;
   o. amino acids 34-175 of SEQ ID NO:63;
   p. amino acids 34-175 of SEQ ID NO:65;
   q. amino acids 34-175 of SEQ ID NO:66;
   r. amino acids 34-175 of SEQ ID NO:67;
   s. amino acids 34-175 of SEQ ID NO:69;
   t. amino acids 42-188 of SEQ ID NO:71;
   u. amino acids 43-189 of SEQ ID NO:73;
   v. amino acids 42-188 of SEQ ID NO:74;
   w. amino acids 42-188 of SEQ ID NO:75;
   x. amino acids 40-186 of SEQ ID NO:78;
   y. amino acids 40-186 of SEQ ID NO:79;
   z. amino acids 40-186 of SEQ ID NO:81;
   aa. amino acids 32-124 of SEQ ID NO:83;
   bb. amino acids 28-120 of SEQ ID NO:85;
   cc. amino acids 28-120 of SEQ ID NO:87;
   dd. amino acids 33-512 of SEQ ID NO:88; and
   ee. amino acids 32-174 of SEQ ID NO:89.

14. The pharmaceutical composition of claim 1, wherein said isolated polypeptide comprises a *C. difficile* type IV pilin antigenic fragment that is an internal fragment of the type IV pilin lacking both the amino and carboxyl terminal amino acids and being 30-100 amino acid residues in length.

15. A pharmaceutical composition for inducing an immune response against *Clostridium difficile* comprising an isolated polypeptide comprising
   i) an antigenic fragment of a *C. difficile* type IV pilin, wherein the antigenic fragment is recombinantly produced, wherein the antigenic fragment is selected from the group consisting of:
   a. amino acids 35-173 of SEQ ID NO:46;
   b. amino acids 35-173 of SEQ ID NO:47;
   c. amino acids 35-173 of SEQ ID NO:48;
   d. amino acids 31-116 of SEQ ID NO:50;
   e. amino acids 31-116 of SEQ ID NO:51;
   f. amino acids 32-162 of SEQ ID NO:52;
   g. amino acids 31-267 of SEQ ID NO:53;
   h. amino acids 36-272 of SEQ ID NO:54;
   i. amino acids 36-272 of SEQ ID NO:55;
   j. amino acids 36-272 of SEQ ID NO:56;
   k. amino acids 31-267 of SEQ ID NO:57;
   l. amino acids 31-267 of SEQ ID NO:58;
   m. amino acids 31-267 of SEQ ID NO:59;
   n. amino acids 31-267 of SEQ ID NO:60;
   o. amino acids 34-175 of SEQ ID NO:63;
   p. amino acids 34-175 of SEQ ID NO:65;
   q. amino acids 34-175 of SEQ ID NO:66;
   r. amino acids 34-175 of SEQ ID NO:67;
   s. amino acids 34-175 of SEQ ID NO:69;
   t. amino acids 42-188 of SEQ ID NO:71;
   u. amino acids 43-189 of SEQ ID NO:73;
   v. amino acids 42-188 of SEQ ID NO:74;
   w. amino acids 42-188 of SEQ ID NO:75;
   x. amino acids 40-186 of SEQ ID NO:78;
   y. amino acids 40-186 of SEQ ID NO:79;
   z. amino acids 40-186 of SEQ ID NO:81;
   aa. amino acids 32-124 of SEQ ID NO:83;
   bb. amino acids 28-120 of SEQ ID NO:85;
   cc. amino acids 28-120 of SEQ ID NO:87;
   dd. amino acids 33-512 of SEQ ID NO:88; and
   ee. amino acids 32-174 of SEQ ID NO:89; and
   ii) an affinity tag sequence to facilitate purification.

* * * * *